(12) United States Patent
Jin et al.

(10) Patent No.: US 7,462,721 B2
(45) Date of Patent: Dec. 9, 2008

(54) AZA-QUINOLINOL PHOSPHONATE INTEGRASE INHIBITOR COMPOUNDS

(75) Inventors: Haolun Jin, Foster City, CA (US); Choung U. Kim, San Carlos, CA (US); Peter H. Nelson, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 515 days.

(21) Appl. No.: 10/944,118

(22) Filed: Sep. 17, 2004

(65) Prior Publication Data
US 2005/0137199 A1 Jun. 23, 2005

Related U.S. Application Data

(60) Provisional application No. 60/504,050, filed on Sep. 19, 2003.

(51) Int. Cl.
C07J 1/00 (2006.01)
C07D 471/02 (2006.01)
(52) U.S. Cl. .............................. 546/118; 546/9; 546/123
(58) Field of Classification Search ................. 546/118, 546/9, 123
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,639,881 A | 6/1997 | Skibo et al. | |
| 5,663,159 A | 9/1997 | Starrett, Jr. et al. | |
| 5,792,756 A | 8/1998 | Starrett, Jr. et al. | |
| 5,798,340 A | 8/1998 | Bischofberger et al. | |
| 5,883,255 A | 3/1999 | Berges et al. | |
| 6,090,821 A | 7/2000 | Patel et al. | |
| 6,114,349 A | 9/2000 | Kirsch et al. | |
| 6,187,907 B1 | 2/2001 | Chen et al. | |
| 6,211,376 B1 | 4/2001 | Romines et al. | |
| 6,245,806 B1 | 6/2001 | Dombrowski et al. | |
| 6,271,402 B1 | 8/2001 | Singh et al. | |
| 6,312,662 B1 | 11/2001 | Erion et al. | |
| 6,395,743 B1 | 5/2002 | Heimbuch et al. | |
| 6,919,351 B2 * | 7/2005 | Anthony et al. ............. | 514/300 |
| 6,921,759 B2 * | 7/2005 | Anthony et al. ........ | 514/211.03 |
| 2002/0055636 A1 | 5/2002 | Vaillancourt et al. | |
| 2002/0103220 A1 | 8/2002 | Schnute | |
| 2003/0119823 A1 | 6/2003 | Anthony et al. | |

FOREIGN PATENT DOCUMENTS

| WO | WO 91/19721 | 12/1991 |
|---|---|---|
| WO | WO 93/17681 | 9/1993 |
| WO | WO 96/15111 | 5/1996 |
| WO | WO 99/62513 A1 | 12/1999 |
| WO | WO 99/62520 A1 | 12/1999 |
| WO | WO 00/75122 A1 | 12/2000 |
| WO | WO 01/00578 A1 | 1/2001 |
| WO | WO 02/30426 A1 | 4/2002 |
| WO | WO 02/30930 | 4/2002 |
| WO | WO 02/30931 A2 | 4/2002 |
| WO | WO 02/36734 | 5/2002 |
| WO | WO 02/055079 | 7/2002 |
| WO | WO 03/016309 | 2/2003 |
| WO | WO 03/016315 | 2/2003 |
| WO | WO 03/031413 | 4/2003 |
| WO | WO 03/077850 | 9/2003 |
| WO | WO 2004/035576 | 4/2004 |

OTHER PUBLICATIONS

Bly et al. "Heterocyclic Studies. XIII. The Aldol Condensation of 2,3-Dihydro-5-methyl-6-phenyl-4H-1,2-diazepin-4-one . . . " 29:2128-2135; J Org. Chem., 1964.
Butula et al. "Reaktionen mit 1-Chlorocarbonylbenzotriazol; II Synthese von Carbamidsaure-estern . . . " p. 704-706; Synth., 1977.
Calheiros et al. "Acyloxymethyl as a Drug Protecting Group. Synthesis and Reactivity of N-Acyloxymethylsulfonamide Prodrugs." 5(9): 937-940 BioOrg. & Med. Chem. Lett., 1995.
Cavalier et al. "New Highly Diastereoselective Synthesis of Phosphoramidates. A Route to Chiral Methyl p-Nitrophenyl Alkylphosphonates." p. 73-75 Synlett, 1998.
Coleman et al. "Synthesis of the aziridino[1,2-a]pyrrolidine substructure of the antitumor agents azinomycin A and B." 57(22):5813-5815, J Org Chem., 1992.
Davies et al. "Dinucleotide Analogues as Inhibitors of Thymidine Kinase, Thymidylate Kinase and Ribonucleotide Reductase" 31:1305-1308; J. Med. Chem, 1988.
Elielet al. "Sterochemistry of Organic Compounds." p. 322-381, 1990.
Furukawa et al. "Convenient Syntheses of Sulfinamide Derivatives." p. 339-340, Synth., 1976.
Greene et al. "Protection For The Hydroxyl Group, Including 1,2- And 1, 3-Diols." p. 10-142, Protective Groups in Organic Synthesis; 1990.
Greene et al. "Protection For the Amino Group" p. 309-405, Protective Groups in Organic Synthesis; , 1990.

(Continued)

Primary Examiner—D. Margaret Seaman

(57) ABSTRACT

Aza-quinolinol phosphonate compounds and methods for inhibition of HIV-integrase are disclosed.

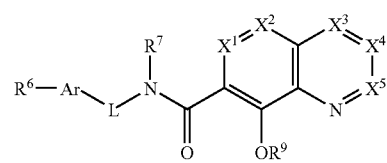

Ar is aryl or heteroaryl connecting $R^6$ to L. L is a bond or a linker connecting a ring atom of Ar to N. The ring atoms, $X^1$-$X^5$ may be N, substituted nitrogen, or substituted carbon, and form rings. The compounds include at least one phosphonate group covalently attached at any site.

47 Claims, No Drawings

OTHER PUBLICATIONS

Greene et al. "Protection for the Amide" p. 397-405, Protective Groups in Organic Synthesis, 1990.

Hakimelahi et al.."Design, Synthesis, and Structure—Activity Relationship of Novel Dinucleotide Analogs As Agents Against Herpes . . . " 38:4648-4659, J Med Chem, 1995.

Hazuda et al. "A novel assay for the DNA strand-transfer reaction of HIV-1 integrase." 22(6):1121-1122; Nuc Acids Res., 1994.

Hazuda et al. "Differential Divalent Cation Requirements Uncouple the Assembly and Catalytic Reactions of Human Immunodeficiency . . . " 71(9): 7005-7011; J Virol., 1997.

Hazuda et al.. "Discovery and Analysis of Inhibitors of the Human Immunodeficiency Integrase." 15:17-24, Drug Design and Discovery, 1997.

Kurita et al. "Trichloromethyl Chloroformate As A Phosgene Equivalent: 3-Isocyanatopropanoyl Chloride." 6:715-718; Org. Syn. Cell, 1988.

Rabjohn et al. "Methods of Preparation." 4:919-921; Org Syn Coll., 1963.

Ratz et al. "Products from Reaction of Hydrazine and Thionooxamic Acid an Their Conversion into Heterocyclic Compounds" 23(12):1931-1934, Org, Chem. 1958.

Razumova et al. "Phosphorus-Containing Heterocycles Condensation of Alkylene and o-Phenylene Ethyl-And (Phenylethynyl) . . . " p. 1834-1837; Zh Obschei Khim., 1974.

Shostakovskii et al. "Synthesis of Full Saturated Esters of 1-Alkylthio-Methylene-2-Chloroprop-2-Enylphosphonic Acid." p. 366-368; J Gen Chem USSR, 1983.

Skwarczynski et al. "Alkylation of Potassium 1-(N-Benzyloxycarbonylamino) Alkylphosphonates and Phosphinates . . . " 25(22):3565-3571 Synthetic Comm., 1995.

Stamm et al. "Reactions with Aziridines XXI The (Michaelis-)Arbusov Reaction with N-Acyl Aziridines and Other Amidoethylations at Phosphorus." 21:1623-1626, Tet Lett., 1980.

Tanaka et al. "Total Synthesis of Tylonolide, The Aglycone of the 16-Membered Ring Macrolide Tylosin, From . . . " 27(31):3651-3654, Tett Lett; 1986.

Tang et al. "The tert-Butanesulfinyl Group: An Ideal Chiral Directing Group and Boc-Surrogate for the Asymmetric Synthesis and . . . " 64:12-13, J. Org. Chem., 1999.

Wessig et al. "A Convenient One-Pot Conversion of N-Boc-B-Aminoalcohols into N-Boc-Aziridines." 8:893-894, Synlett., 1997.

Wolf et al. "The Role of Manganese in Promoting Multimerization and Assembly of Human Immunodeficiency Virus Type 1 Integrase." 70(3):1424-1432; J Virol., 1996.

Anan'Eva et al. "(2-Iodoethyl)Phosphonic Derivatives." 53(3):480-483; J. Gen. Chem. USSR, 1983.

Artico et al."Geometrically and Conformationally Restrained Cinnamoyl Compounds as Inhibitors of HIV-1 Integrase: Synthesis . . . " 41:3948-3960; J Med Chem, 1998.

Asante-Appiah et al."HIV-1 Integrase: Structural Organization, Conformational Changes, and Catalysis" 52:351-369; Advances in Virus Research, 1999.

Balsiger et al."Synthesis of Potential Anticancer Agents. XVIII. Analogs of Carbamoyl Phosphate" 24:434-436; J Org Chem, 1958.

Beauchamp et al. "Amino Acid Ester Prodrugs of Acyclovir" 3(3):157-164; Antiviral Chem & Chemo, 1992.

Bhuta et al"Analogs of Chloramphenicol: Circular Dichroism Spectra, Inhibition of Ribosomal Peptidyltransferase, and Possible Mechanism of Action." 23(12):1299-1305; J Med Ch, 1980.

Bigge et al"Exploration of N-Phosphonoalkyl-, N-Phosphonoalkenyl-, and N (Phosphonoalkyl)phenyl-Spaced . . . " 35(8):1371-1384; J Med Chem, 1992.

Buesen et al."Solid-State Nuclear Magnetic Resonance Analysis of the Conformation of an Inhibitor Bound to Thermolysin" 38:2742-2747; J Med Chem, 1995.

Bundgaard et al"Design and Application of Prodrugs" pp. 113-191; Textbook of Drug, 1991.

Buolamwini et al"CoMFA and CoMSIA 3D OSAR and Docking Studies on Conformationally Restrained Cinnamoyl HIV-1 Integrase . . . " 45:841-852;J Med Chem, 2002.

Burger et al. "Monoesters and Ester-amidates of Aromatic Phosphonic Acids" 79:3575-3579; J Am Chem Soc, 1957.

Benzaria et al."Synthesis, In Vitro Antiviral Evaluation, and Stability Studies of Bis(S-acyl-2-thioethyl) Ester Derviatives of . . . " 39:4958-4965; J Med Chem, 1996.

Campagne et al"(1H-Benzotriazol-1-yloxy)tris(dimethylamino)phosphonium Hexafluorophosphate-and (1H-Benzotriazol-1-yloxy) . . . " 60(16):5214-5223; J Org Chem, 1995.

Carter et al"Carbobenzoxy Chloride and Derivatives" 3:167-169; Org Synth Coll, 1965.

Cates et al. "Phosphorus Analogues of -Aminobutyric Acid, A New Class of Anticonvulsants" 27(5):654-659; J Med Chem, 1984.

Chen et al."Structure-Based Design of a Novel, Potent, and Selective Inhibitor for MMP-13 Utilizing NMR Spectroscopy and Computer-Aided . . . " 122:9648-9654;J Am Chem Soc,2000.

Chen et al. "Anthranilate Sulfonamide Hydroxamate TACE Inhibitors, Part 1: Structure-Based Design of Novel Acetylenic PI' Groups" 12:1195-1198; Bioorg Med Chem Lett, 2002.

Chen et al."Structure-based Design of Potent Inhibitors of Scytalone Dehydratase; Displacement of a Water Molecule from the Active Site" 37:17735-17744;Biochem, 1998.

Chen et al."Design, Synthesis, and Biochemical Evaluation of Phosphonate and Phosphonamidate Analogs of Glutathionylspermidine as Inhibitors . . . " 40(23):3842-3850; J Med Chem, 1997.

Corey et al."Selective Cleavage of Allyl Ethers Under Mild Conditions By Transition Metal Reagants"38(18):3224;J Org Chem, 1973.

Coe et al. "Synthesis of Some Mimics of Nucleoside Triphosphates" pp. 312-314; J. Chem. Soc. Chem. Commun., 1991.

D'Addona et al."Preparation of carbamates from amines and alcholols under mind conditions." 42:5227-5229; Tet Lett, 2001.

De Lombaert et al. "N-Phosphonomethyl Dipeptides and heir Phosphonate Prodrugs, a New Generation of Neutral Endopeptidase (NEP, EC 3.4.24.11) Inhibitor"37:498-511;J Med Chem, 1994.

Darby, G."In search of the perfect antiviral" 6:54-63; Antiviral Chem & Chemo, 1995.

Effenberger et al. "2(1H)-Pyridon als Austrittsgruppe bei Acylierungsreaktionen Anwendungen in der Peptidchemie" 118:468-482; Chem Ber, 1985.

Efimov et al."Synthesis of DNA Analogues with Novel Carboxamidomethyl Phosphonamide and Glycinamide Internucleoside Linkages" 8:1013-1018;Bioorg Med Chem Lett,1998.

Espeseth et al."HIV-1 integrase inhibitors that compete with the target DNA substrate define a unique strand transfer conformation for integrase"97:11244-11249; Proc Natl Aca, 2000.

Farnet et al."Differential inhibition of HIV-1 preintegration complexes and purified integrase protein by small molecules" 93:9742-9747;Proc Natl Acad Sci, 1996.

Farquhar et al. "Biologically Reversible Phosphate-Protective Groups" 72:324-325; J Pharm Sci, 1983.

Galeotti et al."A Straightforward Synthesis of -Amino Phosphonate Monoesters Using BroP or TPyClU "37(23):3997-3998;Tet Lett, 1996.

Gali et al."Facile Ring-Opening Reactions of Phthalimides as a New Strategy to Synthesize Amide-Funtionalized Phosphonates, Primary . . . "65:676-680; J Org Chem, 2000.

Goldgur et al."Structure of the HIV-1 integrase catalytic domain complexed with an inhibitor: A platform for antiviral drug design." 96:13040-13043; Proc Natl Acad Sci, 1999.

Griffin et al. "D-Glucopyranose 5-Deoxy-6-phosphonic Acid. "78(10):2336-2338;J Am Chem Soc., 1956.

Hanse et al. "Partially Protected Polyamines." 404-405; Synthesis, 1982.

Hughes, David L."The Mitsunobu Reaction." 42:335-381;Org Reac vol. 42.,1992.

Hunig et al."The Chemistry of Diimine." 4(4):271-382; Angnew Chem International, 1965.

Hazuda et al."Inhibitors of strand transfer that prevent integration and inhibit HIV-1 replication in cells."287:646-650;Science.,2000.

Jing et al."Potassium-Dependent Folding: A Key to Intracellular Delivery of G-Quartet Olignonucleotides as HIV Inhibitors."41:5397-5403; Biochem., 2002.

Jacob III, Peyton"Resolution of ( )-5-Bromonornicotine. Synthesis of (R)- and (S)- Nornicotine of High Enantiomeric Purity." 47:4165-4167;J Org Chem., 1982.

Katzman et al."Substrate Recognition By Retroviral Integrase." 52:371-395; Advances in Virus Research., 1999.

Khamnei et al."Neighboring Group Catalysis in the Design of Nucleotide Prodrugs."39:4109-4115;J Med Chem, 1996.

Khandazhinskaya et al. "Carbocyclic Dinucleoside Polyphosphonates: Interactions with HIV reverse Transcriptase and Antiviral Activity." 45:1284-1291; J Med Chem.,2002.

Konakahara et al. "A Convenient Method for the Synthesis of Activated N-Methylcarbamates." 103-106; Synthesis., 1993.

Krise et al. "Prodrugs of phosphates, phosphonates, and phosphinates." 19:287-310; Advanced Drug Delivery Reviews., 1996.

Kunz et al. "71. Synthesis of the Glycopeptide Partial Sequence A 80-A84 of Human Fibroblast Interferon." 68:618-622; Helvetica Chimica Acta.,1985.

Lafemina et al. "Requirement of Active Human Immunodeficiency Virus Type 1 Integrase Enzyme for Productive Infection of Human T-Lymphoid Cells." 66:7414-7419; J Virol.,1992.

Lam et al. "Cyclic HIV Protease Inhibitors: Synthesis, Conformational Analysis, P2/P2' Structure-Activitiy Relationship, and Molecular . . . " 39:3514-3525; J Med Chem.,1996.

Lochmuller et al. "Chromatographic Resolution of Enantiomers Selective Review."113:283-302; J Chromatog.,1975.

Lombaert et al."N-Phosphonomethyl Dipeptides and Their Phosphonate Prodrugs, a New Generation of Neutral Endopeptidase (NEP, EC 3.4.24.11) . . . " 37:498-511; J Med Chem, 1994.

Maffre-Lafon et al. "Solid Phase Synthesis of Phosphonopeptides from Fmoc Phosphonodipeptides." 35:4097-4098; J Med Chem.,1994.

Mattson et al."An Improved Method for Reductive Alkylation of Amines Using Titanium (IV) Isopropoxide and S odium Cyanoborohydride."55(8):2552-2554;J Org Chem., 1990.

McKenna et al. "Functional Selectivity in Phosphonate Ester Dealkylation with Bromotrimethylsilane." p. 739; JCS Chem Com.,1979.

Mikhailopulo et al. "Pyrophosphoryl Derivatives of 1-(2-Deoxy-3-O-Phosphonome . . . " 19(10-12):1885-1909; Nucls & Nuclt.,2000.

Mitchell et al. "Bioreversible Protection for the Phospho Group: Bioactivation of the Di(4acyloxybenzyl) and Mono . . . " 2345-2353; J Chem Soc Perkin Trans I.,1992.

Mladenova et al. "An Efficient Synthesis of Enediyne and Arenediyne Lactams." 25(9):1401-1410; Synthetic Comm.,1995.

Morgan et al. "Structure-Based Design of an Inhibitor of the Zinc Peptidase Thermolysin." 116(8):3251-3260;J Am Chem Soc.,1994.

Morr et al. "Formation of Phostonic Acids During The Reduction of Azidonucleosidephosphonic Acids ."42:8841-8843;Tet Lett.,2001.

Morris et al."Vinyl Sulfonyl Esters Amides in the Synthesis of Substituted Sultams and Sultones." 56:3549-3556; J Org Chem., 1991.

Musiol et al. "On the Synthesis of Phosphonamidates Peptides." 59(21):6144-6146; J Org Chem.,1994.

Nair et al. "HIV integrase as a target for antiviral chemotherapy." 12:179-193; Rev. Med. Virol..,2002.

Neamati, Nouri "Patented Small Molecule Inhibotors of HIV-1 Integrase: a 10-year Saga."12(5):709-724;Expert Opin. Ther. Patents., 2002.

Neustadt, Bernard "Facile Preparation of N-(Sulfonyl)carbamates." 35(3):379-380;Tet Lett.,1994.

Okamoto et al. "Optical resolution of dihydropyridine enantiomers by High-performance liquid chromatography using . . . " 513:375-378; Journal of Chromatography.,1990.

Oliyai et al. "Enhanced chemical stability of the intracellular prodrug"179:257-265; Intl Jour Pharm, 1999.

Oliyai et al. "Aryl Ester Prodrugs of Cyclic HPMPC. I: Physicochemical Characterization and In Vitro Biological Stability." 16(11):1687-1693; Pharm Res.,1999.

Pais et al. "Structure Activity of 3-Aryl-1,3-diketo-Containing Compounds as HIV-1 Integrase Inhibitors." 45:3184-3194;J Med Chem.,2002.

Palella et al. "Declining Morbitity and Morality Among Patients with Advances Human Immunodeficiency Virus Infection ."338:853-860;J Med Chem.,1998.

Paquet, Alenka "Introduction of 9-fluorenylmethyloxycarbonyl, trichloroethoxycarbonyl, and benzyloxycarbonyl . . . " 60:976-980; Can J Chem., 1981.

Phillion et al."Synthesis and Reactivity of Diethyl Phosphonomethyltriflate." 27(13):1477-1480; Tet Lett.,1986.

Pommier et al. "Retroviral integrase inhibitors year 2000: update and perspectives." 47:139-148; Antiviral Res.,2000.

Pommier et al. "Inhibitors of Human Immunodeficiency Virus Integrase."52:427-459;Advances in Virus Research., 1999.

Puech et al. "Intracellular delivery of nucleoside monophosphates through a reuctase-mediated activation process." 22:115-174;Antiviral Res.,1993.

Pungente et al. "Synthesis and Sterochemical Elucidation of a 14-Membered Ring Phosphonate" 3(5): 643-646; Org Lett.,2001.

Paquette, Leo A."Three-Membered Rings with One Hetero Atom."Chptr:1; Principals of Modern Heterocyclic Chemistry, 1968.

Paquette, Leo A."The Four-Membered Heterocycles" Chptr:3; Principals of Modern Heterocyclic Chemistry,1968.

Paquette, Leo A. "Furan, Pyrrole, and Thiophene."Chptr:4; Principals of Modern Heterocyclic Chemistry,1968.

Paquette, Leo A. "The Azole ."Chptr:6; Principals of Modern Heterocyclic Chemistry,1968.

Paquette, Leo A. "The Diazines and S-Triazine." Chptr:9; Principals of Modern Heterocyclic Chemistry,1986.

Ratz et al. "Products from Reaction of Hydrazine and Thionooxamic Acid and Their Conversion into Heterocyclic Compounds."23(12):1931-1934; J Org Chem.,1958.

Richman, Douglas "HIV Chemotherapy"410:995-1001; Nature, 2001.

Roach et al. "Fluorescence Detection of Alkylphosphonic Acids Using p-(9-Anthroyloxy)phenacyl Bromide." 59:1056-1059; Anal Chem,1987\.

Rosenberg et al. "Synthesis of Potential Prodrugs and Metabolites of 9-(S)-(3-Hydroxy-2-Phosphonylmethoxypropyl)Adenines" 52:2792-2800; Collect Czech Chem Commun.,1987.

Saady et al."Selective Monodeprotection of Phosphate, Phosphite, Phosphonate, and Phosphoramide Benzyl Esters."60:2946-2947; J Org Chem, 1995.

Sasaki et al."Convenient Synthesis of Some Purine 8,5'-Imino Cyclonucleosides"43(12):2320-2325; J Org Chem.,1978.

Schon et al. "9-Fluorenylmethyl Pentafluorophenyl Carbonate As a Useful Reagant for the Preparation of N-9-Fluorenylm." p. 303-305; Synthesis,1986.

Serafinowska et al. "Synthesis and in Vivo Evalutation of Prodrugs of 9-[2-(Phosphonomethoxy) ethoxy]adenine."38:1372-1379; J Med Chem; 1995.

Sharma et al. "Spermexatin and Spermexatol: New synthetic Spermidine-Based Siderophore anologues." 32:357-367; J Med Chem, 1989.

Sun et al."A General Synthesis of Dioxolenone Prodrug Moieties."43:1161-1164;Tet Lett,2002.

Sardina et al. "Studies on the Synthesis of Side-Chain Hydroxylated Metabolites of Vitamin D. 2. Sterocontrolled Synthesis of 25-Hydroxyvitamin D 2 1."51:1264-1269; J Org Che, 2002.

Thomson et al."Synthesis and Bioactivation of Bis(aroyloxymethyl)and Mono(aroyloxymethyl) Esters of Benzylphosphonate and Phosphonoacetate."19:2303-2308;J Chem Soc Perkin Com, 1993.

Tsushima et al. "Fluorine-Containing Amino Acids and Their Derivatives. 7. Synthesis and Antitumor Activity of and . . . " 44(17):5375-5378; Tetra, 1988.

Vieira de Almeida et al."Synthesis of Deoxy Phosphatidylinositol Analogues and Phosphonate Isosters of Ins (1,4,5)P3" 55:12997-13010; Tetrahedron,1999.

Yamauchi et al."Synthesis of Peptides Analogs Containing(2-aminoethyl)phosphonic acid (ciliatine)."49(7)L1158-1163; J Org Chem, 1984.

Yokomatsu et al."Enzymatic Desymmetrization of Prochiral 2-Benzyl-1, 3-propanediol Derivatives: A Practical Chemoenzymatic Synthesis of Novel . . ."54:9341-9356; Tet, 1998.

Young, Steven "Inhibition of HIV-1 Integrase by small Molecules: The potential for a new class of AIDS chemotherapeutics." 4(4):402-410; Current Opinion in Drug D, 2001.

Yuan et al. "Effect of Carbonate Salts on the Kinetics of Acid-Catalyzed Dimerization of Adefovir Dipivoxil."17:1098-1103; Pharm Res; 2000.

* cited by examiner

AZA-QUINOLINOL PHOSPHONATE INTEGRASE INHIBITOR COMPOUNDS

This application claims the benefit of U.S. Provisional Application(s) No(s). 60/504,050 filed Sep. 19, 2003

FIELD OF THE INVENTION

The invention relates generally to compounds with antiviral activity and more specifically with HIV-integrase inhibitory properties.

BACKGROUND OF THE INVENTION

Human immunodeficiency virus (HIV) infection and related diseases are a major public health problem worldwide. A virally encoded integrase protein mediates specific incorporation and integration of viral DNA into the host genome. Integration is essential for viral replication. Accordingly, inhibition of HIV integrase is an important therapeutic pursuit for treatment of HIV infection and related diseases.

Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, etal *N. Engl. J. Med.* (1998) 338:853-860; Richman, D. D. *Nature* (2001) 410:995-1001). There is a need for new agents directed against alternate sites in the viral life cycle. Integrase has emerged as an attractive target, because it is necessary for stable infection and homologous enzymes are lacking in the human host (LaFemina, etal *J. Virol.* (1992) 66:7414-7419). The function of integrase is to catalyze integration of proviral DNA, resulting from the reverse transcription of viral RNA, into the host genome, by a stepwise fashion of endonucleolytic processing of proviral DNA within a cytoplasmic preintegration complex (termed 3'-processing or "3'-P") with specific DNA sequences at the end of the HIV-1 long terminal repeat (LTR) regions, followed by translocation of the complex into the nuclear compartment where integration of 3'-processed proviral DNA into host DNA occurs in a "strand transfer" (ST) reaction (Hazuda, etal *Science* (2000) 287:646-650; Katzman, etal *Adv. Virus Res.* (1999) 52:371-395; Asante-Applah, etal *Adv. Virus Res.* (1999) 52:351-369). Although numerous agents potently inhibit 3'-P and ST in extracellular assays that employ recombinant integrase and viral long-terminal-repeat oligonucleotide sequences, often such inhibitors lack inhibitory potency when assayed using fully assembled preintegration complexes or fail to show antiviral effects against HIV-infected cells (Pommier, etal *Adv. Virus Res.* (1999) 52:427-458; Farnet, etal *Proc. Natl. Acad. Sci. U.S.A.* (1996) 93:9742-9747; Pommier, etal *Antiviral Res.* (2000) 47:139-148.

Certain HIV integrase inhibitors have been disclosed which block integration in extracellular assays and exhibit good antiviral effects against HIV-infected cells (Anthony, etal WO 02/30426; Anthony, etal WO 02/30930; Anthony, etal WO 02/30931; WO 02/055079; Zhuang, etal WO 02/36734; U.S. Pat. Nos. 6,395,743; 6,245,806; 6,271,402; Fujishita, etal WO 00/039,086; Uenaka etal WO 00/075,122; Selnick, etal WO 99/62513; Young, etal WO 99/62520; Payne, etal WO 01/00578; Jing, etal *Biochemistry* (2002) 41:5397-5403; Pais, etal *Jour. Med. Chem.* (2002) 45:3184-94; Goldgur, etal *Proc. Natl. Acad. Sci. U.S.A.* (1999) 96:13040-13043; Espeseth, etal *Proc. Natl. Acad. Sci. U.S.A.* (2000) 97:11244-11249).

HIV integrase inhibitory compounds with improved antiviral and pharmacokinetic properties are desirable, including enhanced activity against development of HIV resistance, improved oral bioavailability, greater potency and extended effective half-life in vivo (Nair, V. "HIV integrase as a target for antiviral chemotherapy" *Reviews in Medical Virology* (2002) 12(3):179-193; Young (2001) Current Opinion in Drug Discovery & Development, Vol. 4, No. 4, 402-410; Neamati (2002) Expert. Opin. Ther. Patents Vol. 12, No. 5, 709-724). Three-dimensional quantitative structure-activity relationship studies and docking simulations (Buolamwini, etal *Jour. Med. Chem.* (2002) 45:841-852) of conformationally-restrained cinnamoyl-type integrase inhibitors (Artico, etal *Jour. Med. Chem.* (1998) 41:3948-3960) have shown a large contribution of hydrogen-bonding interactions to the inhibitory activity differences among the compounds. Conformationally-constrained hydrogen-bonding functionality such as hydroxyl was correlated with inhibitory activity. Compounds with binding functionality in a pre-organized configuration may possess optimized inhibitory properties against HIV integrase. The prior art does not show or suggest compounds with integrase binding functionality in a pre-organized conformation or molecular structure. In addition to therapeutic uses, the value of compounds in diagnostic assays for HIV, for use in the preparation of polymers and for use as surfactants, and in other industrial utilities will be readily apparent to those skilled in the art.

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g. to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., cytotoxic agents and other anti-cancer or anti-viral drugs) that can be administered. By comparison, although oral administration of drugs is generally recognized as a convenient and economical method of administration, oral administration can result in either (a) uptake of the drug through the cellular and tissue barriers, e.g. blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells. Intracellular targeting may be achieved by methods and compositions which allow accumulation or retention of biologically active agents inside cells.

SUMMARY OF THE INVENTION

The present invention provides compositions and methods for inhibition of HIV-integrase.

The invention provides a compound having the structure:

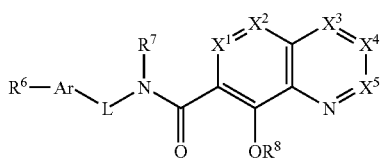

or a pharmaceutically acceptable salt thereof, and including enol and tautomeric resonance isomers;

wherein:

$X^1$ is $CR^1$, NR, or N;

$X^2$ is $CR^2$, NR, or N;

$X^3$ is $CR^3$, NR, or N;

$X^4$ is $CR^4$, NR, or N;

$X^5$ is $CR^5$, NR, or N;

at least one of $X^1$, $X^2$, $X^3$, $X^4$, and $X^5$ is NR or N;

$R^1$, $R^3$, $R^4$, $R^5$, $R^6$, $R^7$ and $R^8$ are independently selected from H, F, Cl, Br, I, OH, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$), arylsulfone (—$SO_2Ar$), arylsulfoxide (—SOAr), arylthio (—SAr), sulfonamide (—$SO_2NR_2$), alkylsulfoxide (—SOR), formyl (—CHO), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, and a prodrug moiety; or when $X^1$ is $CR^1$ and when $X^2$ is $CR^2$, then $CR^1$ and $CR^2$ together may form a ring; when $X^3$ is $CR^3$ and when $X^4$ is $CR^4$, then $CR^3$ and $CR^4$ together may form a ring; or when $X^4$ is $CR^4$ and $X^5$ is $CR^5$, then $CR^4$ and $CR^5$ together may form a ring; wherein the ring is 5, 6, or 7-membered;

$R^2$ is selected from H, F, Cl, Br, I, OH, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$) arylsulfone (—$SO_2Ar$), arylsulfoxide (—SOAr), arylthio (—SAr), sulfonamide (—$SO_2NR_2$), alkylsulfoxide (—SOR), formyl (—CHO), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, a prodrug moiety, OC(=O)OR, OC(=O)$NR_2$, OC(=O)R, $OSO_2NR_2$ (sulfamate), $NR_2$, $NRSO_2R$, SR, S(O)R, $SO_2R$ or $SO_2NR_2$ (sulfonamide), lactam having the structures:

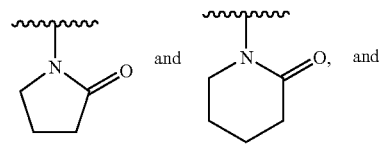

sultam having the structures:

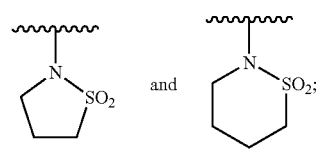

R is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl;

L is selected from a bond, O, S, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, C(=O), S(=O)$_2$, C(=O)NH(CH$_2$)$_n$, and (CH$_2$CH$_2$O)$_n$, where n may be 1, 2, 3, 4, 5, or 6; and Ar is covalently attached to L and to one or more $R^6$ and Ar is selected from $C_6$-$C_{20}$ aryl, $C_6$-$C_{20}$ substituted aryl, $C_2$-$C_{20}$ heteroaryl, and $C_2$-$C_{20}$ substituted heteroaryl;

where at least one of R, $R^1$, $R^2$, $R^3$, $R^4$, $R^5$, $R^6$, $R^7$ and $R^8$ comprises a phosphonate group.

The present invention also provides a compound having the formula:

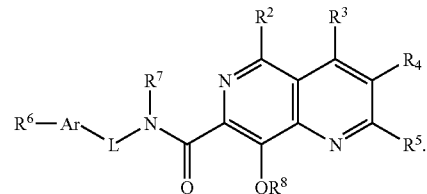

The present invention also provides a compound having the formula:

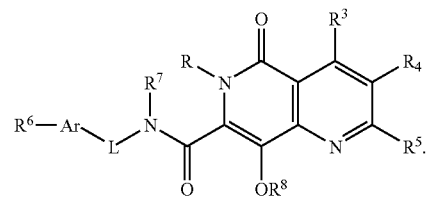

The present invention also provides a compound having the formula:

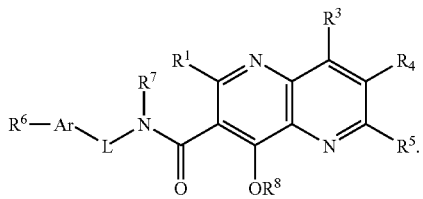

The present invention also provides a compound having the formula:

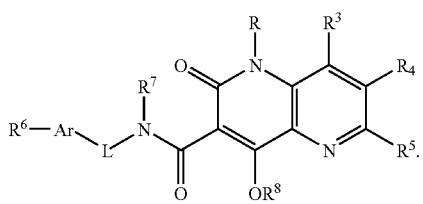

The present invention also provides a compound having the formula:

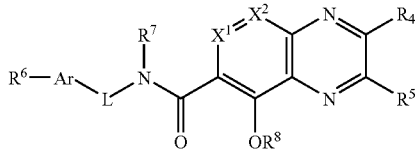

The present invention also provides a compound having the formula:

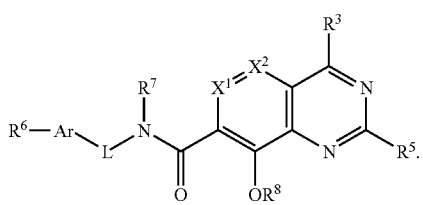

The present invention also provides a compound having the formula:

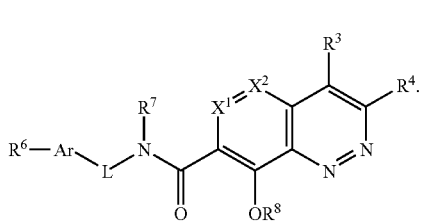

The present invention also provides a compound having the formula:

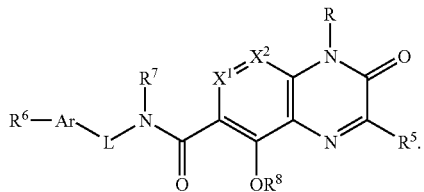

The present invention also provides a compound having the formula:

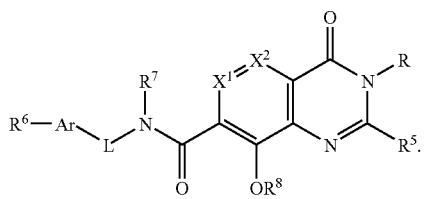

The present invention also provides a compound having the formula:

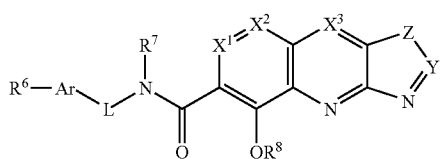

wherein
Y is $CR^5$, NR or N; and
Z is selected from O, S, NR, $CR_2$, CROR, CROC(=O)R, C(=O), C(=S), CRSR, C(=$NR_2$), C=$CR_2$, $CR_2$—$CR_2$, CR=CR, NR—$CR_2$, N=CR, N=N, $SO_2$—NR, C(=O)$CR_2$, S(=O)$CR_2$, $SO_2CR_2$, C(=O)NR, $CR_2$—$CR_2$—$CR_2$, CR=CR—$CR_2$, CRC(=O)NR, $CR_2SO_2CR_2$, $CR_2SO_2$NR, CRC(=S)NR, CR=N—$CR_2$, CR=N—NR, or N=CR—NR.

Also provided in the present invention are compounds of the above formulae wherein substituted alkylene, substituted alkenylene, substituted alkynylene, substituted aryl, and substituted heteroaryl are independently substituted with one or more substituents selected from F, Cl, Br, I, OH, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2$R), arylsulfone (—$SO_2$Ar), arylsulfoxide (—SOAr), arylthio (—SAr), sulfonamide (—$SO_2NR_2$), alkylsulfoxide (—SOR), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, and a prodrug moiety.

Also provided in the present invention are compounds of the above formulae wherein $X^2$ is $CR^2$ and $R^2$ is selected from H, OH, OC(=O)OR, OC(=O)NR$_2$, OC(=O)R, OSO$_2$NR$_2$ (sulfamate), NR$_2$, NRSO$_2$R, SR, S(O)R, SO$_2$R or SO$_2$NR$_2$ (sulfonamide), lactam having the structures:

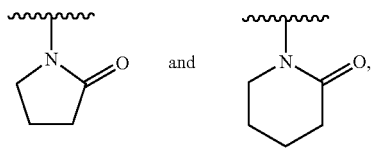 and sultam having the structures:

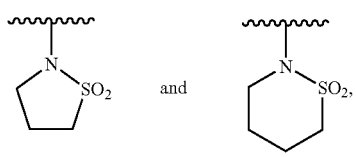 and and a prodrug moiety.

Also provided in the present invention are compounds of the above formulae wherein L is CH$_2$ and Ar is substituted phenyl.

Also provided in the present invention are compounds of the above, formulae where L is CH$_2$ and Ar is 4-fluorophenyl.

Also provided in the present invention are compounds of the above formulae wherein at least one of R$^1$, R$^2$, R$_3$, R$^4$, R$^5$, R$^6$, R$^7$ and R$^8$ comprise a prodrug moiety selected from the structures:

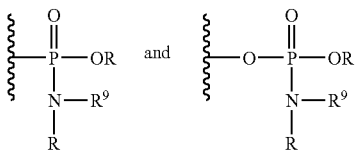

wherein R$^9$ is comprised of an ester, an amide, or a carbamate.

Also provided in the present invention are compounds of the above formulae wherein the phosphonate group has the structure:

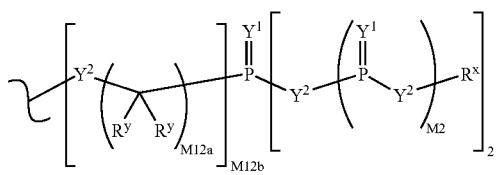

wherein:

Y$^1$ is independently O, S, N(R$^x$), N(O)(R$^x$), N(OR$^x$), N(O)(OR$^x$), or N(N(R$^x$)(R$^x$));

Y$^2$ is independently a bond, O, N(R$^x$), N(O)(R$^x$), N(OR$^x$), N(O)(OR$^x$), N(N(R$^x$)(R$^x$)), —S(O)— (sulfoxide), —S(O)$_2$— (sulfone), —S—(sulfide), or —S—S—(disulfide);

M2 is 0, 1 or 2;

M12a is 1, 2, 3, 4, 5, 6, 7, 8, 9, 10, 11, or 12;

M12b is 0, 1, 2, 3, 4, 5, 6, 7, 8, 9, 10, 11, or 12;

R$^y$ is independently H, alkyl, substituted alkyl, aryl, substituted aryl, or a protecting group, or where taken together at a carbon atom, two vicinal R$^y$ groups form a carbocycle or a heterocycle; and R$^x$ is independently H, alkyl, substituted alkyl, aryl, substituted aryl, or a protecting group, or the formula:

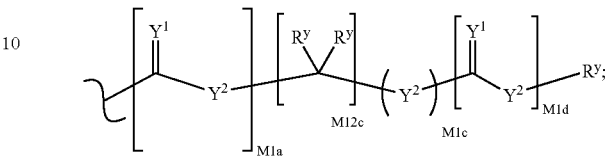

where M1a, M1c, and M1d are independently 0 or 1, and M12c is 0, 1, 2, 3, 4, 5, 6, 7, 8, 9, 10, 11 or 12.

Also provided in the present invention are compounds of the above formulae wherein phosphonate group has the structure:

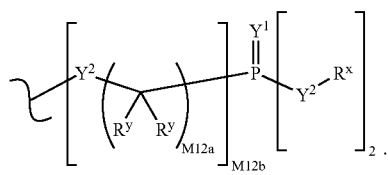

Also provided in the present invention are compounds of the above formulae wherein phosphonate group has the structure:

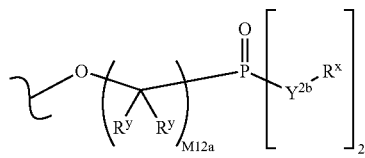

where Y$^{2b}$ is O or N(R$^x$).

Also provided in the present invention are compounds of the above formulae wherein phosphonate group has the structure:

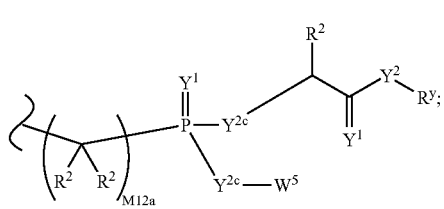

where W$^5$ is a carbocycle, and Y$^{2c}$ is O, N(R$^y$) or S.

Also provided in the present invention are compounds of the above formulae wherein W$^5$ is selected from the structures:

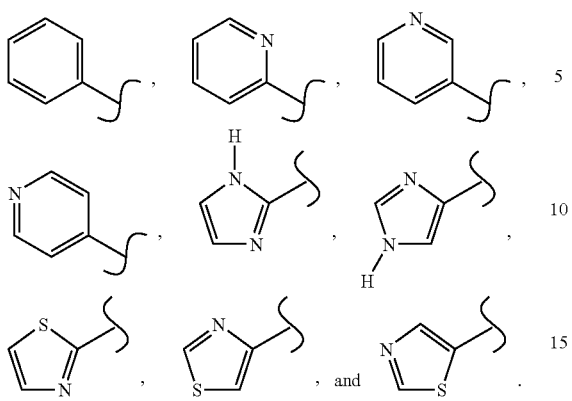

Also provided in the present invention are compounds of the above formulae wherein phosphonate group has the structure:

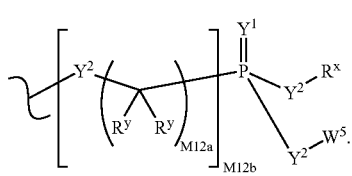

Also provided in the present invention are compounds of the above formulae wherein phosphonate group has the structure:

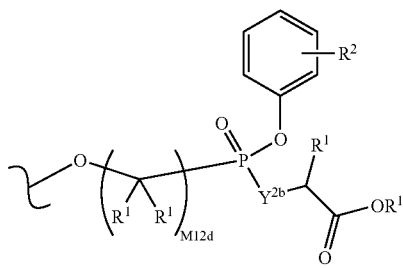

wherein $Y^{2b}$ is O or $N(R^x)$; M12d is 1, 2, 3, 4, 5, 6, 7 or 8; $R^1$ is H or $C_1$-$C_6$ alkyl; and the phenyl carbocycle is substituted with 0 to 3 $R^2$ groups where $R^2$ is $C_1$-$C_6$ alkyl or substituted alkyl.

Also provided in the present invention are compounds of the above formulae wherein phosphonate group has the structure:

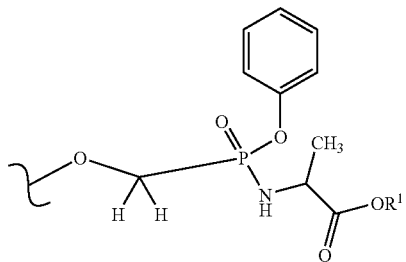

or

-continued

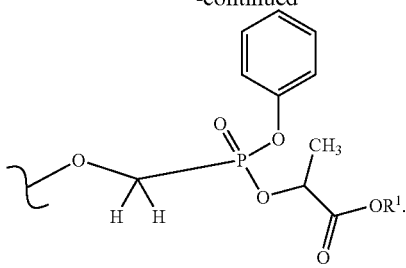

Also provided in the present invention are compounds of the above formulae wherein $R^x$ is selected from the structures:

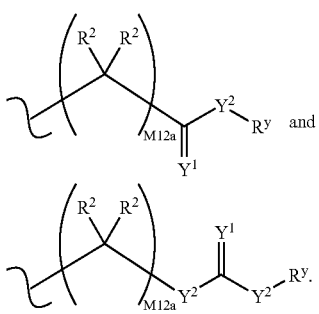

Also provided in the present invention are compounds of the above formulae wherein $X^2$ is $CR^2$ and $R^2$ is selected from the structures:

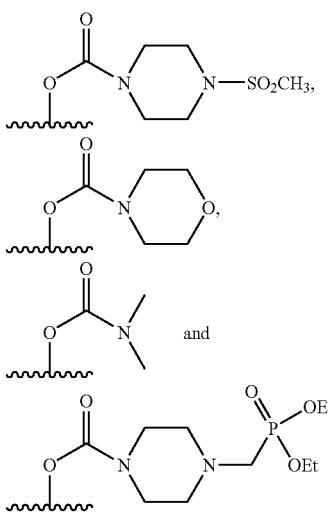

Also provided in the present invention are compounds of the above formulae wherein $X^2$ is $CR^2$ and $R^2$ is selected from the structures:

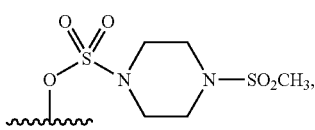

-continued

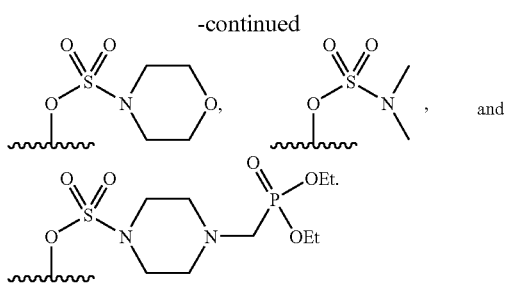

Also provided in the present invention are compounds of the above formulae wherein $X^2$ is $CR^2$ and $R^2$ comprises a phosphonate prodrug moiety.

Also provided in the present invention are compounds of the above formulae wherein Ar-L is selected from the structures:

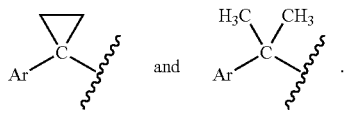

Also provided in the present invention is a compound of the structure:

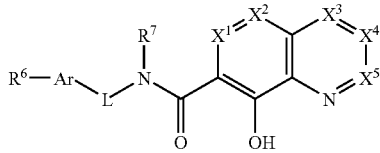

or a pharmaceutically acceptable salt thereof, and including enol and tautomeric resonance isomers;

wherein:

$X^1$ is $CR^1$, NR, or N;
$X^2$ is $CR^2$, NR, or N;
$X^3$ is $CR^3$, NR, or N;
$X^4$ is $CR^4$, NR, or N;
$X^5$ is $CR^5$, NR, or N;

at least one of $X^1$, $X^2$, $X^3$, $X^4$, and $X^5$ is NR or N;

$R^1$, $R^3$, $R^4$, $R^5$, $R^6$, and $R^7$ are independently selected from H, F, Cl, Br, I, OH, amino (—NH$_2$), ammonium (—NH$_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), formyl (—CHO), ester (—C(=O)OR), amido (—C(=O)NR$_2$), 5-7 membered ring lactam, 5-7 membered ring lactone, nitrile (—CN), azido (—N$_3$), nitro (—NO$_2$), $C_1$-$C_8$ alkoxy (—OR), $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, and a prodrug moiety; or when $X^1$ is $CR^1$ and when $X^2$ is $CR^2$, then $CR^1$ and $CR^2$ together may form a ring; when $X^3$ is $CR^3$ and when $X^4$ is $CR^4$, then $CR^3$ and $CR^4$ together may form a ring; or when. $X^4$ is $CR^4$ and $X^5$ is $CR^5$, then $CR^4$ and $CR^5$ together may form a ring; wherein the ring is 5, 6, or 7-membered;

$R^2$ is selected from H, F, Cl, Br, I, OH, amino (—NH$_2$), ammonium (—NH$_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—SO$_2$R) arylsulfone (—SO$_2$Ar), arylsulfoxide (—SOAr), arylthio (—SAr), sulfonamide (—SO$_2$NR$_2$), alkylsulfoxide (—SOR), formyl (—CHO), ester (—C(=O)OR), amido (—C(=O)NR$_2$), 5-7 membered ring lactam, 5-7 membered ring lactone, nitrile (—CN), azido (—N$_3$), nitro (—NO$_2$) $C_1$-$C_8$ alkoxy (—OR), $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, a prodrug moiety, OC(=O)OR, OC(=O)NR$_2$, OC(=O)R, OSO$_2$NR$_2$ (sulfamate), NR$_2$, NRSO$_2$R, SR, S(O)R, SO$_2$R or SO$_2$NR$_2$ (sulfonamide), lactam having the structures:

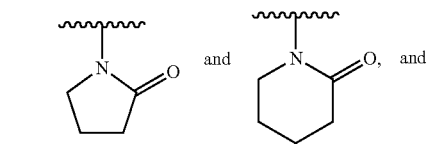

sultam having the structures:

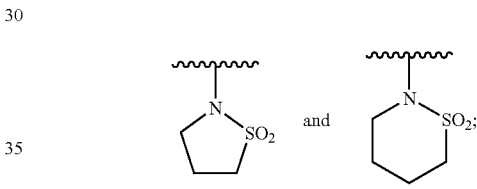

R is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl;

L is selected from a bond, O, S, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, C(=O), S(=O)$_2$, C(=O)NH(CH$_2$)$_n$, and (CH$_2$CH$_2$O)$_n$, where n may be 1, 2, 3, 4, 5, or 6; and Ar is covalently attached to L and to one or more $R^6$ and Ar is selected from $C_6$-$C_{20}$ aryl, $C_6$-$C_{20}$ substituted aryl, $C_2$-$C_{20}$ heteroaryl, and $C_2$-$C_{20}$ substituted heteroaryl;

where at least one of R, $R^1$, $R^2$, $R^3$, $R^4$, $R^5$, $R^6$, and $R^7$ comprises a phosphonate group.

The present invention also provides a compound having the formula:

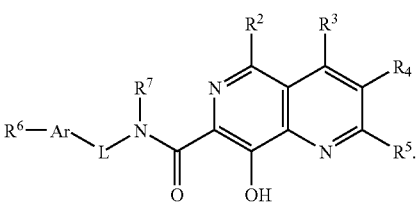

The present invention also provides a compound having the formula:

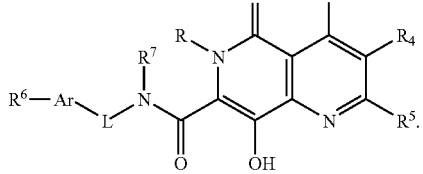

The present invention also provides a compound having the formula:

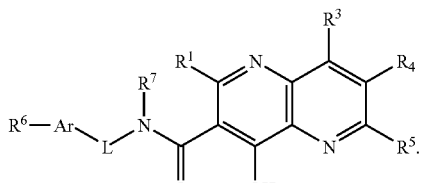

The present invention also provides a compound having the formula:

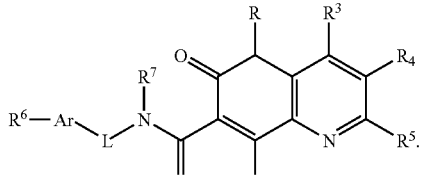

The present invention also provides a compound having the formula:

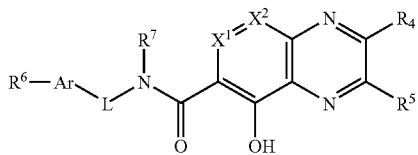

The present invention also provides a compound having the formula:

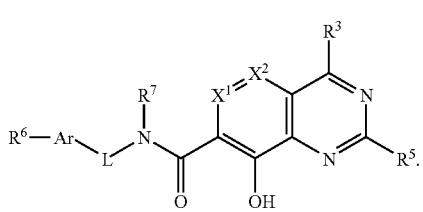

The present invention also provides a compound having the formula:

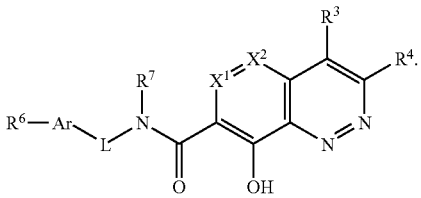

The present invention also provides a compound having the formula:

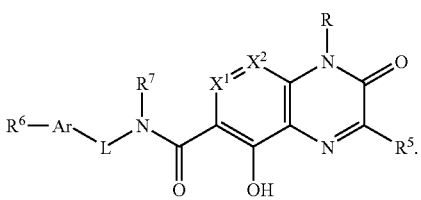

The present invention also provides a compound having the formula:

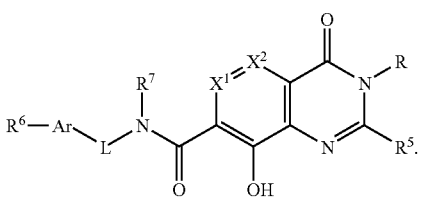

The present invention also provides a compound having the formula:

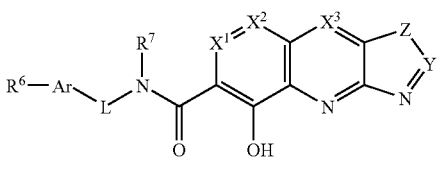

wherein
Y is $CR^5$, NR or N; and
Z is selected from O, S, NR, $CR_2$, CROR, CROC(=O)R, C(=O), C(=S), CRSR, C(=$NR_2$), C=$CR_2$, $CR_2$—$CR_2$, CR=CR, NR—$CR_2$, N=CR, N=N, $SO_2$—NR, C(=O)$CR_2$, S(=O)$CR_2$, $SO_2CR_2$, C(=O)NR, $CR_2$—$CR_2$—$CR_2$, CR=CR—$CR_2$, CRC(=O)NR, $CR_2SO_2CR_2$, $CR_2SO_2$NR, CRC(=S)NR, CR=N—$CR_2$, CR=N—NR, or N=CR—NR.

Also provided in the present invention are compounds of the above formulae wherein substituted alkylene, substituted alkyenylene, substituted alkynylene, substituted aryl, and substituted heteroaryl are independently substituted with one or more substituents selected from F, Cl, Br, I, OH, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$), arylsulfone (—$SO_2Ar$), arylsulfoxide (—SOAr), arylthio (—SAr), sulfonamide (—$SO_2NR_2$), alkylsulfoxide (—SOR), ester (—C(=O)OR), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, and a prodrug moiety.

Also provided in the present invention are compounds of the above formulae wherein $X^2$ is $CR^2$ and $R^2$ is selected from H, OH, OC(=O)OR, OC(=O)$NR_2$, OC(=O)R, $OSO_2NR_2$ (sulfamate), $NR_2$, $NRSO_2R$, SR, S(O)R, $SO_2R$ or $SO_2NR_2$ (sulfonamide), lactam having the structures:

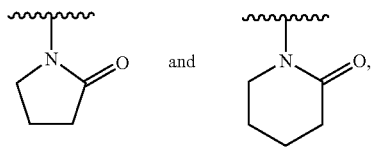 and sultam having the structures:

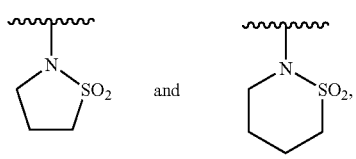 and and a prodrug moiety.

Also provided in the present invention are compounds of the above formulae wherein L is $CH_2$ and Ar is substituted phenyl.

Also provided in the present invention are compounds of the above formulae wherein L is $CH_2$ and Ar is 4-fluorophenyl.

Also provided in the present invention are compounds of the above formulae wherein at least one of $R^1$, $R^2$, $R^3$, $R^4$, $R^5$, $R^6$, and $R^7$ comprise a prodrug moiety selected from the structures:

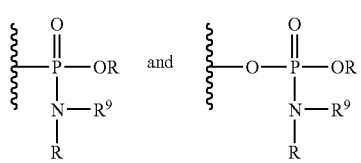

wherein $R^9$ is comprised of an ester, an amide, or a carbamate.

Also provided in the present invention are compounds of the above formulae wherein the phosphonate group has the structure:

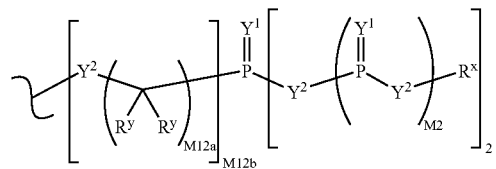

wherein:
$Y^1$ is independently O, S, $N(R^x)$, $N(O)(R^x)$, $N(OR^x)$, $N(O)(OR^x)$, or $N(N(R^x)(R^x))$;
$Y^2$ is independently a bond, O, $N(R^x)$, $N(O)(R^x)$, $N(OR^x)$, $N(O)(OR^x)$, $N(N(R^x)(R^x))$, —S(O)— (sulfoxide), —$S(O)_2$— (sulfone), —S-(sulfide), or —S—S-(disulfide);
M2 is 0, 1 or 2;
M12a is 1, 2, 3, 4, 5, 6, 7, 8, 9, 10, 11, or 12;
M12b is 0, 1, 2, 3, 4, 5, 6, 7, 8, 9, 10, 11, or 12;
$R^y$ is independently H, alkyl, substituted alkyl, aryl, substituted aryl, or a protecting group, or where taken together at a carbon atom, two vicinal $R^y$ groups form a carbocycle or a heterocycle; and
$R^x$ is independently H, alkyl, substituted alkyl, aryl, substituted aryl, or a protecting group, or the formula:

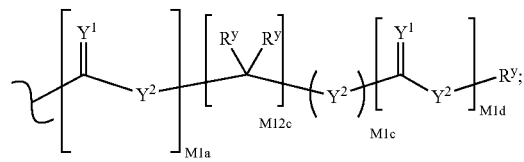

where M1a, M1c, and M1d are independently 0 or 1, and M12c is 0, 1, 2, 3, 4, 5, 6, 7, 8, 9, 10, 11 or 12.

Also provided in the present invention are compounds of the above formulae wherein phosphonate group has the structure:

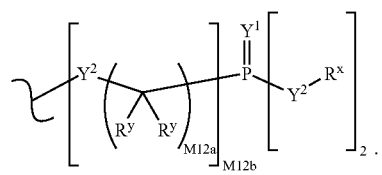

Also provided in the present invention are compounds of the above formulae wherein phosphonate group has the structure:

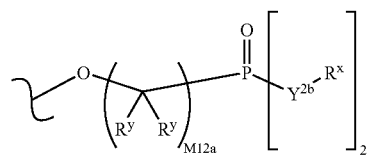

where $Y^{2b}$ is O or $N(R^x)$.

Also provided in the present invention are compounds of the above formulae wherein phosphonate group has the structure:

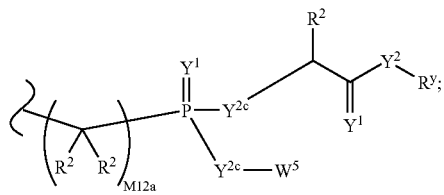

where $W^5$ is a carbocycle, and $Y^{2c}$ is O, $N(R^y)$ or S.

Also provided in the present invention are compounds of the above formulae wherein $W^5$ is selected from the structures:

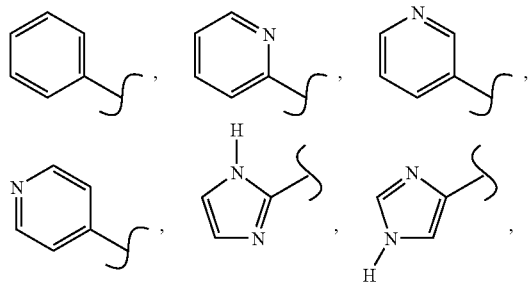

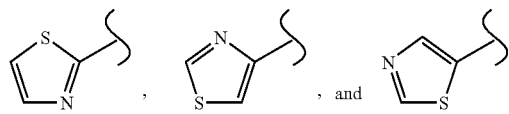

Also provided in the present invention are compounds of the above formulae wherein phosphonate group has the structure:

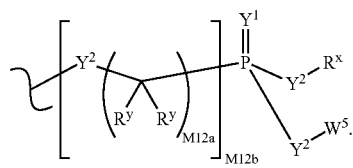

Also provided in the present invention are compounds of the above formulae
wherein phosphonate group has the structure:

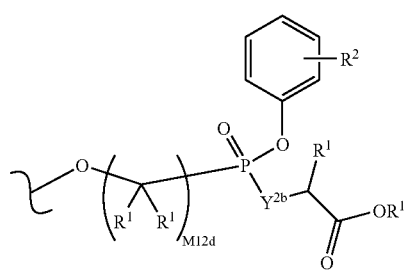

wherein $Y^{2b}$ is O or $N(R^x)$; M12d is 1, 2, 3, 4, 5, 6, 7 or 8; $R^1$ is H or $C_1$-$C_6$ alkyl; and the phenyl carbocycle is substituted with 0 to 3 $R^2$ groups where $R^2$ is $C_1$-$C_6$ alkyl or substituted alkyl.

Also provided in the present invention are compounds of the above formulae wherein phosphonate group has the structure:

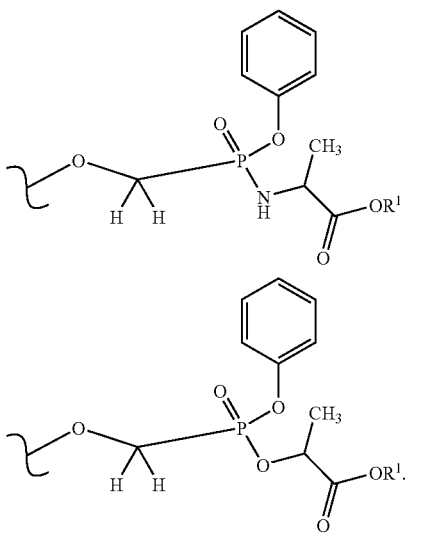

Also provided in the present invention are compounds of the above formulae wherein $R^x$ is selected from the structures:

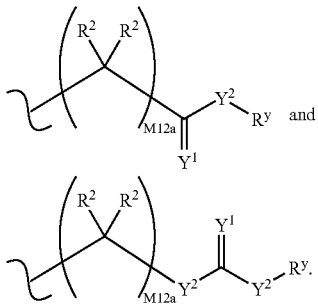

Also provided in the present invention are compounds of the above formulae wherein $X^2$ is $CR^2$ and $R^2$ is selected from the structures:

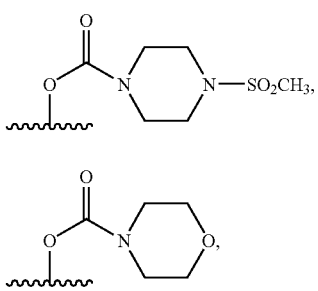

-continued

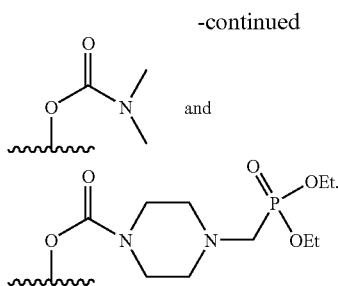

Also provided in the present invention are compounds of the above formulae wherein $X^2$ is $CR^2$ and $R^2$ is selected from the structures:

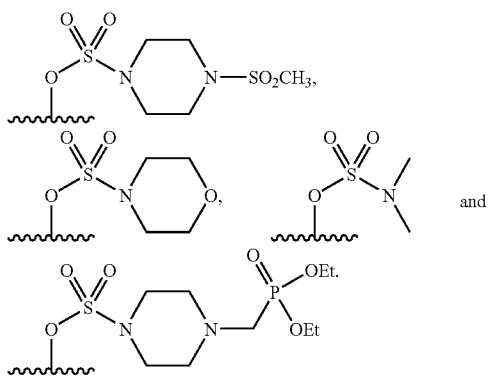

Also provided in the present invention are compounds of the above formulae wherein $X^2$ is $CR^2$ and $R^2$ comprises a phosphonate prodrug moiety.

Also provided in the present invention are compounds of the above formulae wherein Ar-L is selected from the structures:

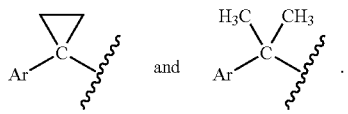

Also provided in the present invention are pharmaceutical composition comprising a therapeutically effective amount of a compound of any of the above formulae and a pharmaceutically acceptable carrier.

Also provided in the present invention are pharmaceutical composition comprising a therapeutically effective amount of a compound of any the above formulae in combination with a therapeutically effective amount of an AIDS treatment agent selected from:

(1) an AIDS antiviral agent,
(2) an anti-infective agent, and
(3) an immunomodulator.

Also provided in the present invention are pharmaceutical compositions as above wherein the antiviral agent is an HIV protease inhibitor.

Also provided in the present invention are pharmaceutical compositions made by combining the compound of any of the above formulae and a pharmaceutically acceptable carrier.

Also provided in the present invention is a process for making a pharmaceutical composition comprising combining a compound of any of the above formulae and a pharmaceutically acceptable carrier.

Also provided in the present invention is a method of inhibiting HIV integrase, comprising the administration to a mammal in need of such treatment of a therapeutically effective amount of a compound of any of the above formulae.

Also provided in the present invention is a method of treating infection by HIV, or of treating AIDS or ARC, comprising administration to a mammal in need of such treatment of a therapeutically effective amount of a compound of any of the above formulae.

The compounds of the invention include at least one phosphonate group covalently attached at any site.

The invention also includes a pharmaceutical composition comprising an effective amount of a compound selected from the above formulae, or a pharmaceutically acceptable salt thereof, in combination with a pharmaceutically acceptable diluent or carrier.

This invention also includes a method of increasing cellular accumulation and retention of drug compounds, thus improving their therapeutic and diagnostic value.

The invention also includes a method of inhibiting HIV, comprising administering to a mammal infected with HIV (HIV positive) an amount of a compound of the above formulae, effective to inhibit the growth of said HIV infected cells.

The invention also includes a compound selected from the above formulae for use in medical therapy (preferably for use in treating cancer, e.g. solid tumors), as well as the use of a compound of the above formulae for the manufacture of a medicament useful for the treatment of cancer, e.g. solid tumors.

The invention also includes processes and novel intermediates disclosed herein which are useful for preparing compounds of the invention. Some of the compounds of the above formulae are useful to prepare other compounds of the above formulae.

In another aspect of the invention, the activity of HIV integrase is inhibited by a method comprising the step of treating a sample suspected of containing HIV virus with a compound or composition of the invention.

Another aspect of the invention provides a method for inhibiting the activity of HIV integrase comprising the step of contacting a sample suspected of containing HIV virus with the composition embodiments of the invention.

In other aspects, novel methods for the synthesis, analysis, separation, isolation, crystallization, purification, characterization, and testing of the compounds of this invention are provided.

DETAILED DESCRIPTION OF EXEMPLARY EMBODIMENTS

Reference will now be made in detail to certain embodiments of the invention, examples of which are illustrated in the accompanying descriptions, structure and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. These substituents may be part of a prodrug moiety. As defined herein, "phosphonate" and "phosphonate group" include molecules with phosphonic acid, phosphonic monoester, phosphonic diester, phosphonamidate, phosphondiamidate, and phosphonthioate functional groups.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Pharmaceutically acceptable prodrug" refers to a compound that is metabolized in the host, for example hydrolyzed or oxidized, by either enzymatic action or by general acid or base solvolysis, to form an active ingredient. Typical examples of prodrugs of the compounds of the invention have biologically labile protecting groups on a functional moiety of the compound. Prodrugs include compounds that can be oxidized, reduced, aminated, deaminated, esterified, deesterified, alkylated, dealkylated, acylated, deacylated, phosphorylated, dephosphorylated, photolyzed, hydrolyzed, or other functional group change or conversion involving forming or breaking chemical bonds on the prodrug.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A "prodrug" is thus a covalently modified analog of a therapeutically-active compound.

Exemplary prodrug moieties include the hydrolytically sensitive or labile acyloxymethyl esters —CH$_2$OC(=O)R$^9$ and acyloxymethyl carbonates —CH$_2$OC(=O)OR$^9$ where R$^9$ is C$_1$-C$_6$ alkyl, C$_1$-C$_6$ substituted alkyl, C$_6$-C$_{20}$ aryl or C$_6$-C$_{20}$ substituted aryl. The acyloxyalkyl ester was first used as a prodrug strategy for carboxylic acids and then applied to phosphates and phosphonates by Farquhar etal (1983) *J. Pharm. Sci.* 72: 324; also U.S. Pat. Nos. 4,816,570, 4,968,788, 5,663,159 and 5,792,756. In certain compounds of the invention, a prodrug moiety is part of a phosphonate group. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —CH$_2$C(=O)C(CH$_3$)$_3$. An exemplary acyloxymethyl carbonate prodrug moiety is pivaloyloxymethylcarbonate (POC) —CH$_2$OC(=O)OC(CH$_3$)$_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (DeLambert etal (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho-or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell etal (1992) *J. Chem. Soc. Perkin Trans. 1* 2345; Brook etal WO 91/19721. Still other benzylic prodrugs have been described containing a carboxylic ester-containing group attached to the benzylic methylene (Glazier etal WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech etal (1993) *Antiviral Res.*, 22: 155-174; Benzaria etal (1996) *J. Med. Chem.* 39: 4958). Cyclic phosphonate esters have also been described as prodrugs of phosphorus-containing compounds (Erion et al, U.S. Pat. No. 6,312,662).

"Protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$.

"Alkenyl" is $C_2$-$C_{18}$ hydrocarbon containing normal, secondary, tertiary or cyclic carbon atoms with at least one site of unsaturation, i.e. a carbon-carbon, sp$^2$ double bond. Examples include, but are not limited to: ethylene or vinyl (—CH═CH$_2$), allyl (—CH$_2$CH═CH$_2$), cyclopentenyl (—C$_5$H$_7$), and 5-hexenyl (—CH$_2$ CH$_2$CH$_2$CH$_2$CH═CH$_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—CH$_2$C≡CH), The terms "alkylene" and "alkyldiyl" each refer to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene, i.e. double carbon-carbon bond moiety. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne, i.e. triple carbon-carbon bond moiety. Typical alkynylene radicals include, but are not limited to: acetylene (—C≡C—), propargyl (—CH$_2$C≡C—), and 4-pentynyl (—CH$_2$CH$_2$CH$_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Heteroaryl" means a monovalent aromatic radical of one or more carbon atoms and one or more atoms selected from N, O, S, or P, derived by the removal of one hydrogen atom from a single atom of a parent aromatic ring system. Heteroaryl groups may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). Heteroaryl bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The heteroaryl group may be bonded to the drug scaffold through a carbon, nitrogen, sulfur, phosphorus or other atom by a stable covalent bond.

Heteroaryl groups include, for example: pyridyl, dihydropyridyl isomers, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

Substituted substituents such as "substituted alkyl", "substituted aryl", "substituted heteroaryl" and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, ═NR, —CX$_3$, —CN, —OCN, —SCN, —N═C═O, —NCS, —NO, —NO$_2$, ═N$_2$, —N$_3$, NC(═O)

R, —C(=O)R, —C(=O)NRR —S(=O)₂O⁻, —S(=O)₂OH, —S(=O)₂R, —OS(=O)₂OR, —S(=O)₂NR, —S(=O)R, —OP(=O)O₂RR, —P(=O)O₂RR —P(=O)(O⁻)₂, —P(=O)(OH)₂, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" means a saturated, unsaturated or aromatic ring system including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

One embodiment of the bis-tetrahydrofuranyl group is:

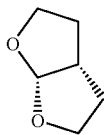

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated, unsaturated or aromatic ring system having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohexyl-enyl, 1-cyclohex-2-enyl, 1-cyclohex-3-enyl, phenyl, spiryl and naphthyl. Carbocycle thus includes some aryl groups.

"Linker" or "link" means a chemical moiety comprising a covalent bond or a chain of atoms that covalently attaches a phosphonate group to a drug, or between the Formula I scaffold and substituents. Linkers include L interposed between Ar and the nitrogen of Formula I compounds. Linkers may also be interposed between a phosphorus containing $A^3$ group and the $R^1$, $R^2$, $R^3$, $R^4$, $R^5$, $R^6$ or $R^7$ positions of Formula I. Linkers include, but are not limited to moieties such as O, S, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, C(=O), S(=O)₂, C(=O)NH(CH₂)ₙ, and (CH₂CH₂O)ₙ, where n may be 1, 2, 3, 4, 5, or 6. Linkers also include repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Aza-Quinolinol Phosphonate Compounds

Novel aza-quinolinol phosphonate compounds with inhibitory activity against HIV integrase are described, as embodied in Formula I, including any pharmaceutically acceptable salts thereof. In one aspect, the compounds include an active form for inhibition of nuclear integration of reverse-transcribed HIV DNA.

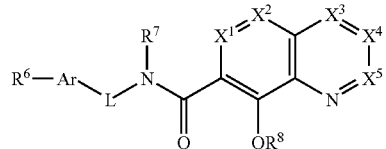

I

Ring atoms, $X^1$, $X^2$, $X^3$, $X^4$ and $X^5$ are independently selected from nitrogen (N), substituted N, or substituted carbon.

The compounds of the invention include all enol and tautomeric resonance isomer forms of Formula I. Formula I includes compounds wherein:

$X^1$ is $CR^1$, NR, or N;
$X^2$ is $CR^2$, NR, or N;
$X^3$ is $CR^3$, NR, or N;
$X^4$ is $CR^4$, NR, or N;
$X^5$ is $CR^5$, NR, or N;

At least one of $X^1$, $X^2$, $X^3$, $X^4$, and $X^5$ is NR or N.

Exemplary structures within Formula I include the following:

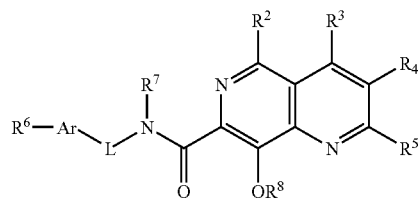

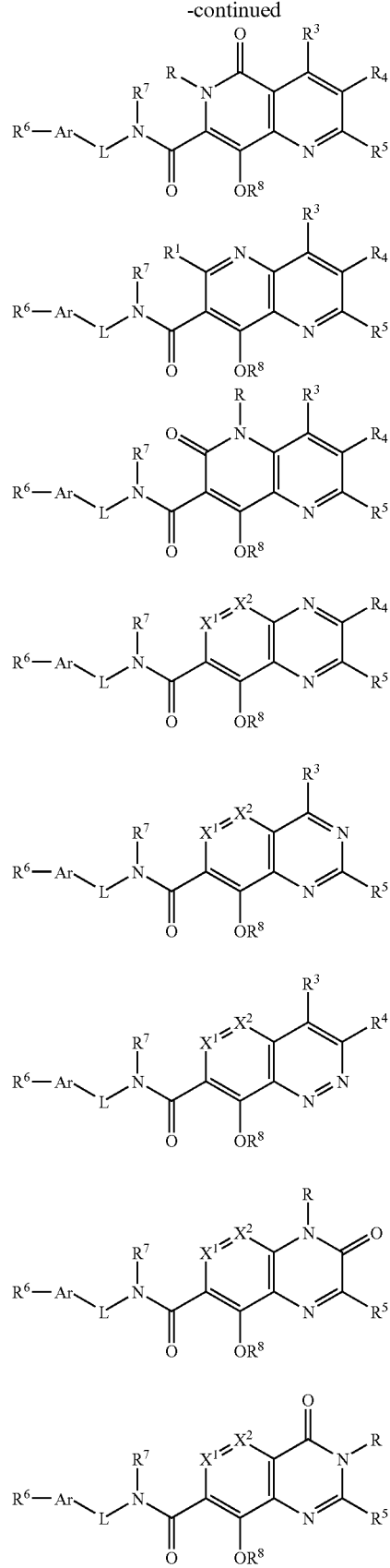

When $X^1$ is $CR^1$ and when $X^2$ is $CR^2$, then $CR^1$ and $CR^2$ together may form a ring. When $X^3$ is $CR^3$ and when $X^4$ is $CR^4$, then $CR^3$ and $CR^4$ together may form a ring. When $X^4$ is $CR^4$ and $X^5$ is $CR^5$, then $CR^4$ and $CR^5$ together may form a ring. The ring may be 5, 6, or 7-membered. The ring may be all carbon atoms or it may have one or more heteroatoms selected from nitrogen, oxygen, and sulfur.

Exemplary structures when $CR^4$ and $CR^5$ form a ring include the following:

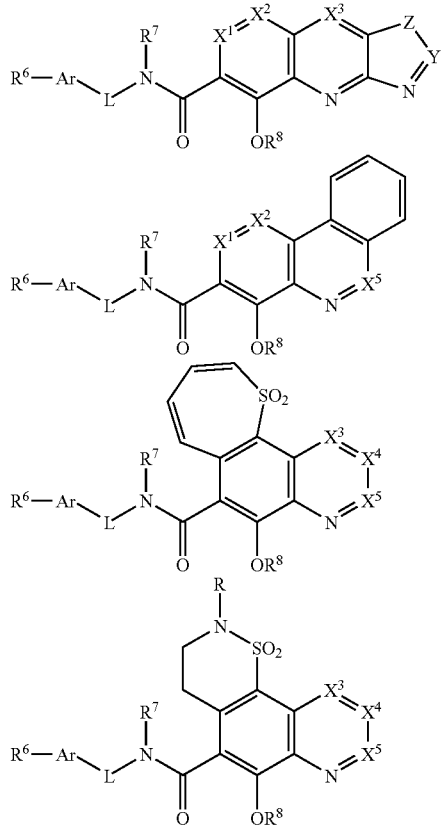

Y is $CR^5$, NR or N. Z is a moiety forming a five, six, or seven membered ring. For example, Z may be O, S, NR, $CR_2$, CROR, CROC(=O)R, C(=O), C(=S), CRSR, C(=$NR_2$), C=$CR_2$, $CR_2$—$CR_2$, CR=CR, NR—$CR_2$, N=CR, N=N, $SO_2$—NR, C(=O)$CR_2$, S(=O)$CR_2$, $SO_2CR_2$, C(=O)NR, $CR_2$—$CR_2$—$CR_2$, CR=CR—$CR_2$, CRC(=O)NR, $CR_2SO_2CR_2$, $CR_2SO_2$NR, CRC(=S)NR, CR=N—$CR_2$, CR=N—NR, or N=CR—NR.

L is a bond or any linker which covalently attaches the Ar group to the tricyclic scaffold. For example, L may be a bond, O, S, S(=O) (sulfoxide), S(=O)$_2$ (sulfone), S(=O)$_2$NR (sulfonamide), N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, C(=O), C(=O)NH(CH$_2$)$_n$, or (CH$_2$CH$_2$O)$_n$, where n may be 1, 2, 3, 4, 5, or 6.

Ar groups may be any saturated, unsaturated or aromatic ring or ring system comprising a mono- or bicyclic carbocycle or heterocycle, e.g. 3 to 10 ring atoms. The rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

For example, Ar may be $C_6$-$C_{20}$ aryl, $C_6$-$C_{20}$ substituted aryl, $C_2$-$C_{20}$ heteroaryl, or $C_2$-$C_{20}$ substituted heteroaryl.

Substituents of Ar, $R^1$, $R^2$, $R^3$, $R^4$, $R^5$, $R^6$, $R^7$ and $R^8$ may independently include H, F, Cl, Br, I, OH, amino (—NH$_2$), ammonium (—NH$_3$+), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), ester (—C(=O)OR), amido (—C(=O)NR$_2$), 5-7 membered ring lactam, 5-7 membered ring lactone, nitrile (—CN), azido (—N$_3$), nitro (—NO$_2$), $C_1$-$C_8$ alkoxy (—OR), $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, and a prodrug moiety.

Exemplary embodiments of $C_6$-$C_{20}$ substituted aryl groups include halo-substituted phenyl such as 4-fluorophenyl, 4-chlorophenyl, 3,5-dichlorophenyl, and 3,5-difluorophenyl.

Ar groups include:

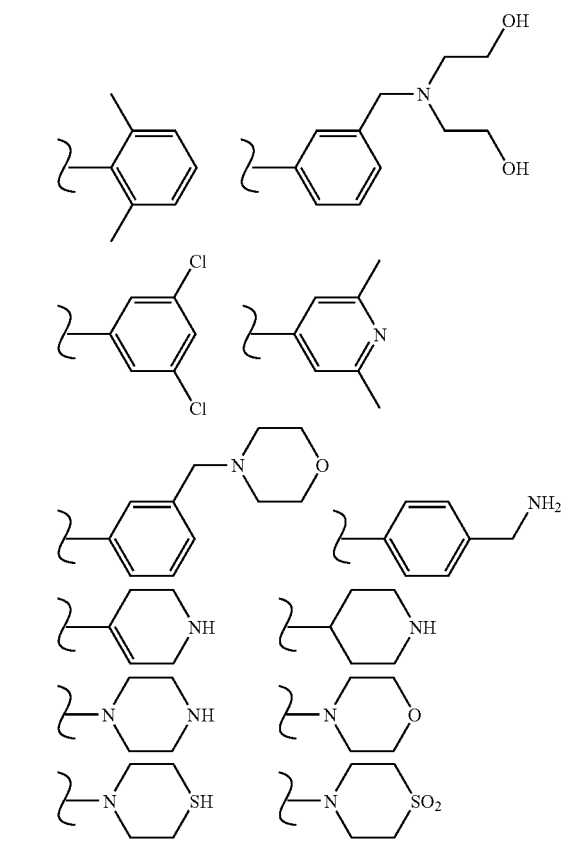

where a wavy line in any orientation, indicates the covalent attachment site of the other structural moieties of the compound.

Examples of substituted phenyl groups include:

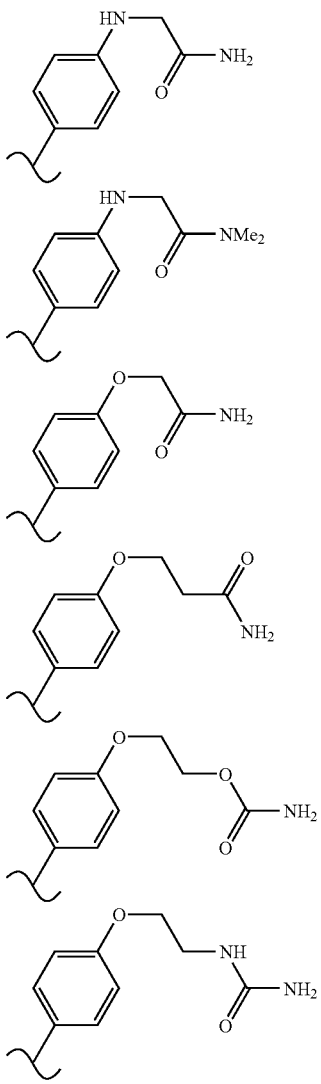

$R^2$ may be —H, —OH, —OC(=O)OR, —OC(=O)NR$_2$, —OC(=S)NR$_2$, —OC(=O)NRNR$_2$, —OC(=O)R, —C(=O)OR, —C(=O)NR$_2$, —C(=O)NRNR$_2$, —C(=O)R, —OSO$_2$NR$_2$ (sulfamate), —NR$_2$, —NRSO$_2$R, —NRC(=S)NR$_2$, —SR, —S(O)R, —SO$_2$R, —SO$_2$NR$_2$ (sulfonamide), —OSO$_2$R (sulfonate), —P(=O)(OR)$_2$, —P(=O)(OR)(NR$_2$), —P(=O)(NR$_2$)$_2$, —P(=S)(OR)$_2$, —P(=S)(OR)(NR$_2$), —P(=S)(NR$_2$)$_2$, and including prodrug substituted forms thereof.

$R^2$ may include a ring, e.g. 4-7 membered ring lactam or sultam, or piperazinyl sulfamate:

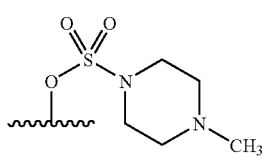

$R^1$, $R^2$, $R^3$, $R^4$, $R^5$, $R^6$, $R^7$ and $R^8$ are independently selected from H, F, Cl, Br, I, OH, amino (—NH$_2$), ammonium (—NH$_3^+$), alkylamino, dialkylamino, trialkylammonium, $C_1$-$C_8$ alkyl $C_1$-$C_8$ alkylhalide (including halomethyl, dihalomethyl, and trihalomethyl such as trifluoromethyl), carboxylate, sulfate, sulfonate, 4-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), ester (—C(=O)OR), amido (—C(=O)NR$_2$), 4-7 membered ring lactam, 4-7 membered ring lactone, nitrile (—CN), azido (—N$_3$), nitro (—NO$_2$), $C_1$-$C_8$ alkoxy (—OR), phenoxy, phenolic, aryl, benzyl, heterocycle, phosphonate, phosphate, polyethyleneoxy, and a prodrug moiety.

R may be independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, $C_2$-$C_{20}$ substituted heteroaryl, and a prodrug moiety.

A tricyclic integrase inhibitor compound of the invention includes one or more phosphonate group or phosphonate prodrug moiety. At least one of R, $R^1$, $R^2$, $R^3$, $R^4$, $R^5$, $R^6$, $R^7$ and $R^8$ comprises a phosphonate group. The phosphonate group may be a prodrug moiety. The phosphonate group may be directly attached to a ring carbon (CR$^1$, CR$^2$, CR$^3$, CR$^4$ or CR$^5$) of Formula I. Alternatively, and by example, R, $R^1$, $R^2$, $R^3$, $R^4$, $R^5$, $R^6$, $R^7$ and $R^8$ may comprise the structure $A^3$, where $A^3$ is:

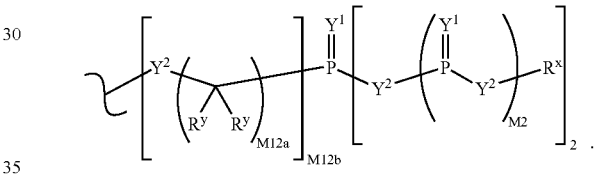

$Y^1$ is independently O, S, N(R$^x$), N(O)(R$^x$), N(OR$^x$), N(O)(OR$^x$), or N(N(R$^x$)(R$^x$)).

$Y^2$ is independently a bond, O, N(R$^x$), N(O)(R$^x$), N(OR$^x$), N(O)(OR$^x$), N(N(R$^x$)(R$^x$)), —S(=O)— (sulfoxide), —S(=O)$_2$— (sulfone), —S-(sulfide), or —S—S-(disulfide).

M2 is 0, 1 or 2.

M12a is 1, 2, 3, 4, 5, 6, 7, 8, 9, 10, 11, or 12.

M12b is 0, 1, 2, 3, 4, 5, 6, 7, 8, 9, 10, 11, or 12.

$R^y$ is independently H, alkyl, substituted alkyl, aryl, substituted aryl, or a protecting group. Alternatively, taken together at a carbon atom, two vicinal $R^y$ groups form a ring, i.e. a spiro carbon. The ring may be all carbon atoms, for example, cyclopropyl, cyclobutyl, cyclopentyl, or cyclohexyl, or alternatively, the ring may contain one or more heteroatoms, for example, piperazinyl, piperidinyl, pyranyl, or tetrahydrofuryl.

$R^x$ is independently H, alkyl, substituted alkyl, aryl, substituted aryl, or a protecting group, or the formula:

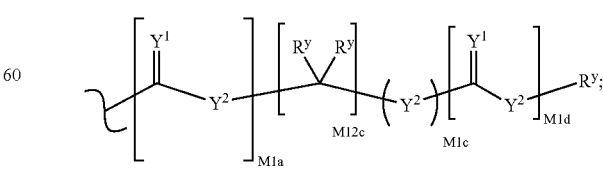

M1a, M1c, and M1d are independently 0 or 1.

M12c is 0, 1, 2, 3, 4, 5, 6, 7, 8, 9, 10, 11 or 12.

A linker may be interposed between positions $R^1$, $R^2$, $R^3$, $R^4$, $R^5$, $R^6$, $R^7$ and $R^8$ and substituent $A^3$. The linker may be O, S, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, C(=O), S(=O)$_2$, C(=O)NH(CH$_2$)$_n$, and (CH$_2$CH$_2$O)$_n$, where n may be 1, 2, 3, 4, 5, or 6. Linkers may also be repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. For example, the linker may comprise propargyl, urea, or alkoxy groups.

Embodiments of $A^3$ include where M2 is 0, such as:

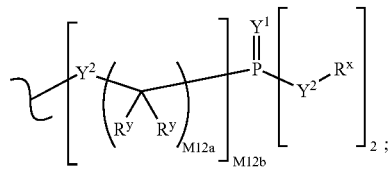

and where M12b is 1, $Y^1$ is oxygen, and $Y^{2b}$ is independently oxygen (O) or nitrogen (N($R^x$)) such as:

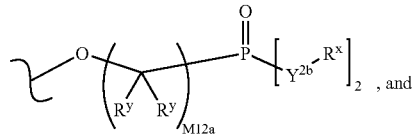

An embodiment of $A^3$ includes:

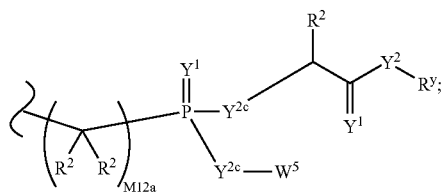

where $W^5$ is a carbocycle such as phenyl or substituted phenyl, and $Y^{2c}$ is independently O, N($R^y$) or S. For example, $R^1$ may be H and n may be 1.

$W^5$ also includes, but is not limited to, aryl and heteroaryl groups such as:

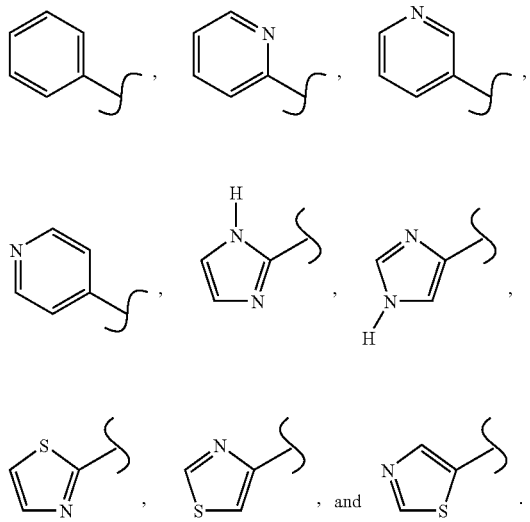

Another embodiment of $A^3$ includes:

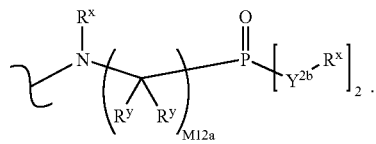

Such embodiments include:

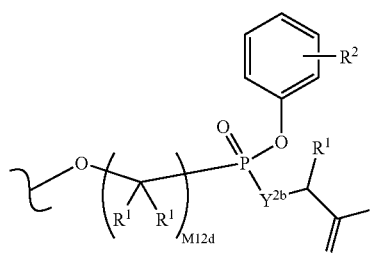

where $Y^{2b}$ is O or N($R^x$); M12d is 1, 2, 3, 4, 5, 6, 7 or 8; $R^1$ is H or $C_1$-$C_6$ alkyl; and the phenyl carbocycle is substituted with 0 to 3 $R^2$ groups where $R^2$ is $C_1$-$C_6$ alkyl or substituted alkyl. Such embodiments of $A^3$ include phenyl phosphonamidate amino acid, e.g. alanate esters and phenyl phosphonate-lactate esters:

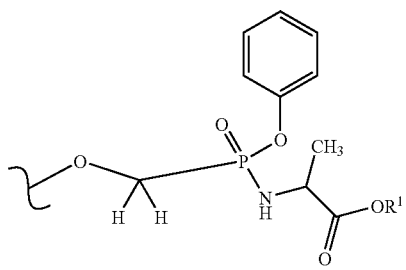

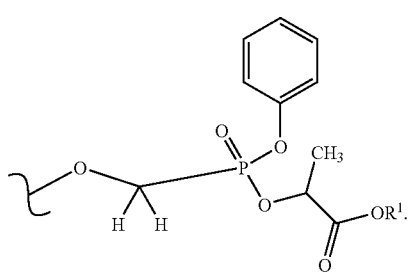

Embodiments of $R^x$ include esters, carbamates, carbonates, thioesters, amides, thioamides, and urea groups:

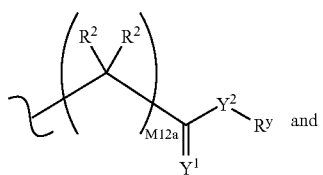

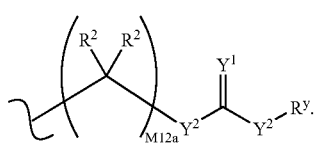

Embodiments of Formula I include Ia-d where, respectively:

Formula Ia

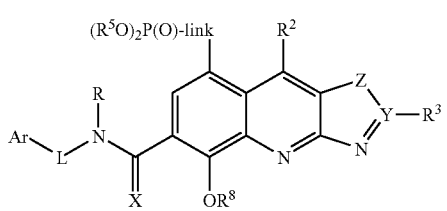

Formula Ib

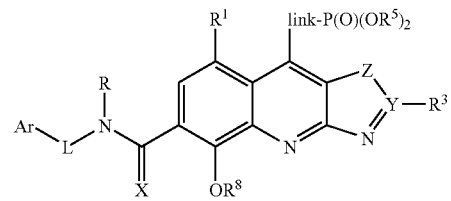

Formula Ic

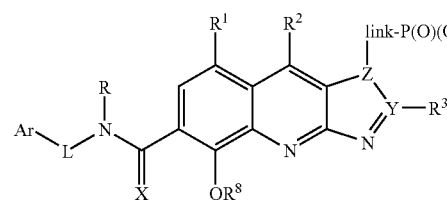

Formula Id

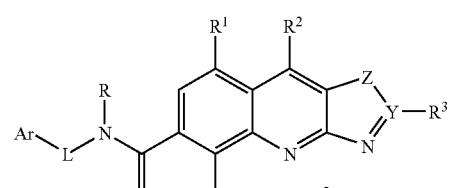

The compounds of the invention may also include one or more prodrug moieties located as a covalently-attached substituent at any location of Formula I, e.g. $R^1$, $R^2$, $R^3$, $R^4$, $R^5$, $R^6$, and $R^7$, or the 8-hydroxyl. One substituent which may be modified as a prodrug moiety is a phosphonate, phosphate, phosphinate or other phosphorus functionality (Oliyai etal *Pharmaceutical Res.* (1999) 16:1687-1693; Krise, J. and Stella, V. *Adv. Drug Del. Reviews* (1996) 19:287-310; Bischofberger et al, U.S. Pat. No. 5,798,340). Prodrug moieties of phosphorus functionality serve to mask anionic charges and decrease polarity. The phosphonate prodrug moiety may be an ester (Oliyai, etal *Intl. Jour. Pharmaceutics* (1999) 179:257-265), e.g. POC and POM (pivaloyloxymethyl, Yuan, etal *Pharmaceutical Res.* (2000) 17:1098-1103), or amidate which separates from the integrase inhibitor compound in vivo or by exposure in vitro to biological conditions, e.g. cells, tissue isolates. The separation may be mediated by general hydrolytic conditions, oxidation, enzymatic action or a combination of steps.

Compounds of the invention bearing one or more prodrug moieties may increase or optimize the bioavailability of the compounds as therapeutic agents. For example, bioavailability after oral administration may be preferred and depend on resistance to metabolic degradation in the gastrointestinal tract or circulatory system, and eventual uptake inside cells. Prodrug moieties are considered to confer said resistance by slowing certain hydrolytic or enzymatic metabolic processes. Lipophilic prodrug moieties may also increase active or passive transport of the compounds of the invention across cellular membranes (Darby, G. *Antiviral Chem. & Chemotherapy* (1995) Supp. 1, 6:54-63).

Exemplary embodiments of the invention includes phosphonamidate and phosphoramidate (collectively "amidate") prodrug compounds. General formulas for phosphonamidate and phosphoramidate prodrug moieties include:

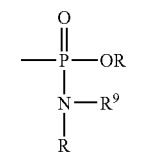

phosphonamidate

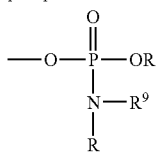

phosphoramidate

The phosphorus atom of the phosphonamidate group is bonded to a carbon atom. The nitrogen substituent $R^9$ may include an ester, an amide, or a carbamate functional group. For example, $R^9$ may be —$CR_2C(=O)OR'$ where R' is H, $C_1$-$C_6$ alkyl, $C_1$-$C_6$ substituted alkyl, $C_6$-$C_{20}$ aryl, $C_6$-$C_{20}$ substituted aryl, $C_2$-$C_{20}$ heteroaryl, or $C_2$-$C_{20}$ substituted heteroaryl. The nitrogen atom may comprise an amino acid residue within the prodrug moiety, such as a glycine, alanine, or valine ester (e.g. valacyclovir, see: Beauchamp, etal *Antiviral Chem. Chemotherapy* (1992) 3:157-164), such as the general structure:

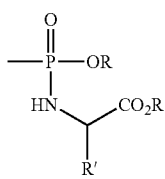

where R' is the amino acid side-chain, e.g. H, $CH_3$, $CH(CH_3)_2$, etc.

An exemplary embodiment of a phosphonamidate prodrug moiety is:

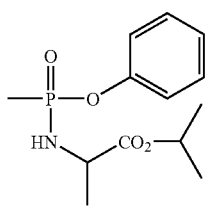

In another aspect of the invention, the compounds have pre-organized binding modes which optimize the binding affinity of designed inhibitors. During binding between an inhibitor and the active site of a target macromolecule or protein, the inhibitor may attain a preferred, low energy conformation (also called bound conformation) in order to interact within an active site. Generally, ligands of molecules with multiple rotational bonds exist in many potential conformational states, most of which are not able to bind to the active site. The greater the number of possible ligand conformations typically results in a greater decrease in efficiency of the entropy contribution to the free energy of binding, and will result in less favorable binding affinities. One aspect of designing pre-organized binding features in an integrase inhibitor compound is incorporating conformational constraints that reduces the total number of conformational states and places the inhibitor into a correct binding conformation (Lam, P. Y. S. et al. *J. Med. Chem*, (1996) 39:3514-3525; Chen, J. M. et al. *Biochemistry* (1998) 37:17735-17744; Chen, J. M. et al. *Jour. Amer. Chem. Soc.* (2000) 122:9648-9654; Chen, J. M. et al U.S. Pat. No. 6,187,907; Chen, et al *Bio. Org. Med. Chem. Letters* (2002) 12:1195-1198). Knowledge of one or more preferred binding conformations is important for rational structure design and avoid inactive lead compounds.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The compounds of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exists in a variety of different forms, the invention is intended to encompass not only forms of the compounds that are in association with counter ions (e.g., dry salts), but also forms that are not in association with counter ions (e.g., aqueous or organic solutions).

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention can also exist as tautomeric, resonance isomers in certain cases. Typically, the structures shown herein exemplify only one tautomeric or resonance form of the compounds. For example, hydrazine, oxime, hydrazone groups may be shown in either the syn or anti configurations. The corresponding alternative configuration is contemplated as well. All possible tautomeric and resonance forms are within the scope of the invention.

One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113: (3) 283-302). Separation of diastereomers formed from the racemic mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers. Alternatively, enantiomers can be separated directly under chiral conditions, method (3).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, α-methoxy-α-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111).

By method (3), a racemic mixture of two asymmetric enantiomers can be separated by chromatography using a chiral stationary phase ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

Enantiomers can be distinguished by methods used to distinguish other chiral molecules with asymmetric carbon atoms, such as optical rotation and circular dichroism.

Synthesis of Aza-Quinolinol Phosphonate Compounds

The compounds of the invention may be prepared by a variety of synthetic routes and methods known to those skilled in the art. The invention also relates to methods of making the compounds of the invention. The compounds are prepared by any of the applicable techniques of organic synthesis. Many such techniques are well known in the art. However, many of the known techniques are elaborated in: "Compendium of Organic Synthetic Methods", John Wiley & Sons, New York, Vol. 1 Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry", Third Edition, John Wiley & Sons, New York, 1985; "Comprehensive Organic Synthesis. Selectivity, Strategy & Efficiency in Modern Organic Chemistry" (9 Volume set) Barry M. Trost, Editor-in-Chief, Pergamon Press, New York, 1993.

A number of exemplary methods for the preparation of the compounds of the invention are provided herein. These methods are intended to illustrate the nature of such preparations are not intended to limit the scope of applicable methods.

Deliberate use may be made of protecting groups to mask reactive functionality and direct reactions regioselectively (Greene, etal (1991) "Protective Groups in Organic Synthesis", 2nd Ed., John Wiley & Sons). For example, useful protecting groups for the 8-hydroxyl group and other hydroxyl substituents include methyl, MOM (methoxymethyl), trialkylsilyl, benzyl, benzoyl, trityl, and tetrahydropyranyl. Certain aryl positions may be blocked from substitution, such as the 2-position as fluorine.

Aza-quinolinol compounds have been prepared, including naphthyridine compounds (US 2003/0119823 A1; WO 03/016315 A1; WO 03/016309 A1; WO 02/30930 A2; WO 02/055079 A2; WO 02/30931 A2; WO 02/30426 A1; WO 02/36734 A2). Quinoline derivatives have been reported (WO 03/031413 A1; US 2002/0103220 A1; US 2002/0055636 A1; U.S. Pat. Nos. 6,211,376; 6,114,349; 6,090,821; 5,883,255; 5,739,148; 5,639,881; 3,113,135).

Preparation of the Intermediate Phosphonate Esters 1-9.

The structures of the intermediate phosphonate esters 1-9 are shown in Chart 1, in which the substituent $R^1$ is H, alkyl, alkenyl, aryl or aralkyl, and the substituents $R^2$, $R^3$, $R^4$, X and $X^1$ are as previously defined. Subsequent chemical modifications to the compounds 1-9 as described below, permit the synthesis of the final compounds of this invention.

The intermediate compounds 1-9 incorporate a phosphonate group $(R^1O)_2P(O)$ connected to the nucleus by means of a variable linking group, designated as "link" in the attached structures. Charts 2 and 3 illustrates examples of the linking groups present in the structures 1-9.

Schemes 1-31 illustrate the syntheses of the intermediate phosphonate compounds of this invention, 1-9, and of the intermediate compounds necessary for their synthesis.

The methods described for the introduction of phosphonate substituents are, with modifications made by one skilled in the art, transferable within the substrates 1-9. For example, reaction sequences which produce the phosphonates 1 are, with appropriate modifications, applicable to the preparation of the phosphonates 2-9. Methods described below for the attachment of phosphonate groups by means of reactive substituents such as OH, Br, $NH_2$, $CH_3$, $CH_2Br$, COOH, CHO etc are applicable to each of the scaffolds 1-9.

Scheme 32 illustrates methods for the interconversion of phosphonate diesters, monoesters and acids, and Scheme 33 illustrates methods for the preparation of carbamates.

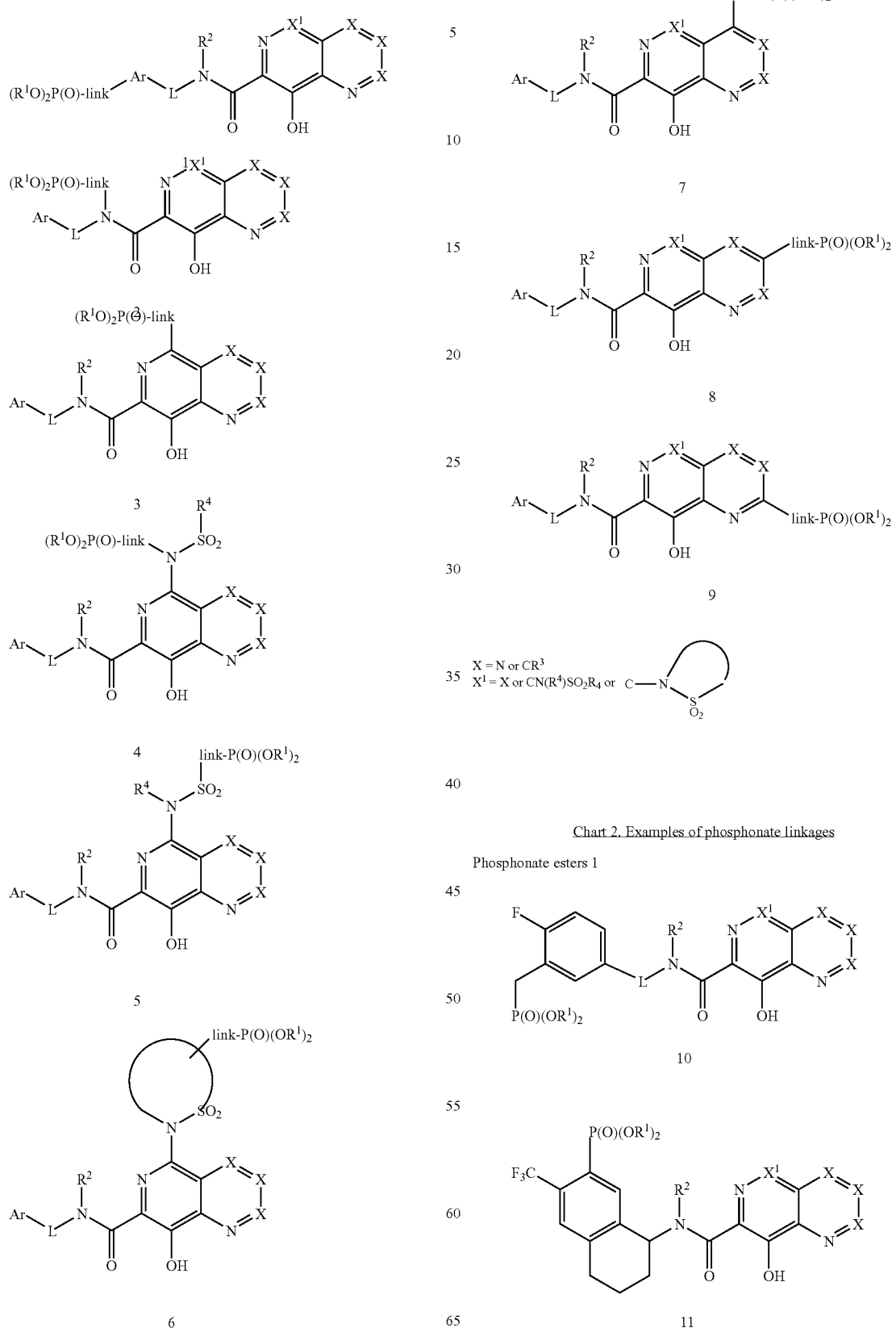

Phosphonate esters 2
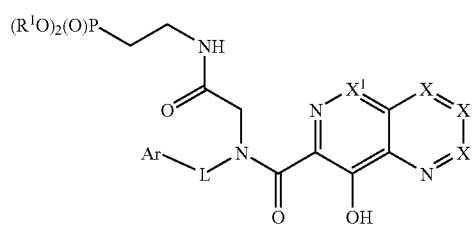
12
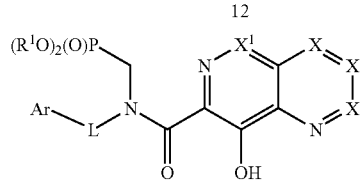
13
Phosphonate esters 3
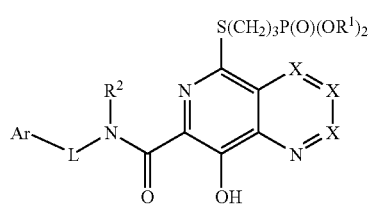
14
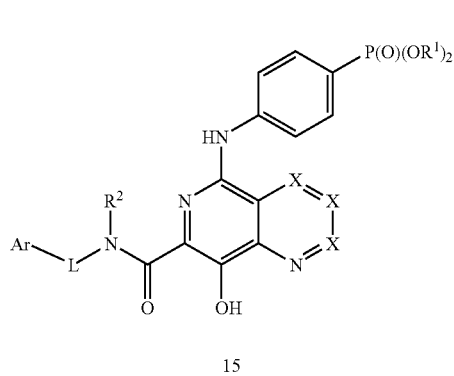
15
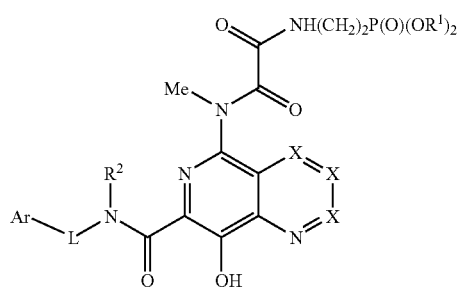
16
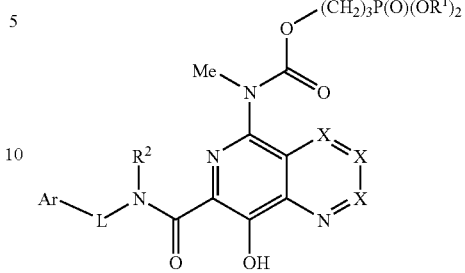
17
Phosphonate esters 4
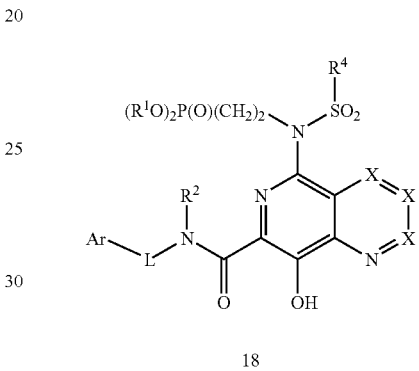
18
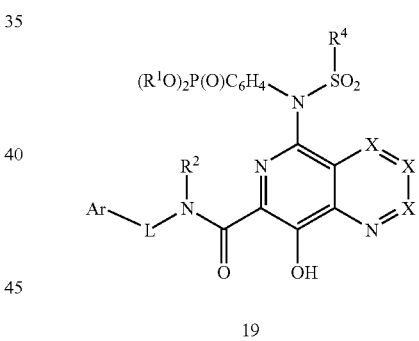
19
Chart 3. Examples of phosphonate linkages
Phosphonate esters 5
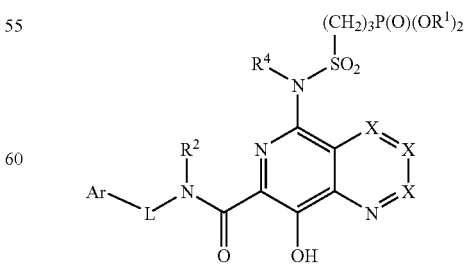
20

-continued
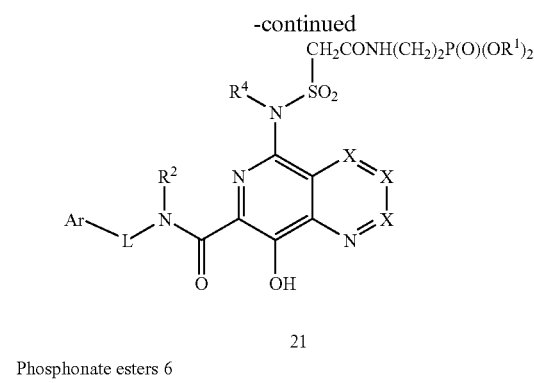
21
Phosphonate esters 6
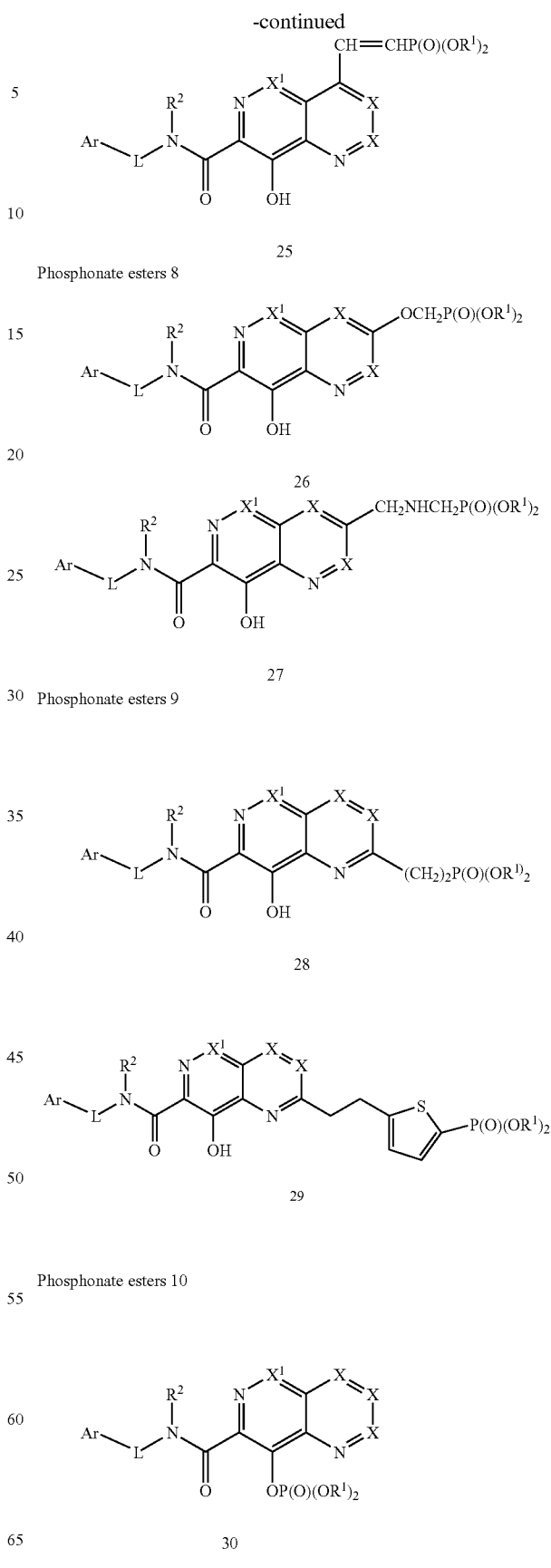
-continued
25
Phosphonate esters 8
26
27
Phosphonate esters 9
28
29
Phosphonate esters 10
30
22
23
Phosphonate esters 7
24

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. Reactive substituents which may be protected are shown in the accompanying schemes as, for example, [OH], [SH], etc.

Preparation of the Intermediate Bicyclic Hydroxyesters and Hydroxyacids.

Scheme 1 illustrates the preparation of bicyclic hydroxyesters 1.2 from the corresponding anhydrides 1.1, in which at least one of the groups X is C—R³. The conversion is effected by means of one or more of the methods described in WO 0230930 A2, Schemes 2, 3, 3A and 5. The resultant ester is then converted into the carboxylic acid 1.3, for example by means of basic hydrolysis using sodium hydroxide, as described in WO 0230930 A2 Scheme 2.

As shown in Example 1, furo[3,4-c]pyridazine-5,7-dione 1.4 (WO 994492) is converted, as described above, into 8-hydroxy-pyrido[4,3-c]pyridazine-7-carboxylic acid methyl ester 1.5, and the ester is hydrolyzed with sodium hydroxide to give 8-hydroxy-pyrido[4,3-c]pyridazine-7-carboxylic acid 1.6.

In a similar manner, as shown in Examples 2 and 3, furo[3,4-b]pyrazine-5,7-dione 1.7 (Aldrich) and furo[3,4-e][1,2,4]triazine-5,7-dione 1.10 (J. Org. Chem., 1958, 23, 1931) are converted respectively into 8-hydroxy-pyrido[3,4-b]pyrazine-7-carboxylic acid methyl ester 1.8 and 8-hydroxy-pyrido[3,4-e][1,2,4]triazine-7-carboxylic acid methyl ester 1.11 and the corresponding carboxylic acids 1.9 and 1.12.

As shown in Example 4, 3-methyl-furo[3,4-b]pyridine-5,7-dione 1.13 is converted, as described above, 8-hydroxy-3-methyl-[1,6]naphthyridine-7-carboxylic acid methyl ester 1.14 and the corresponding carboxylic acid 1.15.

Scheme 1A illustrates the preparation of bicyclic hydroxyesters 1A.3 in which a substituent Nu is introduced at the 5-position. In this procedure, the bicyclic hydroxyester 1A.1, prepared as described in Scheme 1, is halogenated to give the 5-halo product 1A.2 in which Ha is Cl, Br or I. The halogenation reaction is performed, for example, as described in WO 0230930 A2, p. 159, by reaction of the phenolic ester with N-bromosuccinimide in chloroform, to give the product 1A.2 in which Ha is Br. Alternatively, the hydroxyester 1A.1 is reacted with N-iodosuccinimide, as described in WO 0230930 A2 p. 166, to give the product 1A.2 in which Ha is iodo. The halogenated product is then reacted with a nucleophile Nu, to prepare the displacement product 1A.3. Examples of nucleophiles include hydroxy, mercapto or amino compounds, or cyclic or acyclic sulfonamides. The displacement reaction is performed in a polar organic solvent such as pyridine, dimethylformamide, DMPU, dimethylsulfoxide and the like, for example as described in WO 0230930 A2, Examples 57-78. Optionally, the phenolic hydroxyl group is protected prior to the displacement reaction, and deprotected afterwards.

For example, 8-hydroxy-[1,6]naphthyridine-7-carboxylic acid methyl ester 1A.4 (WO 0230930 A2, p. 171) is reacted with one molar equivalent of N-bromosuccinimide in dichloromethane, to yield 5-bromo-8-hydroxy-[1,6]naphthyridine-7-carboxylic acid methyl ester, 1A.5. The phenol is then reacted with p-toluenesulfonyl chloride and triethylamine in chloroform, for example as described in WO 02 30931 A2 p. 72, to give 5-bromo-8-(toluene-4-sulfonyloxy)-[1,6]naphthyridine-7-carboxylic acid methyl ester 1A.6. The product is then reacted with [1,2]thiazinane 1,1-dioxide 1A.7 and cuprous oxide in pyridine at reflux, for example as described in WO 0230931 A2, p. 73, to produce 5-(1,1-dioxo-1,2]thiazinan-2-yl)-8-(toluene-4-sulfonyloxy)-[1,6]naphthyridine-7-carboxylic acid methyl ester 1A.8. Deprotection, for example by reaction with methanolic sodium methoxide in dimethylformamide, as described in WO 0230931 A2 p. 74, then affords the phenol 1A.9.

Using the above procedures, but employing different hydroxyesters 1A.1 in place of the hydroxyester 1A.4, and/or different nucleophiles, the corresponding products 1A.3 are obtained.

Alternative Methods for the Preparation of the Phosphonate Ester Amides 2.4.

As shown in Scheme 2, the hydroxyester 2.1, prepared as described above, is transformed, using the procedures described below, (Schemes 3-31) into the phosphonate ester 2.2. The ester, or the corresponding carboxylic acid, is then converted, using, for example, the procedures described in WO 0230930 A2, Schemes 1, 2, 3 and 5, into the phosphonate amide 2.4.

Alternatively, the ester 2.1, or the corresponding carboxylic acid, is transformed, as described above, into the amide 2.3, and the latter compound is then converted, using the procedures described below, (Schemes 3-31) into the phosphonate amide 2.4. The selection of a suitable stage in the synthetic sequence for the introduction of the phosphonate group is made by one skilled in the art, depending on the reactivities and stabilities of the substrates in a given reaction sequence.

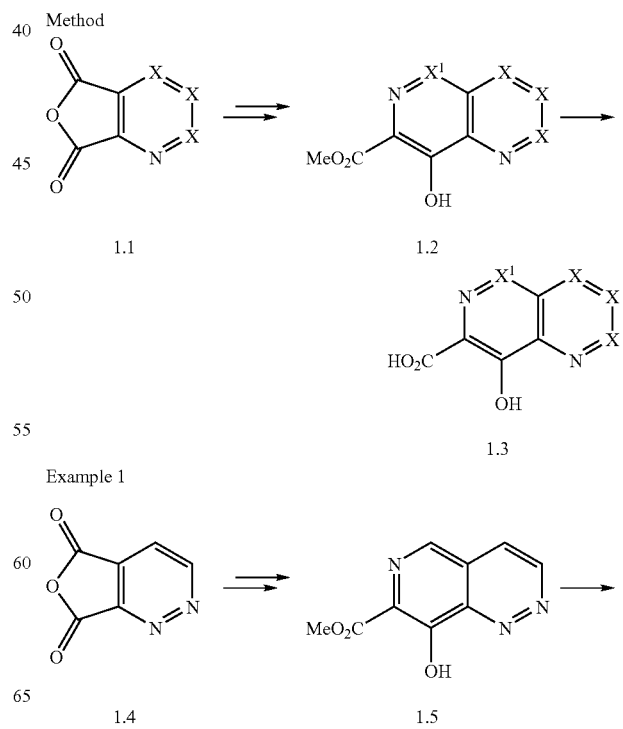

Scheme 1.

Method 1.1 → 1.2 → 1.3

Example 1

1.4 → 1.5

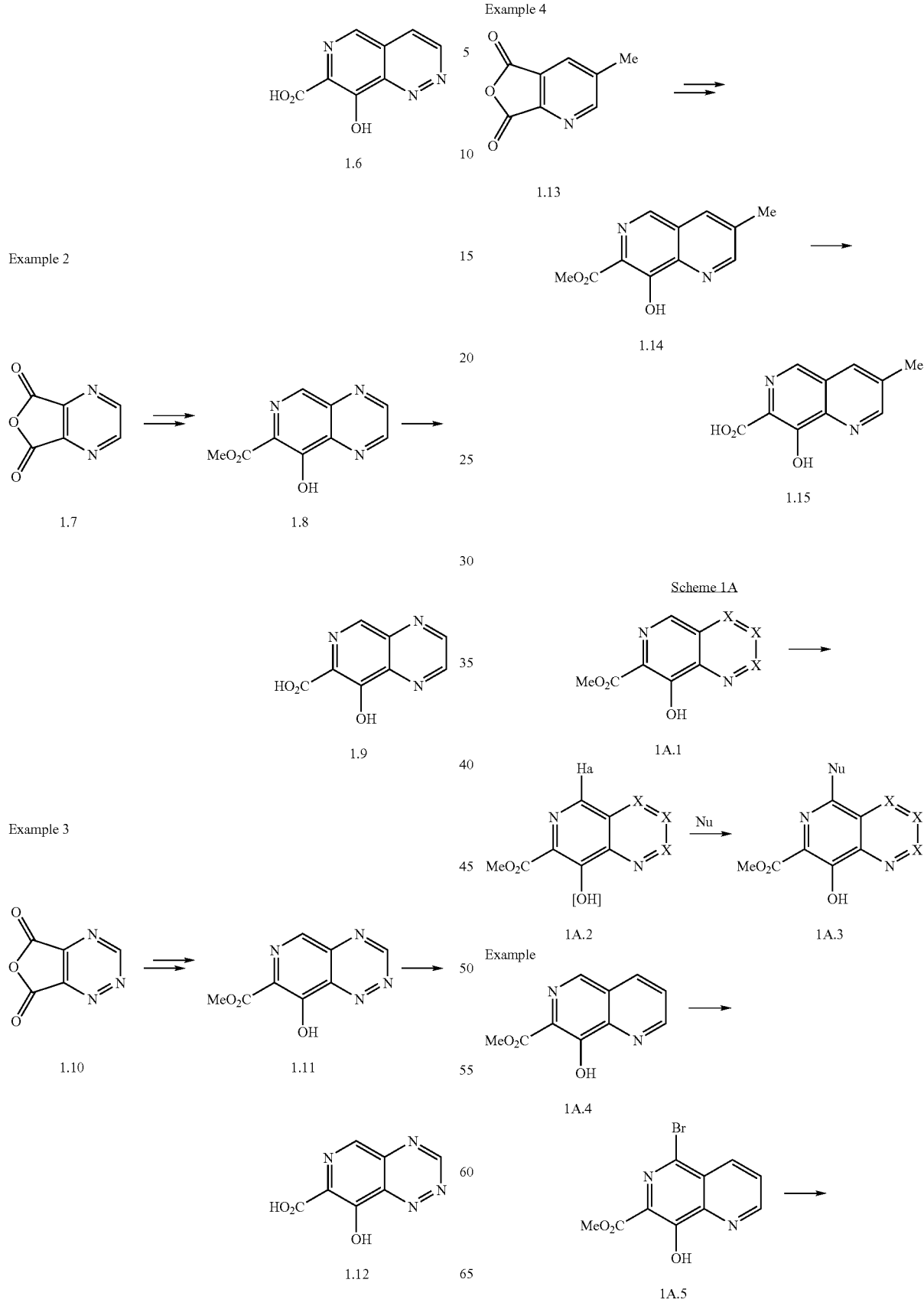

-continued
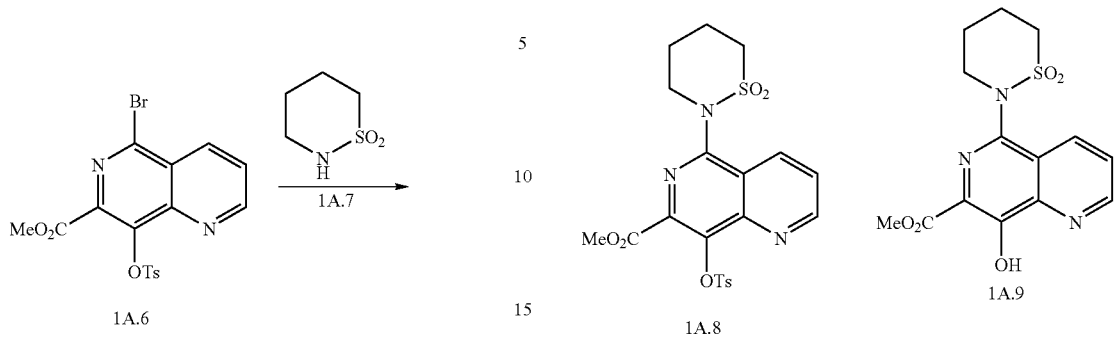
Scheme 2.
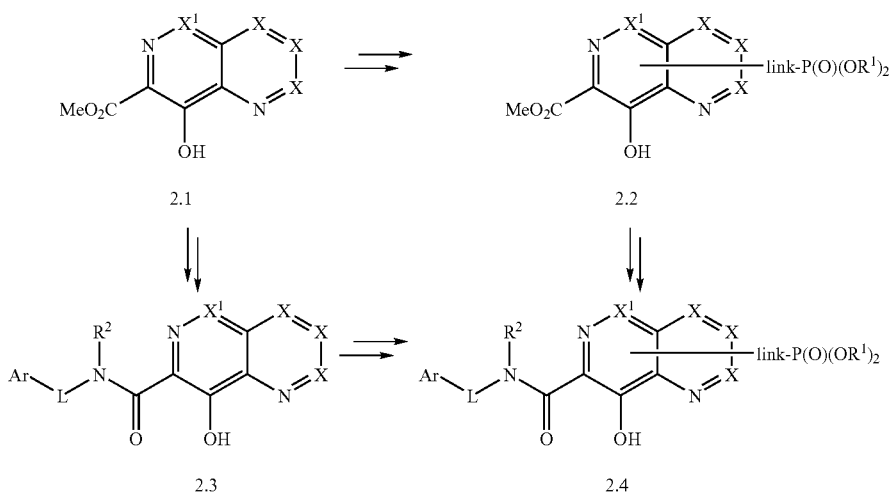
Scheme 2a.
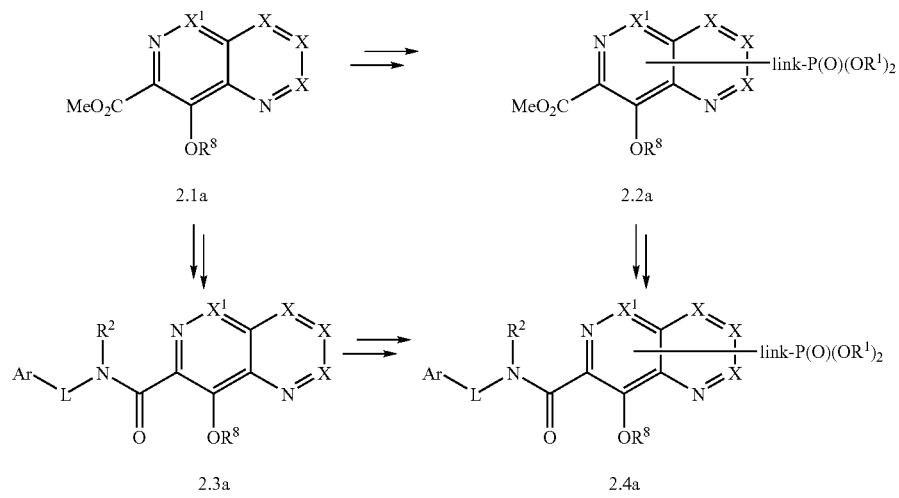

Preparation of the Intermediate Phosphonate Esters 1.

Schemes 3-7 illustrate methods for the preparation of the phosphonate esters 1.

Scheme 3 depicts the preparation of phosphonate esters 1 in which the phosphonate group is directly attached to the group Ar. In this procedure, a bromo-substituted amine 3.1, in which Ar is an aromatic or heteroaromatic group, is reacted, in the presence of a palladium catalyst, with a dialkyl phosphite 3.2 to yield the aryl phosphonate 3.3. The preparation of arylphosphonates by means of a coupling reaction between aryl bromides and dialkyl phosphites is described in J. Med. Chem., 35, 1371, 1992. This reaction is performed in an inert solvent such as toluene, in the presence of a base such as triethylamine and a palladium (0) catalyst such as tetrakis (triphenylphosphine)palladium(0). Optionally, the amine group is protected prior to the coupling reaction, and deprotected afterwards. The amine is then reacted with the ester 3.4 to afford the amide 3.5. The conversion of esters into amides is described in Comprehensive Organic Transformations, by R. C. Larock, VCH, 1989, p. 987. The reactants are combined in a solvent such as toluene or xylene, in the presence of a base such as sodium methoxide under azeotropic conditions, or of a dialkyl aluminum or trialkyl tin derivative of the amine. The use of trimethylaluminum in the conversion of esters to amides is described in J. Med. Chem. Chim. Ther., 34, 1999, 1995, and Syn. Comm., 25, 1401, 1995. The reaction is conducted in an inert solvent such as dichloromethane or toluene. The conversion of bicyclic esters such as 3.4, or the corresponding carboxylic acids, into amides is described in WO 0230930 A2, Schemes 1, 2, 3 and 6. Optionally, the phenolic hydroxyl group of the bicyclic ester 3.4 is protected, for example as a p-toluenesulfonyl derivative, as described in WO 0230930 A2, Example 1, prior to reaction with the amine component 3.3.

For example, 3-bromo-4-fluorobenzylamine 3.6 (Lancaster) is reacted in toluene solution at ca. 100°, with one molar equivalent of a dialkyl phosphite 3.7, triethylamine and 3 mol % of tetrakis(triphenylphosphine)palladium(0), to give the phosphonate product 3.8. The latter compound is then reacted, in toluene solution at reflux temperature with 5-(1, 1-dioxo[1,2]thiazinan-2-yl)-8-hydroxy-[1,6]naphthyridine-7-carboxylic acid methyl ester 3.9, prepared by the methods described in WO 0230930 A2, and Schemes 1, 1A and 2, to yield the amide 3.10.

Using the above procedures, but employing, in place of the amine 3.6, different amines 3.1, and/or different bicyclic esters 3.4, the corresponding amides 3.5 are obtained.

Scheme 4 depicts the preparation of phosphonate esters 1 in which the phosphonate group is attached by means of a saturated or unsaturated alkylene chain. In this procedure, a bromo-substituted amine 4.1, in which Ar is an aryl or heteroaryl group, is subjected to a Heck coupling reaction, in the presence of a palladium catalyst, with a dialkyl alkenyl phosphonate 4.2, in which $R^5$ is a direct bond, an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, to give the amine 4.3. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine) palladium(0) or a palladium(II) catalyst such as palladium(II) acetate, and optionally in the presence of a base such as triethylamine or potassium carbonate. Optionally, the amine substituent is protected prior to the coupling reaction, and deprotected afterwards. The phosphonate amine 4.3 is then coupled, as described above, with the ester 4.4, or the corresponding carboxylic acid, to produce the amide 4.5. Optionally, the double bond is reduced to give the saturated analog 4.6. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane.

For example, 3-bromo-4-methoxybenzylamine 4.7 (Lancaster) is reacted in dioxan solution with one molar equivalent of a dialkyl vinyl phosphonate 4.8 (Aldrich) and potassium carbonate, to yield the olefinic phosphonate 4.9. The product is then reacted, as described above, with 5-(1,1-dioxo-isothiazolidin-2-yl)-8-hydroxy-[1,6]naphthyridine-7-carboxylic acid methyl ester 4.10, prepared as described in Scheme 1A, and by methods described in WO 0230930 A2, to give the amide 4.11. The latter compound is reacted with diimide, prepared by basic hydrolysis of diethyl azodicarboxylate, as described in Angew. Chem. Int. Ed., 4, 271, 1965, to yield the saturated product 4.12.

Using the above procedures, but employing, in place of the amine 4.7, different amines 4.1, and/or different phosphonates 4.2, and/or different bicyclic esters 4.4, the corresponding amides 4.5 and 4.6 are obtained.

Scheme 5 depicts the preparation of phosphonate esters 1 in which the phosphonate group is attached by means of an amide linkage. In this procedure, the amine group of a carboxy-substituted amine 5.1 is protected to afford the derivative 5.2. The protection of amino groups is described in Protective Groups in Organic Synthesis, by T. W. Greene and P. G. M. Wuts, Wiley, Second Edition 1990, p. 309ff. Amino groups are protected, for example by alkylation, such as by mono or dibenzylation, or by acylation. The conversion of amines into mono or dibenzylamines, for example by treatment with benzyl bromide in a polar solvent such as acetonitrile or aqueous ethanol, in the presence of a base such as triethylamine or sodium carbonate, is described in Protective Groups in Organic Synthesis, by T. W. Greene and P. G. M. Wuts, Wiley, Second Edition 1990, p. 364. The N-protected carboxylic acid 5.2 is then coupled with an amino-substituted dialkyl phosphonate 5.3, in which the group $R^5$ is as defined in Scheme 4, to yield the amide 5.4. The preparation of amides from carboxylic acids and derivatives is described, for example, in Organic Functional Group Preparations, by S. R. Sandler and W. Karo, Academic Press, 1968, p. 274, and in Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid is first converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride is effected by treatment of the carboxylic acid with a reagent such as, for example, thionyl chloride or oxalyl chloride in an inert organic solvent such as dichloromethane, optionally in the presence of a catalytic amount of dimethylformamide.

The amino-protecting group is then removed from the product 5.4 to give the free amine 5.5. Deprotection of amines is described in Protective Groups in Organic Synthesis, by T. W. Greene and P. G. M. Wuts, Wiley, Second Edition 1990, p. 309ff. The amine is then coupled with the carboxylic acid 5.6, as described above, to produce the amide 5.7.

For example, 4-carboxycyclohexylmethylamine 5.8 (Aldrich) is converted into the phthalimido derivative 5.9. The conversion of amines into phthalimido derivatives is described in Protective Groups in Organic Synthesis, by T. W. Greene and P. G. M. Wuts, Wiley, Second Edition 1990, p. 358. The conversion is effected by reaction of the amine with an equimolar amount of 2-carbomethoxybenzoyl chloride, N-carboethoxyphthalimide, or preferably, phthalic anhydride. The reaction is performed in an inert solvent such as toluene, dichloromethane or acetonitrile, to prepare the phthalimido derivative 5.9. This material is then reacted with one molar equivalent of a dialkyl aminoethyl phosphonate 5.10, (J. Org. Chem., 2000, 65, 676) and dicyclohexylcarbodiimide in dimethylformamide, to give the amide 5.11. The phthalimido protecting group is then removed, for example by reaction with ethanolic hydrazine at ambient temperature, as described in J. Org. Chem., 43, 2320, 1978, to afford the amine 5.12. This compound is coupled in dimethylformamide solution with 5-(methanesulfonyl-methyl-amino)-8-hydroxy-[1,6]naphthyridine-7-carboxylic acid 5.13, prepared as described in Scheme 1A and WO 0230930 A2 Example 154, and 1-ethyl-3-(dimethylaminopropyl)carbodiimide, to afford the amide 5.14.

Using the above procedures, but employing, in place of the amine 5.8, different amines 5.1, and/or different phosphonates 5.3, and/or different carboxylic acids 5.6, the corresponding products 5.7 are obtained.

Scheme 6 depicts the preparation of phosphonates 1 in which the phosphonate is attached by means of an ether linkage. In this procedure, the amino group of a hydroxy-substituted amine 6.1 is protected, as described above, to give the derivative 6.2. The carbinol is then reacted, with base catalysis, with a dialkyl bromomethyl phosphonate 6.3, in which the group $R^5$ is as defined in Scheme 4. The reaction is conducted in a polar aprotic solvent such as tetrahydrofuran, dimethylformamide or dimethylsulfoxide, in the presence of a base such as potassium carbonate, for cases in which Ar is an aromatic group, or a strong base such as sodium hydride, for cases in which Ar is an aliphatic group. The amino group of the resulting ether 6.4 is then deprotected, as previously described, to give the amine 6.5. The amine is then reacted with the ester 6.6, as described in Scheme 3, to give the amide 6.7.

For example, N-methyl 3-hydroxyphenethylamine 6.8 is reacted with one molar equivalent of acetyl chloride in dichloromethane containing pyridine, to give the N-acetyl product 6.9. The product is then reacted at ca. 60° in dimethylformamide solution with one molar equivalent of a dialkyl 3-bromopropenyl phosphonate 6.10 (Aurora) and cesium carbonate, to produce the ether 6.11. The N-acetyl group is then removed, for example by treatment with hog kidney acylase, as described in Tet., 44, 5375, 1988, to give the amine 6.12.

The product is then reacted in toluene solution at reflux, as described above, with 5-(1,1-dioxo-[1,2]thiazepan-2-yl)-8-hydroxy-[1,6]naphthyridine-7-carboxylic acid methyl ester 6.13, prepared as described in Scheme 1A and in WO 0230931 Example 6, to yield the amide 6.14.

Using the above procedures, but employing, in place of the amine 6.8, different amines 6.1, and/or different phosphonates 6.3, and/or different bicyclic esters 6.6, the corresponding products 6.7 are obtained.

Scheme 7 depicts the preparation of phosphonates 1 in which the phosphonate is attached by means of an ether or thioether linkage. In this procedure, a N-protected hydroxyamine 6.2, in which Ar is an aromatic moiety, is subjected to a Mitsunobu reaction with a hydroxy or mercapto-substituted dialkyl phosphonate 7.1, in which $R^5$ is as defined in Scheme 4, to prepare the ether or thioether product 7.2. The preparation of aromatic ethers and thioethers by means of the Mitsunobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol and the alcohol or thiol component are reacted together in an aprotic solvent such as, for example, tetrahydrofuran or dioxan, in the presence of a dialkyl azodicarboxylate and a triarylphosphine, to afford the ether or thioether products. The N-protecting group is then removed and the resultant amine is converted, as described in Scheme 6, into the amide 7.3.

For example, N-acetyl 3,5-dichloro-4-hydroxybenzylamine 7.4 is reacted tetrahydrofuran solution with one molar equivalent of a dialkyl mercaptoethyl phosphonate 7.5, (Zh. Obschei. Khim., 1973, 43, 2364) diethyl azodicarboxylate and tri-o-tolylphosphine, to afford the thioether product 7.6. The N-acetyl group is removed, as described in Scheme 6, and the amine 7.7 is then reacted with 5-(1,1-dioxo-[1,2,5]thiadiazepan-2-yl)-8-hydroxy-[1,6]naphthyridine-7-carboxylic acid methyl ester 7.8, (see, for example, WO 0230931 Example 3) to afford the amide 7.9.

Using the above procedures, but employing; in place of the amine 7.4, different amines 6.2, and/or different phosphonates 7.2, the corresponding products 7.3 are obtained.

Scheme 3. Phosphonates 1.

Method

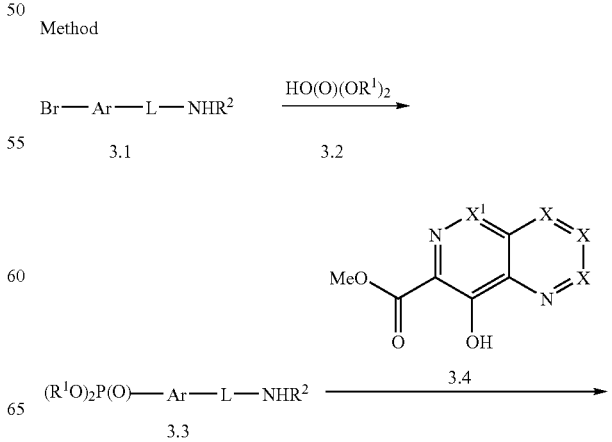

-continued
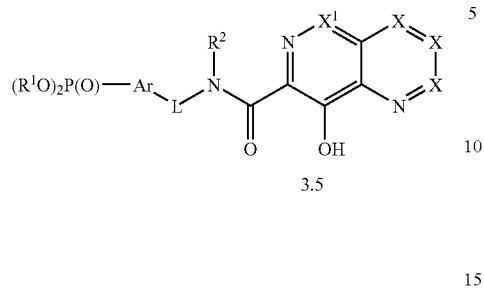
3.5
Example
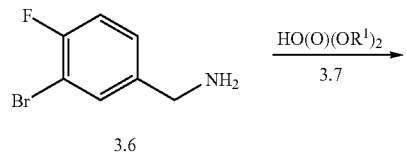
3.6
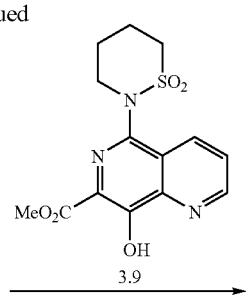
3.9
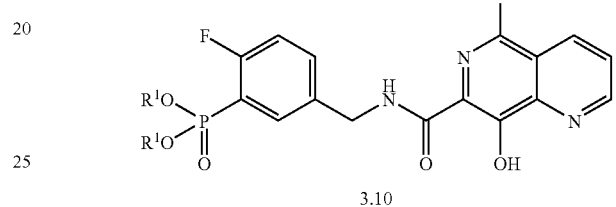
3.10
Scheme 4. Phosphonates 1.
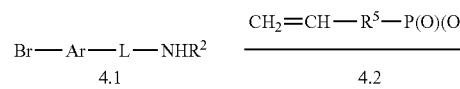
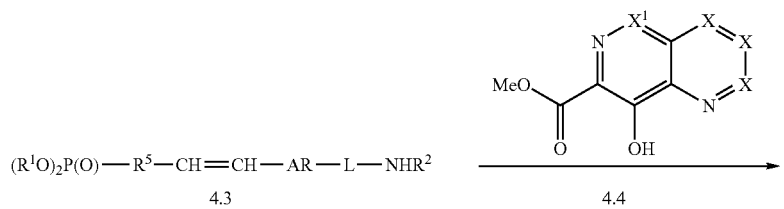
4.5
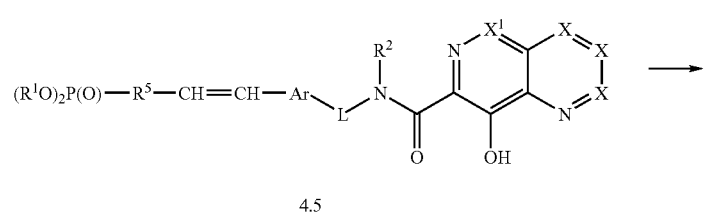
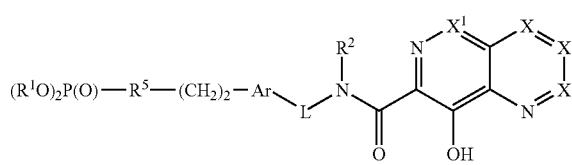
4.6

Example
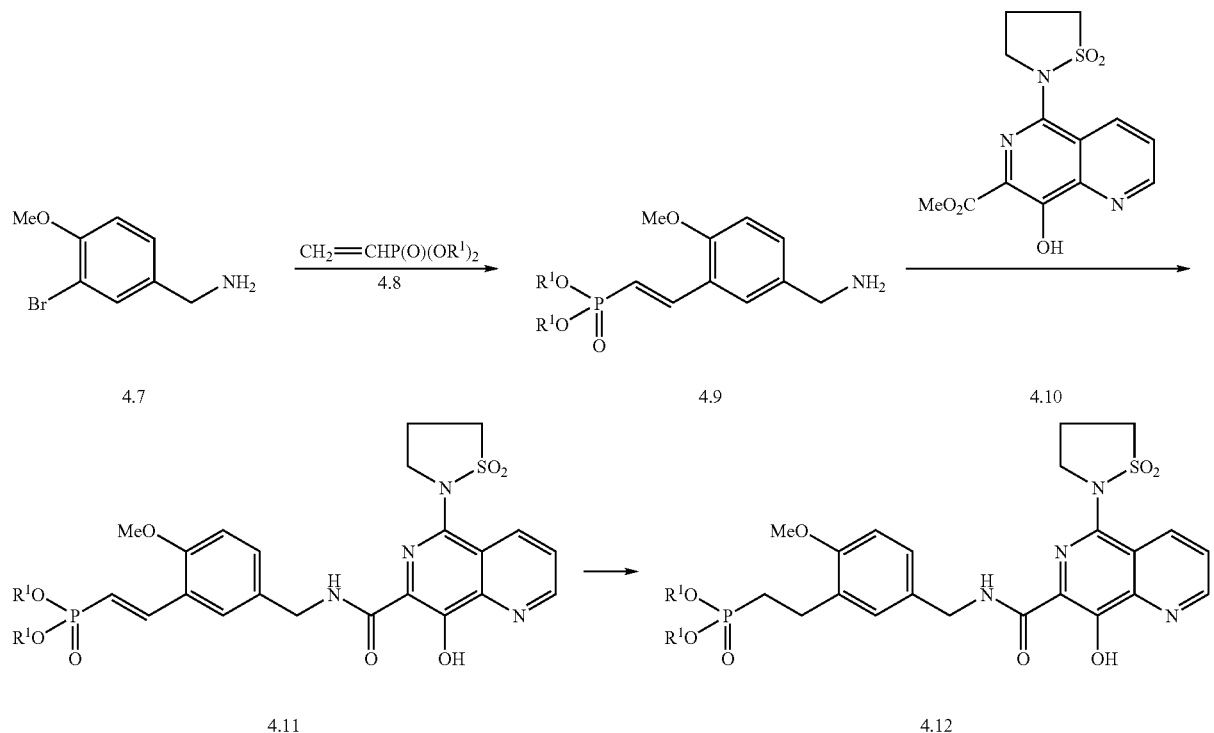
Scheme 5. Phosphonates 1.
Method
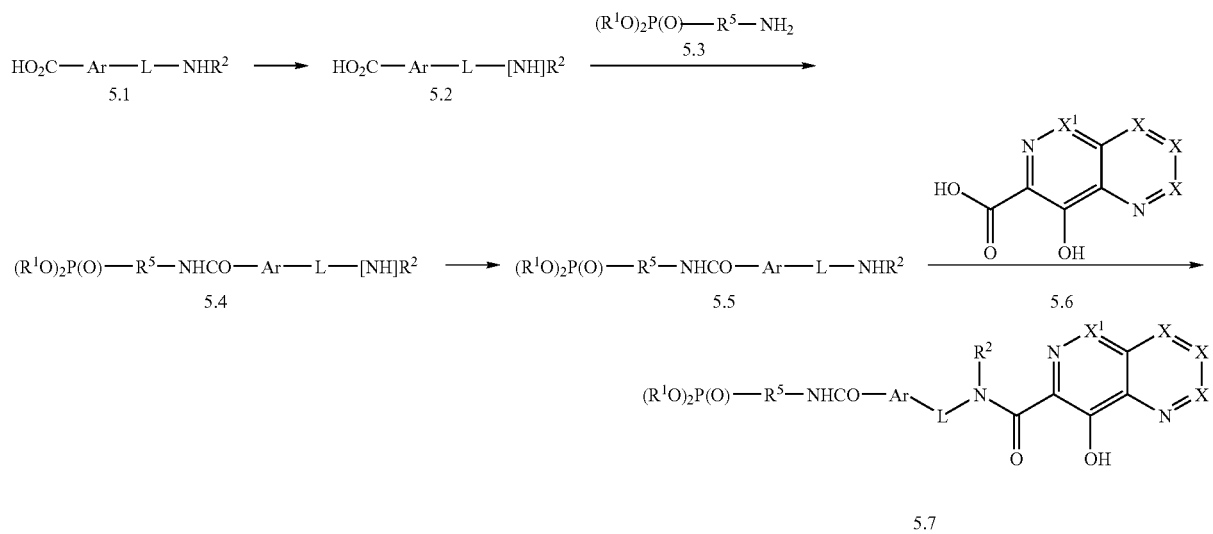
Example
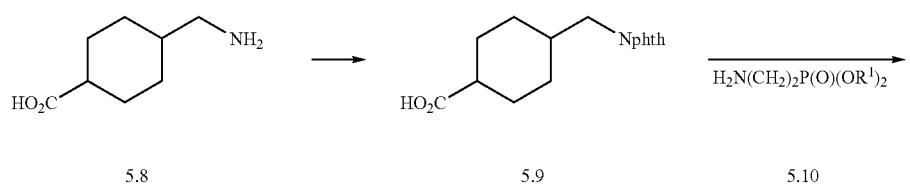

-continued
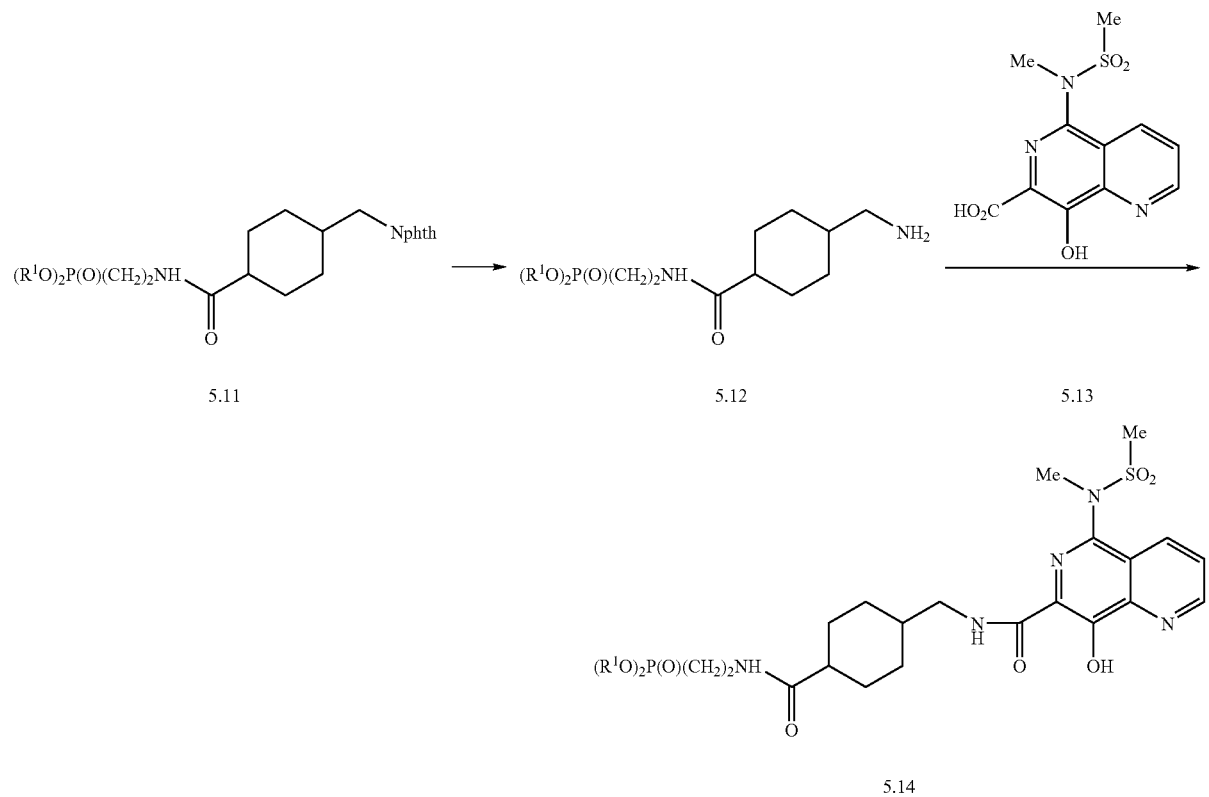
Scheme 6. Phosphonates 1.
Method
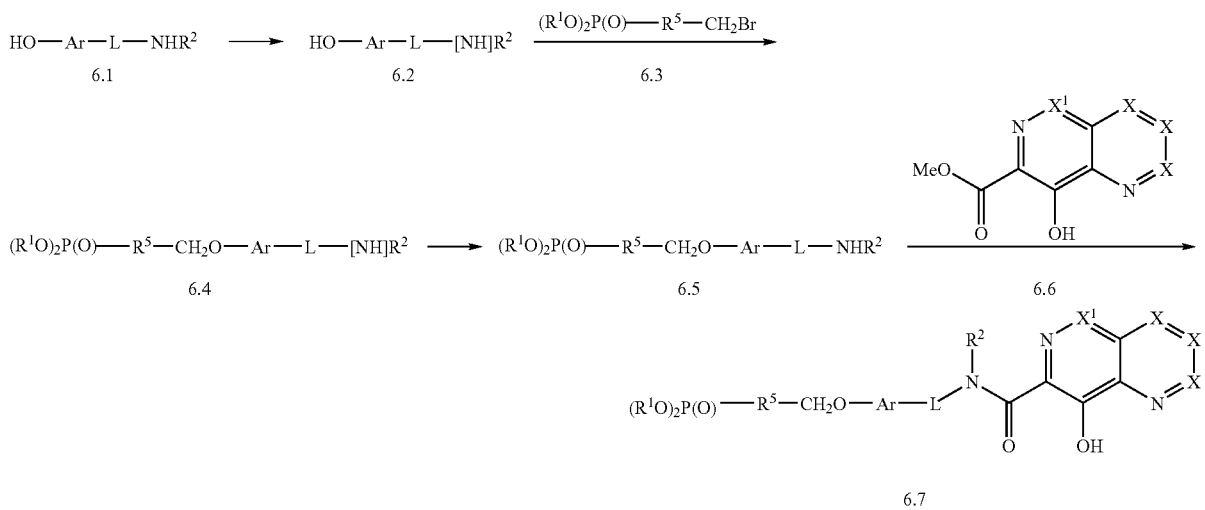
Example
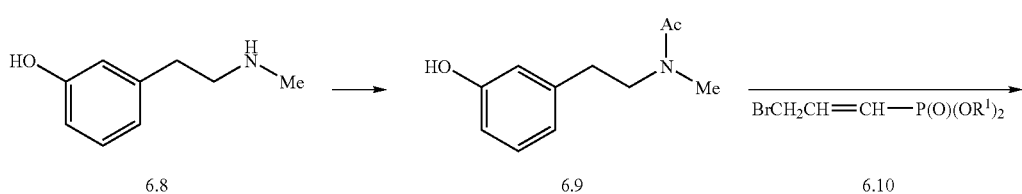

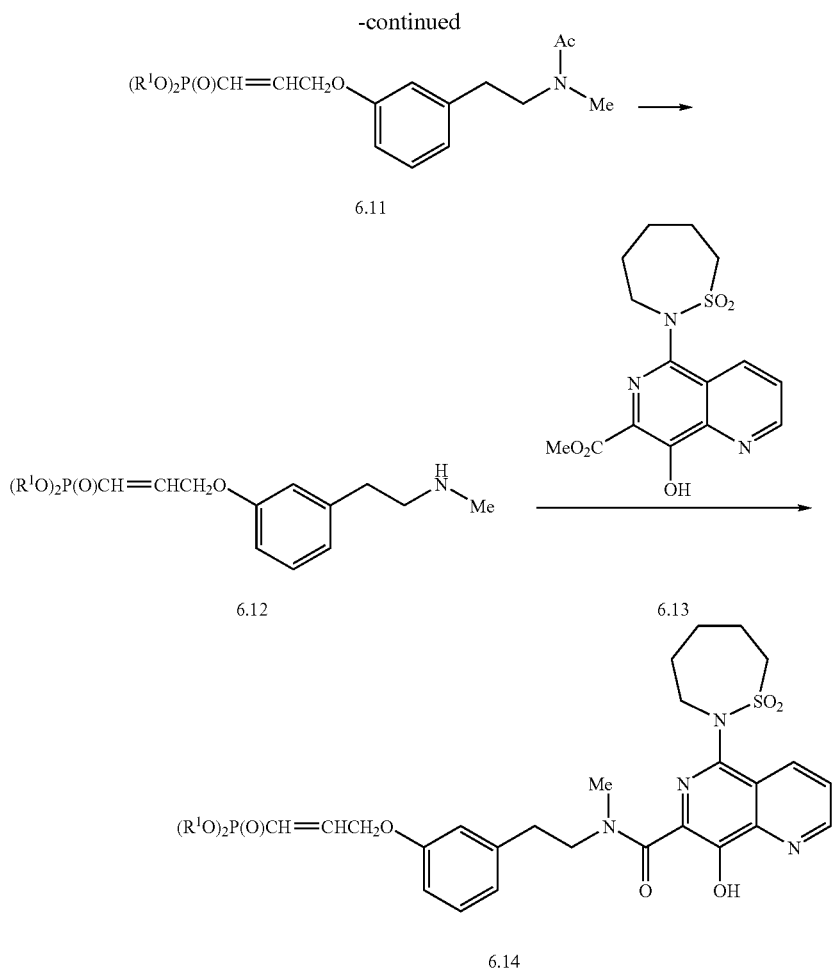

Preparation of the Intermediate Phosphonate Esters 2.

Schemes 8-10 illustrate methods for the preparation of the phosphonate esters 2.

Scheme 8 depicts the preparation of phosphonates 2 in which the phosphonate is attached by means of an alkylene chain incorporating an amide linkage. In this procedure, an amine 8.1 is reacted with a bromoalkyl ester 8.2, in which $R^5$ is as defined in Scheme 4, to yield the alkylated amine 8.3. The preparation of substituted amines by the reaction of amines with alkyl halides is described, for example, in Comprehensive Organic Transformations, by R. C. Larock, VCH, 1989, p. 397. Equimolar amounts of the reactants are combined in a polar solvent such as an alkanol or dimethylformamide and the like, in the presence of a base such as cesium carbonate, diazabicyclononene or dimethylaminopyridine, to yield the substituted amine. The ester group is then hydrolyzed to give the carboxylic acid 8.4, and this compound is then coupled, as described in Scheme 5, with a dialkyl aminoalkyl phosphonate 8.5, to produce the aminoamide 8.6. Optionally, the amino group of the amine 8.4 is protected prior to the coupling reaction, and deprotected afterwards. The product is then reacted with the bicyclic hydroxyester 8.7 to afford the amide 8.8.

For example, 4-trifluoromethylbenzylamine 8.9 is reacted in dimethylformamide with one molar equivalent of methyl bromoacetate 8.10 and potassium carbonate to give the ester 8.11. Hydrolysis, employing one molar equivalent of lithium hydroxide in aqueous dimethoxyethane, affords the carboxylic acid 8.12, and this compound is coupled in tetrahydrofuran solution with a dialkyl aminomethyl phosphonate 8.13 (Aurora), in the presence of dicyclohexylcarbodiimide, to give the aminoamide 8.14. The product is then reacted with 5-(1, 1-dioxo-isothiazolidin-2-yl)-8-hydroxy-[1,6]naphthyridine-7-carboxylic acid methyl ester 8.15, prepared by the methods described above, to yield the amide 8.16.

Using the above procedures, but employing, in place of the amine 8.9, different amines 8.1, and/or different bromoesters 8.2, and/or different phosphonates 8.5, and/or different hydroxyesters 8.7, the corresponding products 8.8 are obtained.

Scheme 9 depicts the preparation of phosphonates 2 in which the phosphonate is attached by means of a variable carbon chain. In this procedure, a primary amine 9.1 is subjected to a reductive amination reaction with a dialkyl formyl-substituted phosphonate 9.2, in which $R^5$ is as defined in Scheme 4, to afford the alkylated amine 9.3. The preparation of amines by means of reductive amination procedures is described, for example, in Comprehensive Organic Transformations, by R. C. Larock, VCH, p. 421, and in Advanced Organic Chemistry, Part B, by F. A. Carey and R. J. Sundberg, Plenum, 2001, p. 269. In this procedure, the amine component and the aldehyde or ketone component are reacted together in a polar solvent in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The product 9.3 is then reacted, as described previously, with the bicyclic ester 9.4 to give the amide 9.5.

For example, 3,4-dichlorobenzylamine is reacted in methanol solution with one molar equivalent of a dialkyl 3-formylphenyl phosphonate 9.7, (Epsilon) and sodium cyanoborohydride, to yield the alkylated product 9.8. This compound is then reacted with 5-(methanesulfonyl-methyl-amino)-8-hydroxy-[1,6]naphthyridine-7-carboxylic acid methyl ester 9.9, prepared using the methods described above, from the corresponding bromo compound and N-methyl methanesulfonamide, to give the amide 9.10.

Using the above procedures, but employing, in place of the amine 9.6, different amines 9.1, and/or different phosphonates 9.2, and/or different bicyclic esters 9.4, the corresponding products 9.5 are obtained.

Scheme 10 depicts an alternative method for the preparation of phosphonates 2 in which the phosphonate is attached by means of a variable carbon chain. In this procedure, the phenolic group of a bicyclic amide 10.1, prepared as described above, and in WO 0230930 A2, is protected to give the product 10.2. The protection of phenolic hydroxyl groups is described in Protective Groups in Organic Synthesis, by T. W. Greene and P. G. M. Wuts, Wiley, Second Edition 1990, p. 10ff. For example, hydroxyl substituents are protected as trialkylsilyloxy ethers. Trialkylsilyl groups are introduced by the reaction of the phenol with a chlorotrialkylsilane and a base such as imidazole, for example as described in Protective Groups in Organic Synthesis, by T. W. Greene and P. G. M. Wuts, Wiley, Second Edition 1990, p. 10, p. 68-86. Alternatively, phenolic hydroxyl groups are protected as benzyl or substituted benzyl ethers, or as acetal ethers such as methoxymethyl or tetrahydropyranyl. The O-protected amide 10.2 is then reacted with the phosphonate-substituted trifluoromethanesulfonate 10.3, in which $R^5$ is as defined in Scheme 4, to produce the alkylated amide 10.4. The alkylation reaction is conducted between equimolar amounts of the reactants in an aprotic organic solvent such as dimethylformamide or dioxan, in the presence of a strong base such as lithium hexamethyl disilylazide or sodium hydride, at from ambient temperature to about 90°. The hydroxyl group is then deprotected to give the phenol 10.5. Deprotection of phenolic hydroxyl groups is described in Protective Groups in Organic Synthesis, by T. W. Greene and P. G. M. Wuts, Wiley, Second Edition 1990, p. 10ff. For example, silyl protecting groups are removed by reaction with tetrabutylammonium fluoride, benzyl groups are removed by catalytic hydrogenation and acetal ethers are removed by treatment with acids.

For example, furo[3,4-b]pyrazine-5,7-dione 10.6, (J. Org. Chem., 1964, 29, 2128) is converted, as described above, (Schemes 1, 1A and 2) and in WO 0230930 A2, into 5-(1,1-dioxo-1,2]thiazinan-2-yl)-8-hydroxy-pyrido[3,4-b]pyrazine-7-carboxylic acid (naphthalen-2-ylmethyl)-amide 10.7. The product is then reacted with one molar equivalent of tert-butyl chlorodimethylsilane and imidazole in dichloromethane, to give the silyl ether 10.8. This compound is then reacted at ambient temperature in dioxan solution with one molar equivalent of sodium hydride, followed by the addition of a dialkyl trifluoromethanesulfonyloxymethyl phosphonate 10.9 (Tet. Lett., 1986, 27, 1477), to afford the alkylated product 10.10. Deprotection, by reaction with tetrabutylammonium fluoride in tetrahydrofuran, then yields the product 10.11.

Using the above procedures, but employing, in place of the amide 10.7, different amides 10.1, and/or different phosphonates 10.3, the corresponding products 10.5 are obtained.

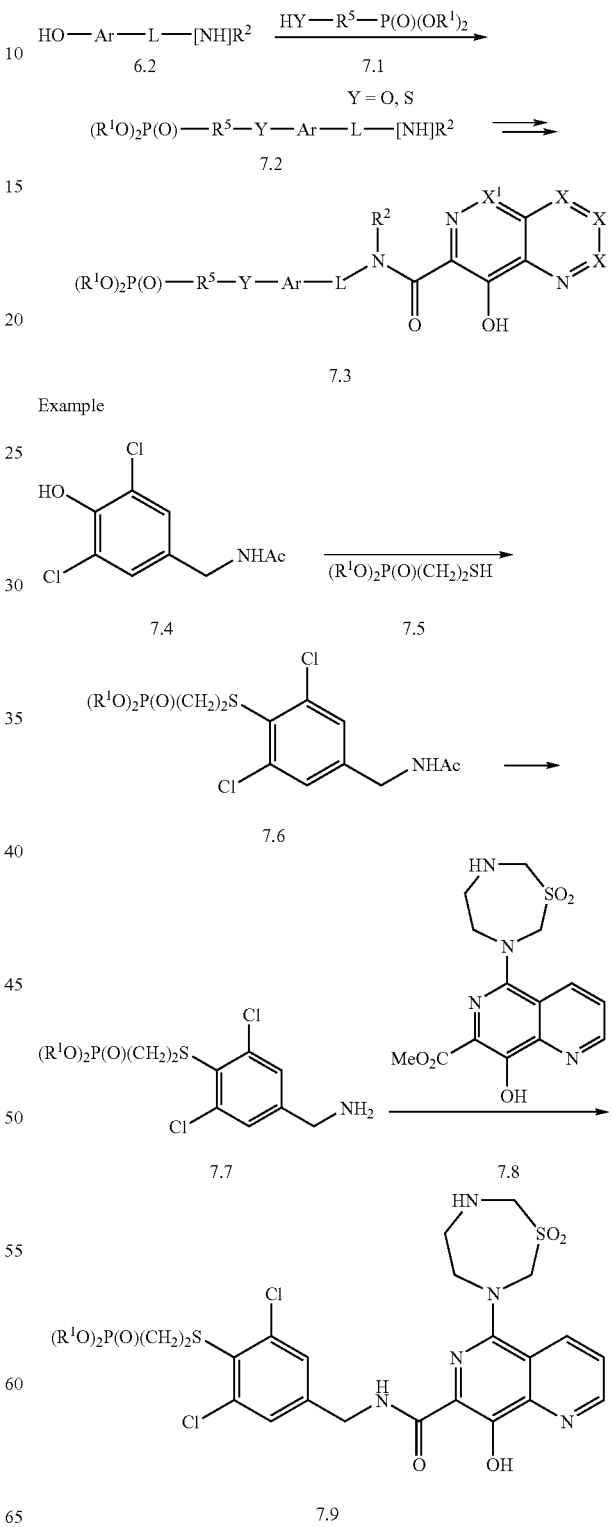

Scheme 8. Phosphonates 2.
Method
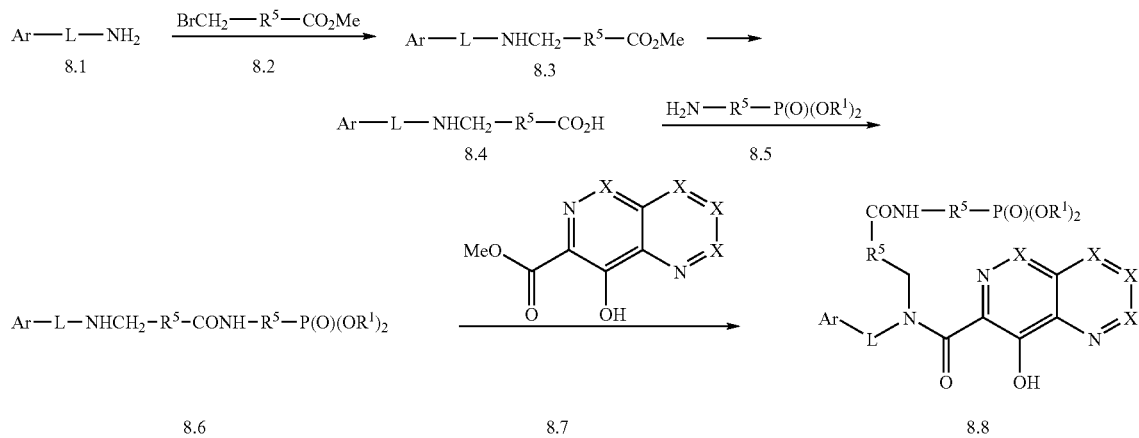
Example
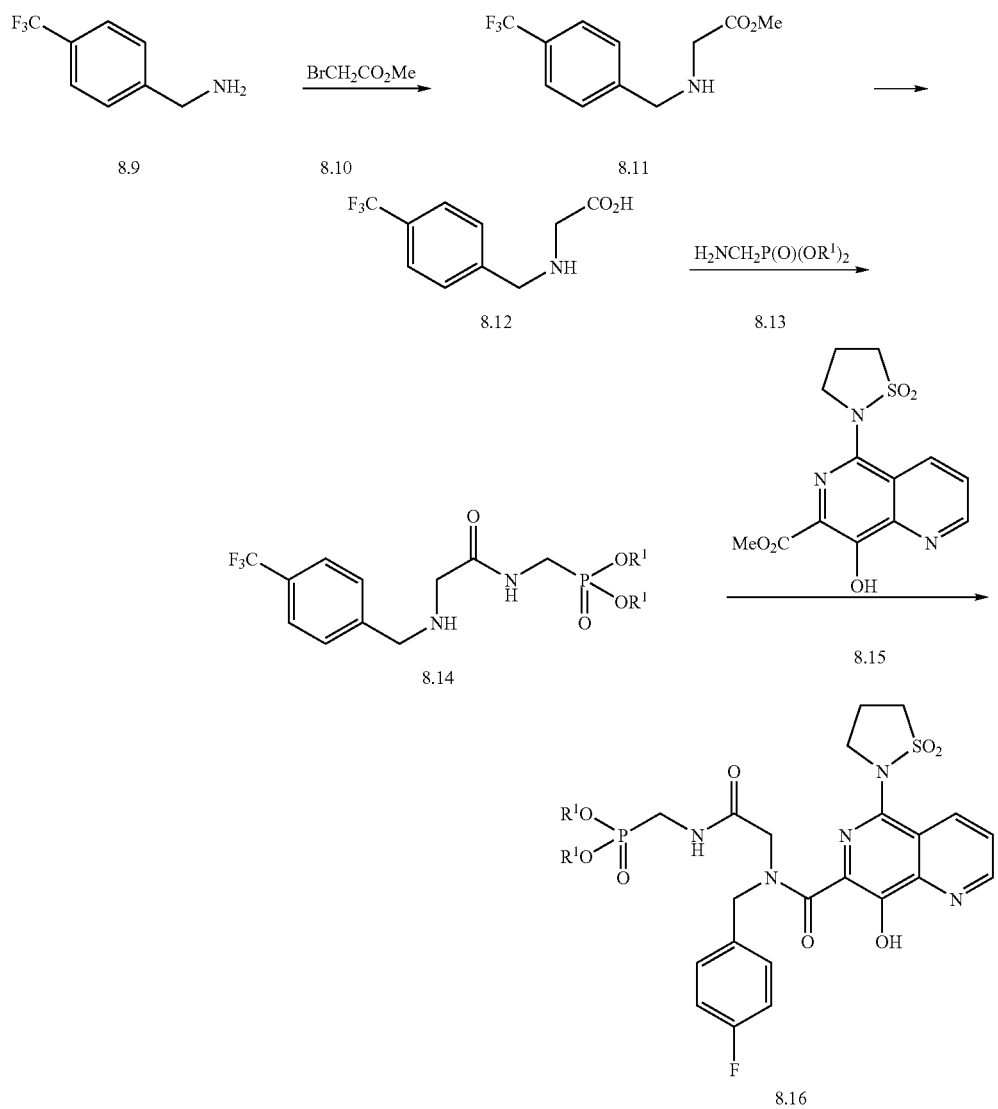

Scheme 9. Phosphonates 2.
Method
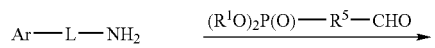
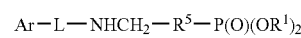
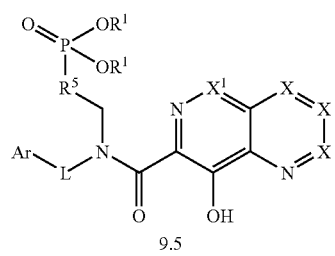
Example
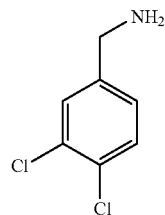 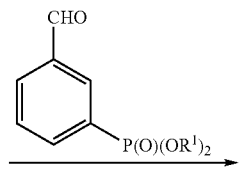
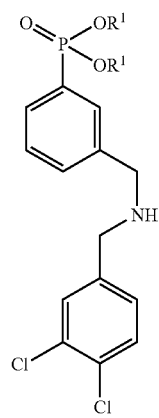 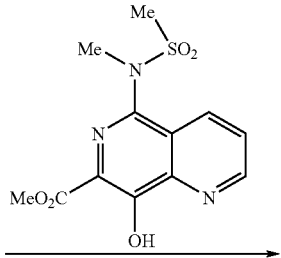
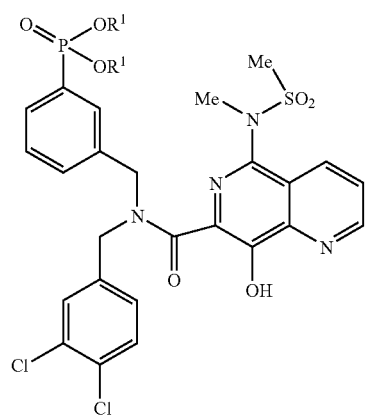
9.10
Scheme 10. Phosphonates 2.
Method
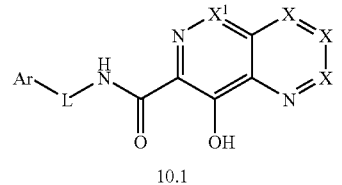
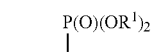
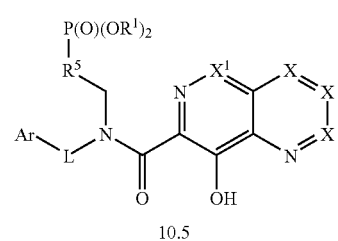

Example

-continued

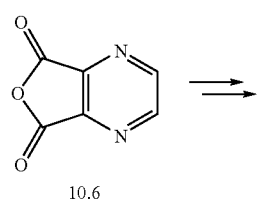

10.6

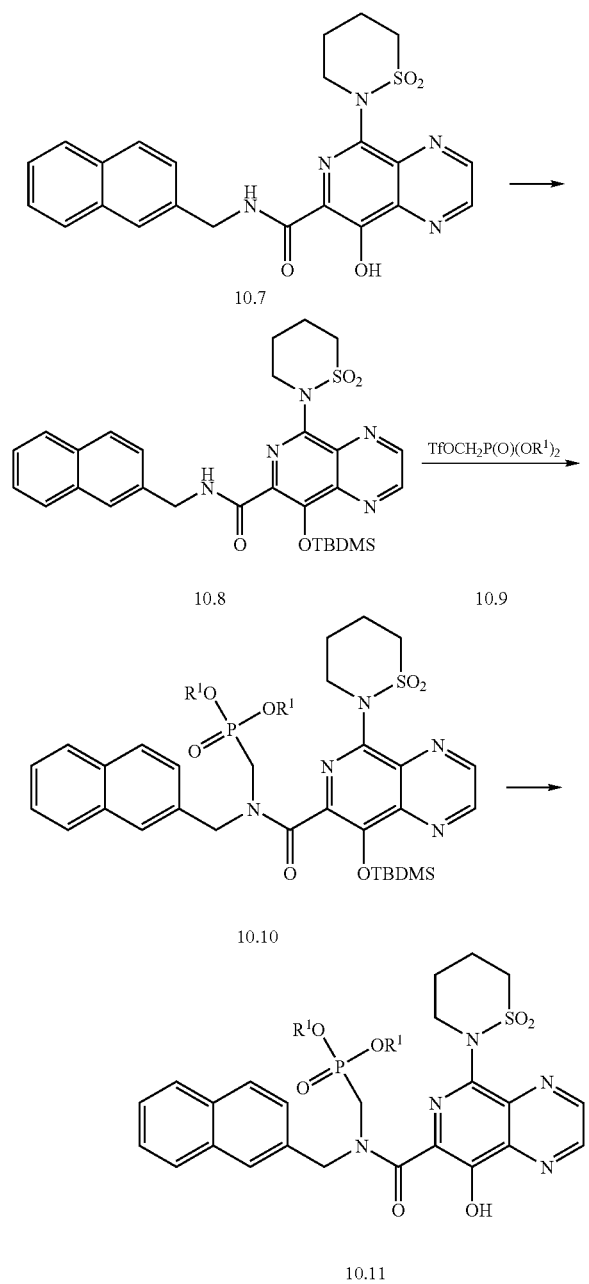

Preparation of the Intermediate Phosphonate Esters 3.

Schemes 11-15 illustrate methods for the preparation of the phosphonate esters 3.

Scheme 11 depicts the preparation of phosphonates 3 in which the phosphonate is attached by means of a heteroatom O, S or N, and a variable carbon chain. In this procedure, a bicyclic amide 11.1, prepared as previously described, is reacted in an aprotic solvent such as dichloromethane, hexachloroethane or ethyl acetate with a free radical brominating agent such as N-bromosuccinimide or N-bromoacetamide, to yield the 5-bromo product 11.2. This compound is then reacted with a dialkyl hydroxy, mercapto or aminosubstituted phosphonate 11.3, in which $R^5$ is as defined as in Scheme 4, to give the ether, thioether or amine product 11.4. The displacement reaction is conducted in a polar aprotic organic solvent such as dimethylformamide or DMPU, at from 100° to about 150°, in the presence of a base such as triethylamine or cesium carbonate, for example as described in WO 0230930 A2, Examples 57-69.

As shown in Example 1, furo[3,4-d]pyrimidine-5,7-dione 11.5 (J. Het. Chem., 1993, 30, 1597) is converted, as described above, into 8-hydroxy-pyrido[4,3-d]pyrimidine-7-carboxylic acid cyclohexylmethyl-amide 11.6. The product is reacted with one molar equivalent of N-bromosuccinimide in dichloromethane to yield the 5-bromo product 11.7. This material is then reacted with a dialkyl mercaptoethyl phosphonate 11.8 (Zh. Obschei. Khim., 1973, 43, 2364) and triethylamine at ca 100° in a pressure vessel, to produce the thioether 11.9.

As shown in Example 2, the anhydride 11.10 is converted, as described previously, into 8-hydroxy-[1,6]naphthyridine-7-carboxylic acid 3,5-dichloro-benzylamide 11.11. Bromination with N-bromosuccinimide in ethyl acetate at reflux temperature then yields the bromo compound 11.12 which is reacted with a dialkyl 3-aminophenyl phosphonate 11.13 (J. Med. Chem., 1984, 27, 654) in dimethylformamide at ca. 130°, using the procedure described in WO 0230930 A2 Example 63, to give the phosphonate 11.14. The product is then reacted with N,N-dimethyloxamide 11.15, (Japanese Patent 540467 18) and dicyclohexylcarbodiimide in dimethylformamide, to yield the amide product 11.16.

Using the above procedures, but employing, in place of the amides 11.6 or 11.11, different amides 11.1, and/or different phosphonates 11.3, the corresponding products 11.4 are obtained.

Scheme 12 depicts the preparation of phosphonates 3 in which the phosphonate is attached by means of a carbamate linkage. In this procedure, a protected bromophenol 12.1 is reacted, as described in Scheme 11, with an amine 12.2 to give the displacement product 12.3. This compound is then reacted with phosgene, triphosgene, carbonyl diimidazole or a functional equivalent thereof, and a dialkyl hydroxyalkyl phosphonate 12.4, in which $R^5$ is as defined in Scheme 4, to yield, after deprotection of the phenol, the carbamate 12.5. Various methods for the preparation of carbamates are described in Scheme 33.

For example, the hydroxyester 12.6 is converted, as described previously, into the amide 12.7. This material is then reacted, in dimethylformamide solution at 100°, with ethylamine and cesium carbonate in dimethylformamide, to afford 8-(tert-butyl-dimethyl-silanyloxy)-5-ethylamino-[1,6]naphthyridine-7-carboxylic acid [2-(4-fluoro-phenyl)-cyclopropyl]-amide 12.9. The amine is treated with equimolar amounts of a dialkyl hydroxypropyl phosphonate 12.10 (Zh. Obschei. Khim., 1974, 44, 1834) and carbonyldiimidazole in dichloromethane, to prepare, after desilylation, the carbamate 12.11.

Using the above procedures, but employing, in place of the amide 12.7, different amides 12.3, and/or different phosphonates 12.4, the corresponding products 12.5 are obtained.

Scheme 13 depicts the preparation of phosphonates 3 in which the phosphonate is attached by means of an arylvinyl or arylethyl linkage. In this procedure, a bromophenol 13.1 is protected to give the product 13.2. This compound is then coupled with tributylvinyltin to yield the 5-vinyl product 13.3. The coupling reaction is effected in dimethylformamide solution at ca. 80° in the presence of a palladium(0) catalyst, such as tris(dibenzylideneacetone)palladium(0), a triarylphosphine such as tri(2-furyl)phosphine and copper(I) iodide, for example as described in WO 0230930A2, Example 176. The vinyl-substituted product is subjected to a palladium-catalyzed Heck coupling reaction, as described in Scheme 4, with a dibromoaromatic or heteroaromatic compound 13.4, to give the bromoaryl product 13.5. The latter compound is then coupled, as described in Scheme 3, with a dialkyl phosphite 13.6, in the presence of a palladium catalyst, to give the aryl phosphonate 13.7. Deprotection then affords the phenol 13.8. Optionally, the double bond is reduced, for example as described in Scheme 4, to give the saturated analog 13.9.

For example, furo[3,4-c]pyridazine-5,7-dione 13.10, (WO9944992) is converted, using the methods described above, into the silyl-protected bromophenol 13.11. The product is coupled, as described above, with tri(n-butyl)vinyltin to produce the 5-vinyl compound 13.12. This material is then coupled, in dimethylformamide solution at 80° with one molar equivalent of 2,5-dibromothiophene, in the presence of tetrakis(triphenylphosphine)palladium(0) and triethylamine, to afford 5-[2-(5-bromo-thiophen-2-yl)-vinyl]-8-(tert-butyl-dimethyl-silanyloxy)-pyrido[4,3-c]pyridazine-7-carboxylic acid 3,5-dichloro-benzylamide 13.14. The product is coupled, in the presence of a palladium(0) catalyst and triethylamine, with a dialkyl phosphite 13.15, to afford the phosphonate 13.16. Deprotection, for example by reaction with tetrabutylammonium fluoride in tetrahydrofuran, then yields the phenol 13.17, and hydrogenation of the latter compound in methanol, using 5% palladium on carbon as catalyst, produces the saturated analog 13.18.

Using the above procedures, but employing, in place of the amide 13.11, different amides 13.1, and/or different dibromides 13.4, the corresponding products 13.8 and 13.9 are obtained.

Scheme 14 depicts the preparation of phosphonates 3 in which the phosphonate is attached by means of an acetylenic bond. In this procedure, a phenol 14.1 is reacted, as described in WO 0230930 A2 p. 166 and Example 112, with N-iodosuccinimide in dichloromethane-dimethylformamide, to give the 5-iodo product; protection of the phenolic hydroxyl group then affords the compound 14.2. This material is coupled, as described in WO 0230930 A2 Example 79, in dimethylformamide solution, in the presence of dichlorobis(triphenylphosphine) palladium (II), copper iodide and triethylamine, with a dialkyl ethynyl phosphonate 14.3, in which $R^5$ is as defined in Scheme 4, to give, after deprotection of the phenol, the acetylenic phosphonate 14.4.

For example, furo[3,4-e][1,2,4]triazine-5,7-dione 14.5, (J. Org. Chem., 1958, 23, 1931) is converted, as described previously, into the hydroxyester 14.6. This material is then converted into 5-iodo-8-(tert-butyl-dimethyl-silanyloxy)-pyrido[3,4-e][1,2,4]triazine-7-carboxylic acid (cyclopent-3-enylmethyl)-amide 14.7, as described above. The product is coupled, as described above, with a dialkyl propynyl phosphonate 14.8, (Syn., 1999, 2027) to yield, after deprotection, the acetylenic phosphonate 14.9.

Using the above procedures, but employing, in place of the iodoamide 14.7, different iodoamides 14.2, and/or different acetylenic phosphonates 14.3, the corresponding products 14.4 are obtained.

Scheme 15 depicts the preparation of phosphonates 3 in which the phosphonate is directly attached to the bicyclic nucleus. In this procedure, a protected bicyclic bromophenol 15.1 is coupled, in the presence of a palladium catalyst, as described in Scheme 3, with a dialkyl phosphite 15.2, to give after deprotection the aryl phosphonate 15.3.

For example, 3-methyl-furo[3,4-b]pyridine-5,7-dione 15.4, (German Patent DE 3707530) is converted, using the procedures described above, into 5-bromo-8-(tert-butyl-dimethyl-silanyloxy)-3-methyl-[1,6]naphthyridine-7-carboxylic acid [1-(3-chloro-4-fluoro-phenyl)-1-methyl-ethyl]-amide 15.5. The product is then coupled, in the presence of tetrakis (triphenylphosphine)palladium(0) and triethylamine, as described in Scheme 3, with a dialkyl phosphite 15.6, to afford, after desilylation of the phenol, the arylphosphonate 15.7.

Using the above procedures, but employing, in place of the bromoamide 15.5, different bromoamides 15.1, the corresponding products 15.3 are obtained.

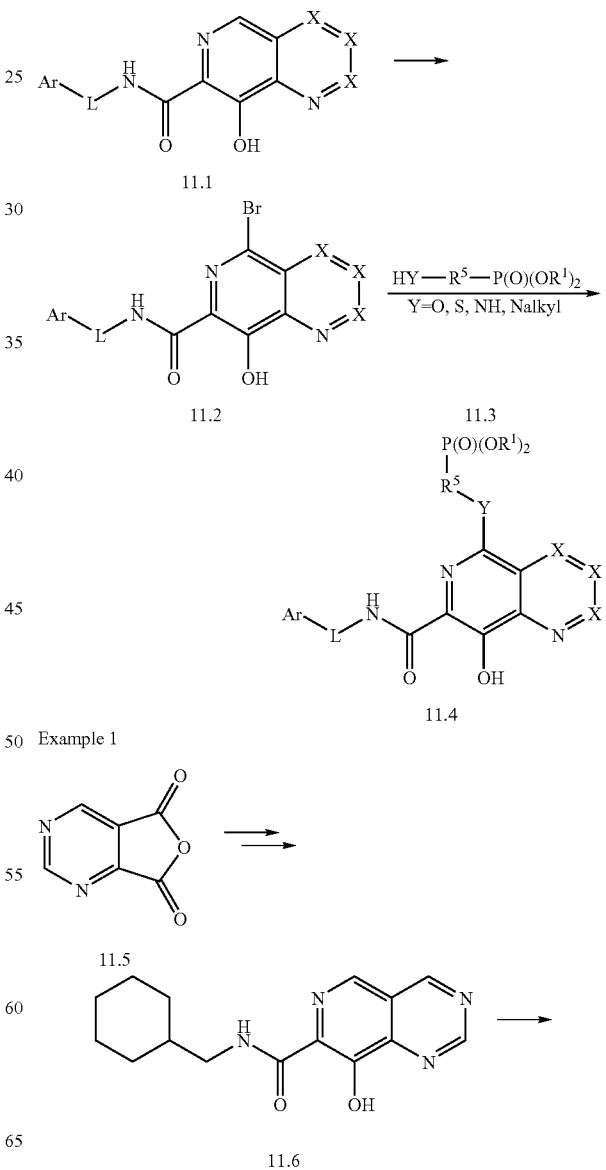

Scheme 11. Phosphonates 3.

Example 1

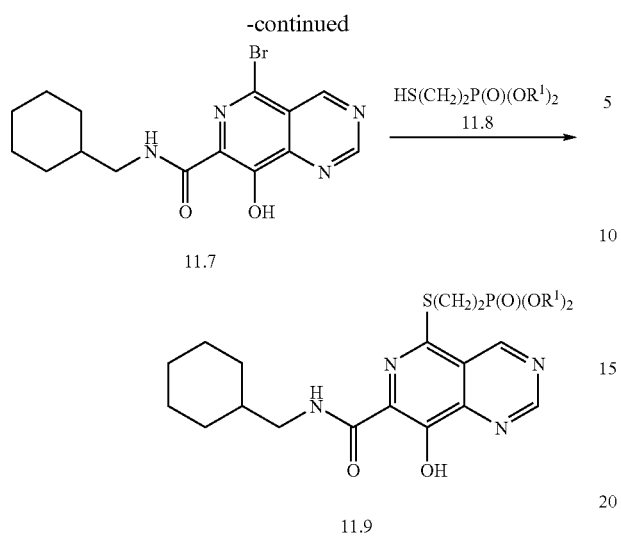
11.7
11.9
Example 2
11.10
11.11
11.12
11.13
11.14
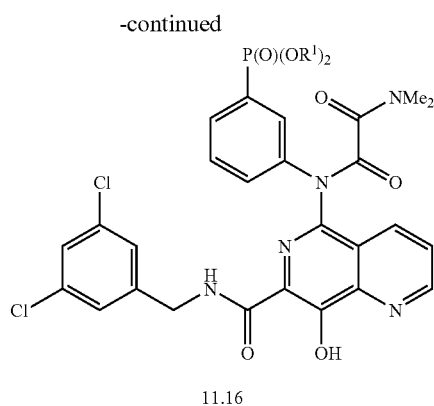
11.16
Scheme 12. Phosphonates 3.
Method
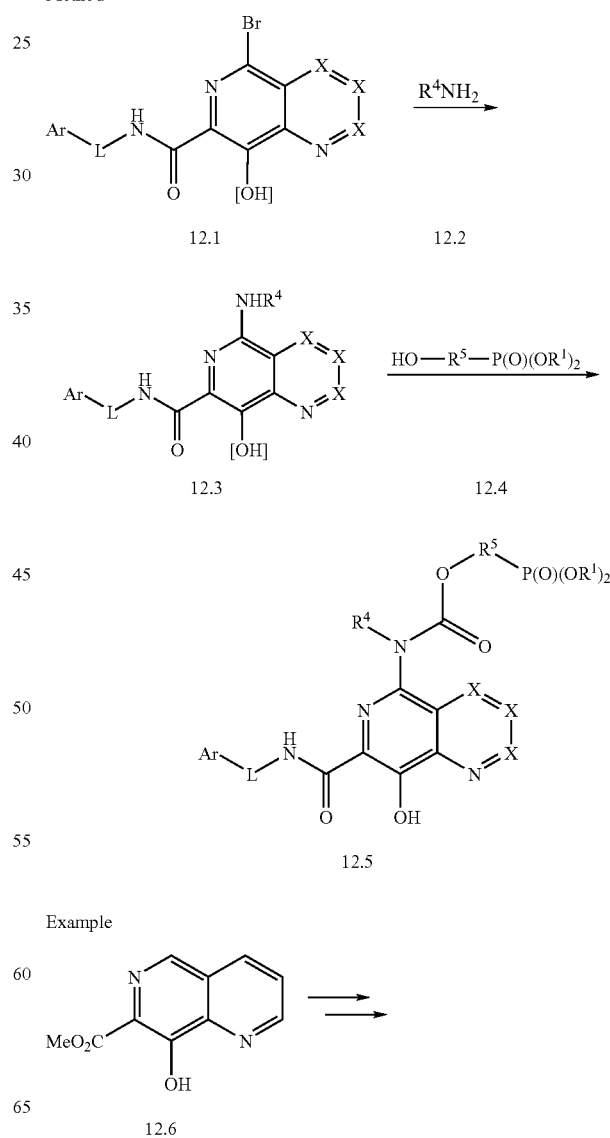
12.1
12.2
12.3
12.4
12.5
Example
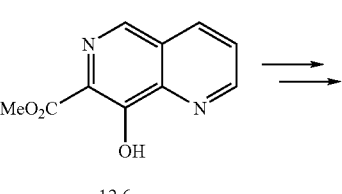
12.6

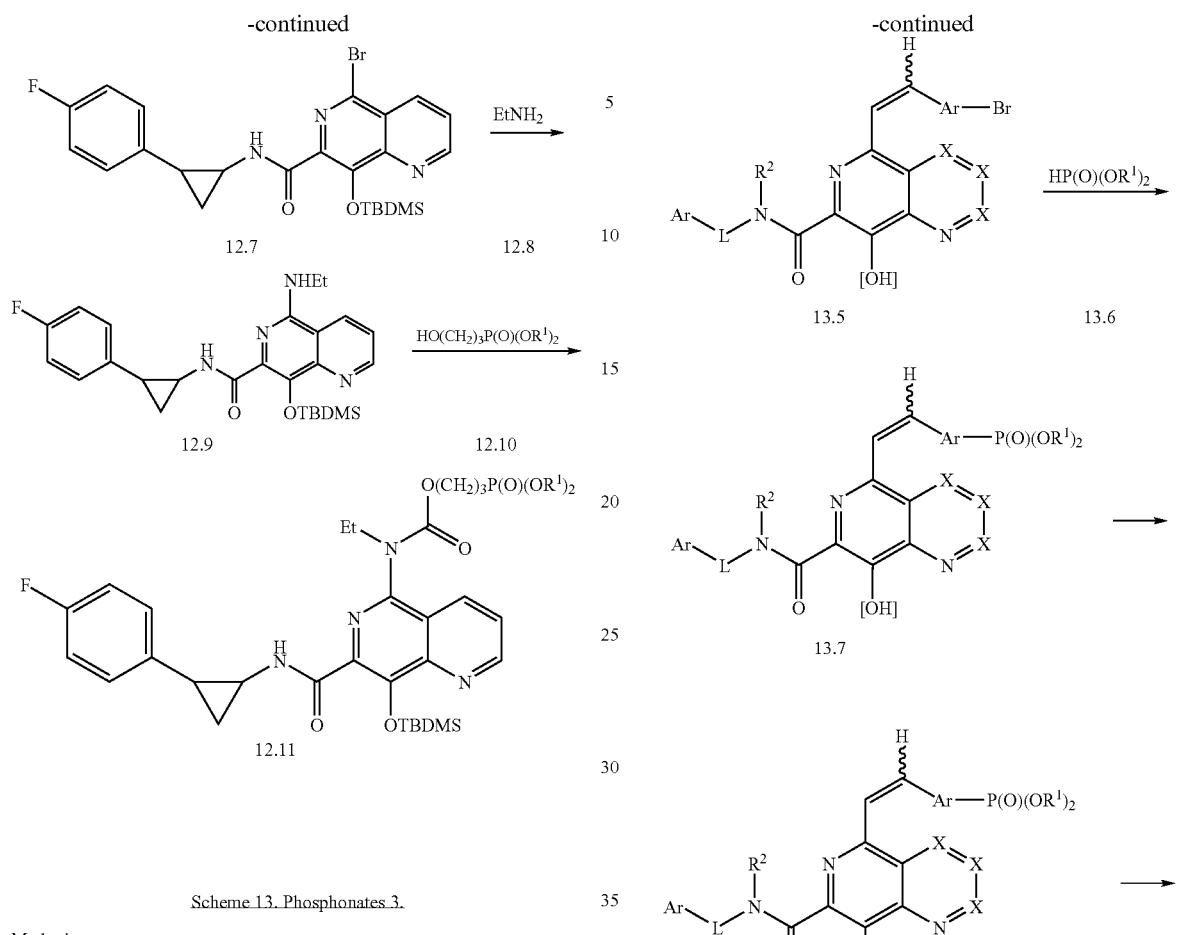
Scheme 13. Phosphonates 3.
Method
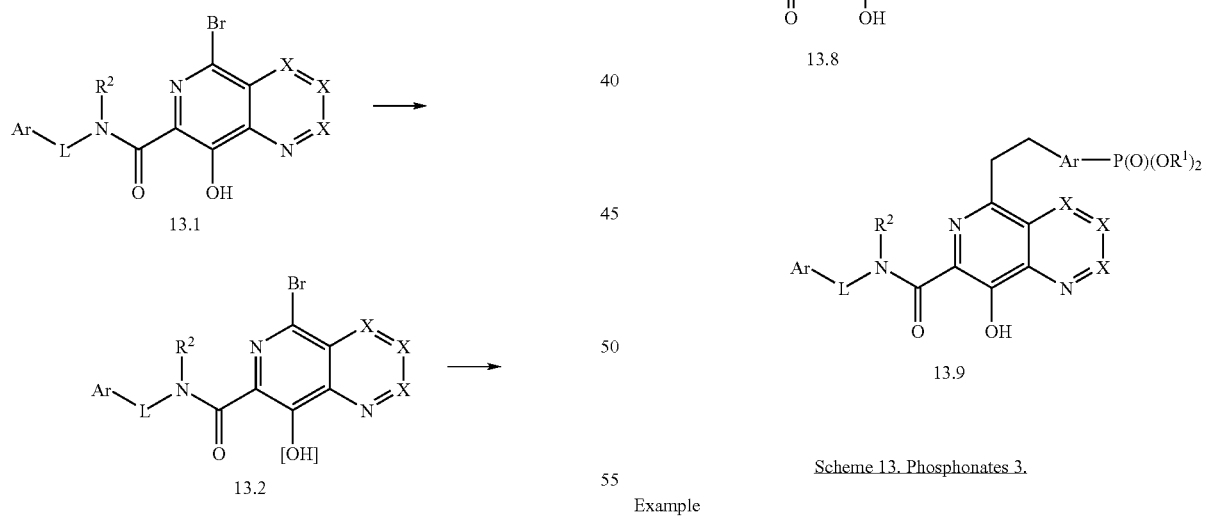
Scheme 13. Phosphonates 3.
Example
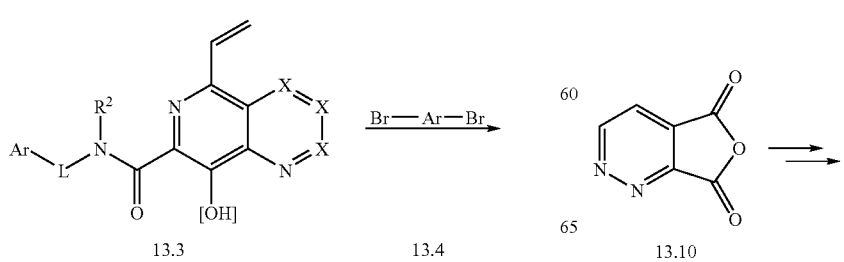

-continued
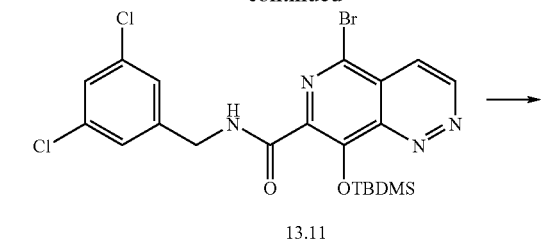
13.11
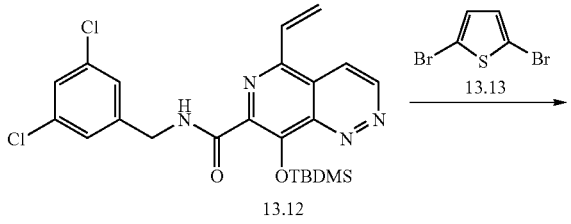
13.12
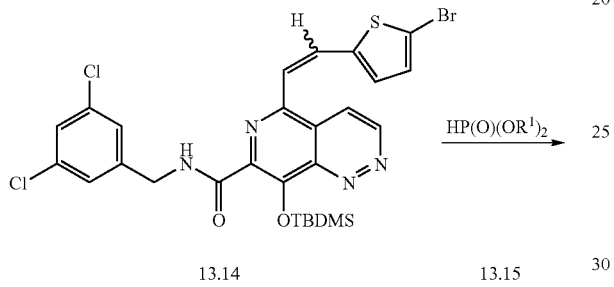
13.14    13.15
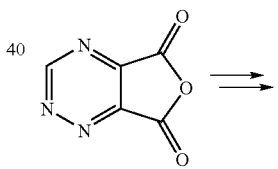
13.16
13.17
13.18
Scheme 14. Phosphonates 3.
Method
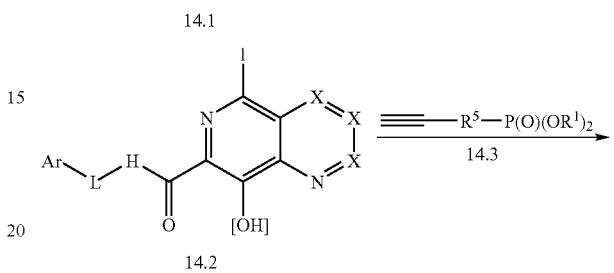
14.1
14.2
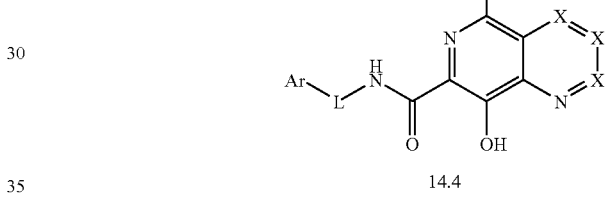
14.4
Example
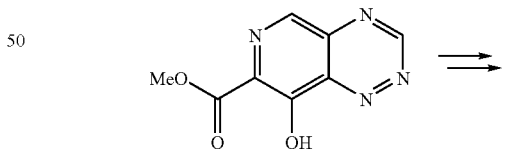
14.5
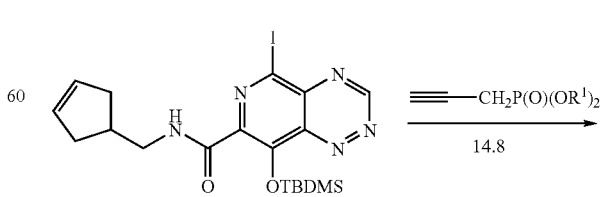
14.6
14.7

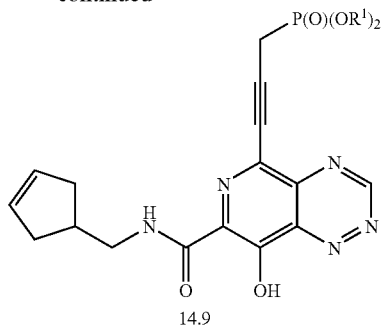

14.9

Scheme 15. Phosphonates 3.

Method

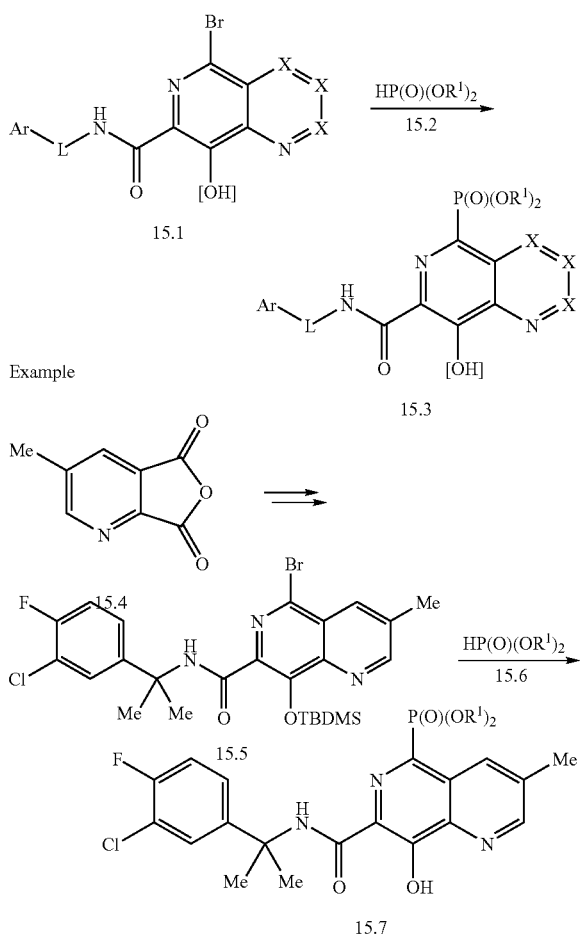

Preparation of the Intermediate Phosphonate Esters 4.

Schemes 16-18 illustrate methods for the preparation of the phosphonate esters 4.

Scheme 16 depicts the preparation of phosphonate esters 4 in which the phosphonate group is attached by means of a variable carbon chain. In this procedure, the phosphonate 16.1, in which the phenolic hydroxyl group is protected, prepared as described in Scheme 11, is reacted with the sulfonyl chloride 16.2 or the sulfonic acid 16.3 to afford after deprotection the sulfonamide 16.4. The reaction between an amine and a sulfonyl chloride, to produce the sulfonamide, is conducted at ambient temperature in an inert solvent such as dichloromethane, in the presence of a tertiary base such as triethylamine. The reaction between a sulfonic acid and an amine to afford a sulfonamide is conducted in a polar solvent such as dimethylformamide, in the presence of a carbodiimide such as dicyclohexyl carbodiimide, for example as described in Syn., 1976, 339.

For example, the protected amine phosphonate 16.5, prepared by the methods described above, is reacted in dichloromethane solution with one molar equivalent of ethyl sulfonyl chloride 16.6 and triethylamine, to produce, after desilylation, the sulfonamide 16.7.

Using the above procedures, but employing, in place of the amine phosphonate 16.5, different phosphonates 16.1, and/or different sulfonyl chlorides 16.2 or sulfonic acids 16.3, the corresponding products 16.4 are obtained.

Scheme 17 depicts an alternative method for the preparation of phosphonate esters 4 in which the phosphonate group is attached by means of a variable carbon chain. In this procedure, a dialkyl amino-substituted phosphonate 17.1, in which the group $R^5$ is as defined in Scheme 4, is reacted with a sulfonyl chloride 17.2 or sulfonic acid 17.3, as described in Scheme 16, to yield the sulfonamide 17.4. The product is then reacted with a bromoamide 17.5, to prepare the displacement product 17.6. The displacement reaction is performed in a basic solvent such as pyridine or quinoline, at from about 80° to reflux temperature, optionally in the presence of a promoter such as copper oxide, as described in WO 0230930 A2 Example 154.

For example, a dialkyl 4-aminophenyl phosphonate 17.7 (Epsilon) is reacted in dichloromethane solution with one molar equivalent of methanesulfonyl chloride 17.8 and triethylamine, to give the sulfonamide 17.9. The product is then reacted in pyridine solution at reflux temperature with 5-bromo-8-hydroxy-pyrido[3,4-b]pyrazine-7-carboxylic acid 4-fluoro-benzylamide 17.10, prepared by the methods described above, and copper oxide, to yield the sulfonamide 17.11.

Using the above procedures, but employing, in place of the amine phosphonate 17.7, different phosphonates 17.1, and/or different sulfonyl chlorides 17.2 or sulfonic acids 17.3, the corresponding products 17.6 are obtained.

Scheme 18 depicts an alternative method for the preparation of phosphonate esters 4 in which the phosphonate group is attached by means of a variable carbon chain. In this procedure, a phenol-protected 5-bromo substituted amide 18.1 is reacted, as described in Scheme 17, with a sulfonamide 18.2, to give the displacement product 18.3. The product is then reacted with a dialkyl bromoalkyl phosphonate 18.4 to afford, after deprotection of the phenol, the alkylated compound 18.5. The alkylation reaction is performed in a polar aprotic solvent such as dimethylformamide or DMPU, at from ambient temperature to about 100°, in the presence of a base such as sodium hydride or lithium hexamethyl disilylazide.

For example, benzoic acid 5-bromo-7-[1-(3-methoxy-phenyl)-1-methyl-ethylcarbamoyl]-[1,6]naphthyridin-8-yl ester 18.6, prepared by the methods described above, is reacted in pyridine solution at reflux temperature with one molar equivalent of propanesulfonamide 18.7 and copper oxide, to afford the sulfonamide 18.8. The product is then reacted in dimethylformamide solution with one molar equivalent of a dialkyl bromoethyl phosphonate 18.9 (Aldrich) and lithium hexamethyl disilylazide, to give after debenzoylation, the sulfonamide phosphonate 18.10. The benzoyl protecting group is removed, for example, by reaction with 1% methanolic sodium hydroxide at ambient temperature, as described in Tet., 26, 803, 1970.

Using the above procedures, but employing, in place of the bromo compound 18.6, different bromo compounds 18.1, and/or different sulfonamides 18.2, and/or different phosphonates 18.4, the corresponding products 18.5 are obtained.
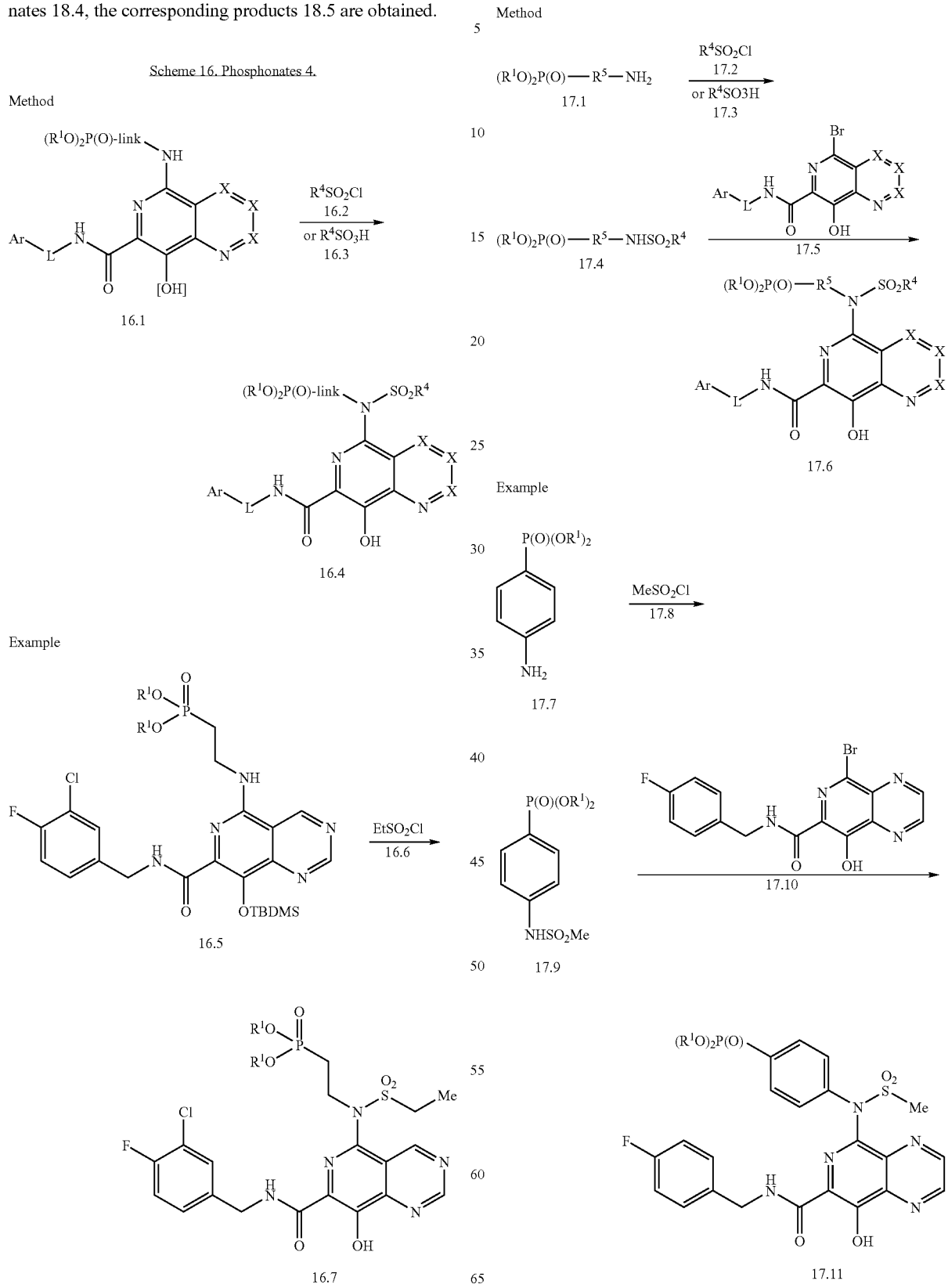

Scheme 18. Phosphonates 4.

Method

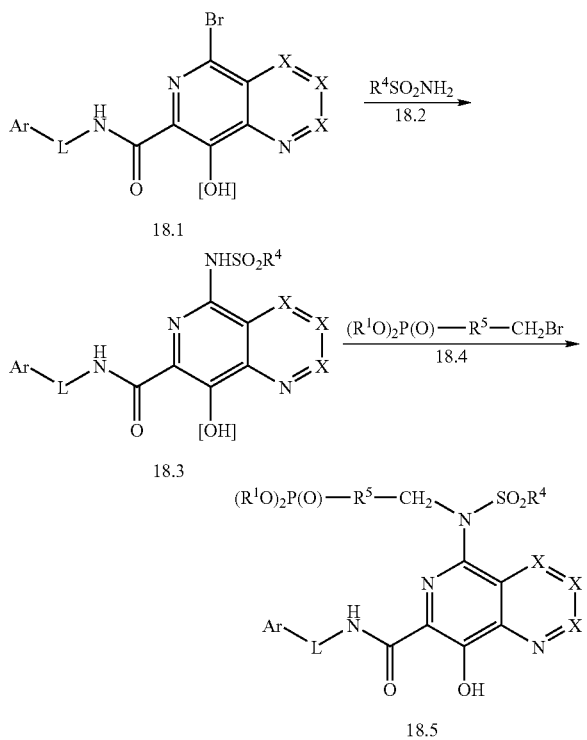

Example

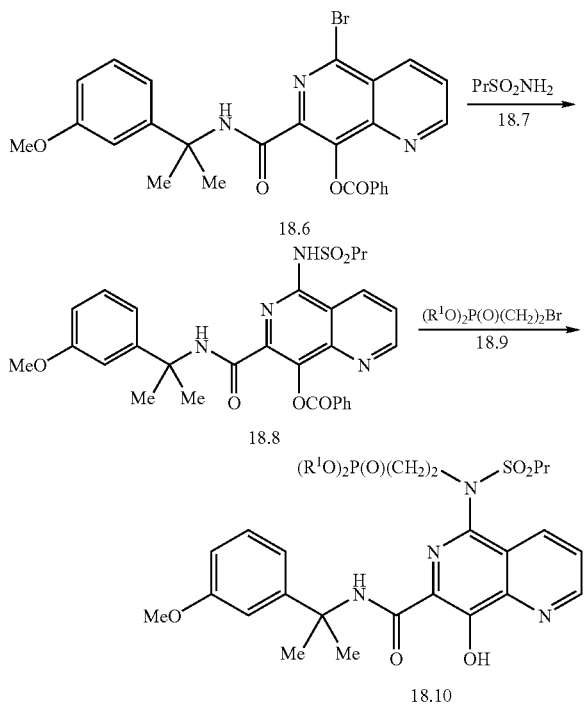

Preparation of the Intermediate Phosphonate Esters 5.

Schemes 19-21 illustrate methods for the preparation of the phosphonate esters 5.

Scheme 19 illustrates the preparation of phosphonates 5 in which the phosphonate group is attached by means of a variable carbon chain. In this procedure, a bromo-substituted sulfonic acid 19.1 is subjected to an Arbuzov reaction with a trialkyl phosphite 19.2 to give the phosphonate 19.3. The Arbuzov reaction is performed by heating the bromo compound with an excess of the trialkyl phosphite at from 100° to 150°, as described in Handb. Organophosphorus Chem., 1992, 115-72. The resulting phosphonate is then reacted with an amine 19.4, either directly, in the presence of a carbodiimide, or by initial conversion to the sulfonyl chloride, as described in Scheme 16, to afford, after deprotection of the phenolic hydroxyl group, the sulfonamide 19.5.

For example, 3-bromopropanesulfonic acid 19.6 (Sigma) is heated at 130° with a trialkyl phosphite 19.7 to give the phosphonate 19.8. The product is then reacted in DMPU solution with 8-(tert-butyl-dimethyl-silanyloxy)-5-ethylamino-[1,6]naphthyridine-7-carboxylic acid 4-fluoro-benzylamide 19.9, prepared by the methods described above, in the presence of dicyclohexylcarbodiimide, to give, after desilylation, by reaction with tetrabutylammonium fluoride in tetrahydrofuran, the sulfonamide 19.10.

Using the above procedures, but employing, in place of the bromo sulfonic acid 19.6, different bromosulfonic acids 19.1, and/or different amines 19.4, the corresponding products 19.5 are obtained.

Scheme 20 illustrates the preparation of phosphonates 5 in which the phosphonate group is attached by means of a saturated or unsaturated carbon chain and an aromatic or heteroaromatic group. In this procedure, a vinyl-substituted sulfonic acid 20.1 is coupled, in a palladium-catalyzed Heck reaction, as described in Scheme 4, with a dibromoaromatic or heteroaromatic compound 20.2, to yield the sulfonic acid 20.3. The product is then coupled, in the presence of a palladium catalyst, as described in Scheme 3, with a dialkyl phosphite $HP(O)(OR^1)_2$, to give the phosphonate 20.4. The latter compound is then reacted, as described above, with an amine 20.5, either directly, in the presence of a carbodiimide, or by initial conversion to the sulfonyl chloride, as described in Scheme 16, to afford, after deprotection of the phenolic hydroxyl group, the sulfonamide 20.6. Optionally, the double bond is reduced, either catalytically or chemically, as described in Scheme 4, to afford the saturated analog 20.7.

For example, vinylsulfonic acid 20.8 (Sigma) is coupled, in dioxan solution, in the presence of tetrakis(triphenylphosphine)palladium (0) and potassium carbonate, with 2,5-dibromothiophene 20.9, to form the coupled product 20.10. The product is then reacted in toluene solution at 100° with a dialkyl phosphite 20.11, triethylamine and a catalytic amount of tetrakis(triphenylphosphine)palladium (0), to produce the phosphonate 20.12. This material is then reacted, in dimethylformamide solution at ambient temperature, as described above, with 8-(tert-butyl-dimethyl-silanyloxy)-5-cyclopropylamino-pyrido[4,3-d]pyrimidine-7-carboxylic acid 4-fluoro-benzylamide 20.13, prepared by the methods described above, in the presence of dicyclohexylcarbodiimide, to give, after desilylation, using tetrabutylammonium fluoride, the sulfonamide 20.14. Hydrogenation of the double bond, for example using 5% palladium on carbon as catalyst, then yields the saturated analog 20.15.

Using the above procedures, but employing, in place of the sulfonic acid 20.8, different sulfonic acids 20.1, and/or different dibromoaromatic compounds 20.2, and/or different amines 20.5, the corresponding products 20.6 and 20.7 are obtained.

Scheme 21 illustrates the preparation of phosphonates 5 in which the phosphonate group is attached by means of a variable carbon chain. In this procedure, an aliphatic bromo-substituted sulfonic acid 21.1 is subjected to an Arbuzov reaction with a trialkyl phosphite, as described in Scheme 19, to give the phosphonate 21.2. Alternatively, an aryl bromosulfonic acid 21.1 is coupled, as described in Scheme 3, with a dialkyl phosphite, to give the phosphonate 21.2. The product is then reacted with an amine 21.3 to afford the sulfonamide 21.4. The latter compound is then reacted, as described in Scheme 17, with a bromoamide 21.5, to give the displacement product 21.6.

For example, 4-bromobenzenesulfonic acid 21.7 is reacted, as described in Scheme 20, with a dialkyl phosphite to form the phosphonate 21.8. The product is then reacted with phosphoryl chloride to afford the corresponding sulfonyl chloride, and the latter compound is reacted, in dichloromethane solution, in the presence of triethylamine, with 2-methoxyethylamine 21.9, to yield the sulfonamide 21.10. This material is then reacted, in pyridine solution at reflux temperature, with 5-bromo-8-hydroxy-[1,6]naphthyridine-7-carboxylic acid 4-fluoro-benzylamide 21.11, prepared by the methods described above, and copper oxide, to give the sulfonamide 21.12.

Using the above procedures, but employing, in place of the sulfonic acid 21.7, different sulfonic acids 21.1, and/or different amines 21.3, and/or different bromo compounds 21.5, the corresponding products 21.6 are obtained.

Preparation of the Intermediate Phosphonate Esters 6.

Schemes 22-24 illustrate methods for the preparation of the phosphonate esters 6.

Scheme 22 depicts the preparation of phosphonates 6 in which the phosphonate group is attached by means of an amide linkage and a variable carbon chain. In this procedure, a cyclic sulfonamide 22.1, incorporating a secondary amine, is coupled, as described in Scheme 5, with a dialkyl carboxy-substituted phosphonate 22.2 to produce the amide 22.3. The product is then reacted with a bromoamide 22.4 to afford the displacement product 22.5.

Alternatively, the cyclic sulfonamide 22.1 is protected to give the analog 22.6. Sulfonamides are protected, for example, by conversion into the N-acyloxymethyl derivatives, such as the pivalyloxymethyl derivative or the benzoyloxymethyl derivative, by reaction with the corresponding acyloxymethyl chloride in the presence of dimethylaminopyridine, as described in Bioorg. Med. Chem. Lett., 1995, 5, 937, or by conversion into the carbamate derivative, for example the tert. butyl carbamate, by reaction with an alkyl, aryl or aralkyl chloroformate, in the presence of a base such as triethylamine, as described in Tet. Lett., 1994, 35, 379. The protected sulfonamide is reacted with a dialkyl bromoalkyl phosphonate 22.7 to form the alkylated product 22.8. The alkylation reaction is effected as described in Scheme 8. The product is then deprotected to yield the sulfonamide 22.9. Deprotection of pivalyloxymethyl amides is effected by treatment with trifluoroacetic acid; deprotection of benzyloxymethyl amides is effected by catalytic hydrogenation, as described in Protective Groups in Organic Synthesis, by T. W. Greene and P. G. M. Wuts, Wiley, Second Edition 1990, p. 398. Sulfonamide carbamates, for example the tert. butyl carbamate, are deprotected by treatment with trifluoroacetic acid. The sulfonamide 22.9 is then reacted with the bromoamide 22.10 to give the displacement product 22.11.

For example, [1,2,5]thiadiazepane 1,1-dioxide 22.11A (WO 0230930 A2 p. 321) is reacted in dioxan solution with equimolar amounts of a dialkyl 3-carboxypropyl phosphonate 23.12, (Epsilon) and dicyclohexyl carbodiimide, to produce the amide 22.13. This material is reacted in pyridine solution at reflux temperature with 5-bromo-8-hydroxy-[1,6]naphthyridine-7-carboxylic acid 4-fluoro-benzylamide 22.14, prepared by the methods described above, and copper oxide, to afford the displacement product 22.15.

As a further example, the sulfonamide 22.11A is reacted in dichloromethane with one molar equivalent of t-Boc anhydride, triethylamine and dimethylaminopyridine, to give 1,1-dioxo-[1,2,5]thiadiazepane-2-carboxylic acid tert-butyl ester 22.16. The product is then reacted at ambient temperature in dimethylformamide solution with a dialkyl 4-bromomethyl benzyl phosphonate 22.17, (Tet., 1998, 54, 9341) and potassium carbonate, to yield the alkylation product 22.18. The BOC group is removed by treatment with trifluoroacetic acid to give the sulfonamide 22.19, and this material is reacted, as described above, with 5-bromo-8-hydroxy-[1,6]naphthyridine-7-carboxylic acid 3-fluoro-benzylamide 22.20, prepared by the methods described above, to afford the displacement product 22.21.

Using the above procedures, but employing, in place of the sulfonamide 22.11A, different sulfonamides 22.1, and/or different carboxylic acids 22.2 or alkyl bromides 22.7, and/or different bromides 22.4, the corresponding products 22.5 and 22.11 are obtained.

Scheme 19. Phosphonates 5.

Method

BrCH$_2$—R$^5$—SO$_3$H $\xrightarrow{\text{P(OR}^1)_3}$
19.1      19.2

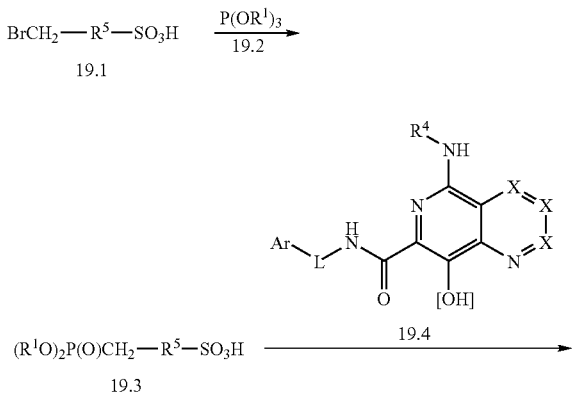

19.4

(R$^1$O)$_2$P(O)CH$_2$—R$^5$—SO$_3$H
19.3

19.5

Example

Br(CH$_2$)$_3$SO$_3$H $\xrightarrow{\text{P(OR}^1)_3}$
19.6      19.7

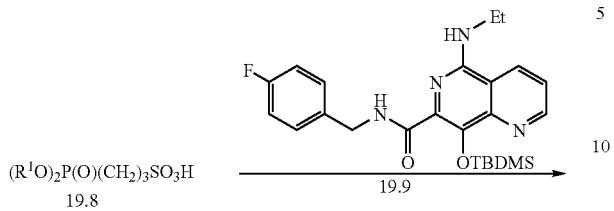
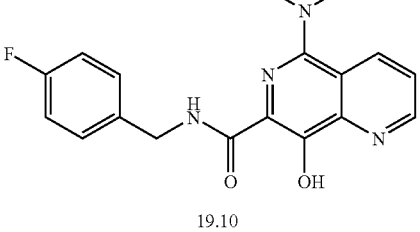
Scheme 20. Phosphonates 5.
Method
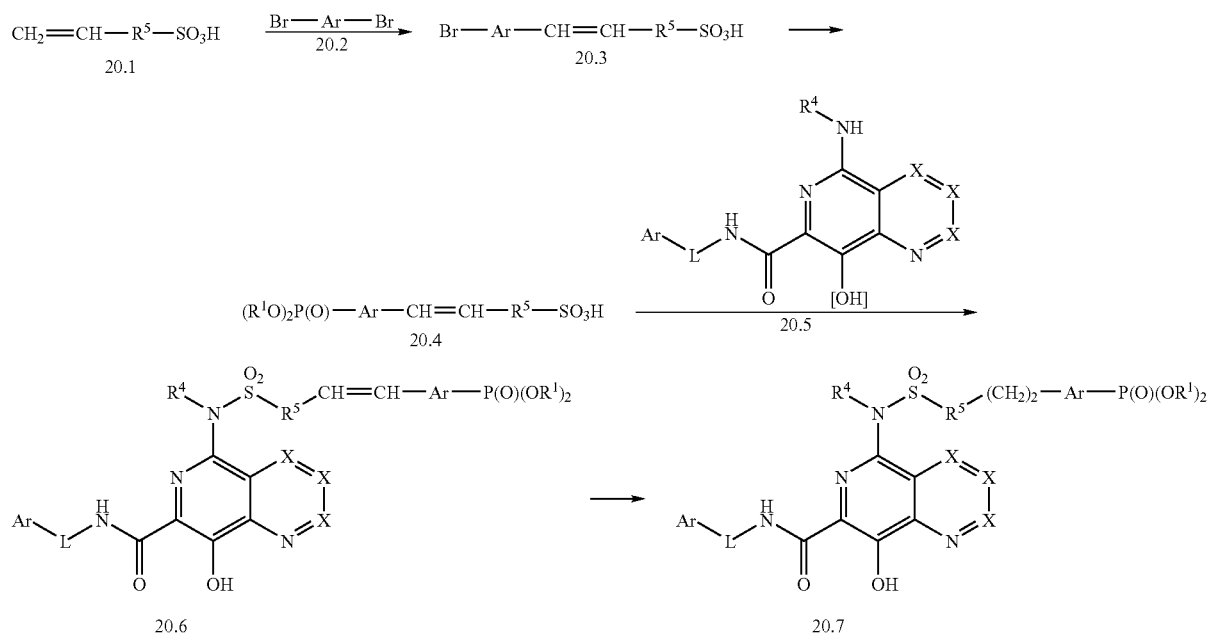
Example
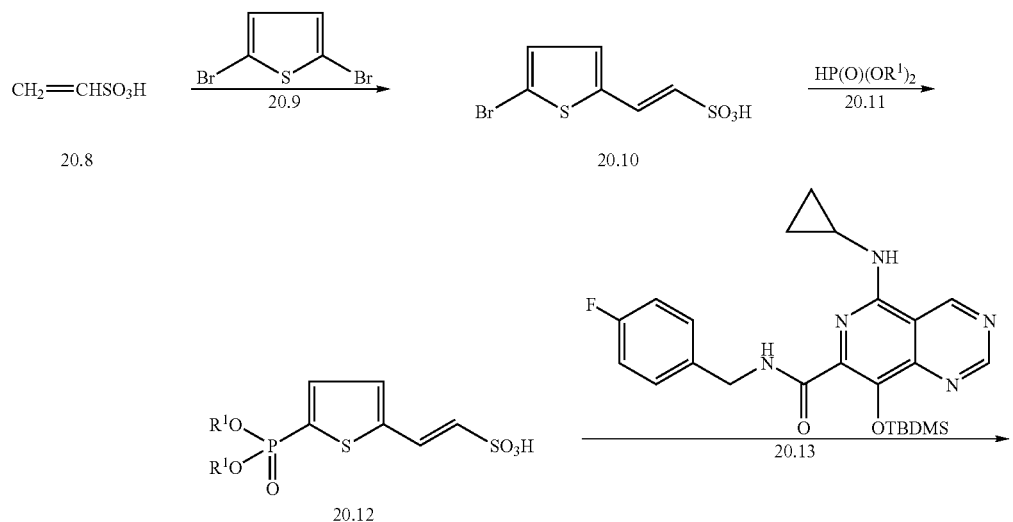

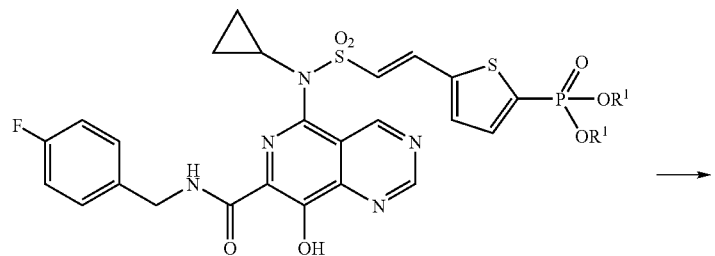
20.14
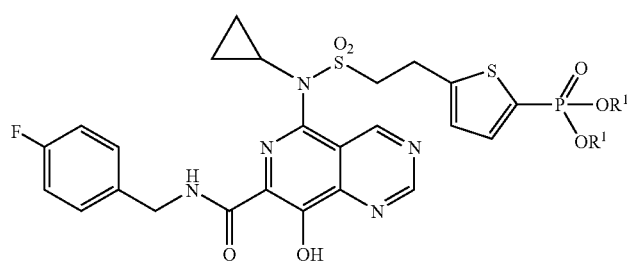
20.15
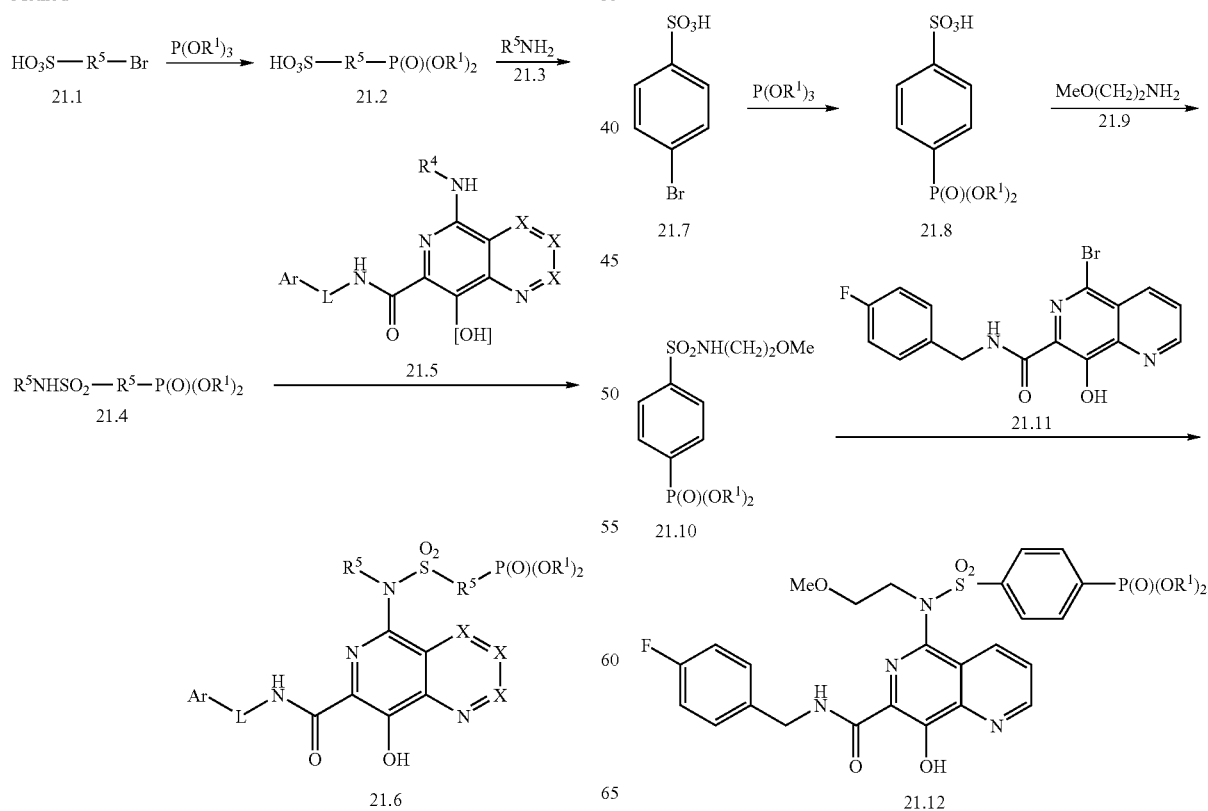

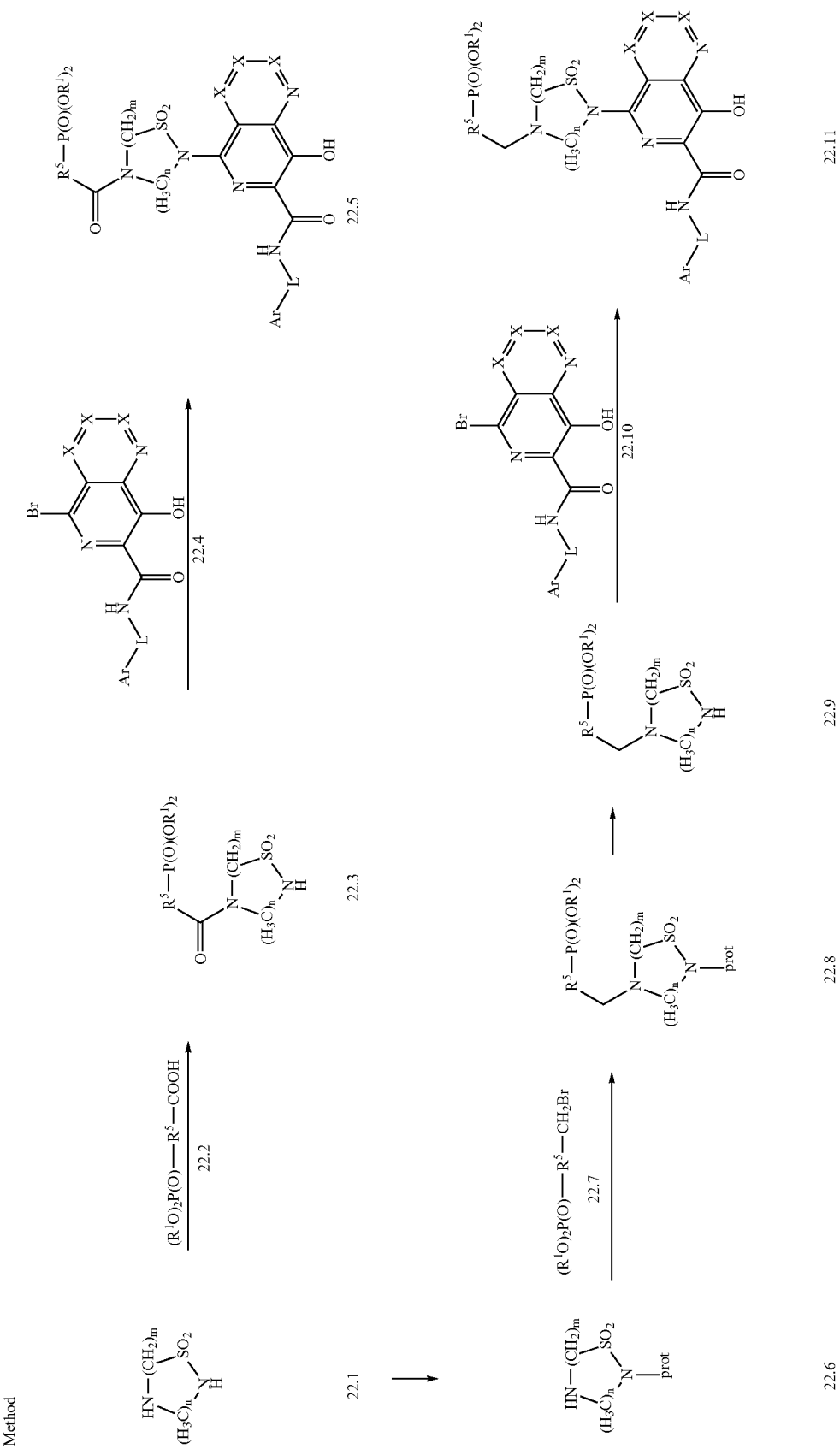

Scheme 22. Phosphonates 5.

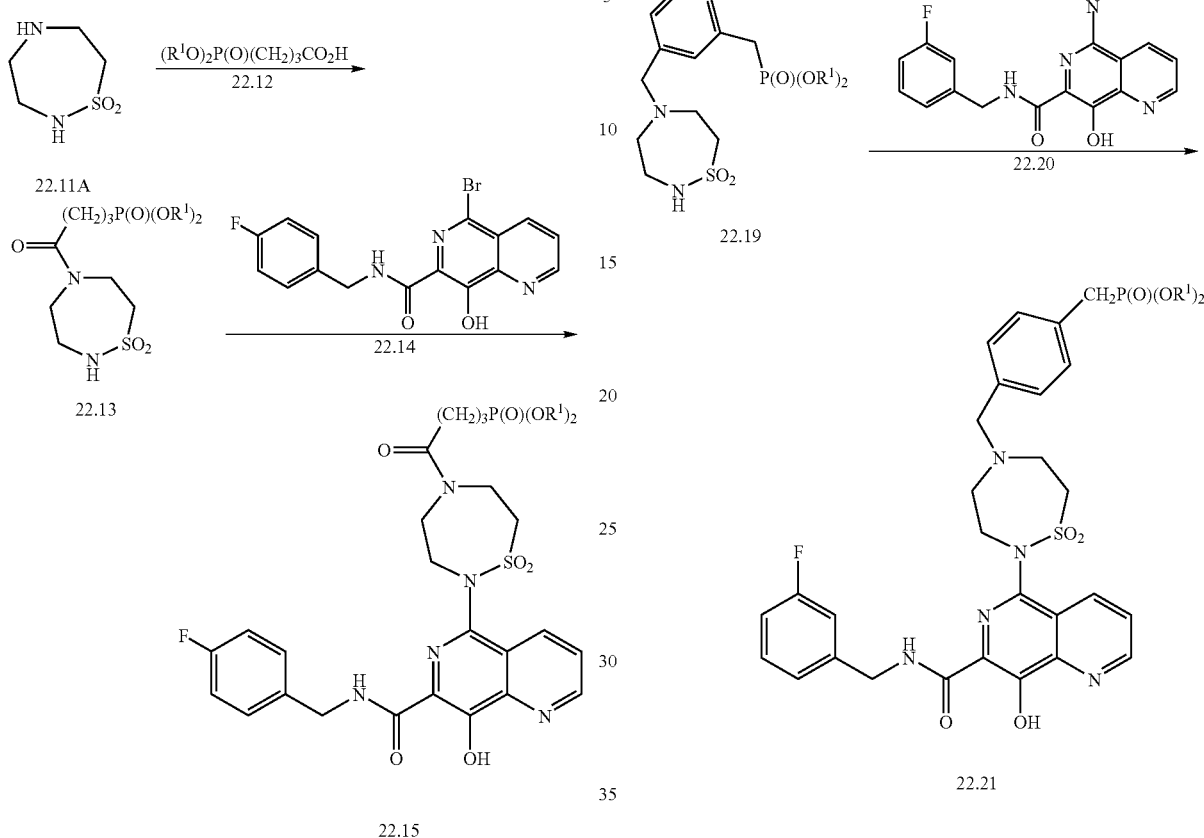

Example 2

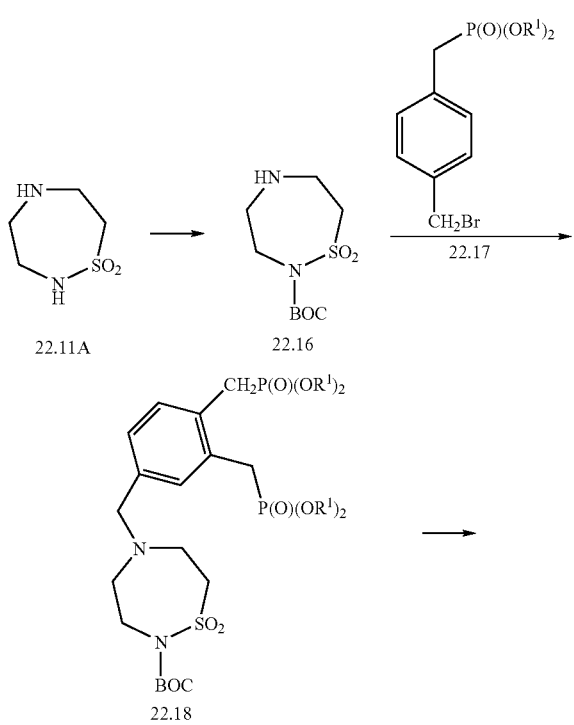

Scheme 23 depicts the preparation of phosphonates 6 in which the phosphonate group is attached by means of an aryl or heteroaryl group. In this procedure, a bromoaryl-substituted cyclic sulfonamide, prepared as described in J. Org. Chem., 1991, 56, 3549, from the corresponding bromoaryl or bromoheteroaryl acetic acid and a vinyl sulfonic ester, is coupled, as described in Scheme 3, with a dialkyl phosphite to afford the phosphonate 23.2. The product is then reacted, as described above, with a bromoamide 23.3 to yield the displacement product 23.4.

For example, 4-(4-bromo-phenyl)-[1,2]thiazinane 1,1-dioxide 23.5 (J. Org. Chem., 1991, 56, 3549) is reacted in dimethylformamide solution with a dialkyl phosphite 23.6 and tetrakis(triphenylphosphine)palladium(0), to give the phosphonate 23.7. The product is then reacted with 5-bromo-8-hydroxy-[1,6]naphthyridine-7-carboxylic acid (5-fluoro-indan-1-yl)-amide 23.8, prepared by the methods described above, to give the phosphonate 23.9.

Using the above procedures, but employing, in place of the sulfonamide 23.5, different sulfonamides 23.1, and/or different bromo compounds 23.3, the corresponding products 23.4 are obtained.

Scheme 24 depicts the preparation of phosphonates 6 in which the phosphonate group is attached by means of an amide linkage. In this procedure, a carboxy-substituted cyclic sulfonamide 24.1 is coupled with an amino-substituted dialkyl phosphonate 24.2, as described in Scheme 5, to give the amide 24.3. The product is then reacted with the bromoamide 24.4 to afford the displacement product 24.5.

For example, 1,1-dioxo-[1,2]thiazinane-3-carboxylic acid 24.6 (Izvest. Akad. Nauk. SSSR Ser. Khim., 1964, 9, 1615) is reacted in dimethylformamide solution with equimolar amounts of an amino-substituted butyl phosphonate 24.7 (Acros) and dicyclohexylcarbodiimide, to afford the amide 24.8. The latter compound is then condensed with 5-bromo-8-hydroxy-[1,6]naphthyridine-7-carboxylic acid [1-(3-chloro-4-fluoro-phenyl)-ethyl]-amide 24.9, prepared by the methods described above, to give the product 24.10.

Using the above procedures, but employing, in place of the sulfonamide 24.6, different sulfonamides 24.1, and/or different bromo compounds 24.4, the corresponding products 24.5 are obtained.

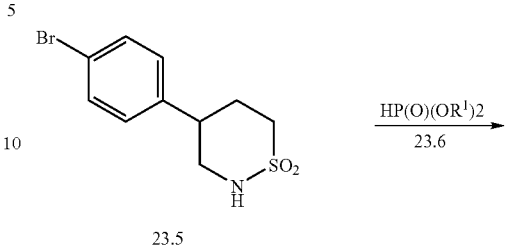

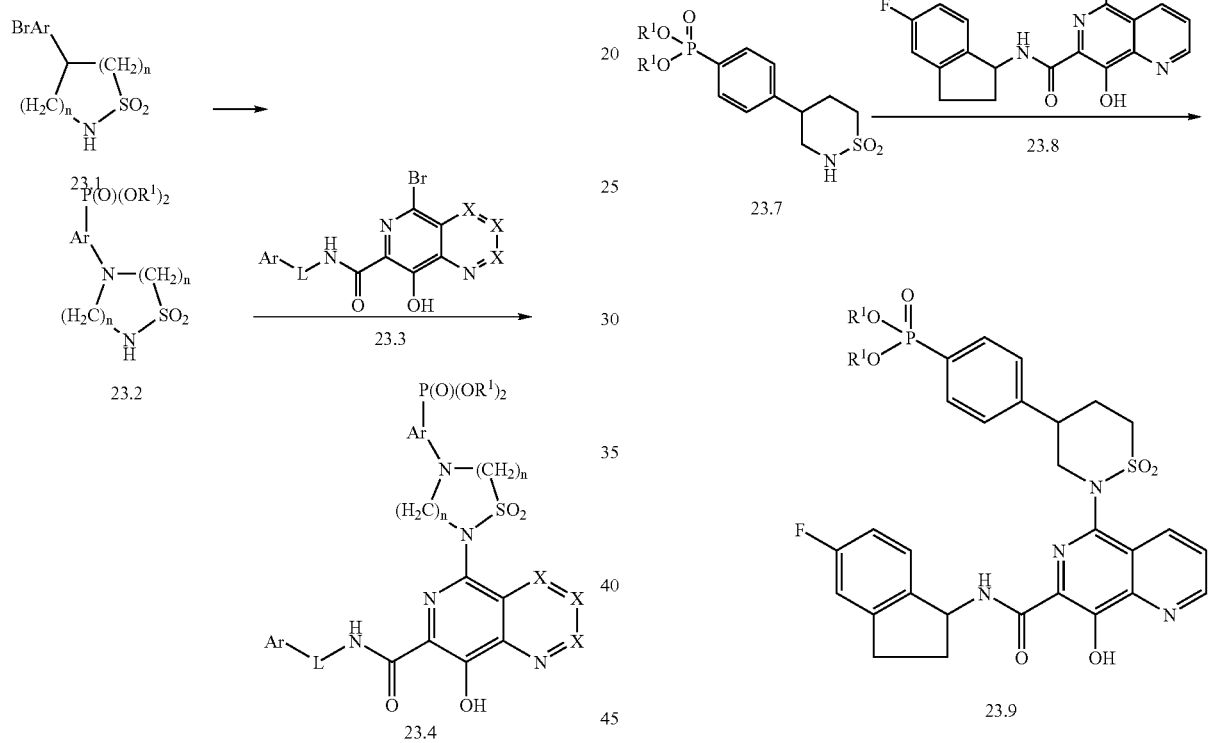

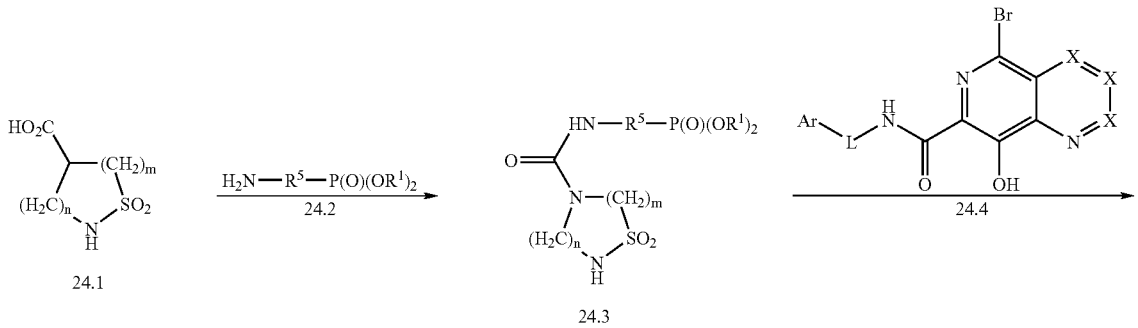

-continued

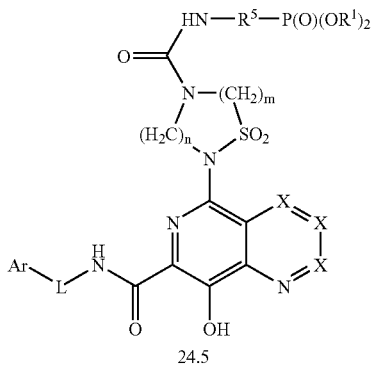

Example

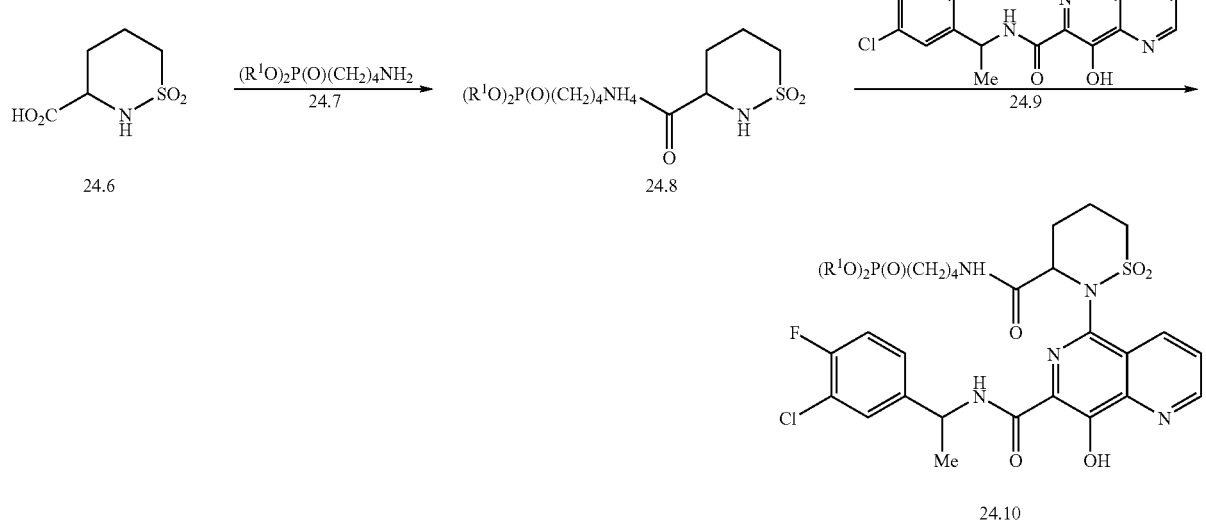

Preparation of the Intermediate Phosphonate Esters 7.

Schemes 25-27 illustrate methods for the preparation of the phosphonate esters 7.

Scheme 25 illustrates the preparation of phosphonate esters 7 in which the phosphonate is attached by means of a carbon link or a variable carbon chain incorporating a heteroatom. In this procedure, a methyl-substituted cyclic anhydride 25.1 is converted, as described in Schemes 1 and 2, into the bicyclic amide 25.2, in which the phenolic hydroxyl group is protected. The compound is reacted with a free radical brominating agent such as N-bromosuccinimide to prepare the bromomethyl derivative 25.3. The benzylic bromination reaction is performed at reflux temperature in an inert organic solvent such as hexachloroethane or ethyl acetate, optionally in the presence of an initiator such as dibenzoyl peroxide. The bromomethyl compound 25.3 is then reacted with a trialkyl phosphite in an Arbuzov reaction, as described in Scheme 19, to give, after deprotection of the phenolic hydroxyl group, the phosphonate 25.4.

Alternatively, the benzylic bromide 25.3 is reacted with a dialkyl hydroxy, mercapto or amino-substituted phosphonate 25.5, to afford, after deprotection of the phenolic hydroxyl group, the displacement product 25.6. The displacement reaction is effected at from ambient temperature to about 100°, in a polar organic solvent such as dimethylformamide or DMPU, in the presence of a suitable base such as sodium hydride or lithium hexamethyldisilazide, for instances in which Y is O, or cesium carbonate or triethylamine for instances in which Y is S or N.

For example, 4-methyl-furo[3,4-b]pyridine-5,7-dione 25.7, (J. Org. Chem., 1961, 26, 808) is converted, using the methods described above, into 5-(1,1-dioxo-isothiazolidin-2-yl)-4-methyl-8-triisopropylsilanyloxy-[1,6]naphthyridine-7-carboxylic acid 4-fluoro-benzylamide 25.8. The compound is then reacted with one molar equivalent of N-bromosuccinimide in ethyl acetate at reflux, to afford the bromomethyl analog 25.9. This product is reacted with a dialkyl hydroxyethyl phosphonate 25.11 (Epsilon) and sodium hydride in dimethylformamide at 80°, to yield, after desilylation, the phosphonate 25.12. Alternatively, the bromomethyl compound 25.9 is reacted at 120° with a trialkyl phosphite, to obtain, after desilylation, the phosphonate 25.10.

Using the above procedures, but employing, in place of the anhydride 25.7, different anhydrides 25.1, and/or different phosphonates 25.5, the corresponding products 25.4 and 25.6 are obtained.

Scheme 26 illustrates the preparation of phosphonate esters 7 in which the phosphonate is attached by means of an aminomethyl linkage. In this procedure, a bromomethyl-substituted bicyclic amide 25.3, prepared as described in Scheme 25, is oxidized to the corresponding aldehyde 26.1. The oxidation of halomethyl compounds to aldehydes is described, for example, in Comprehensive Organic Transformations, by R. C. Larock, VCH, 1989, p. 599ff. The transformation is effected by treatment with dimethylsulfoxide and base, optionally in the presence of a silver salt, or by reaction with trimethylamine N-oxide or hexamethylene tetramine. The aldehyde 26.1 is then reacted with a dialkyl amino-substituted phosphonate 26.2 in a reductive amination reaction, as described in Scheme 9, to yield, after deprotection of the phenolic hydroxyl group, the aminomethyl product 26.3.

For example, 4-bromomethyl-5-(methanesulfonyl-methyl-amino)-8-triisopropylsilanyloxy-[1,6]naphthyridine-7-carboxylic acid 3,5-dichloro-benzylamide 26.4, prepared from the anhydride 25.7, using the methods described in Scheme 25, is reacted with dimethylsulfoxide and 2,4,6-collidine at 90°, as described in J. Org. Chem., 51, 1264, 1986, to afford the aldehyde 26.5. The product is then reacted with one molar equivalent of a dialkyl aminoethyl phosphonate 26.6 (Epsilon) and sodium triacetoxyborohydride to produce, after desilylation, the phosphonate 26.7.

Using the above procedures, but employing, in place of the bromomethyl compound 26.4, different bromomethyl compounds 25.3, and/or different phosphonates 26.2, the corresponding products 26.3 are obtained.

Scheme 27 illustrates the preparation of phosphonate esters 7 in which the phosphonate is attached by means of an amide linkage. In this procedure, an aldehyde 26.1 (Scheme 26) is oxidized to the corresponding carboxylic acid 27.1. The conversion of aldehydes to the corresponding carboxylic acids is described in Comprehensive Organic Transformations, by R. C. Larock, VCH, 1989, p. 838. The reaction is effected by the use of various oxidizing agents such as, for example, potassium permanganate, ruthenium tetroxide, silver oxide or sodium chlorite. The resultant carboxylic acid 27.1 is then coupled, as described in Scheme 5, with a dialkyl amino-substituted phosphonate 27.2, to yield, after deprotection of the phenolic hydroxyl group, the amide 27.3.

For example, the anhydride 27.4 is converted, as described above, and in Schemes 25 and 26, into N-[7-(2-cyclohex-3-enyl-ethylcarbamoyl)-4-formyl-8-triisopropylsilanyloxy-[1,6]naphthyridin-5-yl]-N,N',N'-trimethyl-oxalamide 27.5. The aldehyde is then reacted with silver oxide in aqueous sodium hydroxide, as described in Org. Syn. Coll. Vol. 4, 919, 1963, to afford the carboxylic acid 27.6. The latter compound is then reacted in dioxan solution at ambient temperature with equimolar amounts of a dialkyl aminomethyl phosphonate 27.7 (Interchim) and dicyclohexylcarbodiimide, to give, after desilylation, the amide phosphonate 27.8.

Using the above procedures, but employing, in place of the aldehyde 27.5, different aldehydes 26.1, and/or different phosphonates 27.2, the corresponding products 27.3 are obtained.

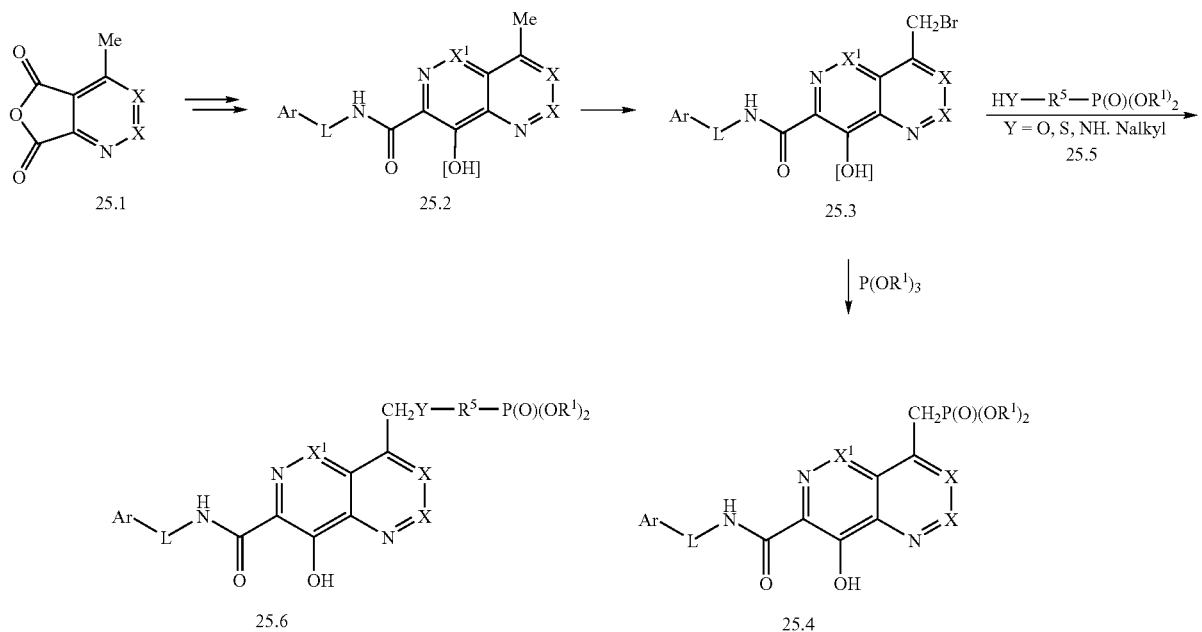

Scheme 25. Phosphonates 7.

Example
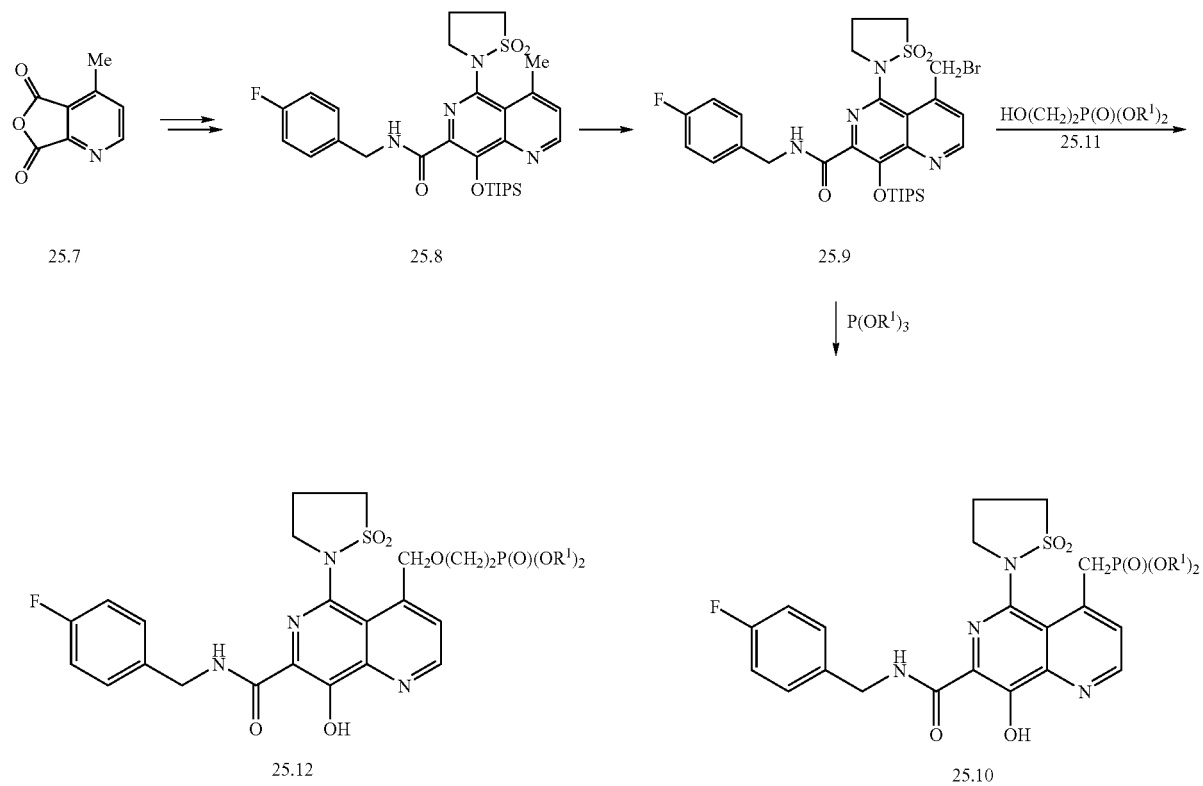
Scheme 26. Phosphonates 7.
Method
Example
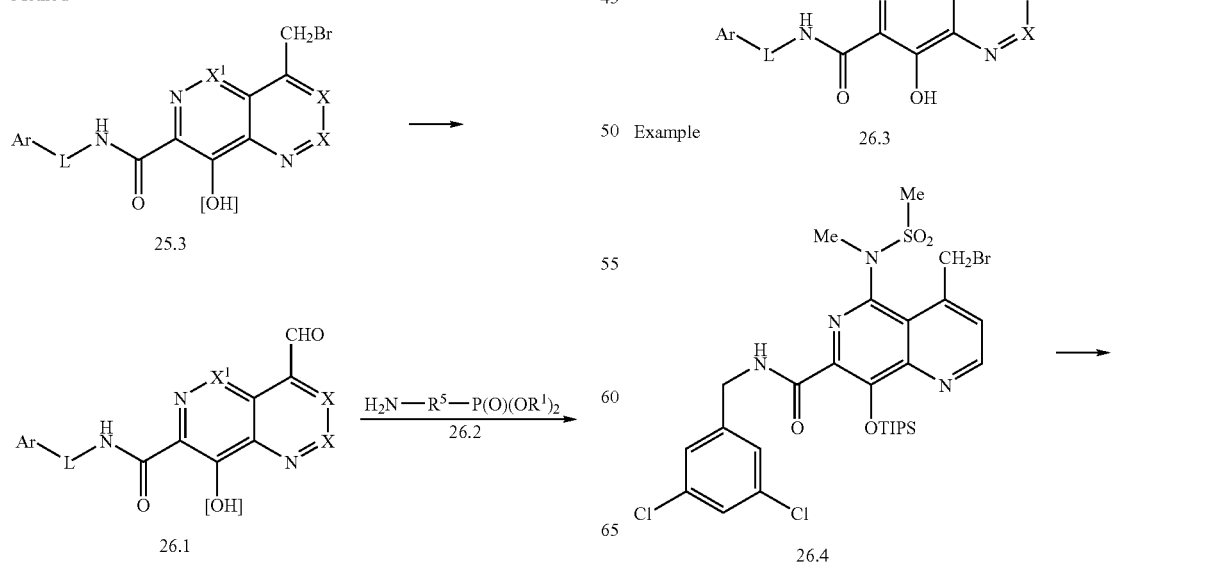

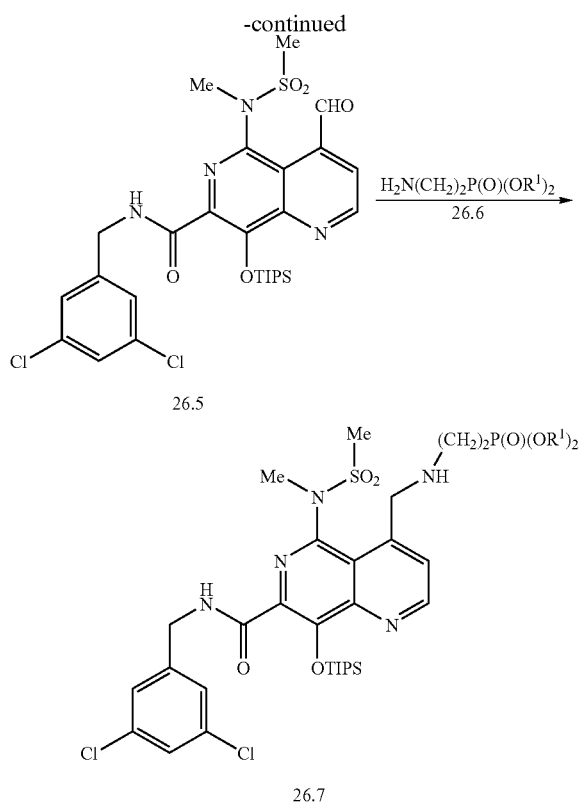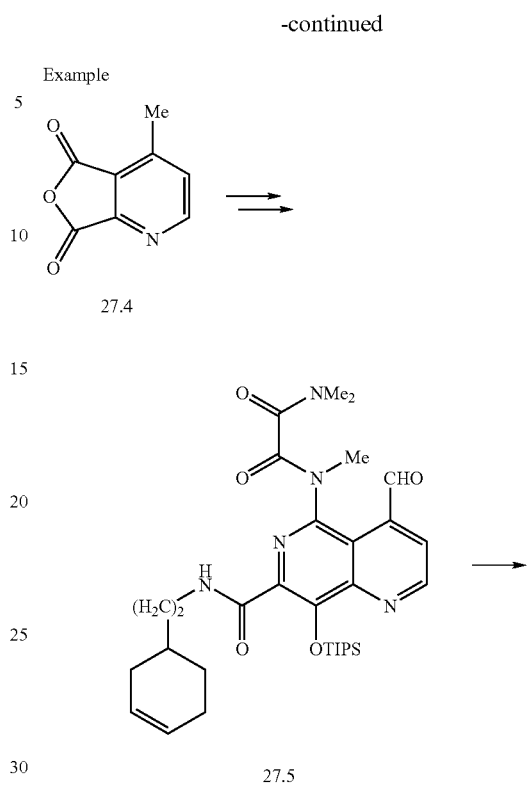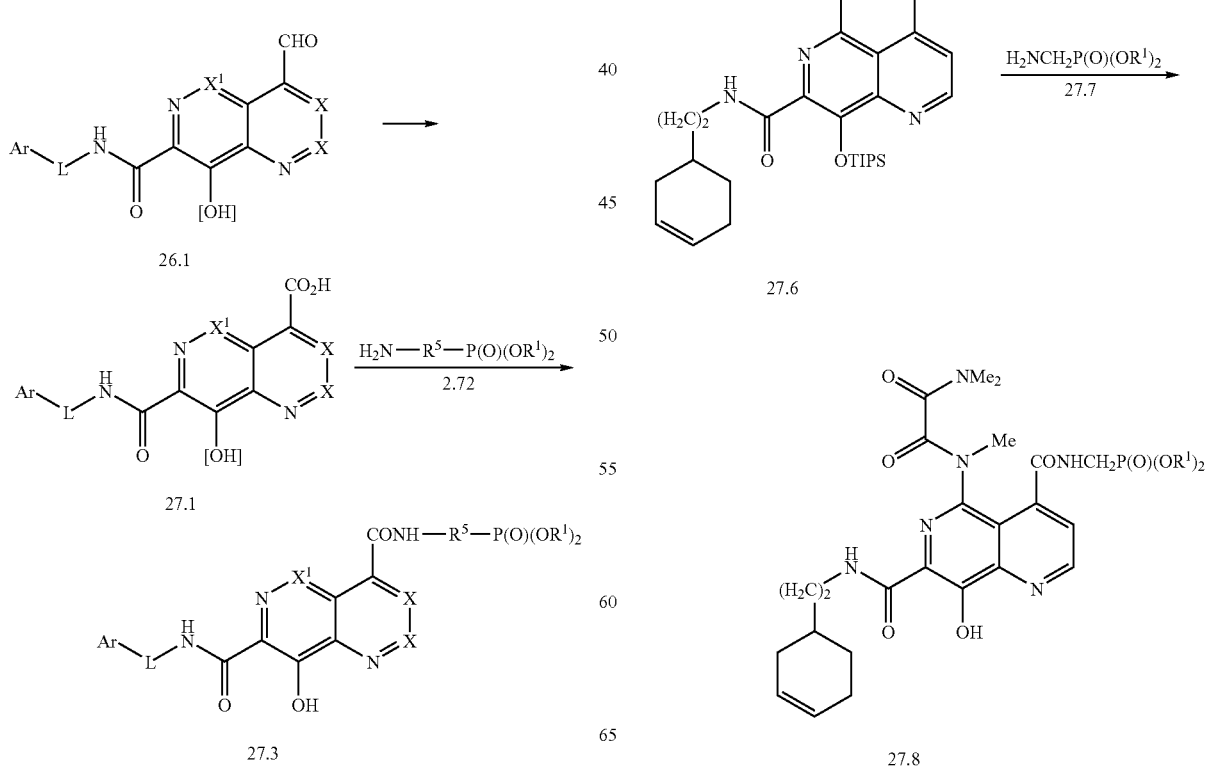

Preparation of the Intermediate Phosphonate Esters 8.

Schemes 28 and 29 illustrate methods for the preparation of the phosphonate esters 8.

Scheme 28 illustrates the preparation of phosphonate esters 8 in which the phosphonate is attached by means of a heteroatom O or S and a variable carbon link. In this procedure, the hydroxyl group of a hydroxy-substituted cyclic anhydride 28.1 is protected to afford the compound 28.2. The product is then converted, as described in Scheme 1, into the bicyclic ester 28.3, in which the phenol protecting groups are different. The original phenolic hydroxyl group is then deprotected to yield the phenol 28.4, and the product is subjected to a Mitsunobu reaction, as described in Scheme 7, with a dialkyl hydroxy or mercapto-substituted phosphonate 28.8, to produce the ether or thioether phosphonate 28.9. This material is then reacted, as described in Scheme 3, with the amine $ArLNR_2H$, to give after deprotection of the phenolic hydroxyl group, the amide 28.10.

Alternatively, the phenol 28.4 is reacted with a dialkyl bromoalkyl-substituted phosphonate 28.5, as described in Scheme 6, to yield the ether 28.6. The latter compound is then transformed, as described above, into the amide 28.7.

For example, 3-hydroxy-furo[3,4-b]pyridine-5,7-dione 28.11 (German Patent 4343923) is reacted in tetrahydrofuran solution at 50° with 4-methoxybenzyl bromide and potassium carbonate, to give the 4-methoxybenzyl ether 28.12. The product is then converted, as described above, into the silyl-protected bicyclic ester 28.13. The 4-methoxybenzyl ether is then removed by reaction with dichlorodicyanobenzoquinone in dichloromethane at ambient temperature, as described in Tet. Lett., 27,3651, 1986, to give the phenol 28.14. The product is then reacted in tetrahydrofuran solution with a dialkyl bromomethyl phosphonate 29.15 (Lancaster) and potassium carbonate, to produce the phosphonate 28.16; the product is then converted, by desilylation, amide formation, bromination, reaction with methylamine and carbamate formation, using the procedures described above, into the hydroxyamide 28.17.

Alternatively, the phenol 28.14 is reacted in tetrahydrofuran solution with one molar equivalent of a dialkyl 2-mercaptoethyl phosphonate 28.18 (Zh. Obschei. Khim., 1973, 43, 2364), diethylazodicarboxylate and triphenylphosphine, to prepare the thioether phosphonate 28.19. The product is then converted, as described above, into the amide 28.20.

Using the above procedures, but employing, in place of the anhydride 28.11, different anhydrides 28.1, and/or different phosphonates 28.5 or 28.8, the corresponding products 28.7 and 28.10 are obtained.

Scheme 29 illustrates the preparation of phosphonate esters 8 in which the phosphonate is attached either directly, or by means of a saturated or unsaturated carbon chain. In this procedure, a bromo-substituted anhydride 29.1 is converted, as described above, into the phenol-protected amide 29.2. The product is then subjected to a Heck coupling reaction, in the presence of a palladium (0) catalyst, as described in Scheme 4, with a dialkyl alkenyl phosphonate 29.3, to afford, after deprotection of the phenol, the phosphonate 29.4. Optionally, the olefinic bond is reduced, as described in Scheme 4, to yield the saturated analog 29.5.

Alternatively, the bromo-substituted amide 29.2 is coupled, as described in Scheme 3, with a dialkyl phosphite, in the presence of a palladium (0) catalyst, to generate, after deprotection of the phenolic hydroxyl group, the amide phosphonate 29.6.

For example, 3-bromo-furo[3,4-b]pyridine-5,7-dione 29.7, (Bioconjugate Chem., 2003, 14, 629) is converted, using the methods described above, into 3-bromo-5-(1,1-dioxo-[1,2]thiazinan-2-yl)-8-triisopropylsilanyloxy-[1,6]naphthyridine-7-carboxylic acid 4-trifluoromethyl-benzylamide 29.8. This compound is then reacted, in dimethylformamide solution at 80°, with one molar equivalent of a dialkyl vinyl phosphonate 29.9, (Aldrich), triethylamine and a catalytic amount of tetrakis(triphenylphosphine)palladium(0) to yield, after desilylation, the unsaturated phosphonate 29.10. The product is then reacted with diimide, prepared by basic hydrolysis of diethyl azodicarboxylate, as described in Angew. Chem. Int. Ed., 4, 271, 1965, to yield the saturated product 29.11.

Alternatively, the bromo compound 29.8 is reacted in toluene solution at ca. 100°, with one molar equivalent of a dialkyl phosphite 29.2, triethylamine and 3 mol % tetrakis(triphenylphosphine)palladium(0), to give, after desilylation, the phosphonate product 29.12.

Using the above procedures, but employing, in place of the anhydride 29.7, different anhydrides 29.1, and/or different phosphonates 29.3, the corresponding products 29.4, 29.5 and 29.6 are obtained.

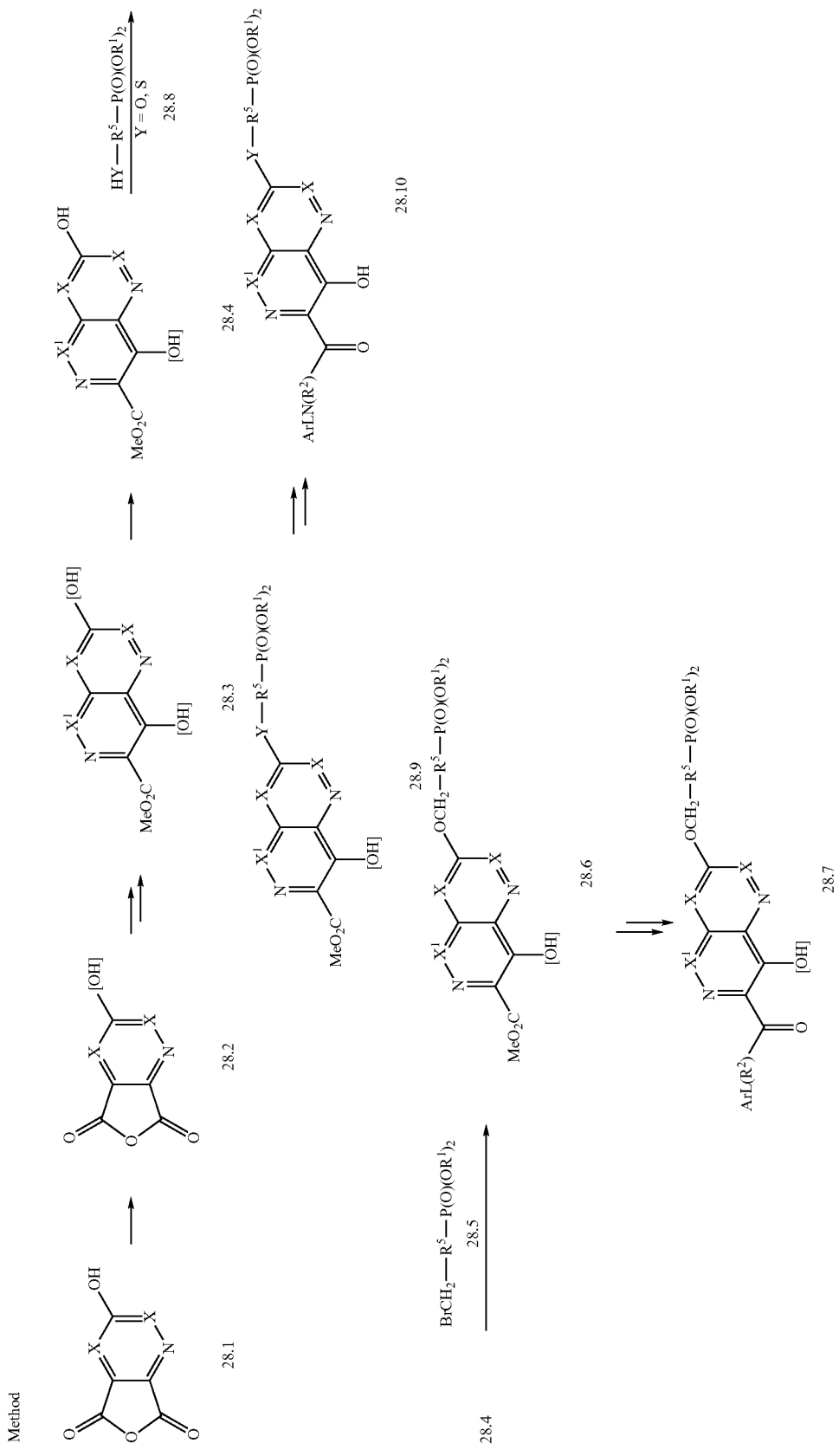

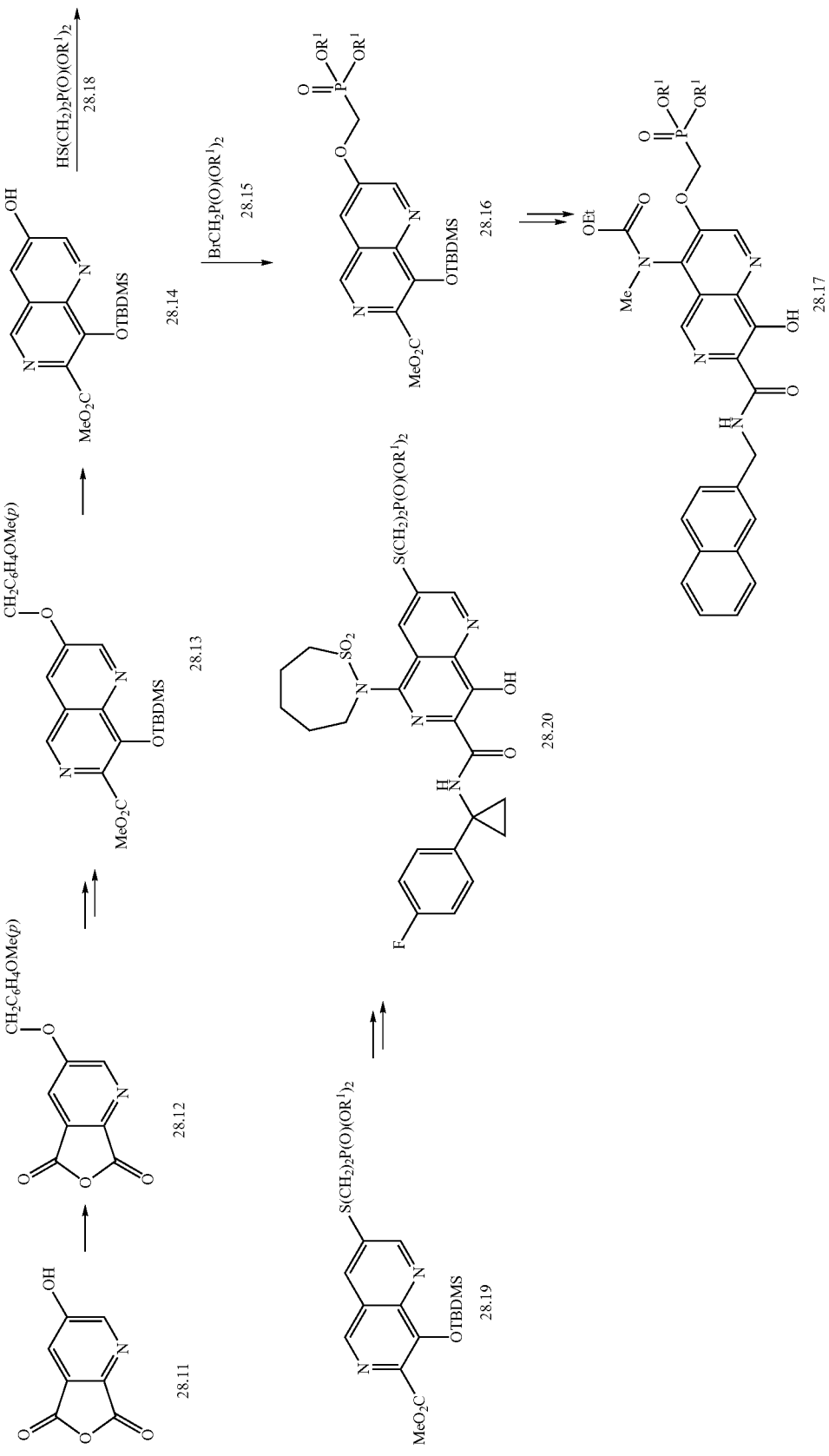

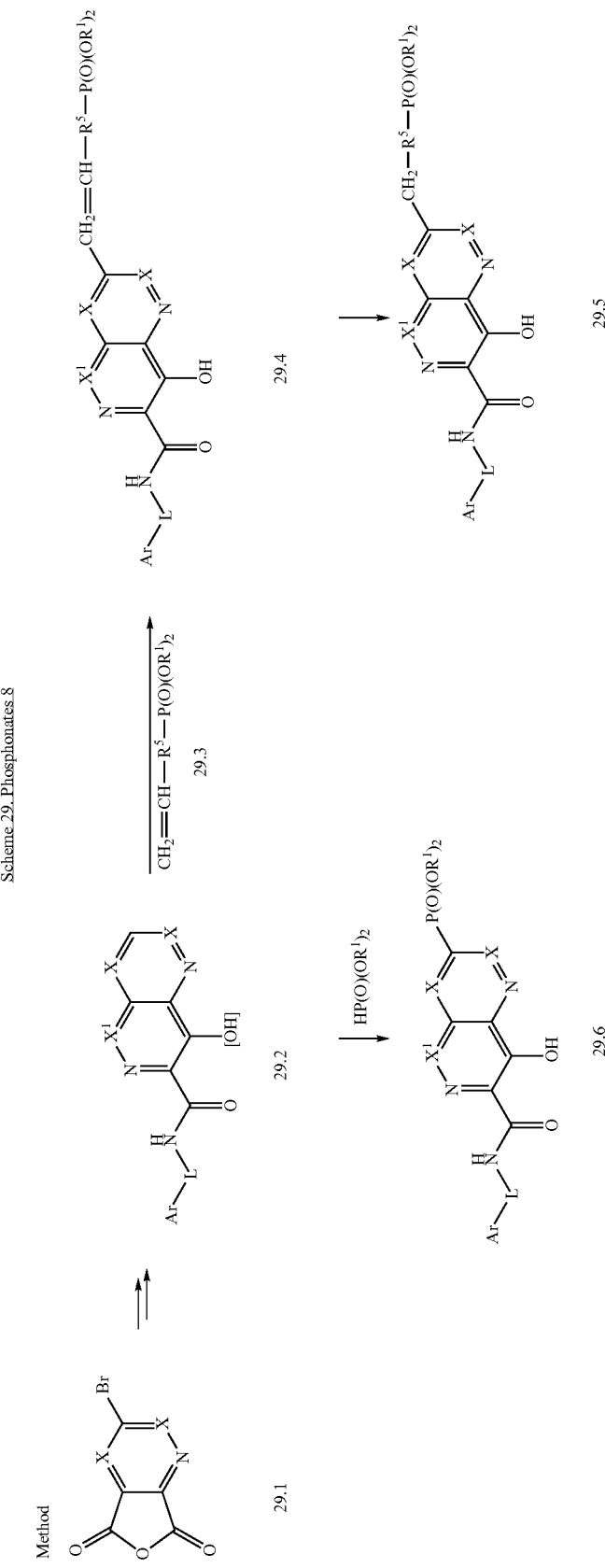

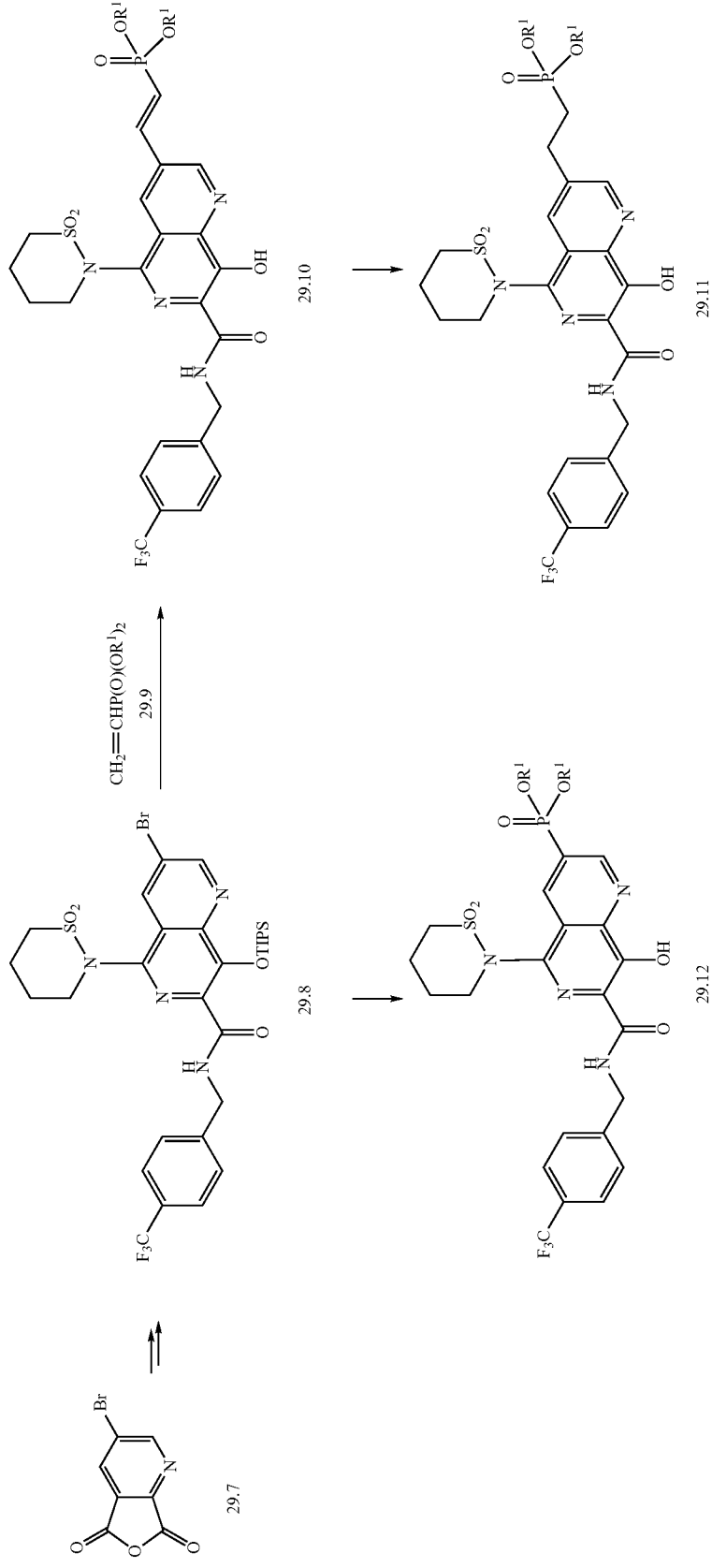

Preparation of the Intermediate Phosphonate Esters 9

Schemes 30 and 31 illustrate methods for the preparation of the phosphonate esters 9.

Scheme 30 illustrates the preparation of phosphonate esters 9 in which the phosphonate is attached by means of a saturated or unsaturated carbon link. In this procedure, a methyl-substituted bicyclic anhydride 30.1 is converted, using the methods described above, into the amide 30.2. The product is then condensed, under basic conditions, with a dialkyl formyl-substituted phosphonate 30.3, to afford the unsaturated phosphonate 30.4. The reaction is conducted at from ambient temperature to about 100°, in a polar aprotic solvent such as dimethylformamide or dioxan, in the presence of a base such as sodium hydride, potassium tert. butoxide or lithium hexamethyldisilazide. Optionally, the product 30.4 is reduced, as described in Scheme 4, to afford the saturated analog 30.5.

For example, 2-methyl-furo[3,4-b]pyrazine-5,7-dione 30.6 (Nippon Noyaku Gakk., 1989, 14, 75) is converted, using the methods described above, into 5-(ethanesulfonyl-methyl-amino)-2-methyl-8-triisopropylsilanyloxy-pyrido[3,4-b]pyrazine-7-carboxylic acid (3,5-dichloro-benzyl)-ethyl-amide 30.7. The product is then reacted, in dimethylformamide solution at 60°, with one molar equivalent of a dialkyl formylmethyl phosphonate 30.8 (Aurora) and sodium hydride, to give, after desilylation, the unsaturated phosphonate 30.9. The product is then reacted with diimide, prepared by basic hydrolysis of diethyl azodicarboxylate, as described in Angew. Chem. Int. Ed., 4, 271,1965, to yield the saturated product 30.10.

Using the above procedures, but employing, in place of the anhydride 30.6, different anhydrides 30.1, and/or different phosphonates 30.3, the corresponding products 30.4, and 30.5 are obtained.

Scheme 31 illustrates the preparation of phosphonate esters 9 in which the phosphonate is attached by means of an oxime linkage. In this procedure, a methyl-substituted bicyclic anhydride 31.1 is converted, using the methods described above, into the methyl-substituted amide 31.2. Benzylic bromination, as described in Scheme 25, then gives the bromomethyl analog 31.3, and oxidation, as described in Scheme 26 affords the corresponding aldehyde. The aldehyde is then converted, by reaction with hydroxylamine, into the oxime 31.5. The latter compound is then reacted, in a polar solvent such as tetrahydrofuran or dimethylformamide, in the presence of a base such as sodium hydroxide or potassium carbonate, with a dialkyl bromomethyl-substituted phosphonate 31.6, to prepare, after deprotection of the phenolic hydroxyl group, the oxime derivative 31.7.

For example, 2-methyl-furo[3,4-b]pyrazine-5,7-dione 30.6 (Nippon Noyaku Gakk., 1989, 14, 75) is converted, using the methods described above, into 5-(ethenesulfonyl-methyl-amino)-2-formyl-8-triisopropylsilanyloxy-pyrido[3,4b]-pyrazine-7-carboxylic acid 4-fluoro-benzylamide 31.9. The aldehyde is then reacted in tetrahydrofuran solution with three molar equivalents of hydroxylamine hydrochloride and sodium acetate, to produce the oxime 31.10. The latter compound is then reacted in dioxan solution at ambient temperature, with one molar equivalent of a dialkyl bromopropyl phosphonate 31.11 (Synthelec) and potassium carbonate, to yield, after desilylation of the phenolic hydroxyl group, the oxime ether 31.12.

Using the above procedures, but employing, in place of the anhydride 31.8, different anhydrides 31.1, and/or different phosphonates 31.6, the corresponding products 31.7 are obtained.

Scheme 30. Phosphonates 9.

Method

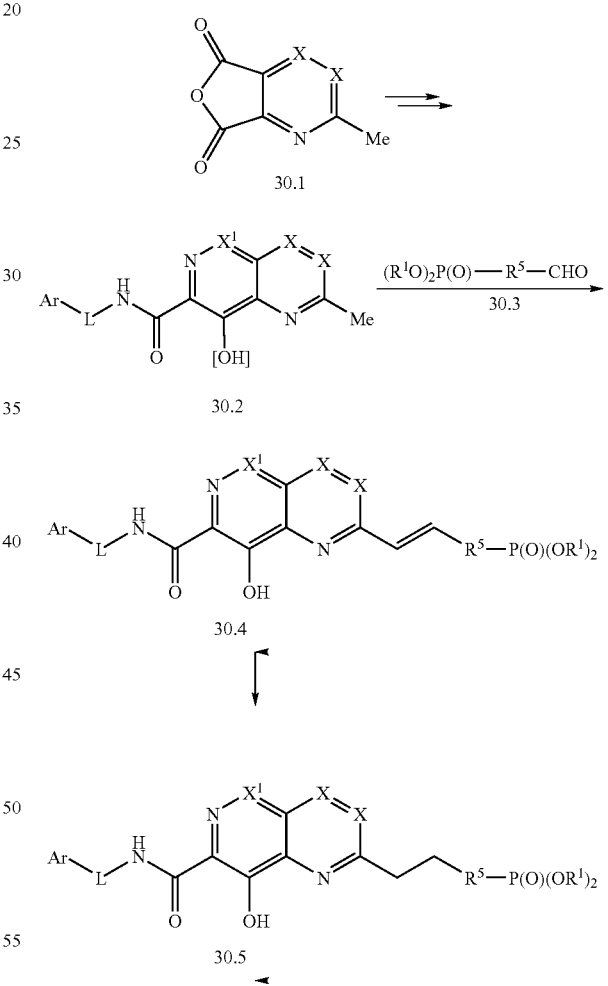

Example

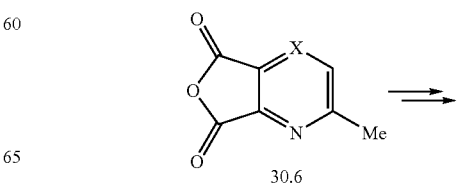

US 7,462,721 B2
119
-continued
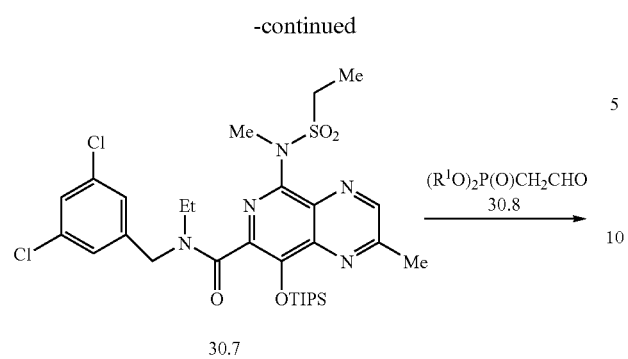
30.7
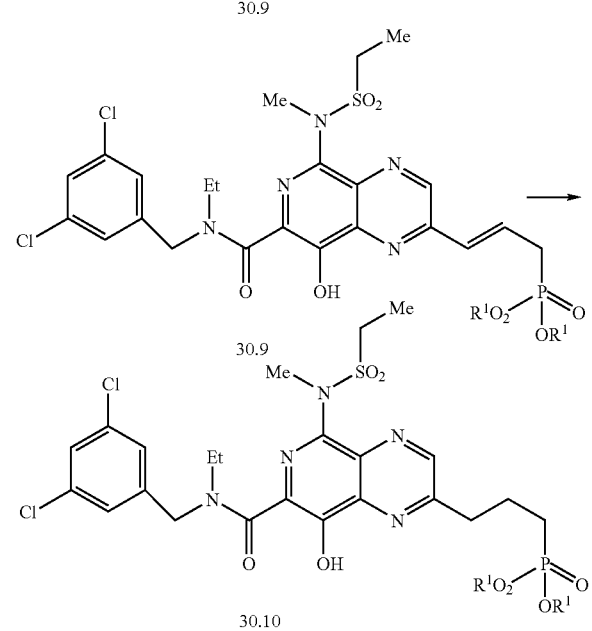
30.9
30.10
Scheme 31. Phosphonates 9.
Method
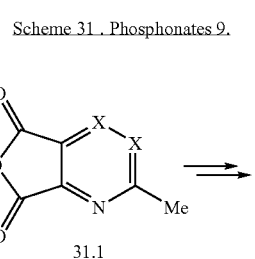
31.1
120
-continued
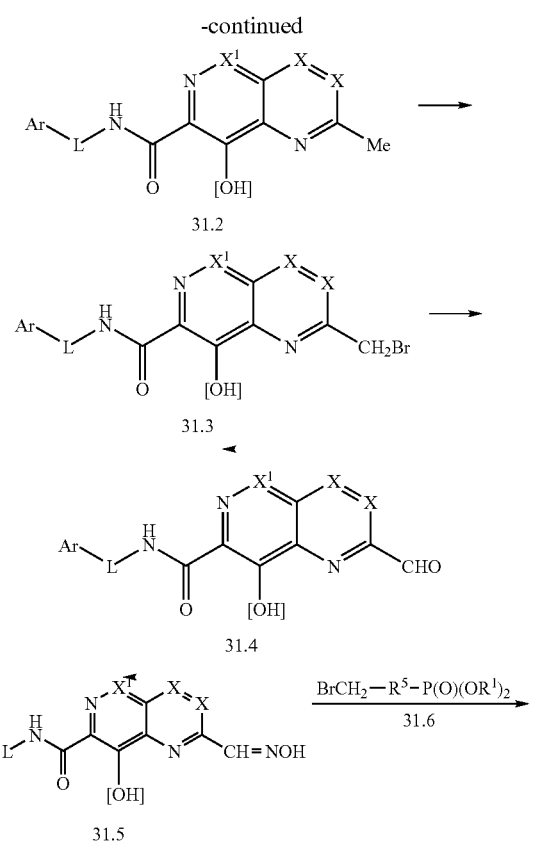
Example
31.8
30.9

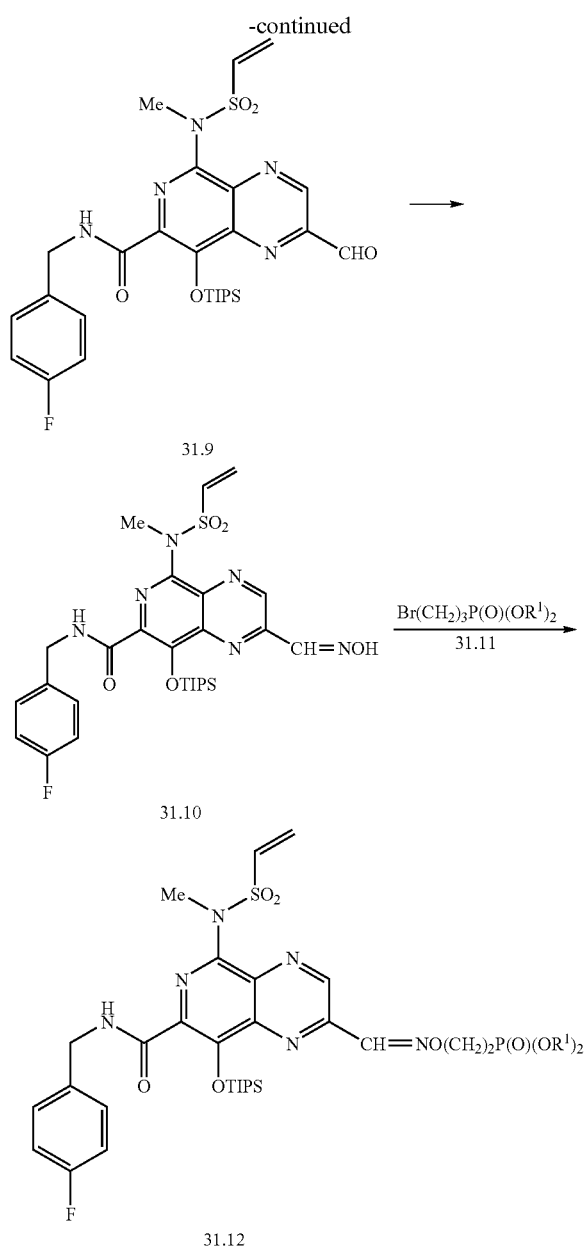

Interconversions of the Phosphonates R-link-P(O)(OR$^1$)$_2$, R-link-P(O)(OR$^1$)(OH) and R-link-P(O)(OH)$_2$ Schemes 1-31 described the preparation of phosphonate esters of the general structure R-link-P(O)(OR$^1$)$_2$, in which the groups R$^1$ may be the same or different. The R$^1$ groups attached to a phosphonate ester 1-9, or to precursors thereto, may be changed using established chemical transformations. The interconversions reactions of phosphonates are illustrated in Scheme 32. The group R in Scheme 32 represents the substructure to which the substituent link-P(O)(OR$^1$)$_2$ is attached, either in the compounds 1-9 or in precursors thereto. The R$^1$ group may be changed, using the procedures described below, either in the precursor compounds, or in the esters 1-9. The methods employed for a given phosphonate transformation depend on the nature of the substituent R$^1$, and of the substrate to which the phosphonate group is attached. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 32.1 into the corresponding phosphonate monoester 32.2 (Scheme 32, Reaction 1) is accomplished by a number of methods. For example, the ester 32.1 in which R$^1$ is an aralkyl group such as benzyl, is converted into the monoester compound 32.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110°. The conversion of the diester 32.1 in which R$^1$ is an aryl group such as phenyl, or an alkenyl group such as allyl, into the monoester 32.2 is effected by treatment of the ester 32.1 with a base such as aqueous sodium hydroxide in acetonitrile or lithium hydroxide in aqueous tetrahydrofuran. Phosphonate diesters 32.1 in which one of the groups R$^1$ is aralkyl, such as benzyl, and the other is alkyl, is converted into the monoesters 32.2 in which R$^1$ is alkyl by hydrogenation, for example using a palladium on carbon catalyst. Phosphonate diesters in which both of the groups R$^1$ are alkenyl, such as allyl, is converted into the monoester 32.2 in which R$^1$ is alkenyl, by treatment with chlorotris(triphenylphosphine)rhodium (Wilkinson's catalyst) in aqueous ethanol at reflux, optionally in the presence of diazabicyclooctane, for example by using the procedure described in J. Org. Chem., 38, 3224, 1973 for the cleavage of allyl carboxylates.

The conversion of a phosphonate diester 32.1 or a phosphonate monoester 32.2 into the corresponding phosphonic acid 32.3 (Scheme 32, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 32.2 in which R$^1$ is aralkyl such as benzyl, is converted into the corresponding phosphonic acid 32.3 by hydrogenation over a palladium catalyst, or by treatment with hydrogen chloride in an ethereal solvent such as dioxan. A phosphonate monoester 32.2 in which R$^1$ is alkenyl such as, for example, allyl, is converted into the phosphonic acid 32.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 32.1 in which R$^1$ is benzyl is described in J. Org. Chem., 24, 434, 1959. Platinum-catalyzed hydrogenolysis of phosphonate esters 32.1 in which R$^1$ is phenyl is described in J. Am. Chem. Soc., 78, 2336, 1956.

The conversion of a phosphonate monoester 32.2 into a phosphonate diester 32.1 (Scheme 32, Reaction 4) in which the newly introduced R$^1$ group is alkyl, aralkyl, haloalkyl such as chloroethyl, or aralkyl is effected by a number of reactions in which the substrate 32.2 is reacted with a hydroxy compound R$^1$OH, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 32.2 to the diester 32.1 is effected by the use of the Mitsunobu reaction, as described above (Scheme 7). The substrate is reacted with the hydroxy compound $R^1OH$, in the presence of diethyl azodicarboxylate and a triarylphosphine such as triphenyl phosphine. Alternatively, the phosphonate monoester 32.2 is transformed into the phosphonate diester 32.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester 32.2 is transformed into the chloro analog $RP(O)(OR^1)Cl$ by reaction with thionyl chloride or oxalyl chloride and the like, as described in Organic Phosphorus Compounds, G. M. Kosolapoff, L. Maeir, eds, Wiley, 1976, p. 17, and the thus-obtained product $RP(O)(OR^1)Cl$ is then reacted with the hydroxy compound $R^1OH$, in the presence of a base such as triethylamine, to afford the phosphonate diester 32.1.

A phosphonic acid $R\text{-link-}P(O)(OH)_2$ is transformed into a phosphonate monoester $RP(O)(OR^1)(OH)$ (Scheme 32, Reaction 5) by means of the methods described above of for the preparation of the phosphonate diester $R\text{-link-}P(O)(OR^1)_2$ 32.1, except that only one molar proportion of the component $R^1OH$ or $R^1Br$ is employed.

A phosphonic acid $R\text{-link-}P(O)(OH)_2$ 32.3 is transformed into a phosphonate diester $R\text{-link-}P(O)(OR^1)_2$ 32.1 (Scheme 32, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine. Alternatively, phosphonic acids 32.3 is transformed into phosphonic esters 32.1 in which $R^1$ is aryl, by means of a coupling reaction employing, for example, dicyclohexylcarbodiimide in pyridine at ca 70°. Alternatively, phosphonic acids 32.3 is transformed into phosphonic esters 32.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 32.1.

Scheme 32

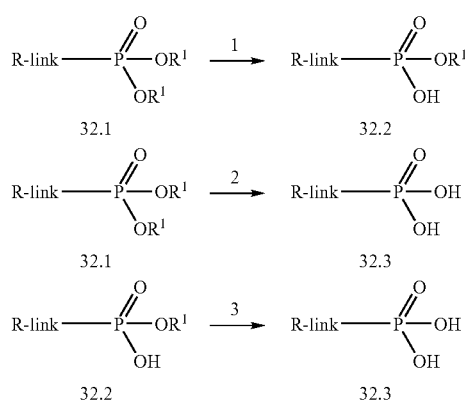

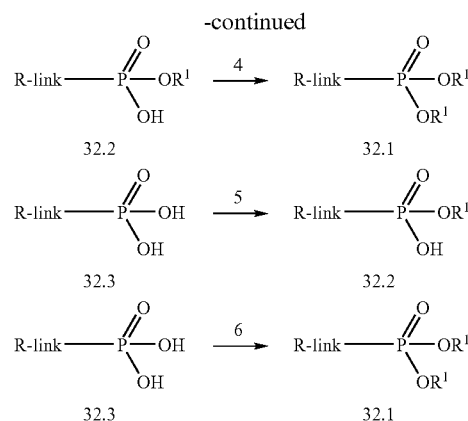

Preparation of Carbamates

The phosphonate esters 1-9 may contain a carbamate linkage. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 33 illustrates various methods by which the carbamate linkage is synthesized. As shown in Scheme 33, in the general reaction generating carbamates, a carbinol 33.1, is converted into the activated derivative 33.2 in which Lv is a leaving group such as halo, imidazolyl, benztriazolyl and the like, as described herein. The activated derivative 33.2 is then reacted with an amine 33.3, to afford the carbamate product 33.4. Examples 1-7 in Scheme 33 depict methods by which the general reaction is effected. Examples 8-10 illustrate alternative methods for the preparation of carbamates.

Scheme 33, Example 1 illustrates the preparation of carbamates employing a chloroformyl derivative of the carbinol 33.5. In this procedure, the carbinol 33.5 is reacted with phosgene, in an inert solvent such as toluene, at about 0°, as described in Org. Syn. Coll. Vol. 3, 167, 1965, or with an equivalent reagent such as trichloromethoxy chloroformate, as described in Org. Syn. Coll. Vol. 6, 715, 1988, to afford the chloroformate 33.6. The latter compound is then reacted with the amine component 33.3, in the presence of an organic or inorganic base, to afford the carbamate 33.7. For example, the chloroformyl compound 33.6 is reacted with the amine 33.3 in a water-miscible solvent such as tetrahydrofuran, in the presence of aqueous sodium hydroxide, as described in Org. Syn. Coll. Vol. 3, 167, 1965, to yield the carbamate 33.7. Alternatively, the reaction is performed in dichloromethane in the presence of an organic base such as diisopropylethylamine or dimethylaminopyridine.

Scheme 33, Example 2 depicts the reaction of the chloroformate compound 33.6 with imidazole to produce the imidazolide 33.8. The imidazolide product is then reacted with the amine 33.3 to yield the carbamate 33.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in J. Med. Chem., 1989, 32, 357.

Scheme 33 Example 3, depicts the reaction of the chloroformate 33.6 with an activated hydroxyl compound R"OH, to yield the mixed carbonate ester 33.10. The reaction is conducted in an inert organic solvent such as ether or dichloromethane, in the presence of a base such as dicyclohexylamine or triethylamine. The hydroxyl component R"OH is selected from the group of compounds 33.19-33.24 shown in Scheme 33, and similar compounds. For example, if the component R"OH is hydroxybenztriazole 33.19, N-hydroxysuccinimide 33.20, or pentachlorophenol, 33.21, the mixed carbonate 33.10 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 33.22 or 2-hydroxypyridine 33.23 is performed in an ethereal solvent in the presence of triethylamine, as described in Syn., 1986, 303, and Chem. Ber. 118, 468, 1985.

Scheme 33 Example 4 illustrates the preparation of carbamates in which an alkyloxycarbonylimidazole 33.8 is employed. In this procedure, a carbinol 33.5 is reacted with an equimolar amount of carbonyl diimidazole 33.11 to prepare the intermediate 33.8. The reaction is conducted in an aprotic organic solvent such as dichloromethane or tetrahydrofuran. The acyloxyimidazole 33.8 is then reacted with an equimolar amount of the amine R'NH$_2$ to afford the carbamate 33.7. The reaction is performed in an aprotic organic solvent such as dichloromethane, as described in Tet. Lett., 42, 2001, 5227, to afford the carbamate 33.7.

Scheme 33, Example 5 illustrates the preparation of carbamates by means of an intermediate alkoxycarbonylbenztriazole 33.13. In this procedure, a carbinol ROH is reacted at ambient temperature with an equimolar amount of benztriazole carbonyl chloride 33.12, to afford the alkoxycarbonyl product 33.13. The reaction is performed in an organic solvent such as benzene or toluene, in the presence of a tertiary organic amine such as triethylamine, as described in Syn., 1977, 704. The product is then reacted with the amine R'NH$_2$ to afford the carbamate 33.7. The reaction is conducted in toluene or ethanol, at from ambient temperature to about 80° as described in Syn., 1977, 704.

Scheme 33, Example 6 illustrates the preparation of carbamates in which a carbonate (R"O)$_2$CO, 33.14, is reacted with a carbinol 33.5 to afford the intermediate alkyloxycarbonyl intermediate 33.15. The latter reagent is then reacted with the amine R'NH$_2$ to afford the carbamate 33.7. The procedure in which the reagent 33.15 is derived from hydroxybenztriazole 33.19 is described in Synthesis, 1993, 908; the procedure in which the reagent 33.15 is derived from N-hydroxysuccinimide 33.20 is described in Tet. Lett., 1992, 2781; the procedure in which the reagent 33.15 is derived from 2-hydroxypyridine 33.23 is described in Tet. Lett., 1991, 4251; the procedure in which the reagent 33.15 is derived from 4-nitrophenol 33.24 is described in Syn. 1993, 103. The reaction between equimolar amounts of the carbinol ROH and the carbonate 33.14 is conducted in an inert organic solvent at ambient temperature.

Scheme 33, Example 7 illustrates the preparation of carbamates from alkoxycarbonyl azides 33.16. In this procedure, an alkyl chloroformate 33.6 is reacted with an azide, for example sodium azide, to afford the alkoxycarbonyl azide 33.16. The latter compound is then reacted with an equimolar amount of the amine R'NH$_2$ to afford the carbamate 33.7. The reaction is conducted at ambient temperature in a polar aprotic solvent such as dimethylsulfoxide, for example as described in Syn., 1982, 404.

Scheme 33, Example 8 illustrates the preparation of carbamates by means of the reaction between a carbinol ROH and the chloroformyl derivative of an amine 33.17. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 33.7.

Scheme 33, Example 9 illustrates the preparation of carbamates by means of the reaction between a carbinol ROH and an isocyanate 33.18. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 33.7.

Scheme 33, Example 10 illustrates the preparation of carbamates by means of the reaction between a carbinol ROH and an amine R'NH$_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 33.7.

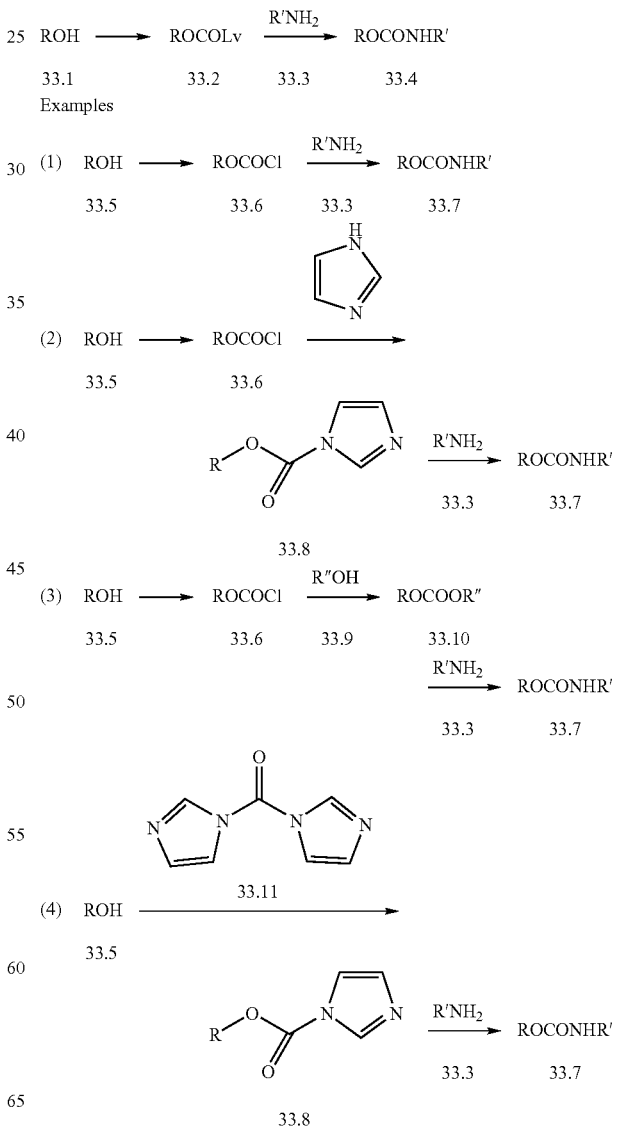

-continued

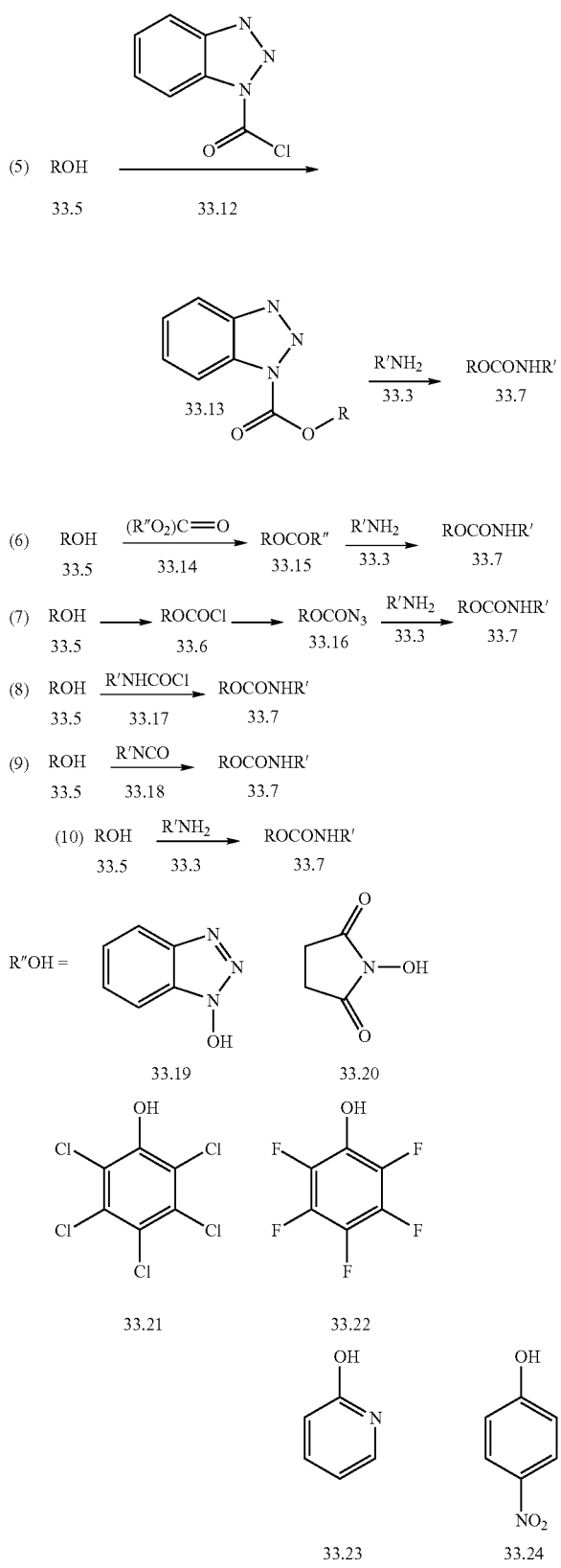

Preparation of Tricyclic Phosphonate Esters

Preparation of the Intermediate Phosphonate Esters Formula 1a

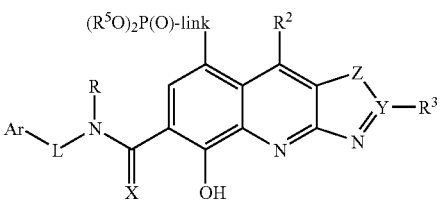

Formula 1a

Scheme A26 illustrates the preparation of phosphonate esters of Formula 1a in which the phosphonate is attached by means of an amide group and a variable carbon linkage. In this procedure, a protected dihydroxyaniline A26.1 is reacted with a 2-halo heterocyclic aldehyde A26.2, in which Y is C or N, to afford the displacement product A26.3. The nucleophilic displacement reaction of 2-halo heterocycles is described, for example, in Heterocyclic Chemistry, by T. L. Gilchrist, Longman, 1992, p. 143. The reaction is catalyzed by acid or base, and is conducted in an inert solvent such as pyridine. The product is cyclized to give the tricyclic ester A26.4. The cyclization of aldehydes to afford quinolines is described, for example, in Heterocyclic Chemistry, by T. L. Gilchrist, Longman, 1992, p. 160. The reaction is catalyzed by a strong acid and is conducted in a high boiling solvent. The ester A26.4 is transformed by reaction with the amine A26.5 into the amide A26.6. Selective deprotection of the less hindered hydroxyl group then generates the phenol A26.7. The product is then reacted, as described above, (Scheme A6) with a dialkyl bromoalkyl phosphonate A26.8 to yield after deprotection the ether phosphonate A26.9.

For example, methyl 3-amino-2,5-dihydroxybenzoate A26.10 is reacted sequentially with one molar equivalent of chlorotriisopropylsilane and imidazole in dichloromethane, and then with excess diphenyldiazomethane, to produce the differentially protected compound A26.11. The product is then reacted, as described above, with 4-bromothiazole-5-carboxaldehyde A26.12 (WO 9317681) to give 5-benzhydryloxy-8-triisopropylsilanyloxy-thiazolo[4,5-b]quinoline-6-carboxylic acid methyl ester A26.13. This material is then coupled, as described above, with 3,5-dichloro-N-methylbenzylamine A26.14 to produce 5-benzhydryloxy-8-triisopropylsilanyloxy-thiazolo[4,5-b]quinoline-6-carboxylic acid 3,5-dichloro-benzylamide A26.15. Treatment of the latter compound with tetrabutylammonium fluoride in tetrahydrofuran then forms the phenol A26.16, which is reacted in dimethylformamide solution with a dialkyl bromoethyl phosphonate A26.17 (Aldrich) and potassium carbonate, to afford after deprotection the phosphonate ether A26.18.

Using the above procedures, but employing, in place of the starting materials A26.10 and A26.12, different starting materials A26.1 and A26.2, and/or different phosphonates A26.8, the corresponding products A26.9 are obtained.

Scheme A26. Phosphonates Formula 1a
Method
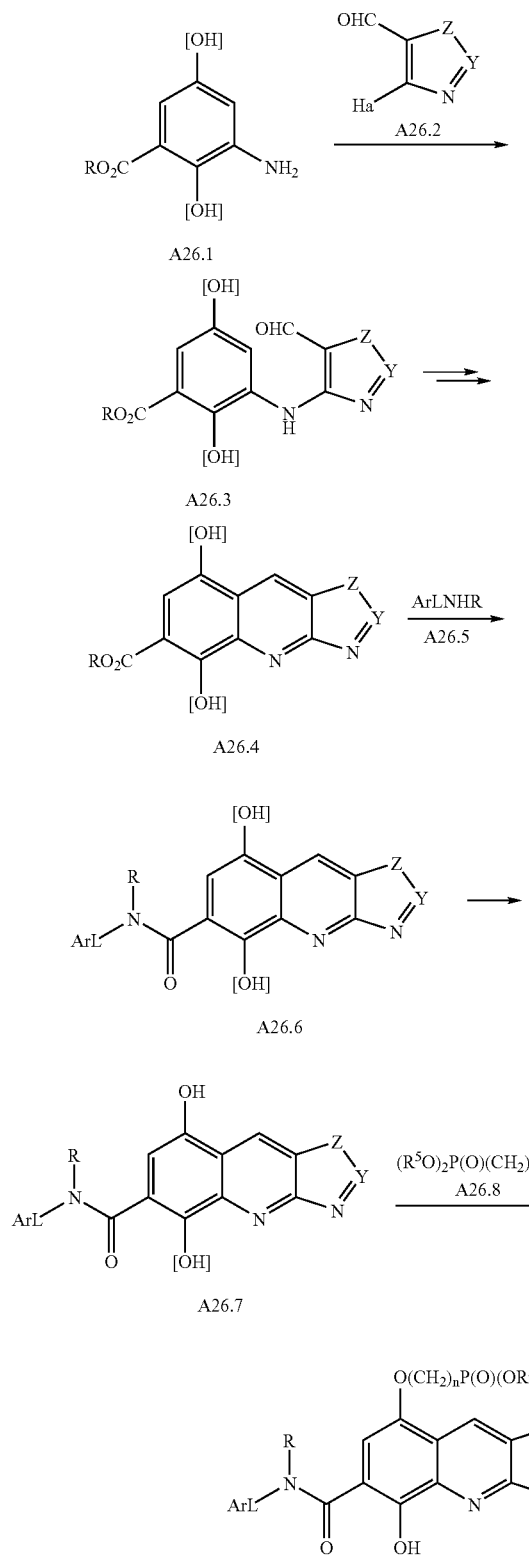
A26.1, A26.2, A26.3, A26.4, A26.5, A26.6, A26.7, A26.8, A26.9
Example A26
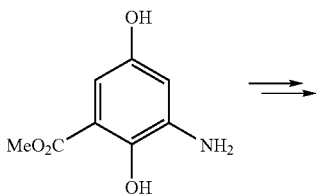
A26.10
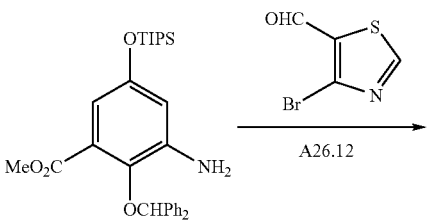
A26.11, A26.12
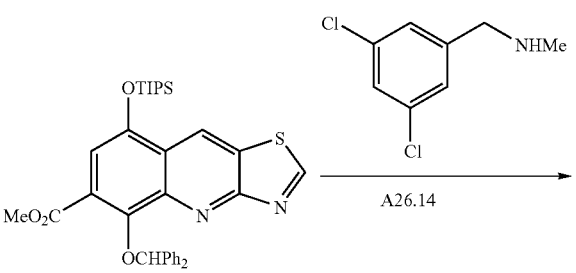
A26.13, A26.14
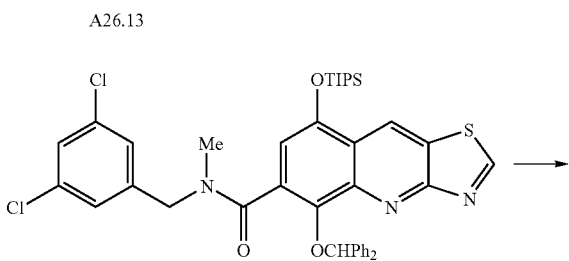
A26.15
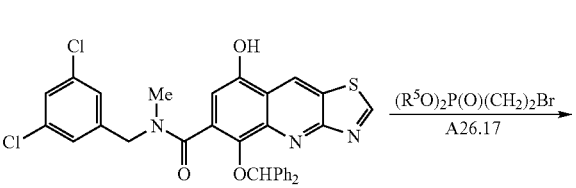
A26.16, A26.17
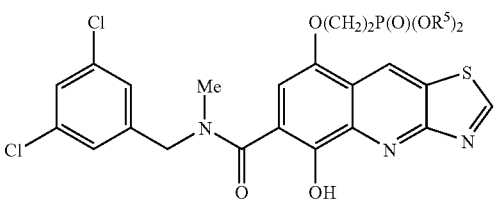
A26.18

Preparation of the Intermediate Phosphonate Esters Formula 1b

Method

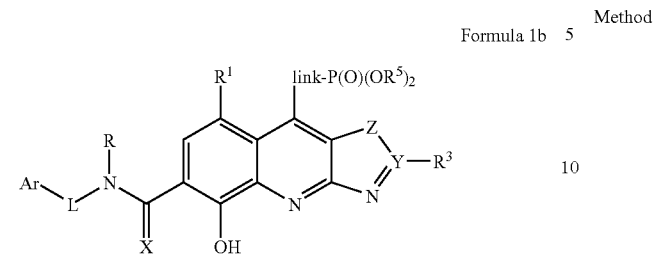

Formula 1b

Scheme A27 illustrates the preparation of phosphonate esters of Formula 1b in which the phosphonate is attached by means of a variable carbon linkage optionally incorporating a heteroatom. In this procedure, a protected 3-amino—2-hydroxy benzoate ester A27.1 is reacted, as described in Scheme A26, with a heterocyclic 2-halo ketone A27.2 to afford the amine A27.3. Thermal cyclization of this compound then affords the tricyclic product A27.4. The compound is then subjected to benzylic bromination to yield the bromomethyl product A27.5. The latter compound is then reacted with a trialkyl phosphite at 120° C. to produce the phosphonate A27.6. The phosphonate is then reacted with the amine ArB-NHR A27.7 and trimethylaluminum to give after deprotection the amide A27.8.

Alternatively, the bromomethyl compound A27.5 is reacted, as described in Scheme A17, with a hydroxy, mercapto or amino-substituted phosphonate A27.9, in which the group $R^a$ is an acyclic or cyclic saturated or unsaturated alkylene, or aryl, aralkyl or heteroaryl moiety. The ether, thioether or amine product is then reacted, as described above, with the amine ArBNHR to prepare after deprotection the phosphonate A27.11.

For example, methyl 3-amino-2-diphenylmethoxybenzoate A27.12 is reacted with 5-acetyl-4-bromothiazole A27.13 (WO 9317681) to afford after cyclization of the initial displacement product, 5-benzhydryloxy-9-methyl-thiazolo[4,5-b]quinoline-6-carboxylic acid methyl ester A27.14. Reaction with N-bromosuccinimide in hexachloroethane then yields the bromomethyl analog A27.15, and this material is reacted with a trialkyl phosphite in an Arbuzov reaction to give the phosphonate A27.16. The product is then reacted with 3,5-dichlorobenzyl methylamine A27.17 and trimethyl aluminum to afford after deprotection the phosphonate A27.18.

As a further example, the bromomethyl compound A27.15 is reacted in acetonitrile solution with a dialkyl 3-hydroxyphenyl phosphonate A27.19 (Epsilon) and potassium carbonate, to obtain the ether product A27.20. This compound is then reacted with cyclopentylmethylamine and trimethylaluminum to give after deprotection the phosphonate A27.21.

Using the above procedures, but employing, in place of the tricyclic starting materials A27.14 or A27.15, different starting materials A27.4 or A27.5, and or different amines A27.7 or phosphonates A27.9, the corresponding products A27.8 and A27.11 are obtained.

Scheme A27. Phosphonates Formula 1b

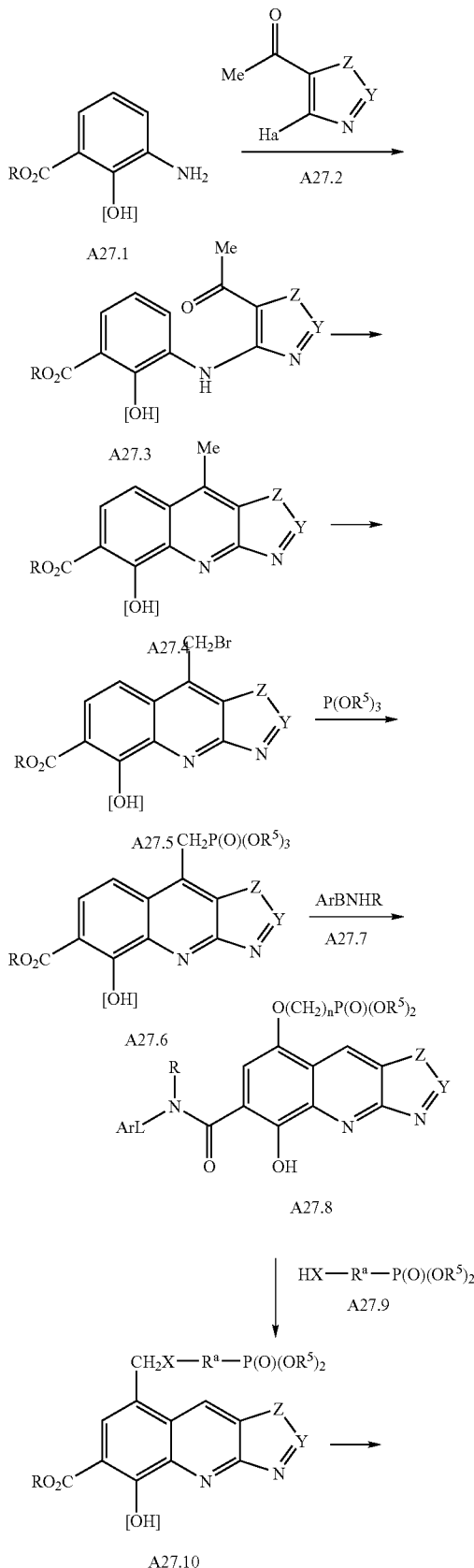

-continued

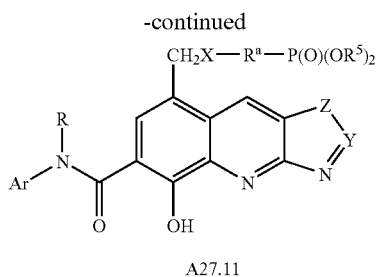

A27.11

Example A27-1

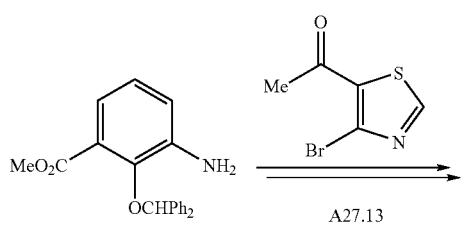

A27.12   A27.13

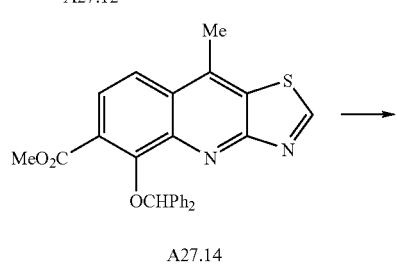

A27.14

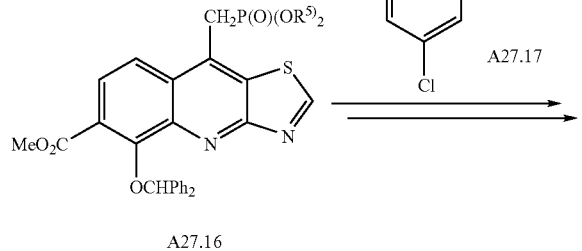

A27.15

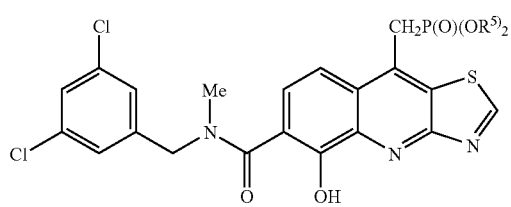

A27.16

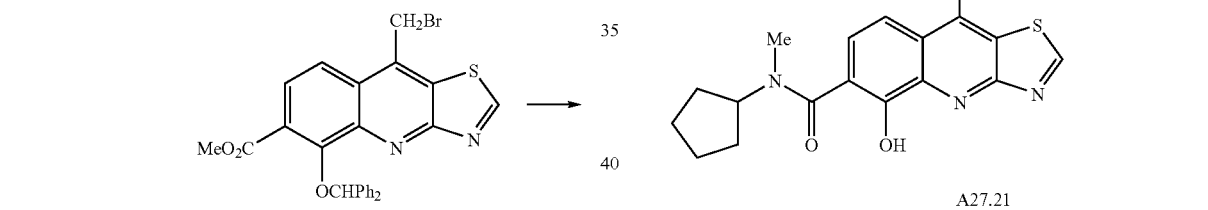

A27.18

-continued

Example A27-2

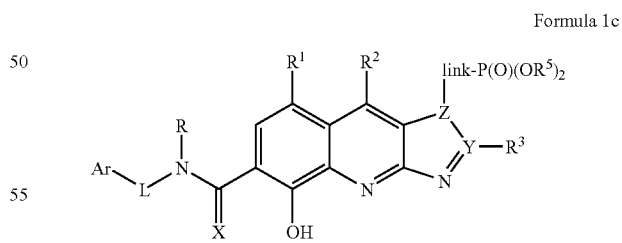

A27.15   A27.19

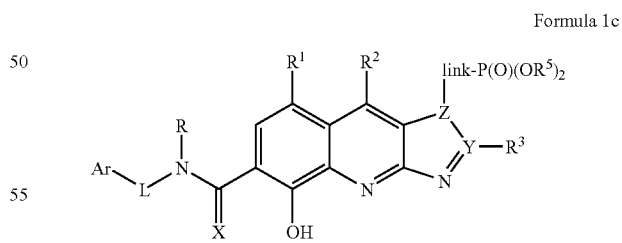

A27.20

A27.21

Preparation of the Intermediate Phosphonate Esters Formula 1c

Formula 1c

Scheme A28 illustrates the preparation of phosphonate esters of Formula 1c in which the phosphonate is attached by means of carbon linkage optionally incorporating a heteroatom. In this procedure, a substituted aniline A28.1 is reacted, using the procedures described in Scheme A26, with a methyl-substituted 2-bromoheterocyclic aldehyde A28.2 to produce the methyl-substituted tricyclic product A28.3. The compound is then subjected to benzylic bromination to give the bromomethyl analog A28.4. The latter compound is then reacted, as described in Scheme A17, with a dialkyl hydroxy, mercapto or amino-substituted phosphonate A28.5 in which the group R is an acyclic or cyclic saturated or unsaturated alkylene, or aryl, aralkyl or heteroaryl moiety, to afford after deprotection the ether, thioether or amine product A28.6.

Alternatively, the bromomethyl compound A28.4 is reacted in an Arbuzov reaction with a trialkyl phosphite to yield after deprotection the phosphonate A28.7.

For example, methyl 3-amino-2-diphenylmethoxybenzoate A28.8 is reacted, as described above, with 2-bromo-4-methylpyridine-3-carboxaldehyde A28.9 (Arkivoc, 2000, 1, 52) to produce after cyclization, the tricyclic ester A28.10. The ester is then reacted with trimethylaluminum and N-methylcyclobutylmethylamine A28.11 to give 9-benzhydryloxy-4-methyl-benzo[b][1,8]naphthyridine-8-carboxylic acid cyclobutylmethyl-methyl-amide A28.12. Benzylic bromination then gives the bromomethyl analog A28.13. The latter compound is heated at 120° C. with excess of a trialkyl phosphite to produce after deprotection the phosphonate A28.14.

As a further example, the bromomethyl compound A28.13 is reacted in acetonitrile solution with a dialkyl mercaptomethyl phosphonate A28.15 (Tet., 1994, 50, 10277) and diisopropylamine to produce after deprotection the thioether phosphonate A28.16.

Using the above procedures, but employing, in place of the starting materials A28.8 and A28.9, different starting materials A28.1 and A28.2, and/or different phosphonates A28.5, the corresponding products A28.6 and A28.7 are obtained.

Scheme A28. Phosphonates Formula 1c.

Method

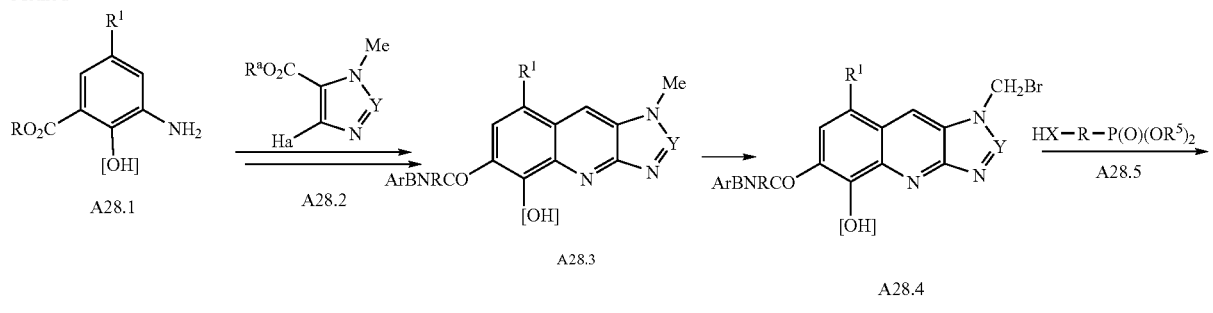

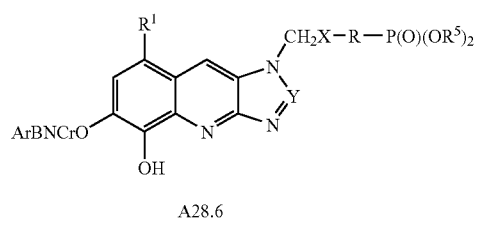

Example A28-1

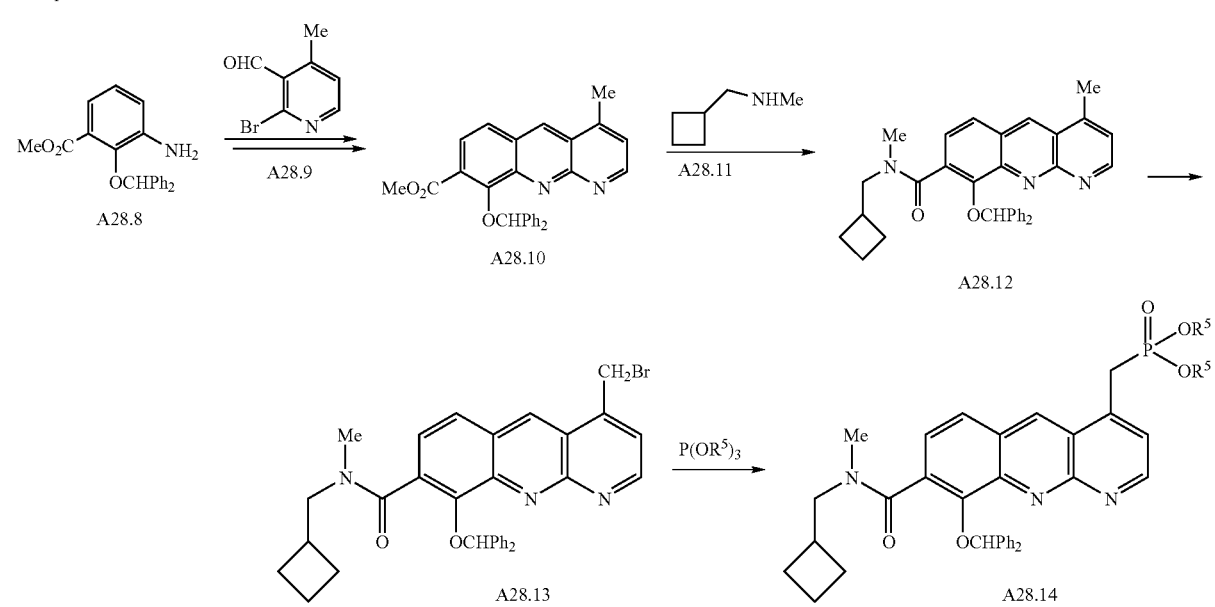

Example A28-2

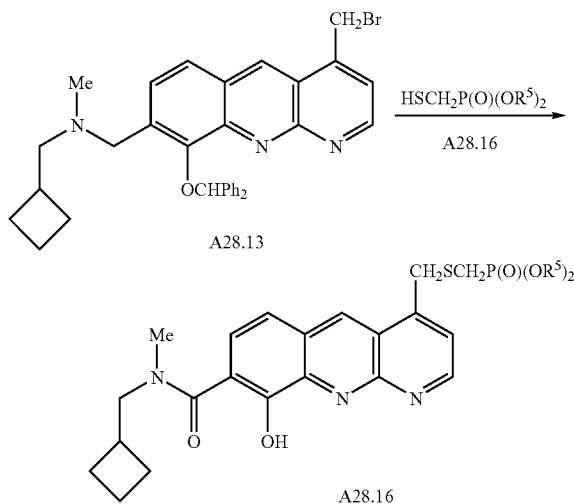

A28.13

A28.16

Preparation of Carboalkoxy-Substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in J. Gen. Chem. USSR, 1983, 53, 480, Zh. Obschei Khim., 1958, 28, 1063, or J. Org. Chem., 1994, 59, 6144, or by reaction with oxalyl chloride, as described in J. Am. Chem. Soc., 1994, 116, 3251, or J. Org. Chem., 1994, 59, 6144, or by reaction with phosphorus pentachloride, as described in J. Org. Chem., 2001, 66, 329, or in J. Med. Chem., 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in J. Chem. Soc., Chem. Comm., 1991, 312, or Nucleosides Nucleotides 2000, 19, 1885. Activated sulfonyloxy derivatives are obtained by the reaction of phosphonic acids with trichloromethylsulfonyl chloride, as described in J. Med. Chem. 1995, 38, 4958, or with triisopropylbenzenesulfonyl chloride, as described in Tet. Lett., 1996, 7857, or Bioorg. Med. Chem. Lett., 1998, 8, 663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in J. Chem. Soc., Chem. Comm., 1991, 312, or J. Med. Chem., 1980, 23, 1299 or Coll. Czech. Chem. Comm., 1987, 52, 2792. The use of ethyl dimethylaminopropyl carbodiimide for activation and coupling of phosphonic acids is described in Tet. Lett., 2001, 42, 8841, or Nucleosides Nucleotides, 2000, 19, 1885.

A number of additional coupling reagents have been described for the preparation of amidates and esters from phosphonic acids. The agents include Aldrithiol-2, and PYBOP and BOP, as described in J. Org. Chem., 1995, 60, 5214, and J. Med. Chem., 1997, 40, 3842, mesitylene-2-sulfonyl-3-nitro-1,2,4-triazole (MSNT), as described in J. Med. Chem., 1996, 39, 4958, diphenylphosphoryl azide, as described in J. Org. Chem., 1984, 49, 1158, 1-(2,4,6-triisopropylbenzenesulfonyl-3-nitro-1,2,4-triazole (TPSNT) as described in Bioorg. Med. Chem. Lett., 1998, 8, 1013, bromotris(dimethylamino)phosphonium hexafluorophosphate (BroP), as described in Tet. Lett., 1996, 37, 3997, 2-chloro-5,5-dimethyl-2-oxo-1,3,2-dioxaphosphinane, as described in Nucleosides Nucleotides 1995, 14, 871, and diphenyl chlorophosphate, as described in J. Med. Chem., 1988, 31, 1305.

Phosphonic acids are converted into amidates and esters by means of the Mitsunobu reaction, in which the phosphonic acid and the amine or hydroxy reactant are combined in the presence of a triaryl phosphine and a dialkyl azodicarboxylate. The procedure is described in Org. Lett., 2001, 3, 643, or J. Med. Chem., 1997, 40, 3842.

Phosphonic esters are also obtained by the reaction between phosphonic acids and halo compounds, in the presence of a suitable base. The method is described, for example, in Anal. Chem., 1987, 59, 1056, or J. Chem. Soc. Perkin Trans., 1, 1993, 19, 2303, or J. Med. Chem., 1995, 38, 1372, or Tet. Lett., 2002, 43, 1161.

Schemes 1-5 illustrate the conversion of phosphonate esters and phosphonic acids into carboalkoxy-substituted phosphorobisamidates (Scheme 1), phosphoroamidates (Scheme 2), phosphonate monoesters (Scheme 3) and phosphonate diesters, (Scheme 4) Scheme 1 illustrates various methods for the conversion of phosphonate diesters 1.1 into phosphorobisamidates 1.5. The diester 1.1, prepared as described previously, is hydrolyzed, either to the monoester 1.2 or to the phosphonic acid 1.6. The methods employed for these transformations are described above. The monoester 1.2 is converted into the monoamidate 1.3 by reaction with an aminoester 1.9, in which the group $R^2$ is H or alkyl, the group $R^4$ is an alkylene moiety such as, for example, $CHCH_3$, $CHPr^1$, $CH(CH_2Ph)$, $CH_2CH(CH_3)$ and the like, or a group present in natural or modified aminoacids, and the group $R^5$ is alkyl. The reactants are combined in the presence of a coupling agent such as a carbodiimide, for example dicyclohexyl carbodiimide, as described in J. Am. Chem. Soc., 1957, 79, 3575, optionally in the presence of an activating agent such as hydroxybenztriazole, to yield the amidate product 1.3. The amidate-forming reaction is also effected in the presence of coupling agents such as BOP, as described in J. Org. Chem., 1995, 60, 5214, Aldrithiol, PYBOP and similar coupling agents used for the preparation of amides and esters. Alternatively, the reactants 1.2 and 1.9 are transformed into the monoamidate 1.3 by means of a Mitsunobu reaction. The preparation of amidates by means of the Mitsunobu reaction is described in J. Med. Chem., 1995, 38, 2742. Equimolar amounts of the reactants are combined in an inert solvent such as tetrahydrofuran in the presence of a triaryl phosphine and a dialkyl azodicarboxylate. The thus-obtained monoamidate ester 1.3 is then transformed into amidate phosphonic acid 1.4. The conditions used for the hydrolysis reaction depend on the nature of the $R^1$ group, as described previously. The phosphonic acid amidate 1.4 is then reacted with an aminoester 1.9, as described above, to yield the bisamidate product 1.5, in which the amino substituents are the same or different.

An example of this procedure is shown in Scheme 1, Example 1. In this procedure, a dibenzyl phosphonate 1.14 is reacted with diazabicyclooctane (DABCO) in toluene at reflux, as described in J. Org. Chem., 1995, 60, 2946, to afford the monobenzyl phosphonate 1.15. The product is then reacted with equimolar amounts of ethyl alaninate 1.16 and dicyclohexyl carbodiimide in pyridine, to yield the amidate product 1.17. The benzyl group is then removed, for example by hydrogenolysis over a palladium catalyst, to give the monoacid product 1.18. This compound is then reacted in a Mitsunobu reaction with ethyl leucinate 1.19, triphenyl phosphine and diethylazodicarboxylate, as described in J. Med. Chem., 1995, 38, 2742, to produce the bisamidate product 1.20.

Using the above procedures, but employing in place of ethyl leucinate 1.19 or ethyl alaninate 1.16, different aminoesters 1.9, the corresponding products 1.5 are obtained.

Alternatively, the phosphonic acid 1.6 is converted into the bisamidate 1.5 by use of the coupling reactions described above. The reaction is performed in one step, in which case the nitrogen-related substituents present in the product 1.5 are the same, or in two steps, in which case the nitrogen-related substituents can be different.

An example of the method is shown in Scheme 1, Example 2. In this procedure, a phosphonic acid 1.6 is reacted in pyridine solution with excess ethyl phenylalaninate 1.21 and dicyclohexylcarbodiimide, for example as described in J. Chem. Soc., Chem. Comm., 1991, 1063, to give the bisamidate product 1.22.

Using the above procedures, but employing, in place of ethyl phenylalaninate, different aminoesters 1.9, the corresponding products 1.5 are obtained.

As a further alternative, the phosphonic acid 1.6 is converted into the mono or bis-activated derivative 1.7, in which Lv is a leaving group such as chloro, imidazolyl, triisopropylbenzenesulfonyloxy etc. The conversion of phosphonic acids into chlorides 1.7 (Lv=Cl) is effected by reaction with thionyl chloride or oxalyl chloride and the like, as described in Organic Phosphorus Compounds, G. M. Kosolapoff, L. Maeir, eds, Wiley, 1976, p. 17. The conversion of phosphonic acids into monoimidazolides 1.7 (Lv=imidazolyl) is described in J. Med. Chem., 2002, 45, 1284 and in J. Chem. Soc. Chem. Comm., 1991, 312. Alternatively, the phosphonic acid is activated by reaction with triisopropylbenzenesulfonyl chloride, as described in Nucleosides and Nucleotides, 2000, 10, 1885. The activated product is then reacted with the aminoester 1.9, in the presence of a base, to give the bisamidate 1.5. The reaction is performed in one step, in which case the nitrogen substituents present in the product 1.5 are the same, or in two steps, via the intermediate 1.11, in which case the nitrogen substituents can be different.

Examples of these methods are shown in Scheme 1, Examples 3 and 5. In the procedure illustrated in Scheme 1, Example 3, a phosphonic acid 1.6 is reacted with ten molar equivalents of thionyl chloride, as described in Zh. Obschei Khim., 1958, 28, 1063, to give the dichloro compound 1.23. The product is then reacted at reflux temperature in a polar aprotic solvent such as acetonitrile, and in the presence of a base such as triethylamine, with butyl serinate 1.24 to afford the bisamidate product 1.25.

Using the above procedures, but employing, in place of butyl serinate 1.24, different aminoesters 1.9, the corresponding products 1.5 are obtained.

In the procedure illustrated in Scheme 1, Example 5, the phosphonic acid-1.6 is reacted, as described in J. Chem. Soc. Chem. Comm., 1991, 312, with carbonyl diimidazole to give the imidazolide 1.32. The product is then reacted in acetonitrile solution at ambient temperature, with one molar equivalent of ethyl alaninate 1.33 to yield the monodisplacement product 1.34. The latter compound is then reacted with carbonyl diimidazole to produce the activated intermediate 1.35, and the product is then reacted, under the same conditions, with ethyl N-methylalaninate 1.33a to give the bisamidate product 1.36.

Using the above procedures, but employing, in place of ethyl alaninate 1.33 or ethyl N-methylalaninate 1.33a, different aminoesters 1.9, the corresponding products 1.5 are obtained.

The intermediate monoamidate 1.3 is also prepared from the monoester 1.2 by first converting the monoester into the activated derivative 1.8 in which Lv is a leaving group such as halo, imidazolyl etc, using the procedures described above. The product 1.8 is then reacted with an aminoester 1.9 in the presence of a base such as pyridine, to give an intermediate monoamidate product 1.3. The latter compound is then converted, by removal of the $R^1$ group and coupling of the product with the aminoester 1.9, as described above, into the bisamidate 1.5.

An example of this procedure, in which the phosphonic acid is activated by conversion to the chloro derivative 1.26, is shown in Scheme 1, Example 4. In this procedure, the phosphonic monobenzyl ester 1.15 is reacted, in dichloromethane, with thionyl chloride, as described in Tet. Let., 1994, 35, 4097, to afford the phosphoryl chloride 1.26. The product is then reacted in acetonitrile solution at ambient temperature with one molar equivalent of ethyl 3-amino-2-methylpropionate 1.27 to yield the monoamidate product 1.28. The latter compound is hydrogenated in ethylacetate over a 5% palladium on carbon catalyst to produce the monoacid product 1.29. The product is subjected to a Mitsunobu coupling procedure, with equimolar amounts of butyl alaninate 1.30, triphenyl phosphine, diethylazodicarboxylate and triethylamine in tetrahydrofuran, to give the bisamidate product 1.31.

Using the above procedures, but employing, in place of ethyl 3-amino-2-methylpropionate 1.27 or butyl alaninate 1.30, different aminoesters 1.9, the corresponding products 1.5 are obtained.

The activated phosphonic acid derivative 1.7 is also converted into the bisamidate 1.5 via the diamino compound 1.10. The conversion of activated phosphonic acid derivatives such as phosphoryl chlorides into the corresponding amino analogs 1.10, by reaction with ammonia, is described in Organic Phosphorus Compounds, G. M. Kosolapoff, L. Maeir, eds, Wiley, 1976. The diamino compound 1.10 is then reacted at elevated temperature with a haloester 1.12, in a polar organic solvent such as dimethylformamide, in the presence of a base such as dimethylaminopyridine or potassium carbonate, to yield the bisamidate 1.5.

An example of this procedure is shown in Scheme 1, Example 6. In this method, a dichlorophosphonate 1.23 is reacted with ammonia to afford the diamide 1.37. The reaction is performed in aqueous, aqueous alcoholic or alcoholic solution, at reflux temperature. The resulting diamino compound is then reacted with two molar equivalents of ethyl 2-bromo-3-methylbutyrate 1.38, in a polar organic solvent such as N-methylpyrrolidinone at ca. 150°, in the presence of a base such as potassium carbonate, and optionally in the presence of a catalytic amount of potassium iodide, to afford the bisamidate product 1.39.

Using the above procedures, but employing, in place of ethyl 2-bromo-3-methylbutyrate 1.38, different haloesters 1.12 the corresponding products 1.5 are obtained.

The procedures shown in Scheme 1 are also applicable to the preparation of bisamidates in which the aminoester moiety incorporates different functional groups. Scheme 1, Example 7 illustrates the preparation of bisamidates derived from tyrosine. In this procedure, the monoimidazolide 1.32 is reacted with propyl tyrosinate 1.40, as described in Example 5, to yield the monoamidate 1.41. The product is reacted with carbonyl diimidazole to give the imidazolide 1.42, and this material is reacted with a further molar equivalent of propyl tyrosinate to produce the bisamidate product 1.43.

Using the above procedures, but employing, in place of propyl tyrosinate 1.40, different aminoesters 1.9, the corresponding products 1.5 are obtained. The aminoesters employed in the two stages of the above procedure can be the same or different, so that bisamidates with the same or different amino substituents are prepared.

Scheme 2 illustrates methods for the preparation of phosphonate monoamidates.

In one procedure, a phosphonate monoester 1.1 is converted, as described in Scheme 1, into the activated derivative 1.8. This compound is then reacted, as described above, with an aminoester 1.9, in the presence of a base, to afford the monoamidate product 2.1.

The procedure is illustrated in Scheme 2, Example 1. In this method, a monophenyl phosphonate 2.7 is reacted with, for example, thionyl chloride, as described in J. Gen. Chem. USSR., 1983, 32, 367, to give the chloro product 2.8. The product is then reacted, as described in Scheme 1, with ethyl alaninate 2.9, to yield the amidate 2.10. Using the above procedures, but employing, in place of ethyl alaninate 2.9, different aminoesters 1.9, the corresponding products 2.1 are obtained.

Alternatively, the phosphonate monoester 1.1 is coupled, as described in Scheme 1, with an aminoester 1.9 to produce the amidate 2.1. If necessary, the $R^1$ substituent is then altered, by initial cleavage to afford the phosphonic acid 2.2. The procedures for this transformation depend on the nature of the $R^1$ group, and are described above. The phosphonic acid is then transformed into the ester amidate product 2.3, by reaction with the hydroxy compound $R^3OH$, in which the group $R^3$ is aryl, heteroaryl, alkyl, cycloalkyl, haloalkyl etc, using the same coupling procedures (carbodiimide, Aldrithiol-2, PYBOP, Mitsunobu reaction etc) described in Scheme 1 for the coupling of amines and phosphonic acids.

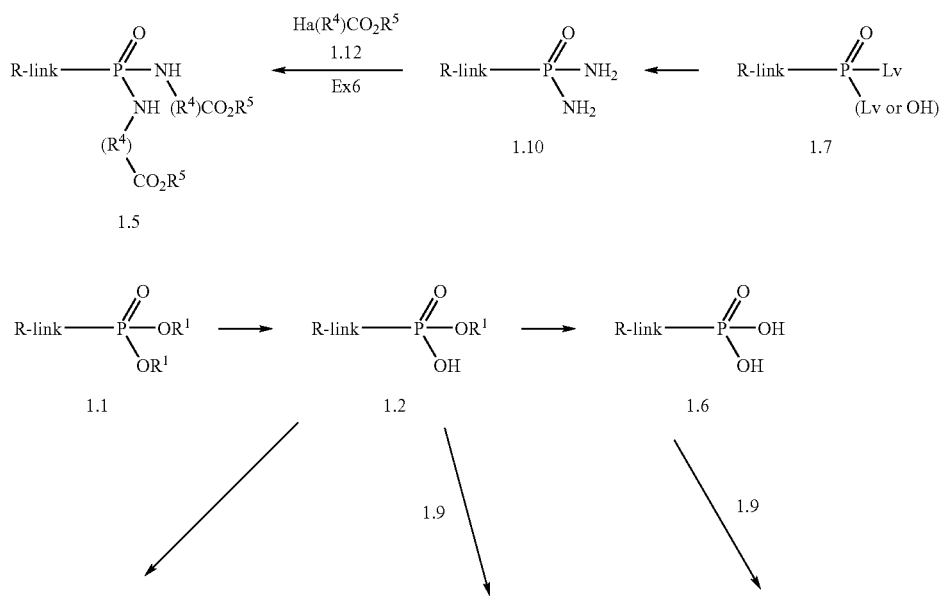

-continued
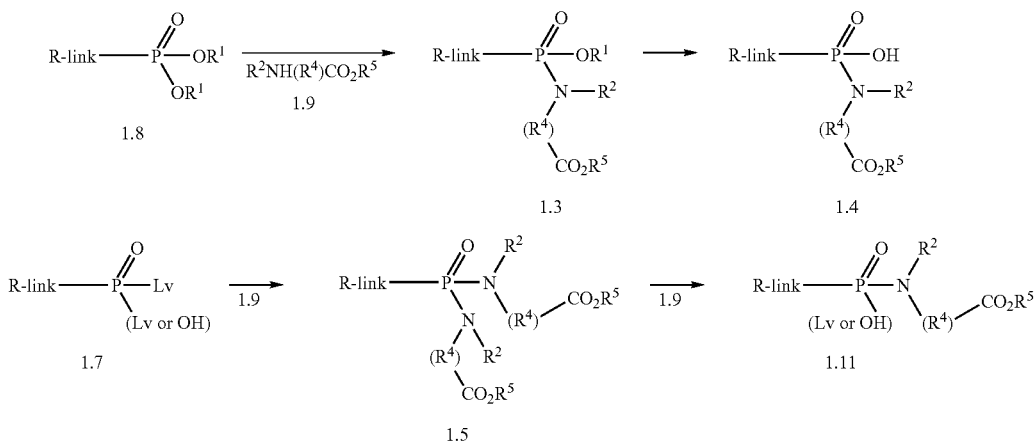
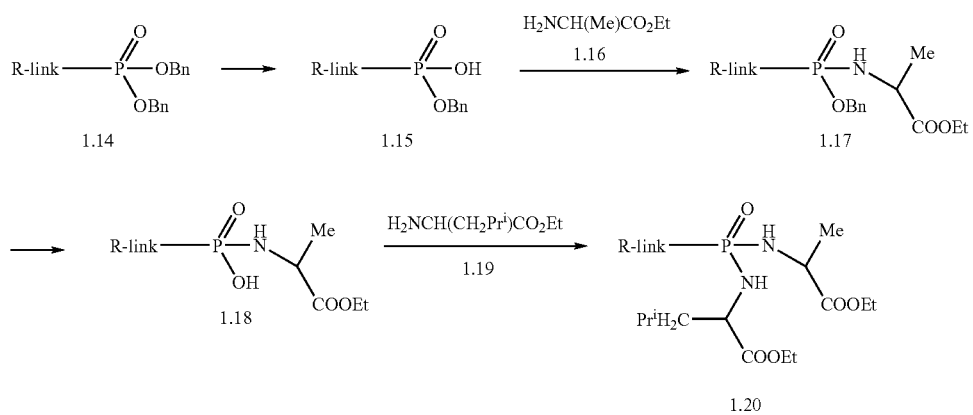
Scheme 1 Example 1
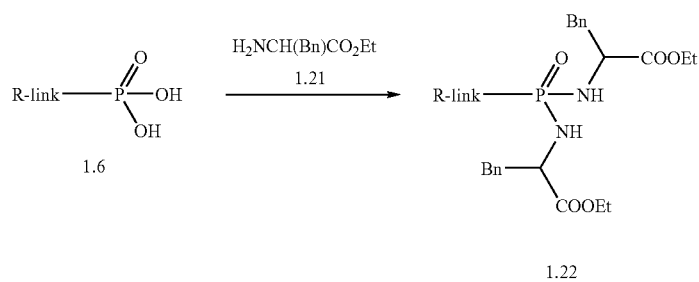
Scheme 1 Example 2
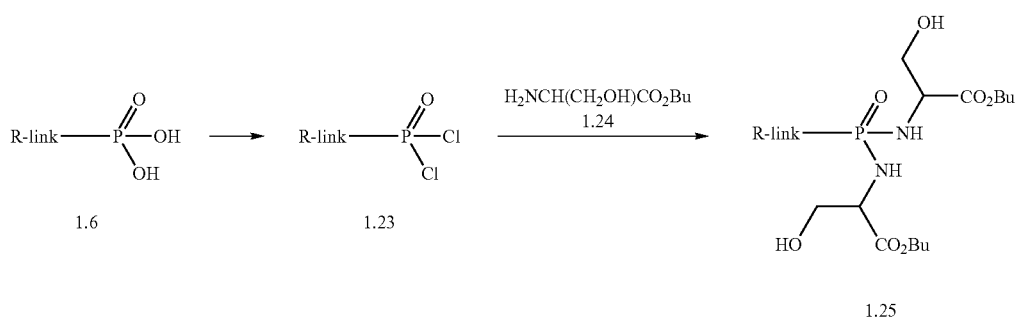
Scheme 1 Example 3

Scheme 1 Example 4
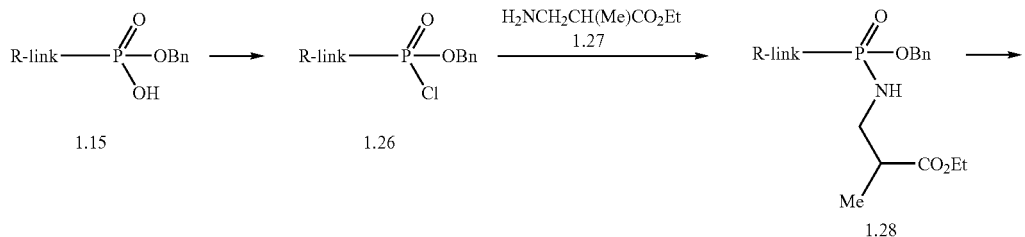
Scheme 1 Example 5
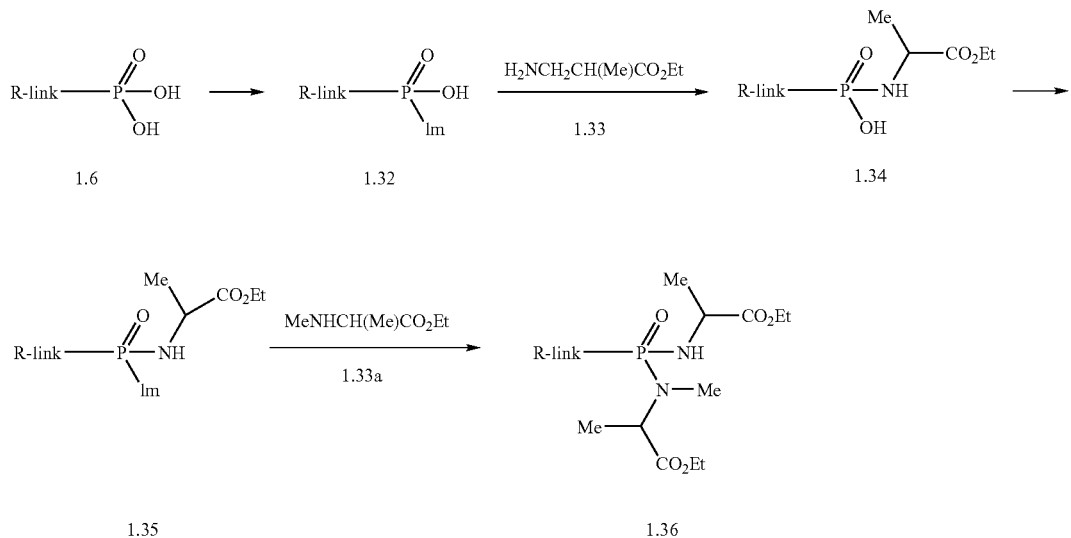
Scheme 1 Example 6
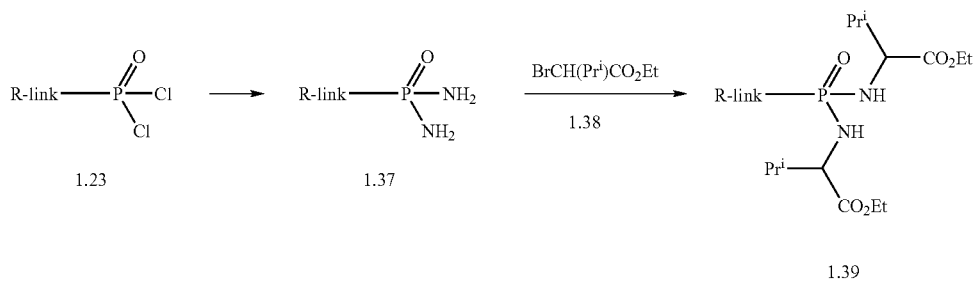

Scheme 1 Example 7

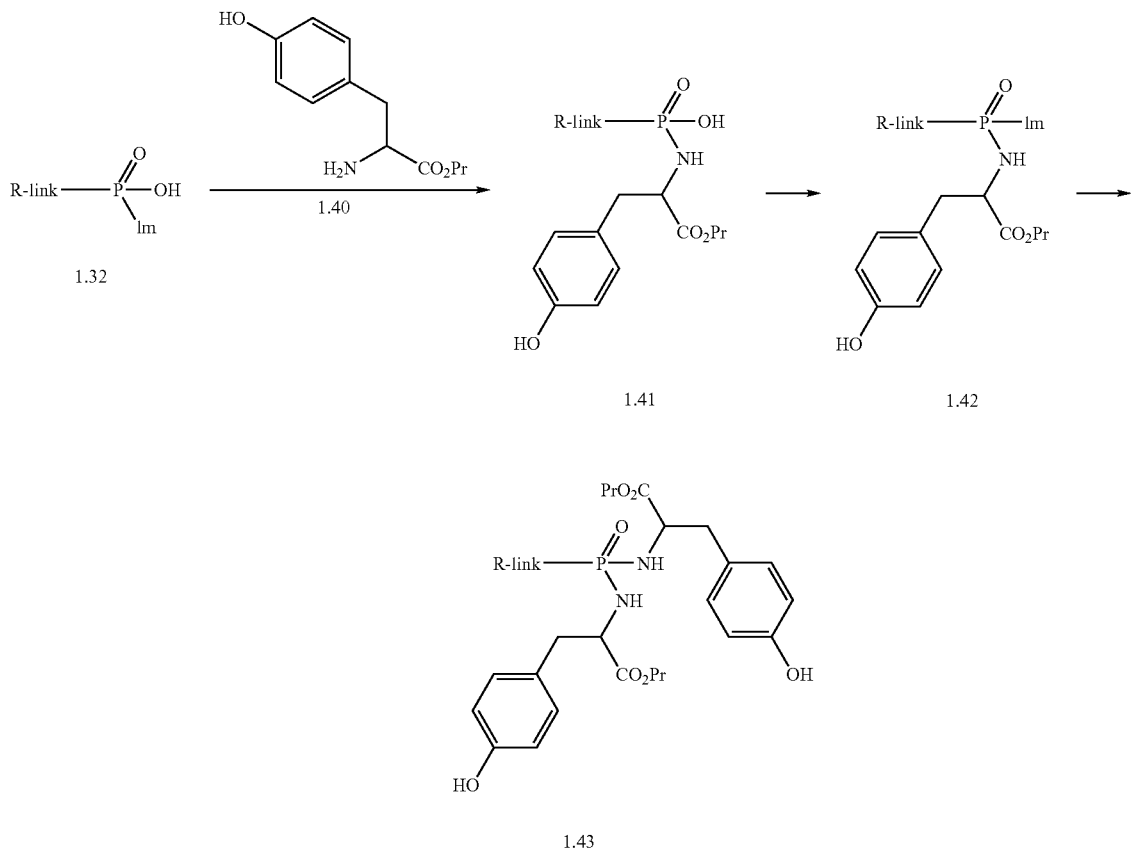

Examples of this method are shown in Scheme 2, Examples and 2 and 3. In the sequence shown in Example 2, a monobenzyl phosphonate 2.11 is transformed by reaction with ethyl alaninate, using one of the methods described above, into the monoamidate 2.12. The benzyl group is then removed by catalytic hydrogenation in ethylacetate solution over a 5% palladium on carbon catalyst, to afford the phosphonic acid amidate 2.13. The product is then reacted in dichloromethane solution at ambient temperature with equimolar amounts of 1-(dimethylaminopropyl)-3-ethylcarbodiimide and trifluoroethanol 2.14, for example as described in Tet. Lett., 2001, 42, 8841, to yield the amidate ester 2.15.

In the sequence shown in Scheme 2, Example 3, the monoamidate 2.13 is coupled, in tetrahydrofuran solution at ambient temperature, with equimolar amounts of dicyclohexyl carbodiimide and 4-hydroxy-N-methylpiperidine 2.16, to produce the amidate ester product 2.17.

Using the above procedures, but employing, in place of the ethyl alaninate product 2.12 different monoacids 2.2, and in place of trifluoroethanol 2.14 or 4-hydroxy-N-methylpiperidine 2.16, different hydroxy compounds $R^3OH$, the corresponding products 2.3 are obtained.

Alternatively, the activated phosphonate ester 1.8 is reacted with ammonia to yield the amidate 2.4. The product is then reacted, as described in Scheme 1, with a haloester 2.5, in the presence of a base, to produce the amidate product 2.6. If appropriate, the nature of the $R^1$ group is changed, using the procedures described above, to give the product 2.3. The method is illustrated in Scheme 2, Example 4. In this sequence, the monophenyl phosphoryl chloride 2.18 is reacted, as described in Scheme 1, with ammonia, to yield the amino product 2.19. This material is then reacted in N-methylpyrrolidinone solution at 170° with butyl 2-bromo-3-phenylpropionate 2.20 and potassium carbonate, to afford the amidate product 2.21.

Using these procedures, but employing, in place of butyl 2-bromo-3-phenylpropionate 2.20, different haloesters 2.5, the corresponding products 2.6 are obtained.

The monoamidate products 2.3 are also prepared from the doubly activated phosphonate derivatives 1.7. In this procedure, examples of which are described in Synlett., 1998, 1, 73, the intermediate 1.7 is reacted with a limited amount of the aminoester 1.9 to give the mono-displacement product 1.11. The latter compound is then reacted with the hydroxy compound $R^3OH$ in a polar organic solvent such as dimethylformamide, in the presence of a base such as diisopropylethylamine, to yield the monoamidate ester 2.3.

The method is illustrated in Scheme 2, Example 5. In this method, the phosphoryl dichloride 2.22 is reacted in dichloromethane solution with one molar equivalent of ethyl N-methyl tyrosinate 2.23 and dimethylaminopyridine, to generate the monoamidate 2.24. The product is then reacted with phenol 2.25 in dimethylformamide containing potassium carbonate, to yield the ester amidate product 2.26.

Using these procedures, but employing, in place of ethyl N-methyl tyrosinate 2.23 or phenol 2.25, the aminoesters 1.9 and/or the hydroxy compounds $R^3OH$, the corresponding products 2.3 are obtained.

Scheme 2
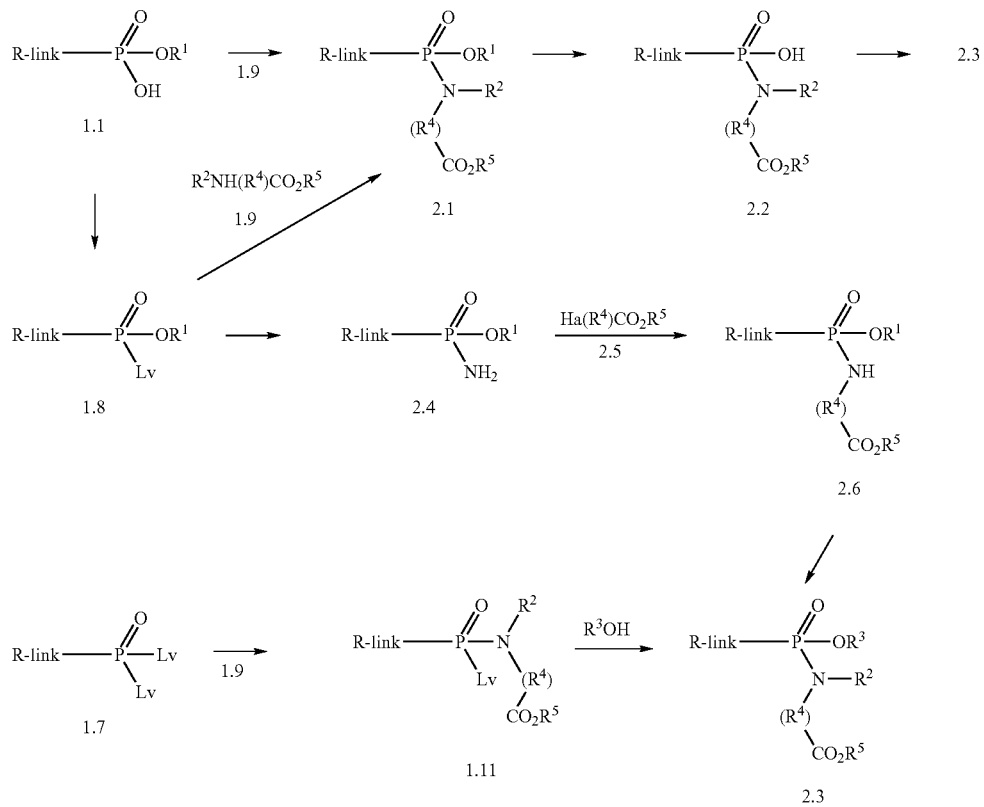
Scheme 2 Example 1
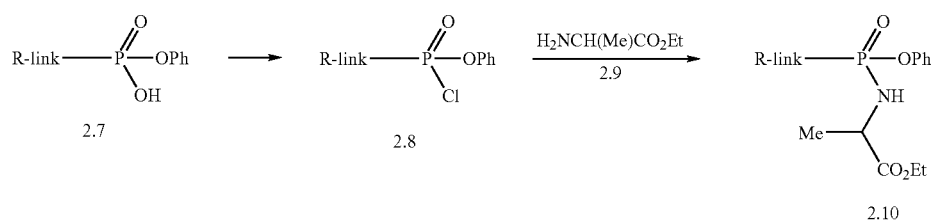
Scheme 2 Example 2
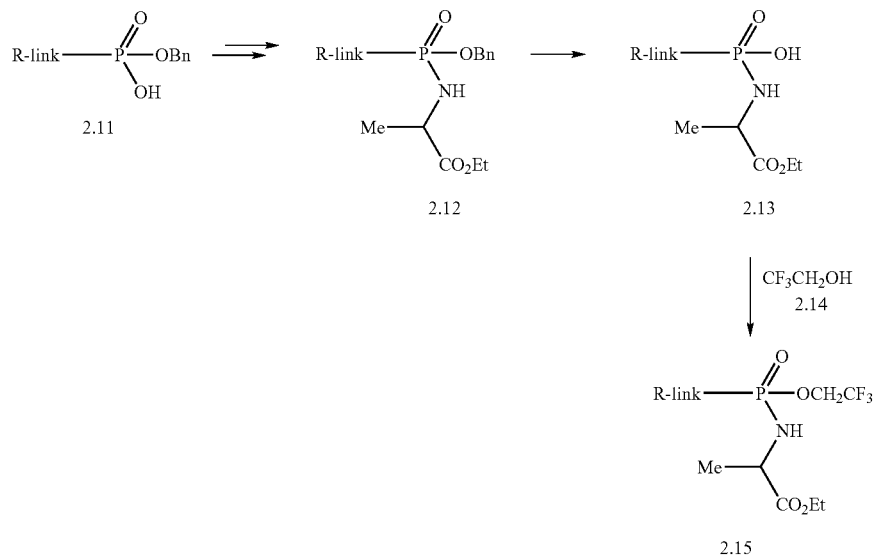

-continued
Scheme 2 Example 3

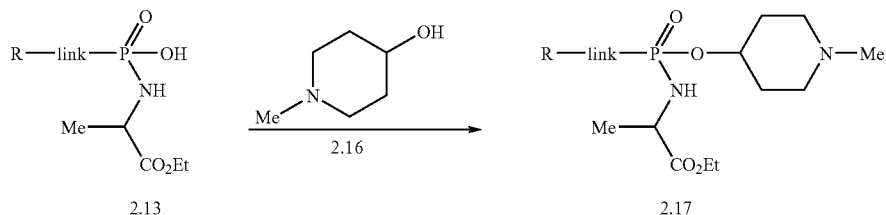

Scheme 2 Example 5

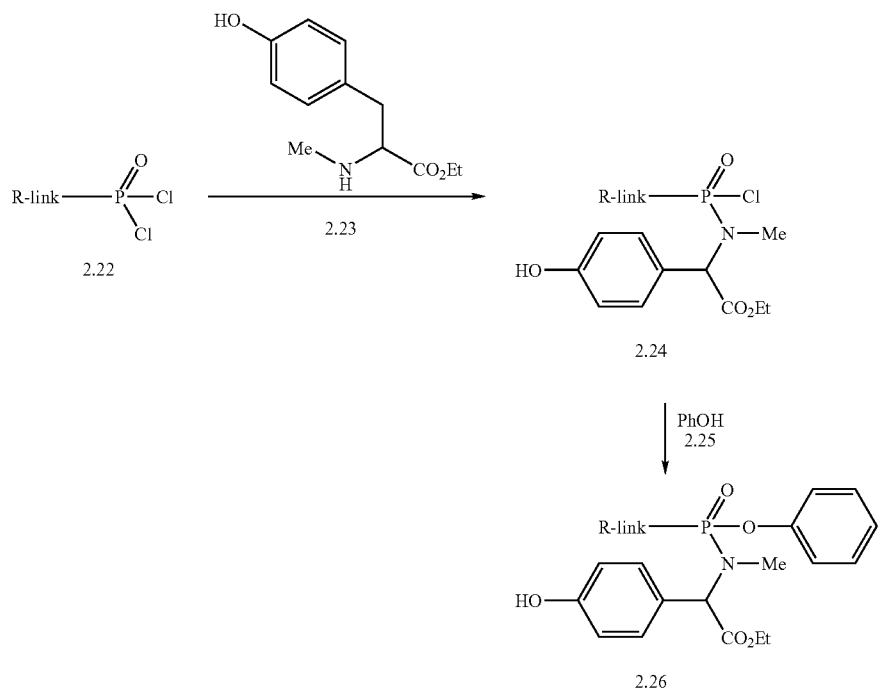

Scheme 3 illustrates methods for the preparation of carboalkoxy-substituted phosphonate diesters in which one of the ester groups incorporates a carboalkoxy substituent.

In one procedure, a phosphonate monoester 1.1, prepared as described above, is coupled, using one of the methods described above, with a hydroxyester 3.1, in which the groups $R^4$ and $R^5$ are as described in Scheme 1. For example, equimolar amounts of the reactants are coupled in the presence of a carbodiimide such as dicyclohexyl carbodiimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 3, Example 1. In this method, a monophenyl phosphonate 3.9 is coupled, in dichloromethane solution in the presence of dicyclohexyl carbodiimide, with ethyl 3-hydroxy-2-methylpropionate 3.10 to yield the phosphonate mixed diester 3.11.

Using this procedure, but employing, in place of ethyl 3-hydroxy-2-methylpropionate 3.10, different hydroxyesters 3.1, the corresponding products 3.2 are obtained.

The conversion of a phosphonate monoester 1.1 into a mixed diester 3.2 is also accomplished by means of a Mitsunobu coupling reaction with the hydroxyester 3.1, as described in Org. Lett., 2001, 643. In this method, the reactants 1.1 and 3.1 are combined in a polar solvent such as tetrahydrofuran, in the presence of a triarylphosphine and a dialkyl azodicarboxylate, to give the mixed diester 3.2. The $R^1$ substituent is varied by cleavage, using the methods described previously, to afford the monoacid product 3.3. The product is then coupled, for example using methods described above, with the hydroxy compound $R^3OH$, to give the diester product 3.4.

The procedure is illustrated in Scheme 3, Example 2. In this method, a monoallyl phosphonate 3.12 is coupled in tetrahydrofuran solution, in the presence of triphenylphosphine and diethylazodicarboxylate, with ethyl lactate 3.13 to give the mixed diester 3.14. The product is reacted with tris(triphenylphosphine) rhodium chloride (Wilkinson catalyst) in acetonitrile, as described previously, to remove the allyl group and produce the monoacid product 3.15. The latter compound is then coupled, in pyridine solution at ambient temperature, in the presence of dicyclohexyl carbodiimide, with one molar equivalent of 3-hydroxypyridine 3.16 to yield the mixed diester 3.17.

Using the above procedures, but employing, in place of the ethyl lactate 3.13 or 3-hydroxypyridine, a different hydroxyester 3.1 and/or a different hydroxy compound $R^3OH$, the corresponding products 3.4 are obtained.

The mixed diesters 3.2 are also obtained from the monoesters 1.1 via the intermediacy of the activated monoesters 3.5. In this procedure, the monoester 1.1 is converted into the activated compound 3.5 by reaction with, for example, phosphorus pentachloride, as described in J. Org. Chem., 2001, 66, 329, or with thionyl chloride or oxalyl chloride (Lv=Cl), or with triisopropylbenzenesulfonyl chloride in pyridine, as described in Nucleosides and Nucleotides, 2000, 19, 1885, or with carbonyl diimidazole, as described in J. Med. Chem., 2002, 45, 1284. The resultant activated monoester is then reacted with the hydroxyester 3.1, as described above, to yield the mixed diester 3.2.

The procedure is illustrated in Scheme 3, Example 3. In this sequence, a monophenyl phosphonate 3.9 is reacted, in acetonitrile solution at 70°, with ten equivalents of thionyl chloride, so as to produce the phosphoryl chloride 3.19. The product is then reacted with ethyl 4-carbamoyl-2-hydroxybutyrate 3.20 in dichloromethane containing triethylamine, to give the mixed diester 3.21.

Using the above procedures, but employing, in place of ethyl 4-carbamoyl-2-hydroxybutyrate 3.20, different hydroxyesters 3.1, the corresponding products 3.2 are obtained.

The mixed phosphonate diesters are also obtained by an alternative route for incorporation of the $R^3O$ group into intermediates 3.3 in which the hydroxyester moiety is already incorporated. In this procedure, the monoacid intermediate 3.3 is converted into the activated derivative 3.6 in which Lv is a leaving group such as chloro, imidazole, and the like, as previously described. The activated intermediate is then reacted with the hydroxy compound $R^3OH$, in the presence of a base, to yield the mixed diester product 3.4.

The method is illustrated in Scheme 3, Example 4. In this sequence, the phosphonate monoacid 3.22 is reacted with trichloromethanesulfonyl chloride in tetrahydrofuran containing collidine, as described in J. Med. Chem., 1995, 38, 4648, to produce the trichloromethanesulfonyloxy product 3.23. This compound is reacted with 3-(morpholinomethyl) phenol 3.24 in dichloromethane containing triethylamine, to yield the mixed diester product 3.25.

Using the above procedures, but employing, in place of with 3-(morpholinomethyl)phenol 3.24, different carbinols $R^3OH$, the corresponding products 3.4 are obtained.

The phosphonate esters 3.4 are also obtained by means of alkylation reactions performed on the monoesters 1.1. The reaction between the monoacid 1.1 and the haloester 3.7 is performed in a polar solvent in the presence of a base such as diisopropylethylamine, as described in Anal. Chem., 1987, 59, 1056, or triethylamine, as described in J. Med. Chem., 1995, 38, 1372, or in a non-polar solvent such as benzene, in the presence of 18-crown-6, as described in Syn. Comm., 1995, 25, 3565.

The method is illustrated in Scheme 3, Example 5. In this procedure, the monoacid 3.26 is reacted with ethyl 2-bromo-3-phenylpropionate 3.27 and diisopropylethylamine in dimethylformamide at 80° C. to afford the mixed diester product 3.28.

Using the above procedure, but employing, in place of ethyl 2-bromo-3-phenylpropionate 3.27, different haloesters 3.7, the corresponding products 3.4 are obtained.

Scheme 3

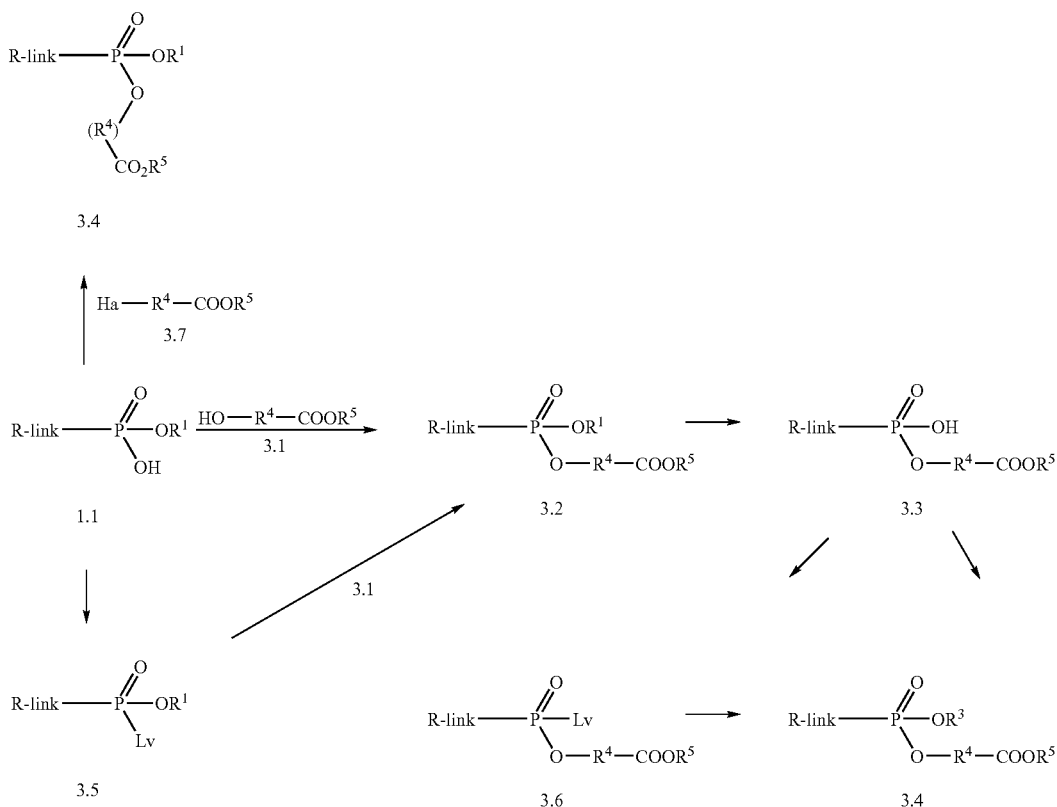

-continued
Scheme 3 Example 1
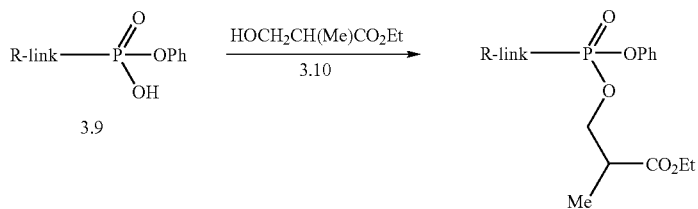
Scheme 3 Example 2
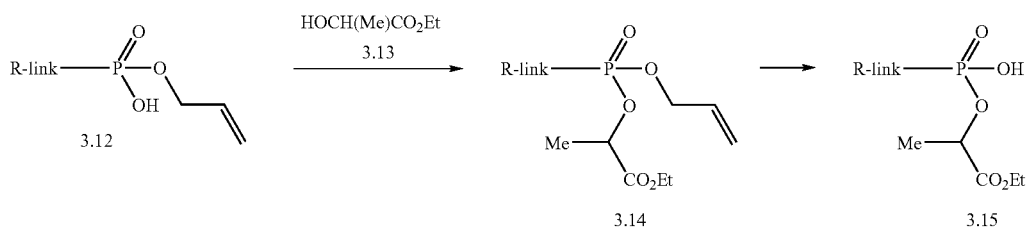
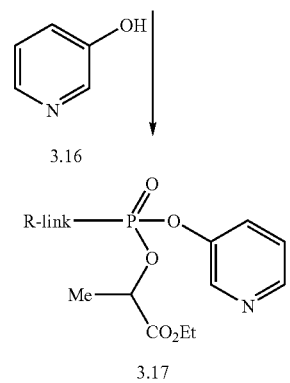
Scheme 3 Example 3
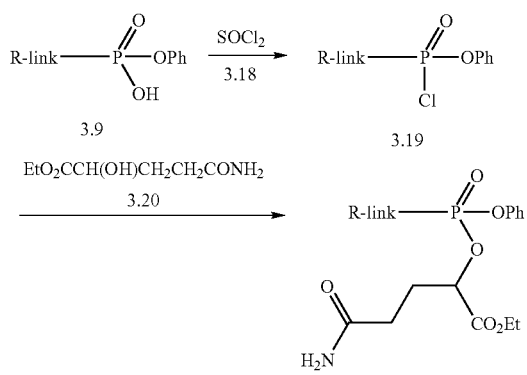
Scheme 3 Example 4
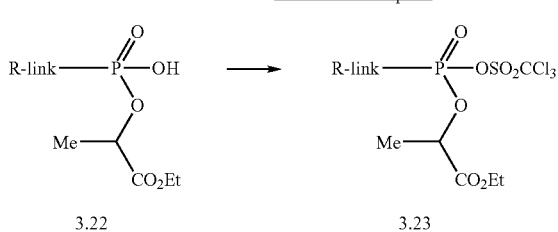

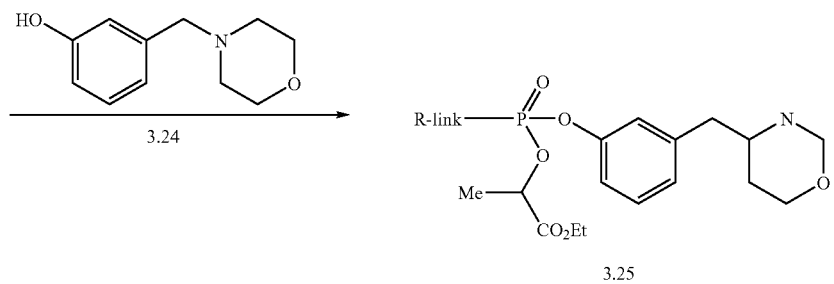

3.24 → 3.25

Scheme 3 Example 5

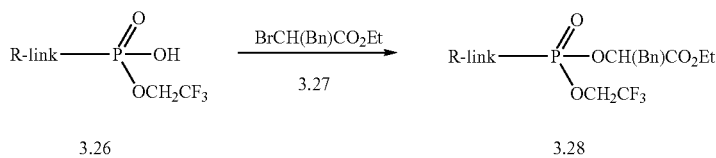

3.26 → 3.28

Scheme 4 illustrates methods for the preparation of phosphonate diesters in which both the ester substituents incorporate carboalkoxy groups.

The compounds are prepared directly or indirectly from the phosphonic acids 1.6. In one alternative, the phosphonic acid is coupled with the hydroxyester 4.2, using the conditions described previously in Schemes 1-3, such as coupling reactions using dicyclohexyl carbodiimide or similar reagents, or under the conditions of the Mitsunobu reaction, to afford the diester product 4.3 in which the ester substituents are identical.

This method is illustrated in Scheme 4, Example 1. In this procedure, the phosphonic acid 1.6 is reacted with three molar equivalents of butyl lactate 4.5 in the presence of Aldrithiol-2 and triphenyl phosphine in pyridine at ca. 70°, to afford the diester 4.6.

Using the above procedure, but employing, in place of butyl lactate 4.5, different hydroxyesters 4.2, the corresponding products 4.3 are obtained.

Alternatively, the diesters 4.3 are obtained by alkylation of the phosphonic acid 1.6 with a haloester 4.1. The alkylation reaction is performed as described in Scheme 3 for the preparation of the esters 3.4.

This method is illustrated in Scheme 4, Example 2. In this procedure, the phosphonic acid 1.6 is reacted with excess ethyl 3-bromo-2-methylpropionate 4.7 and diisopropylethylamine in dimethylformamide at ca. 80°, as described in Anal. Chem., 1987, 59, 1056, to produce the diester 4.8.

Using the above procedure, but employing, in place of ethyl 3-bromo-2-methylpropionate 4.7, different haloesters 4.1, the corresponding products 4.3 are obtained.

The diesters 4.3 are also obtained by displacement reactions of activated derivatives 1.7 of the phosphonic acid with the hydroxyesters 4.2. The displacement reaction is performed in a polar solvent in the presence of a suitable base, as described in Scheme 3. The displacement reaction is performed in the presence of an excess of the hydroxyester, to afford the diester product 4.3 in which the ester substituents are identical, or sequentially with limited amounts of different hydroxyesters, to prepare diesters 4.3 in which the ester substituents are different.

The methods are illustrated in Scheme 4, Examples 3 and 4. As shown in Example 3, the phosphoryl dichloride 2.22 is reacted with three molar equivalents of ethyl 3-hydroxy-2-(hydroxymethyl)propionate 4.9 in tetrahydrofuran containing potassium carbonate, to obtain the diester product 4.10.

Using the above procedure, but employing, in place of ethyl 3-hydroxy-2-(hydroxymethyl)propionate 4.9, different hydroxyesters 4.2, the corresponding products 4.3 are obtained.

Scheme 4, Example 4 depicts the displacement reaction between equimolar amounts of the phosphoryl dichloride 2.22 and ethyl 2-methyl-3-hydroxypropionate 4.11, to yield the monoester product 4.12. The reaction is conducted in acetonitrile at 70° in the presence of diisopropylethylamine. The product 4.12 is then reacted, under the same conditions, with one molar equivalent of ethyl lactate 4.13, to give the diester product 4.14.

Using the above procedures, but employing, in place of ethyl 2-methyl-3-hydroxypropionate 4.11 and ethyl lactate 4.13, sequential reactions with different hydroxyesters 4.2, the corresponding products 4.3 are obtained.

Scheme 4

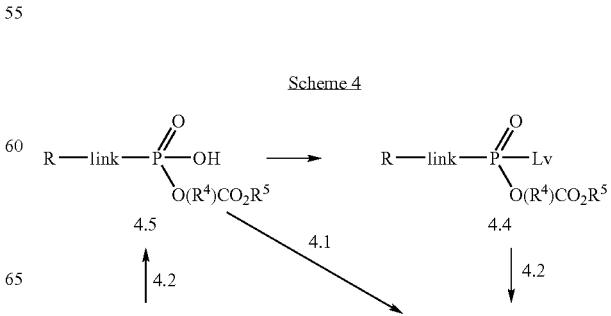

-continued

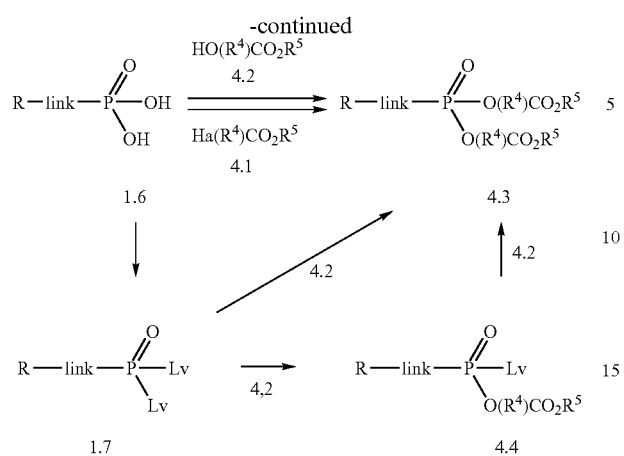

Scheme 4 Example 1

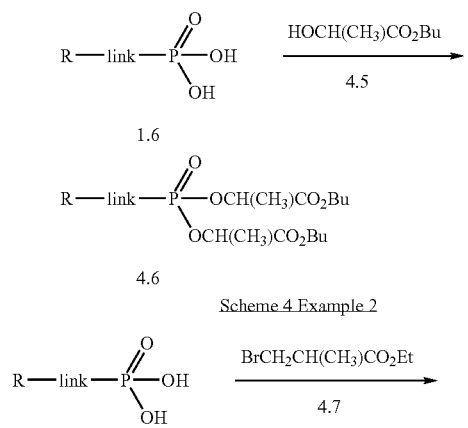

Scheme 4 Example 2

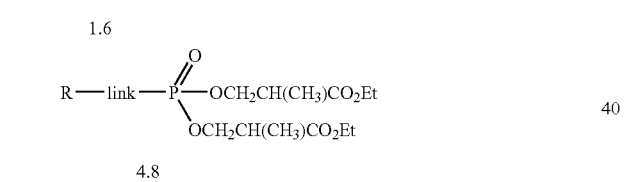

Scheme 4 Example 3

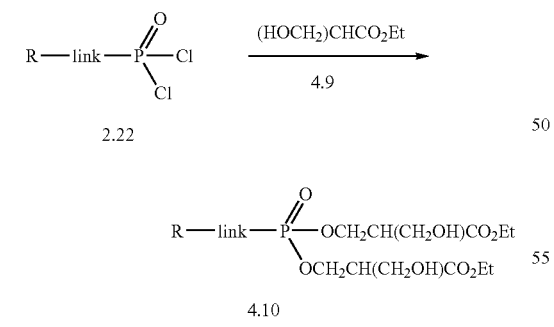

Scheme 4 Example 3

-continued

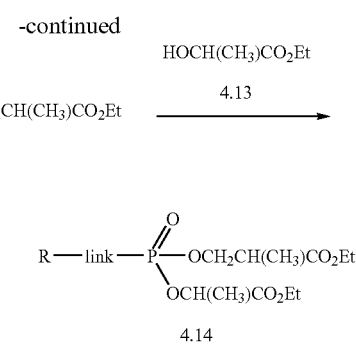

2,2-Dimethyl-2-aminoethylphosphonic acid intermediates can be prepared by the route in Scheme 5. Condensation of 2-methyl-2-propanesulfinamide with acetone give sulfinyl imine 11 (*J. Org. Chem.* 1999, 64, 12). Addition of dimethyl methylphosphonate lithium to 11 afford 12. Acidic methanolysis of 12 provide amine 13. Protection of amine with Cbz group and removal of methyl groups yield phosphonic acid 14, which can be converted to desired 15 (Scheme 5a) using methods reported earlier on. An alternative synthesis of compound 14 is also shown in Scheme 5b. Commercially available 2-amino-2-methyl-1-propanol is converted to aziridines 16 according to literature methods (*J. Org. Chem.* 1992, 57, 5813; *Syn. Lett.* 1997, 8, 893). Aziridine opening with phosphite give 17 (*Tetrahedron Lett.* 1980, 21, 1623). Reprotection) of 17 affords 14.

Scheme 5a

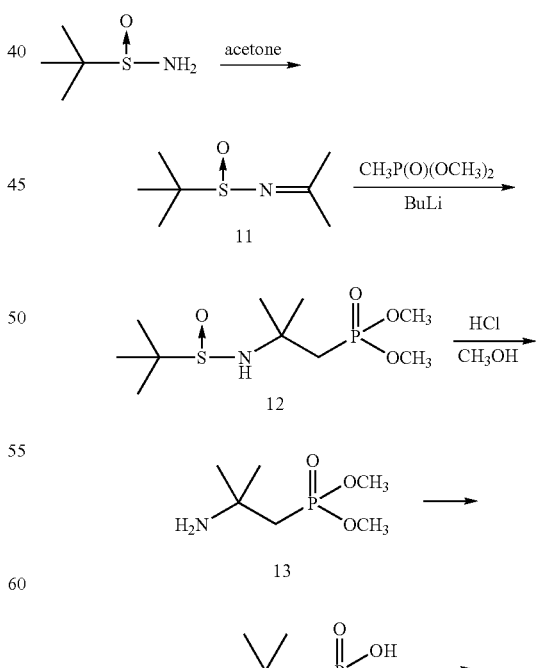

-continued

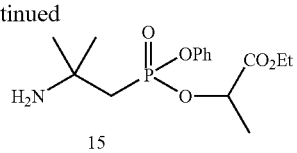

15

Scheme 5b

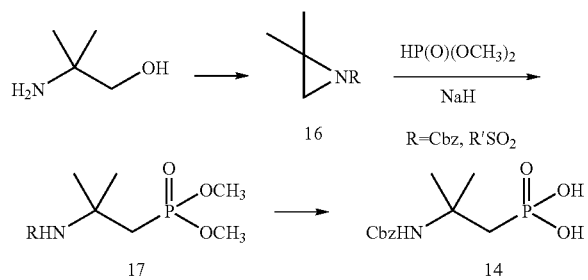

Biological Activity of HIV-Integrase Inhibitor Compounds

Representative compounds of the invention are tested for biological activity by methods including anti-HIV assay, measuring inhibition of HIV-integrase strand transfer catalysis, and cytotoxicity. See: Wolfe, et al *J. Virol.* (1996) 70:1424-1432; Hazuda, et al *Nucleic Acids Res.* (1994) 22:1121-22; Hazuda, et al *J. Virol.* (1997) 71:7005-7011; Hazuda, et al *Drug Design and Discovery* (1997) 15:17-24; and Hazuda, et al *Science* (2000) 287:646-650. The antiviral activity of a compound of the invention can be determined using pharmacological models which are well known in the art. While many of the compounds of the present invention demonstrate inhibition of integration of HIV reverse-transcribed DNA, there may be other mechanisms of action whereby HIV replication or proliferation is affected. The compounds of the invention may be active via inhibition of HIV-integrase or other enzymes associated with HIV infection, AIDS, or ARC. Furthermore, the compounds of the invention may have significant activity against other viral diseases. Thus, the specific assays embodied in Examples x-y are not meant to limit the present invention to a specific mechanism of action.

Pharmaceutical Formulations and Routes of Administration

The compounds of the invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more pharmaceutically acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpes viruses (CMV, HSV 1, HSV 2, VZV, and the like), retroviruses, adenoviruses and the like. The controlled release formulations can be used to treat HIV infections and related conditions such as tuberculosis, malaria, pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus (HTLV)-I and IV and HIV-2 infections. The invention accordingly provides pharmaceutical formulations for use in the treatment or prophylaxis of the above-mentioned human or veterinary conditions and microbial infections.

Combination Therapy

The compounds of the invention may be employed in combination with other therapeutic agents for the treatment or prophylaxis of the infections or conditions indicated above. Examples of such further therapeutic agents include agents that are effective for the treatment or prophylaxis of viral, parasitic or bacterial infections or associated conditions or for treatment of tumors or related conditions include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5,1-jk)-(1,4)-benzodiazepin-2 (1H)-thione (TIBO), 2'-nor-cyclicGMP, 6-methoxypurine arabinoside (ara-M), 6-methoxypurine arabinoside 2'-O-valerate, cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI), acyclic nucleosides such as acyclovir, penciclovir, famciclovir, ganciclovir, HPMPC, PMEA, PMEG, PMPA, PMPDAP, FPMPA, HPMPA, HPMPDAP, (2R, 5R)-9->tetrahydro-5-(phosphonomethoxy)-2-furanyladenine, (2R, 5R)-1->tetrahydro-5-(phosphonomethoxy)-2-furanylthymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), antibacterial agents including bactericidal fluoroquinolones (ciprofloxacin, pefloxacin and the like), aminoglycoside bactericidal antibiotics (streptomycin, gentamicin, amicacin and the like) β-lactamase inhibitors (cephalosporins, penicillins and the like), other antibacterials including tetracycline, isoniazid, rifampin, cefoperazone, claithromycin and azithromycin, antiparasite or antifungal agents including pentamidine (1,5-bis(4'-aminophenoxy)pentane), 9-deaza-inosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin, renal excretion inhibitors such as probenicid, nucleoside transport inhibitors such as dipyridamole, dilazep and nitrobenzylthioinosine, immunomodulators such as FK506, cyclosporin A, thymosin α-1, cytokines including TNF and TGF-β, interferons including IFN-α, IFN-β, and IFN-γ, interleukins including various interleukins, macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and the like.

Assay Protocol Examples

HIV Integrase Assay (IC$_{50}$ Determination)

IC50 (also referred to as CC50, CD50, TC50, TD50 or cytotoxicity) is the inhibitory concentration that reduces cellular growth or viability of uninfected cells by 50%. HIV Integrase assay is carried out in Reacti-Bind High Binding Capacity Streptavidin coated plates (Pierce #15502) in 100 µl reactions. The wells of the plate are rinsed once with PBS. Each well is then coated at room temperature for 1 h with 100 µl of 0.14 µM double-stranded, 5'-biotin labelled donor DNA.

After coating, the plate is washed twice with PBS. 3' Processing of the donor DNA is started by adding 80 µl of Integrase/buffer mixture (25 mM HEPES, pH 7.3, 12.5 mM DTT, 93.75 mM NaCl, 12.5 mM MgCl$_2$, 1.25% Glycerol, 0.3125 µM integrase) to each well. 3'-Processing is allowed to proceed for 30 min at 37° C., after which, 10 µl of test compound and 10 µl of 2.5 µM 3'-DIG (digitoxigenin)-labeled, double-stranded Target DNA are added to each well to allow strand transfer to proceed for 30 min at 37° C. The plate is then washed three times with 2× SSC for 5 min and rinsed once with PBS. For detection of integrated product, 100 µl of a 1/2000 dilution of HRP-conjugated anti-DIG antibody (Pierce #31468) are added to each well and incubated for 1 hour. The plate is then washed three times for 5 min each, with 0.05% Tween-20 in PBS. For signal development and amplification, 100 µl of SuperSignal ELISA Femto Substrate (Pierce #37075) are added to each well. Chemiluminescence (in relative light units) is read immediately at 425 nm in the SPECTRAmax GEMINI Microplate Spectrophotometer using the end point mode at 5 sec per well. For IC$_{50}$ determinations, eight concentrations of test compounds in a 1/2.2 dilution series are used. Certain compounds of the invention, including those in Tables 1-5, had a strand transfer IC$_{50}$ less than about 10 µM.

Anti-HIV Assay (EC$_{50}$ Determination)

EC50 (also commonly referred to as ED50 or IC50) is the effective concentration that inhibits 50% of viral production, 50% of viral infectivity, or 50% of the virus-induced cytopathic effect.

Anti-HIV assay is carried out in 96-well Clear Bottom Black Assay Plate (Costar # 3603) in 100 µl of culture medium, using the CellTiter-Glo™ Reagent (Promega # G7570) for signal detection. MT-2 cells (1.54×10$^4$ cells) are infected with wild-type virus at an m.o.i. (multiplicity of infection, i.e. the ratio between the number of infectious viral particles and cells in an assay) of about 0.025, and grown in the presence of various drug concentrations (serial 5-fold dilutions) in 100 µl of RPMI medium containing 10% FBS, 2% glutamine, 1% HEPES and 1% penicillin/streptomycin for 5 days. At the end of the incubation period, 100 µl of CellTiter-Glo™ Reagent is added to each well in the Assay Plate and the chemiluminescence (in relative light units) is measured after 10 mins of incubation with the Wallac Victor$^2$ 1420 MultiLabel Counter. Certain compounds of the invention, including those in Tables 1-5, had an anti-HIV MT2 EC$_{50}$ less than about 10 µM.

Cytotoxicity Assay (CC$_{50}$ Determination)

For the determination of compound cytotoxicity, the plate and reagents are the same as those of anti-HIV assay. Uninfected MT-2 cells (1.54×10$^4$ cells) are grown in the presence of various drug concentrations (serial 2-fold dilutions) in 100 µl of RPMI medium containing 10% FBS, 2% glutamine, 1% HEPES and 1% penicillin/streptomycin for 5 days. At the end of the incubation period, 100 µl of CellTiter-Glo™ Reagent is added to each well in the assay plate and the chemiluminescence (in relative light units) is measured after 10 mins of incubation with the Wallac Victor$^2$ 1420 MultiLabel Counter.

The invention claimed is:

1. A compound having the formula:

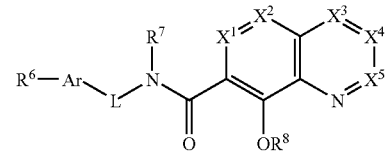

or a pharmaceutically acceptable salt thereof, and including enol and tautomeric resonance isomers;
wherein:
$X^1$ is NR, or N;
$X^2$ is CR$^2$;
$X^3$ is CR$^3$; $X^4$ is CR$^4$; $X^5$ is CR$^5$;
$R^3$, $R^4$, $R^5$, $R^6$, $R^7$ and $R^8$ are independently selected from H, F, Cl, Br, I, OH, amino (—NH$_2$), ammonium (—NH$_3^+$), alkylamino, dialkylamino, trialkylammonium, C$_1$-C$_8$ alkyl, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), formyl (—CHO), ester (—C(=O)OR), amido (—C(=O)NR$_2$), 5-7 membered ring lactam, 5-7 membered ring lactone, nitrile (—CN), azido (—N$_3$), nitro (—NO$_2$), C$_1$-C$_8$ alkoxy (—OR), C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, phosphonate, phosphate, polyethyleneoxy, and a phosphonate prodrug moiety;

R$^2$ is selected from H, F, Cl, Br, I, OH, amino (—NH$_2$), ammonium (—NH$_3^+$) alkylamino, dialkylamino, trialkylammonium, C$_1$-C$_8$ alkyl, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), formyl (—CHO), ester (—C(=O)OR), amido (—C(=O)NR$_2$), 5-7 membered ring lactam, 5-7 membered ring lactone, nitrile (—CN), azido (—N$_3$), nitro (—NO$_2$), C$_1$-C$_8$ alkoxy (—OR), C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, phosphonate, phosphate, polyethyleneoxy, a phosphonate prodrug moiety, OC(=O)OR, OC(=O)NR$_2$, OC(=O)R, OSO$_2$NR$_2$ (sulfamate), NR$_2$, NRSO$_2$R, SR, S(O)R, SO$_2$R or SO$_2$NR$_2$ (sulfonamide), lactam having the structures:

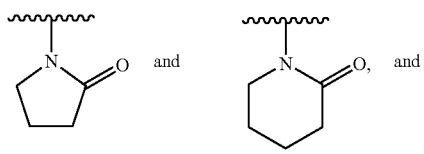

sultam having the structures:

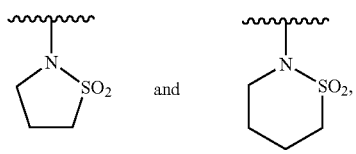

R is independently selected from H, C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl;

L is selected from a bond, O, S, NR, N—OR, C$_1$-C$_{12}$ alkylene, C$_1$-C$_{12}$ substituted alkylene, C$_2$-C$_{12}$ alkenylene, C$_2$-C$_{12}$ substituted alkenylene, C$_2$-C$_{12}$ alkynylene, C$_2$-C$_{12}$ substituted alkynylene, C(=O)NH, C(=O), S(=O)$_2$, C(=O)NH(CH$_2$)$_n$, and (CH$_2$CH$_2$O)$_n$, where n may be 1, 2, 3, 4, 5, or 6; and Ar is covalently attached to L and to one or more R$^6$ and Ar is selected from C$_6$-C$_{20}$ aryl, C$_6$-C$_{20}$ substituted aryl, C$_2$-C$_{20}$ heteroaryl, and C$_2$-C$_{20}$ substituted heteroaryl;

where at least one of R, R$^1$, R$^2$, R$^3$, R$^4$, R$^5$, R$^6$, R$^7$ and R$^8$ comprises a phosphonate group.

2. A compound according to claim 1 having the formula:

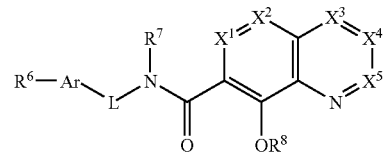

3. A compound according to claim 1 having the formula:

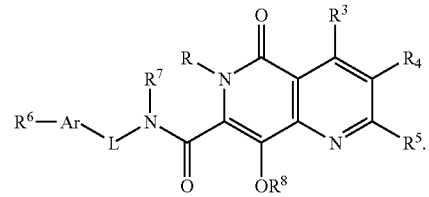

4. The compound of claim 1 wherein substituted alkylene, substituted alkenylene, substituted alkynylene, substituted aryl, and substituted heteroaryl are independently substituted with one or more substituents selected from F, Cl, Br, I, OH, amino (—NH$_2$), ammonium (—NH$_3^+$), alkylamino, dialkylamino, trialkylammonium, C$_1$-C$_8$ alkyl, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), ester (—C(=O)OR), amido (—C(=O)NR$_2$), 5-7 membered ring lactam, 5-7 membered ring lactone, nitrile (—CN), azido (—N$_3$), nitro (—NO$_2$), C$_1$-C$_8$ alkoxy (—OR), C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, phosphonate, phosphate, polyethyleneoxy, and a phosphonate prodrug moiety.

5. A compound of claim 1 wherein X$^2$ is CR$^2$ and R$^2$ is selected from H, OH, OC(=O)OR, OC(=O)NR$_2$, OC(=O)R, OSO$_2$NR$_2$ (sulfamate), NR$_2$, NRSO$_2$R, SR, S(O)R, SO$_2$R or SO$_2$NR$_2$ (sulfonamide), lactam having the structures:

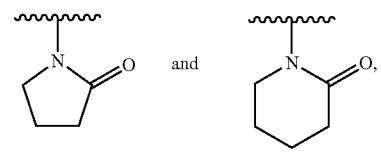

sultam having the structures:

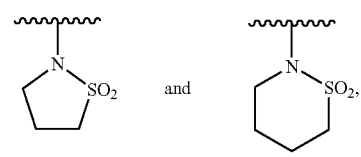

and a phosphonate prodrug moiety.

6. The compound of claim 1 wherein L is $CH_2$ and Ar is substituted phenyl.

7. The compound of claim 1 where L is $CH_2$ and Ar is 4-fluorophenyl.

8. The compound of claim 1 wherein at least one of $R^1$, $R^2$, $R^3$, $R^4$, $R^5$, $R^6$, $R^7$ and $R^8$ comprise a phosphonate prodrug moiety selected from the structures:

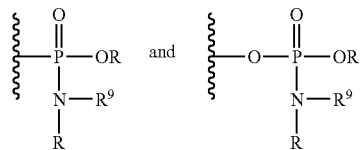

wherein $R^9$ is comprised of an ester, an amide, or a carbamate.

9. The compound of claim 1 wherein the phosphonate group has the structure:

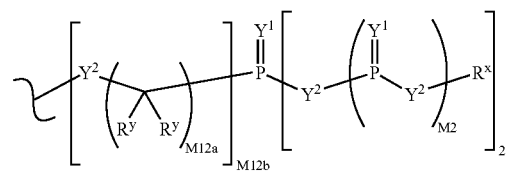

wherein:
$Y^1$ is independently O, S, $N(R^x)$, $N(O)(R^x)$, $N(OR^x)$, $N(O)(OR^x)$, or $N(N(R^x)(R^x))$;
$Y^2$ is independently a bond, O, $N(R^x)$, $N(O)(R^x)$, $N(OR^x)$, $N(O)(OR^x)$, $N(N(R^x)(R^x))$, —S(O)— (sulfoxide), —S(O)$_2$— (sulfone), —S— (sulfide), or —S—S— (disulfide);
M2 is 0, 1 or 2;
M12a is 1, 2, 3, 4, 5, 6, 7, 8, 9, 10, 11, or 12;
M12b is 0, 1, 2, 3, 4, 5, 6, 7, 8, 9, 10, 11, or 12;
$R^y$ is independently H, alkyl, substituted alkyl, aryl, substituted aryl, or a protecting group, or where taken together at a carbon atom, two vicinal $R^y$ groups form a carbocycle or a heterocycle; and
$R^x$ is independently H, alkyl, substituted alkyl, aryl, substituted aryl, or a protecting group, or the formula:

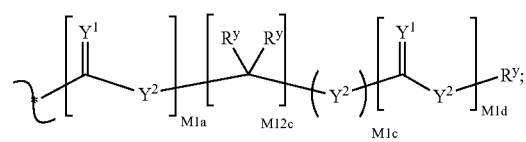

where M1a, M1c, and M1d are independently 0 or 1, and M12c is 0, 1, 2, 3, 4, 5, 6, 7, 8, 9, 10, 11 or 12.

10. The compound of claim 9 wherein the phosphonate group has the structure:

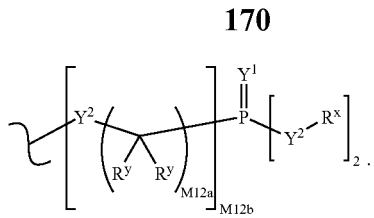

11. The compound of claim 10 wherein the phosphonate group has the structure:

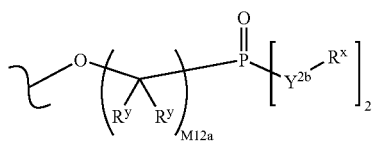

where $Y^{2b}$ is O or $N(R^x)$.

12. The compound of claim 10 wherein the phosphonate group has the structure:

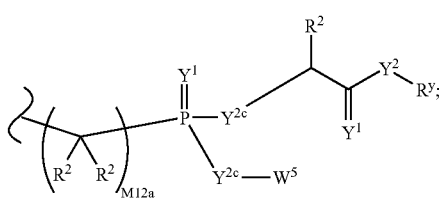

where $W^5$ is a carbocycle, and $Y^{2c}$ is O, $N(R^y)$ or S.

13. The compound of claim 12 wherein $W^5$ is selected from the structures:

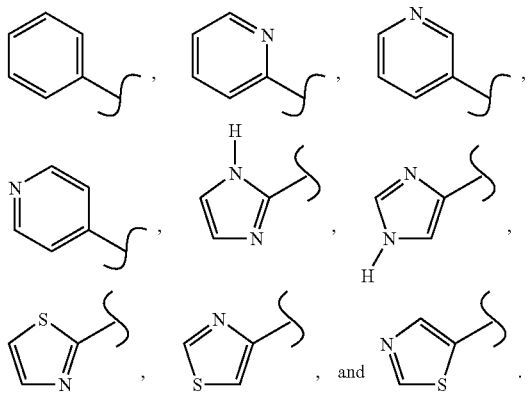

14. The compound of claim 9 wherein the phosphonate group has the structure:

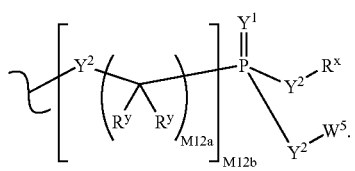

15. The compound of claim 14 wherein the phosphonate group has the structure:

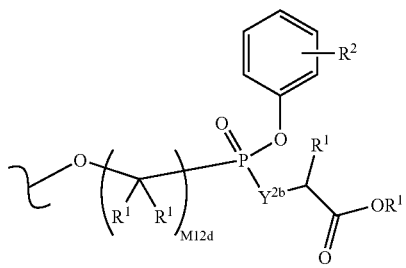

wherein $Y^{2b}$ is O or $N(R^x)$; M12d is 1, 2, 3, 4, 5, 6, 7 or 8; $R^1$ is H or $C_1$-$C_6$ alkyl; and the phenyl carbocycle is substituted with 0 to 3 $R^2$ groups where $R^2$ is $C_1$-$C_6$ alkyl or substituted alkyl.

16. The compound of claim 15 wherein the phosphonate group has the structure:

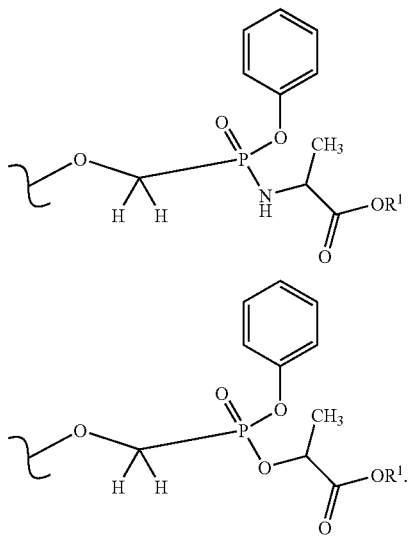

or

17. The compound of claim 9 wherein $R^x$ is selected from the structures:

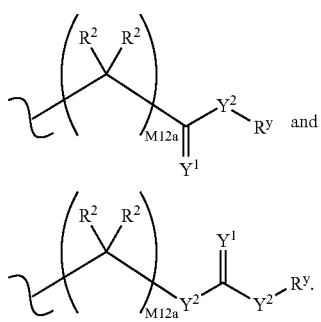

18. The compound of claim 17 wherein $X^2$ is $CR^2$ and $R^2$ is selected from the structures:

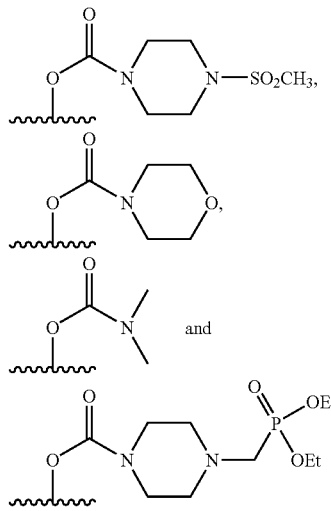

19. The compound of claim 17 wherein $X^2$ is $CR^2$ and $R^2$ is selected from the structures:

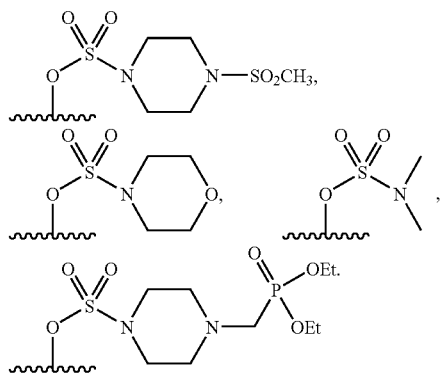

20. A compound of claim 1 wherein $X^2$ is $CR^2$ and $R^2$ comprises a phosphonate prodrug moiety.

21. The compound of claim 1 wherein Ar-L is selected from the structures:

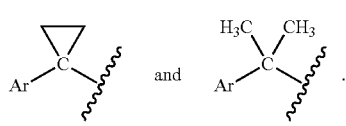

22. A compound having the formula:

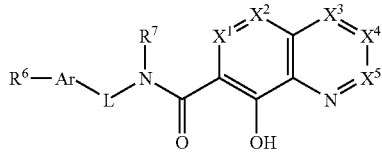

or a pharmaceutically acceptable salt thereof, and including enol and tautomeric resonance isomers;

wherein:

X$^1$ is NR, or N;

X$^2$ is CR$^2$;

X$^3$ is CR$^3$;

X$^4$ is CR$^4$;

X$^5$ is CR$^5$;

R$^1$, R$^3$, R$^4$, R$^5$, R$^6$, R$^7$, and R$^8$ are independently selected from H, F, Cl, Br, I, OH, amino (—NH$_2$), ammonium (—NH$_3$$^+$), alkylamino, dialkylamino, trialkylammonium, C$_1$-C$_8$ alkyl, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), formyl (—CHO), ester (—C(=O)OR), amido (—C(=O)NR$_2$), 5-7 membered ring lactam, 5-7 membered ring lactone, nitrile (—CN), azido (—N$_3$), nitro (—NO$_2$), C$_1$-C$_8$ alkoxy (—OR), C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, phosphonate, phosphate, polyethyleneoxy, and a phosphonate prodrug moiety; or when X$^1$ is CR$^1$ and when X$^2$ is CR$^2$, then CR$^1$ and CR$^2$ together may form a ring; when X$^3$ is CR$^3$ and when X$^4$ is CR$^4$, then CR$^3$ and CR$^4$ together may form a ring; or when. X$^4$ is CR$^4$ and X$^5$ is CR$^5$, then CR$^4$ and CR$^5$ together may form a ring; wherein the ring is 5, 6, or 7-membered;

R$^2$ is selected from H, F, Cl, Br, I,OH, amino (—NH$_2$), ammonium (—NH$_3$$^+$) alkylamino, dialkylamino, trialkylammonium, C$_1$-C$_8$ alkyl, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), formyl (—CHO), ester (—C(=O)OR), amido (—C(=O)NR$_2$), 5-7 membered ring lactam, 5-7 membered ring lactone, nitrile (—CN), azido (—N$_3$), nitro (—NO$_2$), C$_1$-C$_8$ alkoxy (—OR), C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, phosphonate, phosphate, polyethyleneoxy, a phosphonate prodrug moiety, OC(=O)OR, OC(=O)NR$_2$, OC(=O)R, OSO$_2$NR$_2$ (sulfamate), NR$_2$, NRSO$_2$R, SR, S(O)R, SO$_2$R or SO$_2$NR$_2$ (sulfonamide), lactam having the structures:

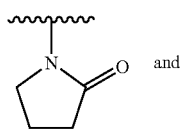 and 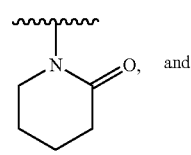 and sultam having the structures:

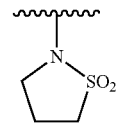 and 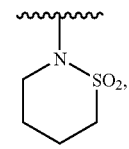

R is independently selected from H, C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl;

L is selected from a bond, O, S, NR, N—OR, C$_1$-C$_{12}$ alkylene, C$_1$-C$_{12}$ substituted alkylene, C$_2$-C$_{12}$ alkenylene, C$_2$-C$_{12}$ substituted alkenylene, C$_2$-C$_{12}$ alkynylene, C$_2$-C$_{12}$ substituted alkynylene, C(=O)NH, C(=O), S(=O)$_2$, C(=O)NH(CH$_2$)$_n$, and (CH$_2$CH$_2$O)$_n$, where n may be 1, 2, 3, 4, 5, or 6; and Ar is covalently attached to L and to one or more R$^6$ and Ar is selected from C$_6$-C$_{20}$ aryl, C$_6$-C$_{20}$ substituted aryl, C$_2$-C$_{20}$ heteroaryl, and C$_2$-C$_{20}$ substituted heteroaryl;

where at least one of R, R$^1$, R$^2$, R$^3$, R$^4$, R$^5$, R$^6$, and R$^7$ comprises a phosphonate group.

23. A compound according to claim 22 having the formula:

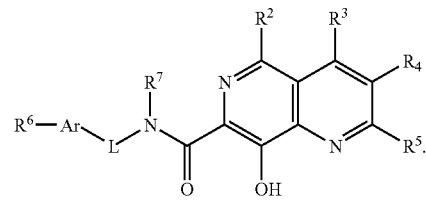

24. A compound according to claim 22 having the formula:

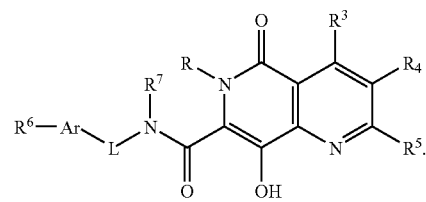

25. The compound of claim 22 wherein substituted alkylene, substituted alkenylene, substituted alkynylene, substituted aryl, and substituted heteroaryl are independently substituted with one or more substituents selected from F, Cl, Br, I, OH, amino (—NH$_2$), ammonium (—NH$_3$$^+$), alkylamino, dialkylamino, trialkylammonium, C$_1$-C$_8$ alkyl, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), ester (—C(=O)OR), amido (—C(=O)NR$_2$), 5-7 membered ring lactam, 5-7 membered ring lactone, nitrile (—CN), azido (—N$_3$), nitro (—NO₂), $C_1$-$C_8$ alkoxy (—OR), $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, and a prodrug moiety.

26. A compound of claim 22 wherein $X^2$ is $CR^2$ and $R^2$ is selected from H, OH, OC(=O)OR, OC(=O)NR₂, OC(=O)R, OSO₂NR₂ (sulfamate), NR₂, NRSO₂R, SR, S(O)R, SO₂R or SO₂NR₂ (sulfonamide), lactam having the structures:

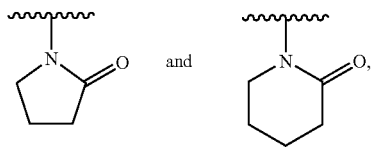

sultam having the structures:

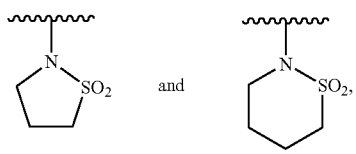

and a phosphonate prodrug moiety.

27. The compound of claim 22 wherein L is $CH_2$ and Ar is substituted phenyl.

28. The compound of claim 22 where L is $CH_2$ and Ar is 4-fluorophenyl.

29. The compound of claim 22 wherein at least one of $R^1$, $R^2$, $R^3$, $R^4$, $R^5$, $R^6$, and $R^7$ comprise a phosphonate prodrug moiety selected from the structures:

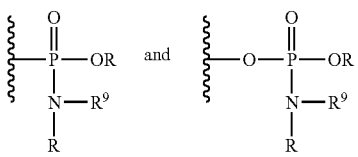

wherein $R^9$ is comprised of an ester, an amide, or a carbamate.

30. The compound of claim 22 wherein the phosphonate group has the structure:

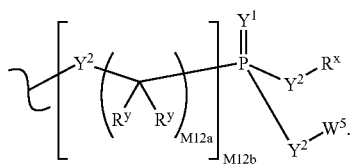

wherein:
$Y^1$ is independently O, S, N($R^x$), N(O)($R^x$), N(O$R^x$), N(O)(O$R^x$), or N(N($R^x$)($R^x$));
$Y^2$ is independently a bond, O, N($R^x$), N(O)($R^x$), N(O$R^x$), N(O)(O$R^x$), N(N($R^x$)($R^x$)), —S(O)— (sulfoxide), —S(O)₂— (sulfone), —S— (sulfide), or —S—S— (disulfide);
M2 is 0, 1 or 2;
M12a is 1, 2, 3, 4, 5, 6, 7, 8, 9, 10, 11, or 12;
M12b is 0, 1, 2, 3, 4, 5, 6, 7, 8, 9, 10, 11, or 12;

$R^y$ is independently H, alkyl, substituted alkyl, aryl, substituted aryl, or a protecting group, or where taken together at a carbon atom, two vicinal $R^y$ groups form a carbocycle or a heterocycle; and $R^x$ is independently H, alkyl, substituted alkyl, aryl, substituted aryl, or a protecting group, or the formula:

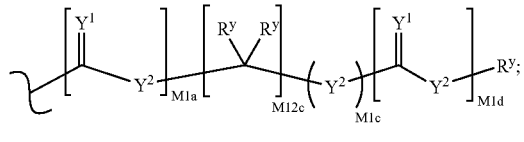

where M1a, M1c, and M1d are independently 0 or 1, and M12c is 0, 1, 2, 3, 4, 5, 6, 7, 8, 9, 10, 11 or 12.

31. The compound of claim 30 wherein the phosphonate group has the structure:

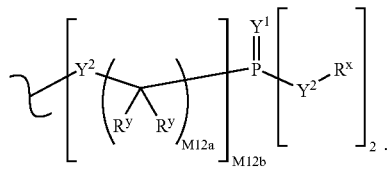

32. The compound of claim 31 wherein the phosphonate group has the structure:

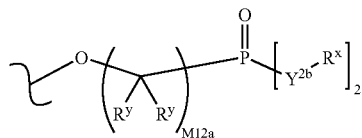

where $Y^{2b}$ is O or N($R^x$).

33. The compound of claim 31 wherein the phosphonate group has the structure:

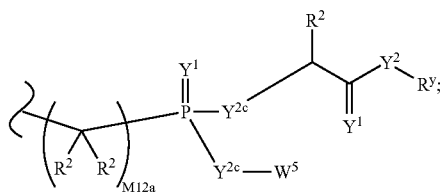

where $W^5$ is a carbocycle, and $Y^{2c}$ is O, N($R^y$) or S.

34. The compound of claim 33 wherein $W^5$ is selected from the structures:

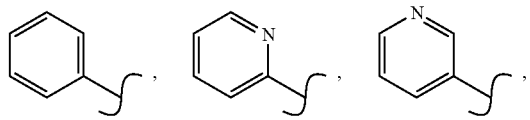

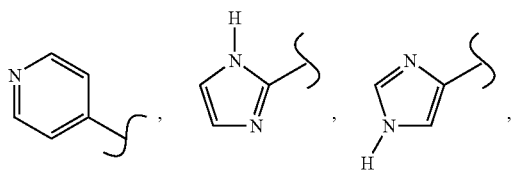

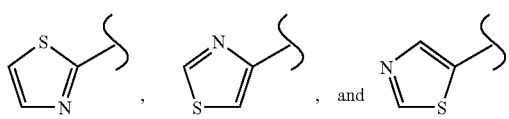

35. The compound of claim 30 wherein the phosphonate group has the structure:

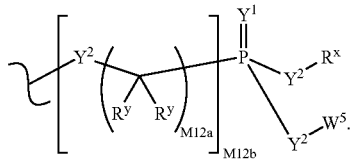

36. The compound of claim 35 wherein the phosphonate group has the structure:

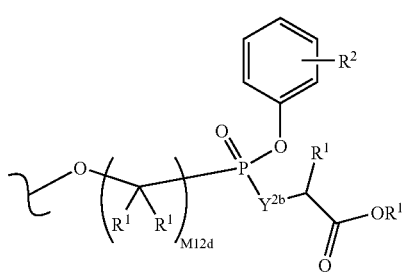

wherein $Y^{2b}$ is O or $N(R^x)$; M12d is 1, 2, 3, 4, 5, 6, 7 or 8; $R^1$ is H or $C_1$-$C_6$ alkyl; and the phenyl carbocycle is substituted with 0 to 3 $R^2$ groups where $R^2$ is $C_1$-$C_6$ alkyl or substituted alkyl.

37. The compound of claim 36 wherein the phosphonate group has the structure:

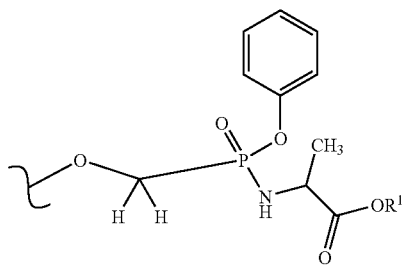

or

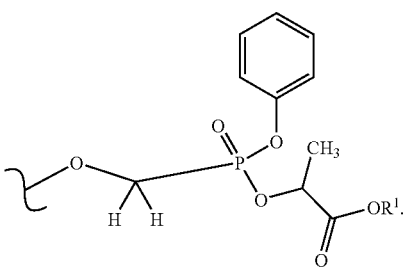

38. The compound of claim 30 wherein $R^x$ is selected from the structures:

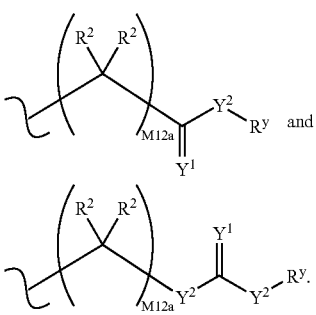

39. The compound of claim 38 wherein $X^2$ is $CR^2$ and $R^2$ is selected from the structures:

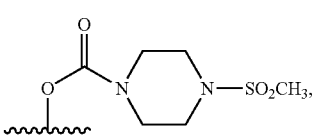

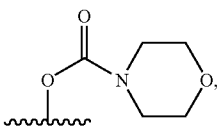

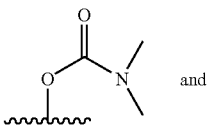

and

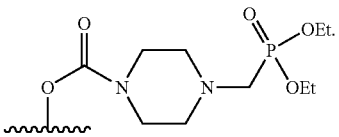

40. The compound of claim 38 wherein $X^2$ is $CR^2$ and $R^2$ is selected from the structures:

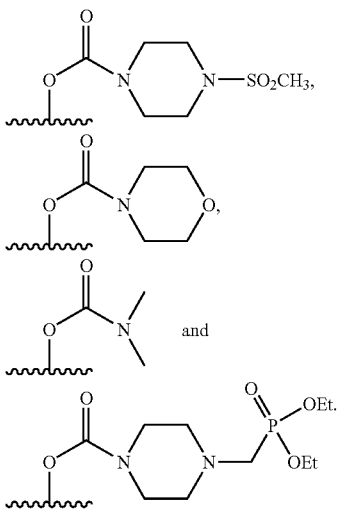

41. A compound of claim 22 wherein $X^2$ is $CR^2$ and $R^2$ comprises a phosphonate prodrug moiety.

42. The compound of claim 23 wherein Ar-L is selected from the structures:

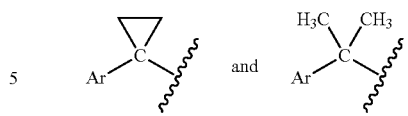

43. A pharmaceutical composition comprising a therapeutically effective amount of a compound of claim 1 and a pharmaceutically acceptable carrier.

44. A pharmaceutical composition comprising a therapeutically effective amount of a compound of claim 1 in combination with a therapeutically effective amount of an AIDS treatment agent selected from:
    (1) an AIDS antiviral agent,
    (2) an anti-infective agent, and
    (3) an immunomodulator.

45. The composition of claim 44 wherein the antiviral agent is an HIV protease inhibitor.

46. A pharmaceutical composition made by combining the compound of claim 1 and a pharmaceutically acceptable carrier.

47. A process for making a pharmaceutical composition comprising combining a compound of claim 1 and a pharmaceutically acceptable carrier.

* * * * *